United States Patent
Vandendriessche et al.

(10) Patent No.: US 12,427,205 B2
(45) Date of Patent: Sep. 30, 2025

(54) MUSCLE-SPECIFIC NUCLEIC ACID REGULATORY ELEMENTS AND METHODS AND USE THEREOF

(71) Applicant: VRIJE UNIVERSITEIT BRUSSEL, Brussels (BE)

(72) Inventors: Thierry Vandendriessche, Bierbeek (BE); Lay Khim Chuah, Bierbeek (BE)

(73) Assignee: VRIJE UNIVERSITEIT BRUSSEL, Brussels (BE)

( * ) Notice: Subject to any disclaimer, the term of this patent is extended or adjusted under 35 U.S.C. 154(b) by 496 days.

(21) Appl. No.: 17/760,333

(22) PCT Filed: Feb. 18, 2021

(86) PCT No.: PCT/EP2021/053945
§ 371 (c)(1),
(2) Date: Aug. 8, 2022

(87) PCT Pub. No.: WO2021/165353
PCT Pub. Date: Aug. 26, 2021

(65) Prior Publication Data
US 2023/0226220 A1    Jul. 20, 2023

(30) Foreign Application Priority Data
Feb. 18, 2020 (EP) .................... 20158057

(51) Int. Cl.
C12N 15/86    (2006.01)
A61K 48/00    (2006.01)
C07K 14/47    (2006.01)

(52) U.S. Cl.
CPC ...... A61K 48/0058 (2013.01); C07K 14/4716 (2013.01); C12N 15/86 (2013.01);
(Continued)

(58) Field of Classification Search
None
See application file for complete search history.

(56) References Cited

FOREIGN PATENT DOCUMENTS

WO    WO 2015/110449 A1    7/2015
WO    WO 2018/178067 A1    10/2018

OTHER PUBLICATIONS

Talbot GE, Waddington SN, Bales O, Tchen RC, Antoniou MN. Desmin-regulated lentiviral vectors for skeletal muscle gene transfer . Mol Ther. Mar. 2010;18(3):601-8. doi: 10.1038/mt.2009.267. Epub Nov. 24, 2009. PMID: 19935780; PMCID: PMC2839432. (Year: 2010).*

(Continued)

*Primary Examiner* — Evelyn Y Pyla
*Assistant Examiner* — Jagamya Vijayaraghavan
(74) *Attorney, Agent, or Firm* — Knobbe, Martens, Olson & Bear, LLP

(57) ABSTRACT

Nucleic acid regulatory elements that are able to enhance muscle-specific expression of genes, in particular expression in muscle cells and/or tissues such as in diaphragm, smooth muscle, heart and/or skeletal muscle, including at least two diaphragm-specific regulatory elements and a heart- and skeletal muscle-specific regulatory element. Expression cassettes and vectors containing these nucleic acid regulatory elements, as well as uses thereof such as applications using gene therapy of muscle-related disorders, more particularly diaphragm, heart and/or skeletal muscle-directed gene therapy, and for vaccination purposes.

10 Claims, 16 Drawing Sheets
Specification includes a Sequence Listing.

(52) U.S. Cl.
CPC .............. *C12N 2750/14143* (2013.01); *C12N 2750/14145* (2013.01); *C12N 2750/14171* (2013.01); *C12N 2830/008* (2013.01)

(56) References Cited

OTHER PUBLICATIONS

Niederriter, A.R.; Varshney, A.; Parker, S.C.J.; Martin, D.M. Super Enhancers in Cancers, Complex Disease, and Developmental Disorders. Genes 2015, 6, 1183-1200. https://doi.org/10.3390/genes6041183 (Year: 2015).*

Pozsgai et al., "[beta]-Sarcoglycan gene transfer decreases fibrosis and restores force in LGMD2E mice", Gene Therapy, vol. 23, No. 1, 2016, pp. 57-66.

Wang et al., "Construction and analysis of compact muscle-specific promoters for AAV vectors", Gene Therapy, vol. 15, No. 22, Nov. 19, 2008 (Nov. 19, 2008), pp. 1489-1499.

International Search Report and Written Opinion issued in PCT/EP2021/053945, mailed Jun. 11, 2021.

* cited by examiner

Fig. 1

(A) CSk-SH5 (SEQ ID NO:1)
CAGTTTACTCACCAGGGATTCAGAGGCAGCACTGCTGAACCCTGAGCCCTTGGCACATCAGGTTGGCTGTCAG
AAGTCGGCCTTTGTACATACACAGTTCCCTTGTGAGGCCCAGCTGCGTGTCCTAGGAGCGGGGCCTCTCTCCA
CAGCAGAGCTCAGCCTCTCAAGTGTATGGACAGCACGGGTGCCTGATGGGTGGATTTAGCCATGAGTTGAAGG
TGGCTTGGGGAGAATGAGAGTTCTAGAGATAGGGAGAAGGGGTTGCCAATAGGAGAGTGGAATTCCTGAGCAC
CTCGTCACAGGCAGCCGACAGAACATGAGCCGCAGGGCCCAGGCTATTTATACCTCGCCTGTCACTATCAGGG
TCCCCACAGCTCCCCCCACCTCCAGCCACACACAGCAGGTCCTTTTGCTCTTTCTGGTCCCTTCTCTACTCCT
CCCCCTCCCTACCTAA (B) Dph-CRE02 (SEQ ID NO:2)
GACAGGTGCGGTTCCCGGAGCGCAGGCGCACACATGCACCCACCGGCGAACGCGGTGACCCTCGCCCCACCCC
ATCCCCTCCGGCGGGCAACTGGGTCGGGTCAGGAGGGGCAAACCCGCTAGGGAGACACTCCATATACGGCCCG
GCCCGCGTTACCTGGGACCGGGCCAACCCGCTCCTTCTTTGGTCAACGCAGGGGACCCGGGCGGGGGCCCAGG
CCGCGAACCGGCCGAGGGAGGGGGCTCTAGTGCCCAACACCCAAATATGGCTCGAGAAGGGCAGCGACATTCC
TGCGGGGTGGCGCGGAGGGAATGCCCGCGGGCTATATAAACCTGAGCAGAGGGACAAGCGGCCACCGCAGCG
GACAGCGCCAAGTGAAGCCTCGCTTCCCCTCCGCGGCGACCAGGGCCCGAGCCGAGAGTAGCAGTTGTAGCTA
CCCGCCCAGGTAGG (C) Dph-CRE04 (SEQ ID NO:3)
CCTTTTAGAGAATCCACACCTGTCCCAGTTGCTGGGTTCCACTACCAAAAGTGAATTGCAACTATTTTAGGAG
CACTTAAGCACATCCGAAAAATGAGTGATTCTGTTCTGGCCCACACCACATCACTGATGTACCCCCTTAAAGC
ATGTCCCTGAGTTCATCACAGAAGACTGCTCCTCCTGTGCCCTCCACAAGGTTAGAACTGTCCTTGTCTTAGG
GAAAAAGGAGAGAGAGAGAGAGAGAGAGAGAGAGAGAGAGAGAGAGAGAGAGGGACAGGCACCAACT
GGGTAACCTCTGCTGACCCCCACTCTACTTTACCATAAGTAGCTCCAAATCCTTCTAGAAAATCTGAAAGGCA
TAGCCCCATATATCAGTGATATAAATAGAACCTGCAGCAGGCTCTGGTAAATGATGACTACAAGGTGGACTGG
GAGGCAGCCCGGCCTTGGCAGGCATCATCCTCTAAATATAAAGATGAGTTTGTTCAGCCTTTGCAGAAGGA (D) Dph-CRE06 (SEQ ID NO:4)
GGGCCAGGGGACGGTGGCTTCTACGTGCTTGGGACGTTCCCAGCCACCGTCCCATGTTCCCGGCGGGGGCCA
GCTGTCCCCACCGCCAGCCCAACTCAGCACTTGGTCAGGGTATCAGCTTGGTGGGGGGCGTGAGCCCAGCCC
CTGGGGCGGCTCAGCCCATACAAGGCCATGGGGCTGGGCGCAAAGCATGCCTGGGTTCAGGGTGGGTATGGTG
CGGGAGCAGGGAGGTGAGAGGCTCAGCTGCCCTCCAGAACTCCTCCCTGGGGACAACCCCTCCCAGCCAATAG
CACAGCCTAGGTCCCCCTATATAAGGCCACGGCTGCTGGCCCTTCCTTTGGGTCAGTGTCACCTCCAGGATAC
AGACAGCCCCCCTTCAGCCCAGCCCAGCCAGGTAC (E) Dph-CRE02-CRE04 (SEQ ID NO:5)
GACAGGTGCGGTTCCCGGAGCGCAGGCGCACACATGCACCCACCGGCGAACGCGGTGACCCTCGCCCCACCCC
ATCCCCTCCGGCGGGCAACTGGGTCGGGTCAGGAGGGGCAAACCCGCTAGGGAGACACTCCATATACGGCCCG
GCCCGCGTTACCTGGGACCGGGCCAACCCGCTCCTTCTTTGGTCAACGCAGGGGACCCGGGCGGGGGCCCAGG
CCGCGAACCGGCCGAGGGAGGGGGCTCTAGTGCCCAACACCCAAATATGGCTCGAGAAGGGCAGCGACATTCC
TGCGGGGTGGCGCGGAGGGAATGCCCGCGGGCTATATAAACCTGAGCAGAGGGACAAGCGGCCACCGCAGCG
GACAGCGCCAAGTGAAGCCTCGCTTCCCCTCCGCGGCGACCAGGGCCCGAGCCGAGAGTAGCAGTTGTAGCTA
CCCGCCCAGGTAGGGGCGCGCCGTCGACGGATCCCCTTTTAGAGAATCCACACCTGTCCCAGTTGCTGGGTTC
CACTACCAAAAGTGAATTGCAACTATTTTAGGAGCACTTAAGCACATCCGAAAAATGAGTGATTCTGTTCTGG
CCCACACCACATCACTGATGTACCCCCTTAAAGCATGTCCCTGAGTTCATCACAGAAGACTGCTCCTCCTGTG
CCCTCCACAAGGTTAGAACTGTCCTTGTCTTAGGGAAAAAGGAGAGAGAGAGAGAGAGAGAGAGAGAGAGAGA
GAGAGAGAGAGAGAGGGACAGGCACCAACTGGGTAACCTCTGCTGACCCCCACTCTACTTTACCATAAG
TAGCTCCAAATCCTTCTAGAAAATCTGAAAGGCATAGCCCCATATATCAGTGATATAAATAGAACCTGCAGCA
GGCTCTGGTAAATGATGACTACAAGGTGGACTGGGAGGCAGCCCGGCCTTGGCAGGCATCATCCTCTAAATAT
AAAGATGAGTTTGTTCAGCCTTTGCAGAAGGA

Fig. 1 (cont.)

(F) Dph-CRE02-CRE06 (SEQ ID NO: 6)
GACAGGTGCGGTTCCCGGAGCGCAGGCGCACACATGCACCCACCGGCGAACGCGGTGACCCTCGCCCCACCCC
ATCCCCTCCGGCGGGCAACTGGGTCGGGTCAGGAGGGGCAAACCCGCTAGGGAGACACTCCATATACGGCCCG
GCCCGCGTTACCTGGGACCGGGCCAACCCGCTCCTTCTTTGGTCAACGCAGGGGACCCGGGCGGGGGCCCAGG
CCGCGAACCGGCCGAGGGAGGGGGCTCTAGTGCCCAACACCCAAATATGGCTCGAGAAGGGCAGCGACATTCC
TGCGGGGTGGCGCGGAGGGAATGCCCGCGGCTATATAAAACCTGAGCAGAGGGACAAGCGGCCACCGCAGCG
GACAGCGCCAAGTGAAGCCTCGCTTCCCCTCCGCGGCGACCAGGGCCCGAGCCGAGAGTAGCAGTTGTAGCTA
CCCGCCCAGGTAGGGGCGCGCCGTCGACGGATCCGGGCCAGGGGACGGTGGCTTCTACGTGCTTGGGACGTTC
CCAGCCACCGTCCCATGTTCCCGGCGGGGGCCAGCTGTCCCCACCGCCAGCCCAACTCAGCACTTGGTCAGG
GTATCAGCTTGGTGGGGGGCGTGAGCCCAGCCCTGGGGCGGCTCAGCCCATACAAGGCCATGGGGCTGGGC
GCAAAGCATGCCTGGGTTCAGGGTGGGTATGGTGCGGGAGCAGGGAGGTGAGAGGCTCAGCTGCCCTCCAGAA
CTCCTCCCTGGGGACAACCCCTCCCAGCCAATAGCACAGCCTAGGTCCCCCTATATAAGGCCACGGCTGCTGG
CCCTTCCTTTGGGTCAGTGTCACCTCCAGGATACAGACAGCCCCCCTTCAGCCCAGCCCAGCCAGGTAC (G) Dph-CRE04-CRE06 (SEQ ID NO: 7)
CCTTTTAGAGAATCCACACCTGTCCCAGTTGCTGGGTTCCACTACCAAAAGTGAATTGCAACTATTTTAGGAG
CACTTAAGCACATCCGAAAAATGAGTGATTCTGTTCTGGCCCACACCACATCACTGATGTACCCCCTTAAAGC
ATGTCCCTGAGTTCATCACAGAAGACTGCTCCTCCTGTGCCCTCCACAAGGTTAGAACTGTCCTTGTCTTAGG
GAAAAAGGAGAGAGAGAGAGAGAGAGAGAGAGAGAGAGAGAGAGAGAGAGAGAGAGAGAGAGGGACAGGCACCAACT
GGGTAACCTCTGCTGACCCCCACTCTACTTTACCATAAGTAGCTCCAAATCCTTCTAGAAAATCTGAAAGGCA
TAGCCCCATATATCAGTGATATAAATAGAACCTGCAGCAGGCTCTGGTAAATGATGACTACAAGGTGGACTGG
GAGGCAGCCCGGCCTTGGCAGGCATCATCCTCTAAATATAAAGATGAGTTTGTTCAGCCTTTGCAGAAGGAGG
CGCGCCGTCGACGGATCCGGGCCAGGGGACGGTGGCTTCTACGTGCTTGGGACGTTCCCAGCCACCGTCCCAT
GTTCCCGGCGGGGGCCAGCTGTCCCCACCGCCAGCCCAACTCAGCACTTGGTCAGGGTATCAGCTTGGTGGG
GGGCGTGAGCCCAGCCCCTGGGGCGGCTCAGCCCATACAAGGCCATGGGGCTGGGCGCAAAGCATGCCTGGG
TTCAGGGTGGGTATGGTGCGGGAGCAGGGAGGTGAGAGGCTCAGCTGCCCTCCAGAACTCCTCCCTGGGGACA
ACCCCTCCCAGCCAATAGCACAGCCTAGGTCCCCCTATATAAGGCCACGGCTGCTGGCCCTTCCTTTGGGTCA
GTGTCACCTCCAGGATACAGACAGCCCCCCTTCAGCCCAGCCCAGCCAGGTAC (H) Dph-CRE06-CRE04 (SEQ ID NO:8)
GGGCCAGGGGACGGTGGCTTCTACGTGCTTGGGACGTTCCCAGCCACCGTCCCATGTTCCCGGCGGGGGCCA
GCTGTCCCCACCGCCAGCCCAACTCAGCACTTGGTCAGGGTATCAGCTTGGTGGGGGGCGTGAGCCCAGCCC
CTGGGGCGGCTCAGCCCATACAAGGCCATGGGGCTGGGCGCAAAGCATGCCTGGGTTCAGGGTGGGTATGGTG
CGGGAGCAGGGAGGTGAGAGGCTCAGCTGCCCTCCAGAACTCCTCCCTGGGGACAACCCCTCCCAGCCAATAG
CACAGCCTAGGTCCCCCTATATAAGGCCACGGCTGCTGGCCCTTCCTTTGGGTCAGTGTCACCTCCAGGATAC
AGACAGCCCCCCTTCAGCCCAGCCCAGCCAGGTACGGCGCGCCGTCGACGGATCCCCTTTTAGAGAATCCACA
CCTGTCCCAGTTGCTGGGTTCCACTACCAAAAGTGAATTGCAACTATTTTAGGAGCACTTAAGCACATCCGAA
AAATGAGTGATTCTGTTCTGGCCCACACCACATCACTGATGTACCCCCTTAAAGCATGTCCCTGAGTTCATCA
CAGAAGACTGCTCCTCCTGTGCCCTCCACAAGGTTAGAACTGTCCTTGTCTTAGGGAAAAAGGAGAGAGAGAG
AGAGAGAGAGAGAGAGAGAGAGAGAGAGAGAGAGAGAGAGGGACAGGCACCAACTGGGTAACCTCTGCTGACC
CCCACTCTACTTTACCATAAGTAGCTCCAAATCCTTCTAGAAAATCTGAAAGGCATAGCCCCATATATCAGTG
ATATAAATAGAACCTGCAGCAGGCTCTGGTAAATGATGACTACAAGGTGGACTGGGAGGCAGCCCGGCCTTGG
CAGGCATCATCCTCTAAATATAAAGATGAGTTTGTTCAGCCTTTGCAGAAGGA

Fig. 1 (cont.)

(I) Dph-CRE02-CRE04-CRE06 (SEQ ID NO:9)
GACAGGTGCGGTTCCCGGAGCGCAGGCGCACACATGCACCCACCGGCGAACGCGGTGACCCTCGCCCCACCCC
ATCCCCTCCGGCGGGCAACTGGGTCGGGTCAGGAGGGGCAAACCCGCTAGGGAGACACTCCATATACGGCCCG
GCCCGCGTTACCTGGGACCGGGCCAACCCGCTCCTTCTTTGGTCAACGCAGGGGACCCGGGCGGGGGCCCAGG
CCGCGAACCGGCCGAGGGAGGGGGCTCTAGTGCCCAACACCCAAATATGGCTCGAGAAGGGCAGCGACATTCC
TGCGGGGTGGCGCGGAGGGAATGCCCGCGGGCTATATAAACCTGAGCAGAGGGACAAGCGGCCACCGCAGCG
GACAGCGCCAAGTGAAGCCTCGCTTCCCCTCCGCGGCGACCAGGGCCCGAGCCGAGAGTAGCAGTTGTAGCTA
CCCGCCCAGGTAGGGGCGCGCCGTACGGTCGACGGATCCCCTTTTAGAGAATCCACACCTGTCCCAGTTGCT
GGGTTCCACTACCAAAAGTGAATTGCAACTATTTTAGGAGCACTTAAGCACATCCGAAAAATGAGTGATTCTG
TTCTGGCCCACACCACATCACTGATGTACCCCCTTAAAGCATGTCCCTGAGTTCATCACAGAAGACTGCTCCT
CCTGTGCCCTCCACAAGGTTAGAACTGTCCTTGTCTTAGGGAAAAAGGAGAGAGAGAGAGAGAGAGAGAGAGA
GAGAGAGAGAGAGAGAGAGAGAGGGACAGGCACCAACTGGGTAACCTCTGCTGACCCCCACTCTACTTTAC
CATAAGTAGCTCCAAATCCTTCTAGAAAATCTGAAAGGCATAGCCCCATATATCAGTGATATAAATAGAACCT
GCAGCAGGCTCTGGTAAATGATGACTACAAGGTGGACTGGGAGGCAGCCCGGCCTTGGCAGGCATCATCCTCT
AAATATAAAGATGAGTTTGTTCAGCCTTTGCAGAAGGAGGCGCGCCGTCGACGGATCCGGGCCAGGGGACGGT
GGCTTCTACGTGCTTGGGACGTTCCCAGCCACCGTCCCATGTTCCCGGCGGGGGCCAGCTGTCCCCACCGCC
AGCCCAACTCAGCACTTGGTCAGGGTATCAGCTTGGTGGGGGGCGTGAGCCCAGCCCCTGGGCGGCTCAGC
CCATACAAGGCCATGGGGCTGGGCGCAAAGCATGCCTGGGTTCAGGGTGGGTATGGTGCGGGAGCAGGGAGGT
GAGAGGCTCAGCTGCCCTCCAGAACTCCTCCCTGGGGACAACCCCTCCCAGCCAATAGCACAGCCTAGGTCCC
CCTATATAAGGCCACGGCTGCTGGCCCTTCCTTTGGGTCAGTGTCACCTCCAGGATACAGACAGCCCCCCTTC
AGCCCAGCCCAGCCAGGTAC (J) Dph-CRE02-CRE04-CSk-SH5 (SEQ ID NO:10)
GACAGGTGCGGTTCCCGGAGCGCAGGCGCACACATGCACCCACCGGCGAACGCGGTGACCCTCGCCCCACCCC
ATCCCCTCCGGCGGGCAACTGGGTCGGGTCAGGAGGGGCAAACCCGCTAGGGAGACACTCCATATACGGCCCG
GCCCGCGTTACCTGGGACCGGGCCAACCCGCTCCTTCTTTGGTCAACGCAGGGGACCCGGGCGGGGGCCCAGG
CCGCGAACCGGCCGAGGGAGGGGGCTCTAGTGCCCAACACCCAAATATGGCTCGAGAAGGGCAGCGACATTCC
TGCGGGGTGGCGCGGAGGGAATGCCCGCGGGCTATATAAACCTGAGCAGAGGGACAAGCGGCCACCGCAGCG
GACAGCGCCAAGTGAAGCCTCGCTTCCCCTCCGCGGCGACCAGGGCCCGAGCCGAGAGTAGCAGTTGTAGCTA
CCCGCCCAGGTAGGGGCGCGCCGTCGACGGATCCCCTTTTAGAGAATCCACACCTGTCCCAGTTGCTGGGTTC
CACTACCAAAAGTGAATTGCAACTATTTTAGGAGCACTTAAGCACATCCGAAAAATGAGTGATTCTGTTCTGG
CCCACACCACATCACTGATGTACCCCCTTAAAGCATGTCCCTGAGTTCATCACAGAAGACTGCTCCTCCTGTG
CCCTCCACAAGGTTAGAACTGTCCTTGTCTTAGGGAAAAAGGAGAGAGAGAGAGAGAGAGAGAGAGAGAGAGA
GAGAGAGAGAGAGAGGGACAGGCACCAACTGGGTAACCTCTGCTGACCCCCACTCTACTTTACCATAAG
TAGCTCCAAATCCTTCTAGAAAATCTGAAAGGCATAGCCCCATATATCAGTGATATAAATAGAACCTGCAGCA
GGCTCTGGTAAATGATGACTACAAGGTGGACTGGGAGGCAGCCCGGCCTTGGCAGGCATCATCCTCTAAATAT
AAAGATGAGTTTGTTCAGCCTTTGCAGAAGGAGGATCCGTCGACGGCGCGCCACGCGTCAGTTACTCACCAG
GGATTCAGAGGCAGCACTGCTGAACCCTGAGCCCTTGGCACATCAGGTTGGCTGTCAGAAGTCGGCCTTTGTA
CATACACAGTTCCCTTGTGAGGCCAGCTGCGTGTCCTAGGAGCGGGGCCTCTCTCCACAGCAGAGCTCAGCC
TCTCAAGTGTATGGACAGCACGGGTGCCTGATGGGTGGATTTAGCCATGAGTTGAAGGTGGCTTGGGAGAAT
GAGAGTTCTAGAGATAGGGAGAAGGGGTTGCCAATAGGAGAGTGGAATTCCTGAGCACCTCGTCACAGGCAGC
CGACAGAACATGAGCCGCAGGGCCCAGGCTATTTATACCTCGCCTGTCACTATCAGGGTCCCCACAGCTCCCC
CCACCTCCAGCCACACACAGCAGGTCCTTTTGCTCTTTCTGGTCCCTTCTCTACTCCTCCCCCTCCCTACCTA
A

Fig. 1 (cont.)

(K) Dph-CRE02-CRE06–Csk-SH5 (SEQ ID NO:11)
GACAGGTGCGGTTCCCGGAGCGCAGGCGCACACATGCACCCACCGGCGAACGCGGTGACCCTCGCCCCACCCC
ATCCCCTCCGGCGGGCAACTGGGTCGGGTCAGGAGGGGCAAACCCGCTAGGGAGACACTCCATATACGGCCCG
GCCCGCGTTACCTGGGACCGGGCCAACCCGCTCCTTCTTTGGTCAACGCAGGGGACCCGGGCGGGGGCCCAGG
CCGCGAACCGGCCGAGGGAGGGGGCTCTAGTGCCCAACACCCAAATATGGCTCGAGAAGGGCAGCGACATTCC
TGCGGGGTGGCGCGGAGGGAATGCCCGCGGGCTATATAAACCTGAGCAGAGGGACAAGCGGCCACCGCAGCG
GACAGCGCCAAGTGAAGCCTCGCTTCCCCTCCGCGGCGACCAGGGCCCGAGCCGAGAGTAGCAGTTGTAGCTA
CCCGCCCAGGTAGGGGCGCGCCGTCGACGGATCCGGGCCAGGGGACGGTGGCTTCTACGTGCTTGGGACGTTC
CCAGCCACCGTCCCATGTTCCCGGCGGGGGCCAGCTGTCCCCACCGCCAGCCCAACTCAGCACTTGGTCAGG
GTATCAGCTTGGTGGGGGGCGTGAGCCCAGCCCCTGGGGCGGCTCAGCCCATACAAGGCCATGGGGCTGGGC
GCAAAGCATGCCTGGGTTCAGGGTGGGTATGGTGCGGGAGCAGGGAGGTGAGAGGCTCAGCTGCCCTCCAGAA
CTCCTCCCTGGGGACAACCCCTCCCAGCCAATAGCACAGCCTAGGTCCCCTATATAAGGCCACGGCTGCTGG
CCCTTCCTTTGGGTCAGTGTCACCTCCAGGATACAGACAGCCCCCCTTCAGCCCAGCCCAGCCAGGTACGGAT
CCGTCGACGGCGCGCCACGCGTCAGTTTACTCACCAGGGATTCAGAGGCAGCACTGCTGAACCCTGAGCCCTT
GGCACATCAGGTTGGCTGTCAGAAGTCGGCCTTTGTACATACACAGTTCCCTTGTGAGGCCCAGCTGCGTGTC
CTAGGAGCGGGGCCTCTCTCCACAGCAGAGCTCAGCCTCTCAAGTGTATGGACAGCACGGGTGCCTGATGGGT
GGATTTAGCCATGAGTTGAAGGTGGCTTGGGGAGAATGAGAGTTCTAGAGATAGGGAGAAGGGGTTGCCAATA
GGAGAGTGGAATTCCTGAGCACCTCGTCACAGGCAGCCGACAGAACATGAGCCGCAGGGCCCAGGCTATTTAT
ACCTCGCCTGTCACTATCAGGGTCCCCACAGCTCCCCCCACCTCCAGCCACACACAGCAGGTCCTTTTGCTCT
TTCTGGTCCCTTCTCTACTCCTCCCCCTCCCTACCTAA (L) Dph-CRE04-CRE06–Csk-SH5 (SEQ ID NO:12)
CCTTTTAGAGAATCCACACCTGTCCCAGTTGCTGGGTTCCACTACCAAAAGTGAATTGCAACTATTTTAGGAG
CACTTAAGCACATCCGAAAAATGAGTGATTCTGTTCTGGCCCACACCACATCACTGATGTACCCCCTTAAAGC
ATGTCCCTGAGTTCATCACAGAAGACTGCTCCTCCTGTGCCCTCCACAAGGTTAGAACTGTCCTTGTCTTAGG
GAAAAAGGAGAGAGAGAGAGAGAGAGAGAGAGAGAGAGAGAGAGAGAGAGAGAGAGAGGGACAGGCACCAACT
GGGTAACCTCTGCTGACCCCCACTCTACTTTACCATAAGTAGCTCCAAATCCTTCTAGAAAATCTGAAAGGCA
TAGCCCCATATATCAGTGATATAAATAGAACCTGCAGCAGGCTCTGGTAAATGATGACTACAAGGTGGACTGG
GAGGCAGCCCGGCCTTGGCAGGCATCATCCTCTAAATATAAAGATGAGTTTGTTCAGCCTTTGCAGAAGGAGG
CGCGCCGTCGACGGATCCGGGCCAGGGGACGGTGGCTTCTACGTGCTTGGGACGTTCCCAGCCACCGTCCCAT
GTTCCCGGCGGGGGCCAGCTGTCCCCACCGCCAGCCCAACTCAGCACTTGGTCAGGGTATCAGCTTGGTGGG
GGGCGTGAGCCCAGCCCCTGGGGCGGCTCAGCCCATACAAGGCCATGGGGCTGGGCGCAAAGCATGCCTGGG
TTCAGGGTGGGTATGGTGCGGGAGCAGGGAGGTGAGAGGCTCAGCTGCCCTCCAGAACTCCTCCCTGGGGACA
ACCCCTCCCAGCCAATAGCACAGCCTAGGTCCCCTATATAAGGCCACGGCTGCTGGCCCTTCCTTTGGGTCA
GTGTCACCTCCAGGATACAGACAGCCCCCCTTCAGCCCAGCCCAGCCAGGTACGGATCCGTCGACGGCGCGCC
ACGCGTCAGTTTACTCACCAGGGATTCAGAGGCAGCACTGCTGAACCCTGAGCCCTTGGCACATCAGGTTGGC
TGTCAGAAGTCGGCCTTTGTACATACACAGTTCCCTTGTGAGGCCCAGCTGCGTGTCCTAGGAGCGGGGCCTC
TCTCCACAGCAGAGCTCAGCCTCTCAAGTGTATGGACAGCACGGGTGCCTGATGGGTGGATTTAGCCATGAGT
TGAAGGTGGCTTGGGGAGAATGAGAGTTCTAGAGATAGGGAGAAGGGGTTGCCAATAGGAGAGTGGAATTCCT
GAGCACCTCGTCACAGGCAGCCGACAGAACATGAGCCGCAGGGCCCAGGCTATTTATACCTCGCCTGTCACTA
TCAGGGTCCCCACAGCTCCCCCCACCTCCAGCCACACACAGCAGGTCCTTTTGCTCTTTCTGGTCCCTTCTCT
ACTCCTCCCCCTCCCTACCTAA

Fig. 1 (cont.)

(M) Dph-CRE06-CRE04–Csk-SH5 (SEQ ID NO:13)
GGGCCAGGGGACGGTGGCTTCTACGTGCTTGGGACGTTCCCAGCCACCGTCCCATGTTCCCGGCGGGGGGCCA
GCTGTCCCCACCGCCAGCCCAACTCAGCACTTGGTCAGGGTATCAGCTTGGTGGGGGGCGTGAGCCCAGCCC
CTGGGGCGGCTCAGCCCATACAAGGCCATGGGGCTGGGCGCAAAGCATGCCTGGGTTCAGGGTGGGTATGGTG
CGGGAGCAGGGAGGTGAGAGGCTCAGCTGCCCTCCAGAACTCCTCCCTGGGGACAACCCCTCCCAGCCAATAG
CACAGCCTAGGTCCCCCTATATAAGGCCACGGCTGCTGGCCCTTCCTTTGGGTCAGTGTCACCTCCAGGATAC
AGACAGCCCCCCTTCAGCCCAGCCCAGCCAGGTACGGCGCGCCGTCGACGGATCCCCTTTTAGAGAATCCACA
CCTGTCCCAGTTGCTGGGTTCCACTACCAAAAGTGAATTGCAACTATTTTAGGAGCACTTAAGCACATCCGAA
AAATGAGTGATTCTGTTCTGGCCCACACCACATCACTGATGTACCCCCTTAAAGCATGTCCCTGAGTTCATCA
CAGAAGACTGCTCCTCCTGTGCCCTCCACAAGGTTAGAACTGTCCTTGTCTTAGGGAAAAAGGAGAGAGAGAG
AGAGAGAGAGAGAGAGAGAGAGAGAGAGAGAGAGAGAGGGACAGGCACCAACTGGGTAACCTCTGCTGACC
CCCACTCTACTTTACCATAAGTAGCTCCAAATCCTTCTAGAAAATCTGAAAGGCATAGCCCCATATATCAGTG
ATATAAATAGAACCTGCAGCAGGCTCTGGTAAATGATGACTACAAGGTGGACTGGGAGGCAGCCCGGCCTTGG
CAGGCATCATCCTCTAAATATAAAGATGAGTTTGTTCAGCCTTTGCAGAAGGAGGATCCGTCGACGGCGCGCC
ACGCGTCAGTTTACTCACCAGGGATTCAGAGGCAGCACTGCTGAACCCTGAGCCCTTGGCACATCAGGTTGGC
TGTCAGAAGTCGGCCTTTGTACATACACAGTTCCCTTGTGAGGCCCAGCTGCGTGTCCTAGGAGCGGGGCCTC
TCTCCACAGCAGAGCTCAGCCTCTCAAGTGTATGGACAGCACGGGTGCCTGATGGGTGGATTTAGCCATGAGT
TGAAGGTGGCTTGGGGAGAATGAGAGTTCTAGAGATAGGGAGAAGGGGTTGCCAATAGGAGAGTGGAATTCCT
GAGCACCTCGTCACAGGCAGCCGACAGAACATGAGCCGCAGGGCCCAGGCTATTTATACCTCGCCTGTCACTA
TCAGGGTCCCCACAGCTCCCCCCACCTCCAGCCACACACAGCAGGTCCTTTTGCTCTTTCTGGTCCCTTCTCT
ACTCCTCCCCCTCCCTACCTAA (N) Dph-CRE02-CRE04-CRE06–Csk-SH5 (SEQ ID NO:14)
GACAGGTGCGGTTCCCGGAGCGCAGGCGCACACATGCACCCACCGGCGAACGCGGTGACCCTCGCCCCACCCC
ATCCCCTCCGGCGGGCAACTGGGTCGGGTCAGGAGGGGCAAACCCGCTAGGGAGACACTCCATATACGGCCCG
GCCCGCGTTACCTGGGACCGGGCCAACCCGCTCCTTCTTTGGTCAACGCAGGGGACCCGGGCGGGGGCCCAGG
CCGCGAACCGGCCGAGGGAGGGGGCTCTAGTGCCCAACACCCAAATATGGCTCGAGAAGGGCAGCGACATTCC
TGCGGGGTGGCGCGGAGGGAATGCCCGCGGGCTATATAAACCTGAGCAGAGGGACAAGCGGCCACCGCAGCG
GACAGCGCCAAGTGAAGCCTCGCTTCCCCTCCGCGGCGACCAGGGCCCGAGCCGAGAGTAGCAGTTGTAGCTA
CCCGCCCAGGTAGGGGCGCGCCCGTACGGTCGACGGATCCCCTTTTAGAGAATCCACACCTGTCCCAGTTGCT
GGGTTCCACTACCAAAAGTGAATTGCAACTATTTTAGGAGCACTTAAGCACATCCGAAAAATGAGTGATTCTG
TTCTGGCCCACACCACATCACTGATGTACCCCCTTAAAGCATGTCCCTGAGTTCATCACAGAAGACTGCTCCT
CCTGTGCCCTCCACAAGGTTAGAACTGTCCTTGTCTTAGGGAAAAAGGAGAGAGAGAGAGAGAGAGAGAGAGA
GAGAGAGAGAGAGAGAGAGAGGGACAGGCACCAACTGGGTAACCTCTGCTGACCCCCACTCTACTTTAC
CATAAGTAGCTCCAAATCCTTCTAGAAAATCTGAAAGGCATAGCCCCATATATCAGTGATATAAATAGAACCT
GCAGCAGGCTCTGGTAAATGATGACTACAAGGTGGACTGGGAGGCAGCCCGGCCTTGGCAGGCATCATCCTCT
AAATATAAAGATGAGTTTGTTCAGCCTTTGCAGAAGGAGCGCGCCGTCGACGGATCCGGGCCAGGGGACGGT
GGCTTCTACGTGCTTGGGACGTTCCCAGCCACCGTCCCATGTTCCCGGCGGGGGCCAGCTGTCCCCACCGCC
AGCCCAACTCAGCACTTGGTCAGGGTATCAGCTTGGTGGGGGGCGTGAGCCCAGCCCCTGGGCGGCTCAGC
CCATACAAGGCCATGGGGCTGGGCGCAAAGCATGCCTGGGTTCAGGGTGGGTATGGTGCGGGAGCAGGGAGGT
GAGAGGCTCAGCTGCCCTCCAGAACTCCTCCCTGGGGACAACCCCTCCCAGCCAATAGCACAGCCTAGGTCCC
CCTATATAAGGCCACGGCTGCTGGCCCTTCCTTTGGGTCAGTGTCACCTCCAGGATACAGACAGCCCCCCTTC
AGCCCAGCCCAGCCAGGTACGGATCCGTCGACCGTACGGGCGCGCCACGCGTCAGTTTACTCACCAGGGATTC
AGAGGCAGCACTGCTGAACCCTGAGCCCTTGGCACATCAGGTTGGCTGTCAGAAGTCGGCCTTTGTACATACA
CAGTTCCCTTGTGAGGCCCAGCTGCGTGTCCTAGGAGCGGGGCCTCTCTCCACAGCAGAGCTCAGCCTCTCAA
GTGTATGGACAGCACGGGTGCCTGATGGGTGGATTTAGCCATGAGTTGAAGGTGGCTTGGGGAGAATGAGAGT
TCTAGAGATAGGGAGAAGGGGTTGCCAATAGGAGAGTGGAATTCCTGAGCACCTCGTCACAGGCAGCCGACAG
AACATGAGCCGCAGGGCCCAGGCTATTTATACCTCGCCTGTCACTATCAGGGTCCCCACAGCTCCCCCCACCT
CCAGCCACACACAGCAGGTCCTTTTGCTCTTTCTGGTCCCTTCTCTACTCCTCCCCCTCCCTACCTAA

Fig. 2
(A)
AAV-CSk-SH5-SPc5-12-MVM-hβsgco-pA
(B)
AAV-CSk-SH5-SPc5-12-MVM-hβsg-pA
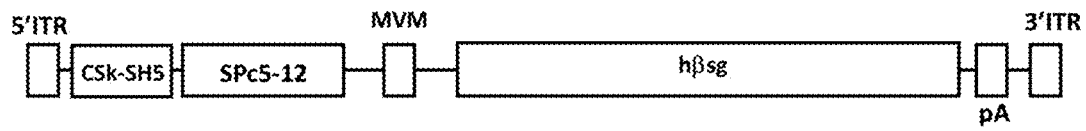
(C)
AAV-CRE02-CSk-SH5-SPc5-12-MVM-hβsgco-pA
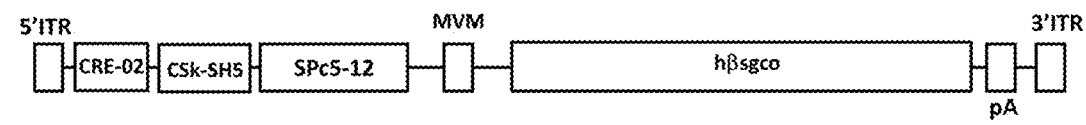
(D)
AAV-CRE04-CSk-SH5-SPc5-12-MVM-hβsgco-pA
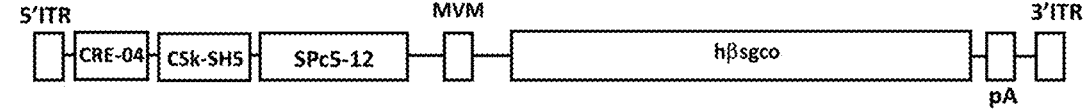
(E)
AAV-CRE06-CSk-SH5-SPc5-12-MVM-hβsgco-pA
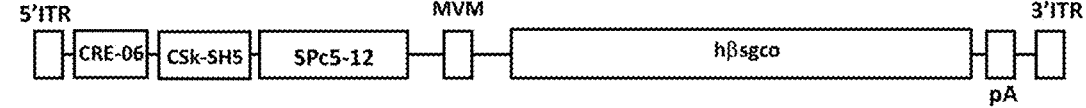
(F)
AAV-CRE02-CRE04-CSk-SH5-SPc5-12-MVM-hβsgco-pA
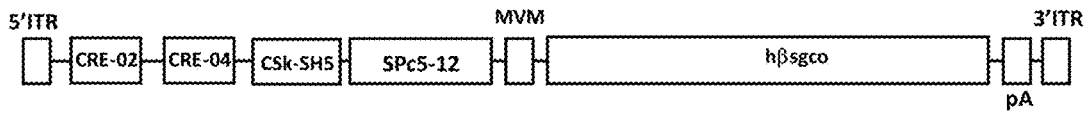
(G)
AAV-CRE02-CRE04-CSk-SH5-SPc5-12-MVM-hβsg-pA
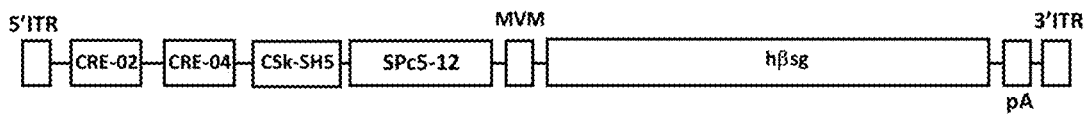

Fig. 2 (cont.)
(H)
AAV-CRE04-CRE06-CSk-SH5-SPc5-12-MVM-hβsgco-pA
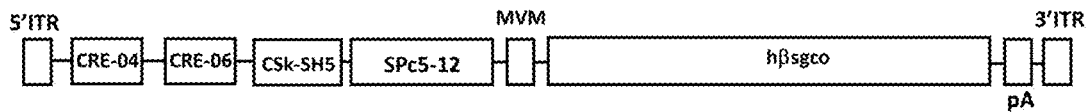
(I)
AAV-CRE04-CRE06-CSk-SH5-SPc5-12-MVM-hβsg-pA
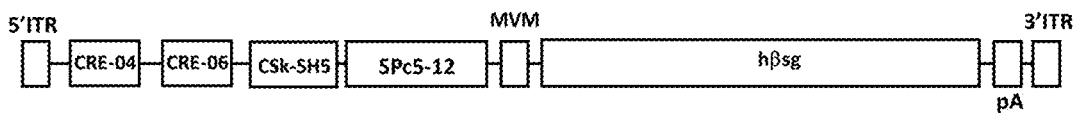
(J)
AAV-CRE06-CRE04-CSk-SH5-SPc5-12-MVM-hβsgco-pA
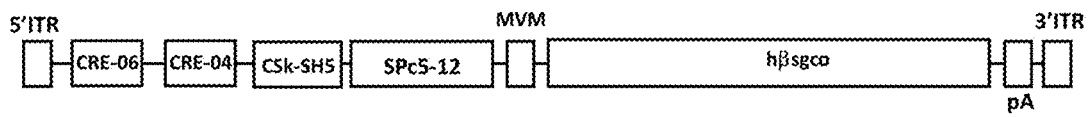
(K)
AAV-CRE06-CRE04-CSk-SH5-SPc5-12-MVM-hβsg-pA
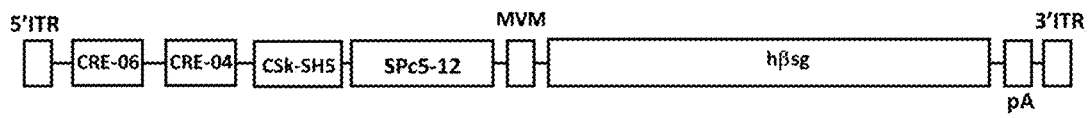
(L)
AAV-CRE02-CRE06-CSk-SH5-SPc5-12-MVM-hβsgco-pA
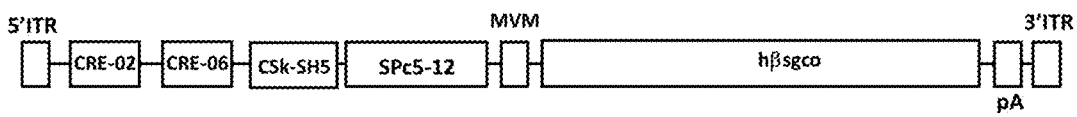
(M)
AAV-CRE02-CRE06-CSk-SH5-SPc5-12-MVM-hβsg-pA
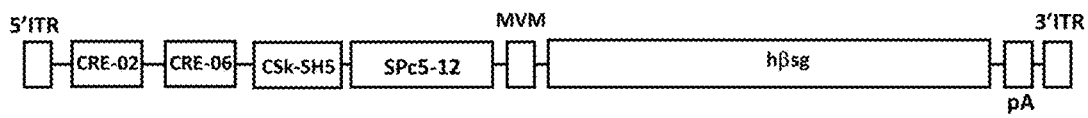
(N)
AAV-CRE02-CRE04-CRE06-CSk-SH5-SPc5-12-MVM-hβsgco-pA
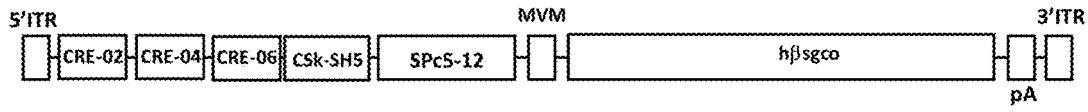

Fig. 2 (cont.)
(O) AAV-CRE02-CRE04-CRE06-CSk-SH5-SPc5-12-MVM-hβsg-pA
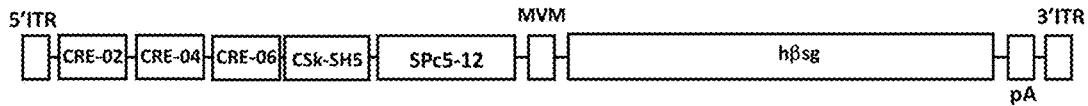
(P) AAV-CRE06-CSk-SH5-SPc5-12-MVM-Luc-pA
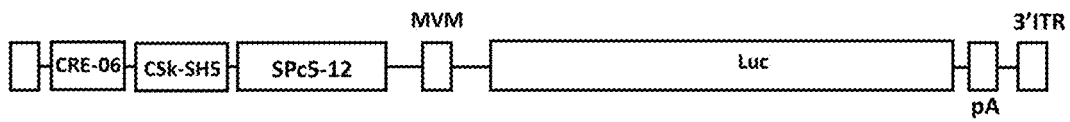
(Q) AAV-CRE04-CSk-SH5-SPc5-12-MVM-Luc-pA
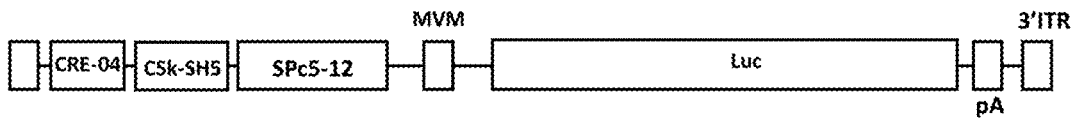
(R) AAV-CRE02-CSk-SH5-SPc5-12-MVM-Luc-pA
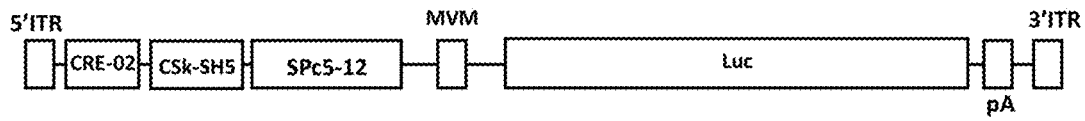
(S) AAV-CRE06-CRE04-CSk-SH5-SPc5-12-MVM-Luc-pA
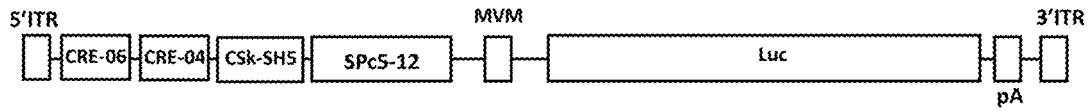
(T) AAV-CRE04-CRE06-CSk-SH5-SPc5-12-MVM-Luc-pA
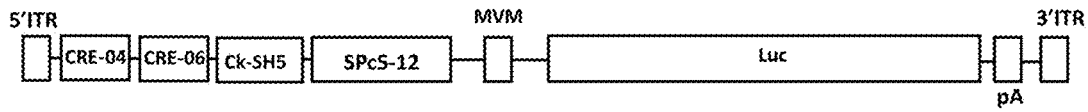
(U) AAV-CRE02-CRE06-CSk-SH5-SPc5-12-MVM-Luc-pA
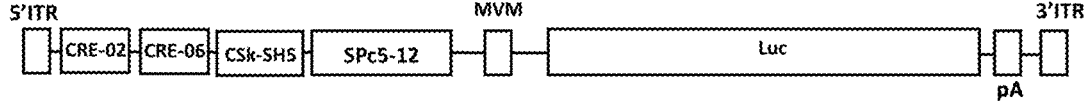

AAV-CRE02-CRE04-CSk-SH5-SPc5-12-MVM-Luc-pA

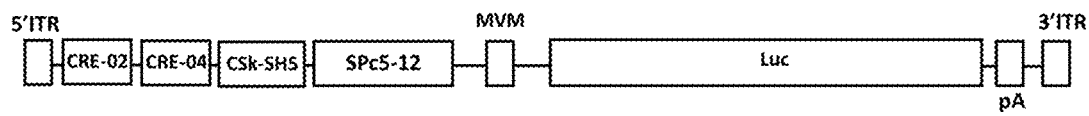

(W)

AAV-CRE02-CRE04-CRE06-CSk-SH5-SPc5-12-MVM-Luc-pA

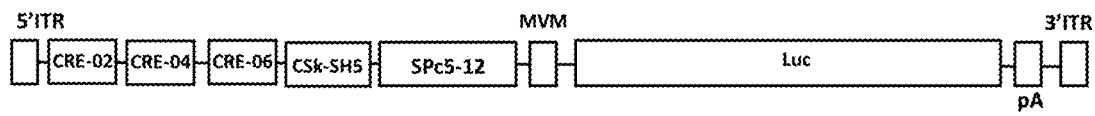

(X)

AAV-SPc5-12-MVM-hβsg-pA

(Y)

AAV-SPc5-12-MVM-hβsgco-pA

(Z)

AAV-SPc5-12-MVM-Luc-pA

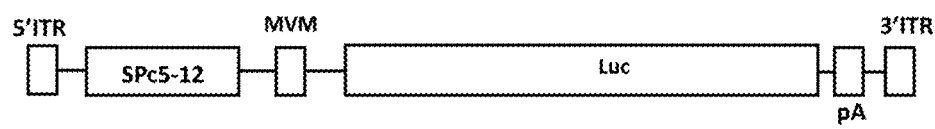

(A1)

AAV-CSk-SH5-SPc5-12-MVM-Luc-pA

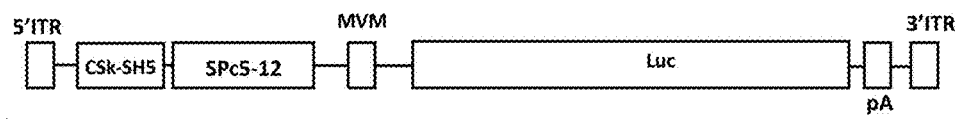

SPc5-12 (SEQ ID NO:15)
tggccaccgccttcggcaccatcctcacgacacccaaatatggcgacgggtgaggaatggtggggagttattt
ttagagcggtgaggaaggtgggcaggcagcaggtgttggcgctctaaaaataactcccgggagttattttag
agcggaggaatggtggacacccaaatatggcgacggttcctcaccgtcgccatatttgggtgtccgccctcg
gccggggccgcattcctgggggccgggcggtgctcccgcccgcctcgataaaaggctccggggccggcggcgg
cccacgagctaccggaggagcgggaggcgccaagctctaga

Fig. 2 (cont.)

MVM (SEQ ID NO:16)
aagaggtaagggtttaagggatggttggttggtggggtattaatgtttaattacctggagcacctgcctgaaa
tcactttttttcaggttgg pA (SEQ ID NO:17)
aataaaagatctttatttcattagatctgtgtgttggttttttgtgtg hβsg (SEQ ID NO: 18)
ATGGCGGCAGCGGCGGCGGCTGCAGAACAGCAAAGTTCCAATGGTCCTGTAAAGAAGTCCATGCGTGAGAAGGC
TGTTGAGAGAAGGAGTGTCAATAAAGAGCACAACAGTAACTTTAAAGCTGGATACATTCCGATTGATGAAGATCGTC
TCCACAAAACAGGGTTGAGAGGAAGAAAGGGCAATTTAGCCATCTGTGTGATTATCCTCTTGTTTATCCTGGCTGTC
ATCAATTTAATAATAACACTTGTTATTTGGGCCGTGATTCGCATTGGACCAAATGGCTGTGATAGTATGGAGTTTCA
TGAAAGTGGCCTGCTTCGATTTAAGCAAGTATCTGACATGGGAGTGATCCACCCTCTTTATAAAAGCACAGTAGGAG
GAAGGCGAAATGAAAATTTGGTCATCACTGGCAACAACCAGCCTATTGTTTTTCAGCAAGGGACAACAAAGCTCAGT
GTAGAAAACAACAAAACTTCTATTACAAGTGACATCGGCATGCAGTTTTTTGACCCGAGGACTCAAAATATCTTATT
CAGCACAGACTATGAAACTCATGAGTTTCATTTGCCAAGTGGAGTGAAAAGTTTGAATGTTCAAAAGGCATCTACTG
AAAGGATTACCAGCAATGCTACCAGTGATTTAAATATAAAGTTGATGGGCGTGCTATTGTGCGTGGAAATGAAGGT
GTATTCATTATGGGCAAAACCATTGAATTTCACATGGGTGGTAATATGGAGTTAAAGGCGGAAAACAGTATCATCCT
AAATGGATCTGTGATGGTCAGCACCACCCGCCTACCCAGTTCCTCCAGTGGAGACCAGTTGGGTAGTGGTGACTGGG
TACGCTACAAGCTCTGCATGTGTGCTGATGGGACGCTCTTCAAGGTGCAAGTAACCAGCCAGAACATGGGCTGCCAA
ATCTCAGACAACCCCTGTGGAAACACTCATTAA hβsgco (SEQ ID NO: 19)
ATGGCTGCTGCCGCTGCTGCTGCAGCTGAACAGCAATCTAGCAACGGCCCCGTGAAGAAATCCATGCGCGAGAAGGC
CGTCGAGCGGAGATCTGTGAACAAAGAGCACAACAGCAACTTCAAGGCCGGCTACATCCCCATCGACGAGGACAGAC
TGCACAAGACAGGCCTGAGAGGCAGAAAGGGCAATCTGGCCATCTGCGTGATCATCCTGCTGTTCATCCTGGCCGTG
ATCAACCTGATCATCACCCTGGTCATCTGGGCCGTGATTAGAATCGGCCCCAACGGCTGCGACAGCATGGAATTTCA
CGAGAGCGGCCTGCTGCGGTTCAAACAGGTGTCCGATATGGGCGTGATCCATCCACTGTACAAGAGCACCGTTGGCG
GCAGAAGAAACGAGAATCTGGTCATCACCGGCAACAACCAGCCTATCGTGTTTCAGCAGGGCACCACCAAGCTGAGC
GTGGAAAACAACAAGACCAGCATCACCAGCGACATCGGCATGCAGTTCTTCGACCCCAGAACACAGAACATCCTGTT
CAGCACCGACTACGAGACACACGAGTTCCATCTGCCTAGCGGCGTGAAGTCCCTGAATGTGCAGAAGGCCAGCACCG
AGAGAATCACCAGCAATGCCACCTCCGACCTGAACATCAAAGTGGACGGCAGAGCCATCGTGCGGGGAAATGAGGGC
GTGTTCATCATGGGCAAGACCATCGAGTTCCACATGGGCGGCAACATGGAACTGAAGGCCGAGAACAGCATCATCCT
GAACGGCAGCGTGATGGTGTCCACCACAAGACTGCCAAGCAGCAGCTCTGGCGATCAGCTTGGATCTGGCGACTGGG
TCCGATACAAGCTGTGTATGTGTGCCGACGGCACCCTGTTCAAGGTGCAAGTGACAAGCCAGAACATGGGCTGCCAG
ATCAGCGACAACCCTTGCGGCAATACCCACTGA

Luc (SEQ ID NO: 20)
ATGGAAGATGCCAAAAACATTAAGAAGGGCCCAGCGCCATTCTACCCACTCGAAGACGGGACCGCCGGCGAGCAGCT
GCACAAAGCCATGAAGCGCTACGCCCTGGTGCCCGGCACCATCGCCTTTACCGACGCACATATCGAGGTGGACATTA
CCTACGCCGAGTACTTCGAGATGAGCGTTCGGCTGGCAGAAGCTATGAAGCGCTATGGGCTGAATACAAACCATCGG
ATCGTGGTGTGCAGCGAGAATAGCTTGCAGTTCTTCATGCCCGTGTTGGGTGCCCTGTTCATCGGTGTGGCTGTGGC
CCCAGCTAACGACATCTACAACGAGCGCGAGCTGCTGAACAGCATGGGCATCAGCCAGCCCACCGTCGTATTCGTGA
GCAAGAAAGGGCTGCAAAAGATCCTCAACGTGCAAAAGAAGCTACCGATATACAAAAGATCATCATCATGGATAGC
AAGACCGACTACCAGGGCTTCCAAAGCATGTACACCTTCGTGACTTCCCATTTGCCACCCGGCTTCAACGAGTACGA
CTTCGTGCCCGAGAGCTTCGACCGGGACAAAACCATCGCCCTGATCATGAACAGTAGTGGCAGTACCGGATTGCCCA
AGGGCGTAGCCCTACCGCACCGCACCGCTTGTGTCCGATTCAGTCATGCCCGCGACCCCATCTTCGGCAACCAGATC
ATCCCCGACACCGCTATCCTCAGCGTGGTGCCATTTCACCACGGCTTCGGCATGTTCACCACGCTGGGCTACTTGAT
CTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAAC
TTGCACGAGATCGCCAGCGGCGGGGCGCCGCTCAGCAAGGAGGTAGGTGAGGCCGTGGCCAAACGCTTCCACCTACC
AGGCATCCGCCAGGGCTACGGCCTGACAGAAACAACCAGCGCCATTCTGATCACCCCCGAAGGGGACGACAAGCCTG
GCGCAGTAGGCAAGGTGGTGCCCTTCTTCGAGGCTAAGGTGGTGGACTTGGACACCGGTAAGACACTGGGTGTGAAC
CAGCGCGGCGAGCTGTGCGTCCGTGGCCCCATGATCATGAGCGGCTACGTTAACAACCCCGAGGCTACAAACGCTCT
CATCGACAAGGACGGCTGGCTGCACAGCGGCGACATCGCCTACTGGGACGAGGACGAGCACTTCTTCATCGTGGACC
GGCTGAAGAGCCTGATCAAATACAAGGGCTACCAGGTAGCCCCAGCCGAACTGGAGAGCATCCTGCTGCAACACCCC
AACATCTTCGACGCCGGGGTCGCCGGCCTGCCCGACGACGATGCCGGCGAGCTGCCCGCCGCAGTCGTCGTGCTGGA
ACACGGTAAAACCATGACCGAGAAGGAGATCGTGGACTATGTGGCCAGCCAGGTTACAACCGCCAAGAAGCTGCGCG
GTGGTGTTGTGTTCGTGGACGAGGTGCCTAAAGGACTGACCGGCAAGTTGGACGCCCGCAAGATCCGCGAGATTCTC
ATTAAGGCCAAGAAGGGCGGCAAGATCGCCGTGTAA

Fig. 4
(A)
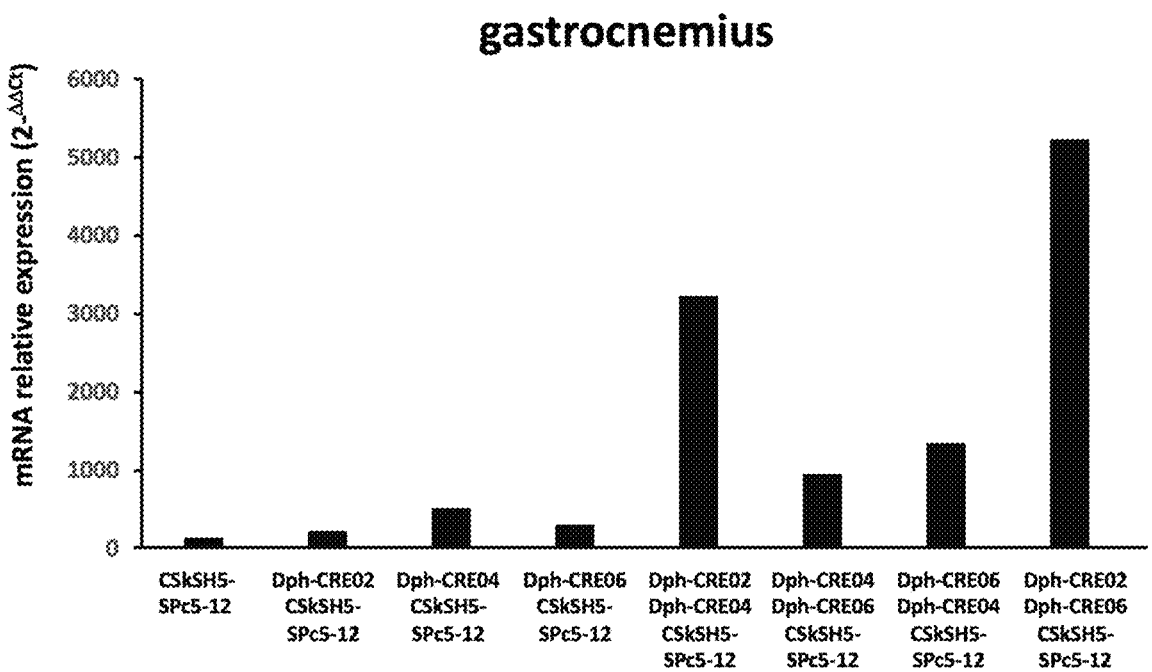
(B)
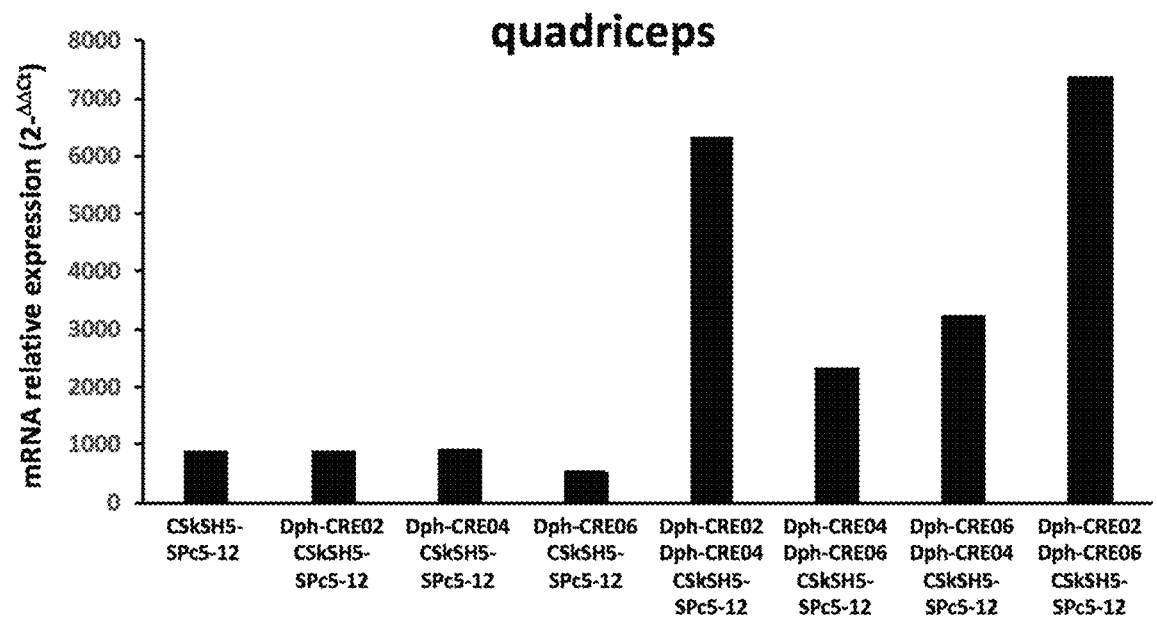

Fig. 4 (cont.)
(C)
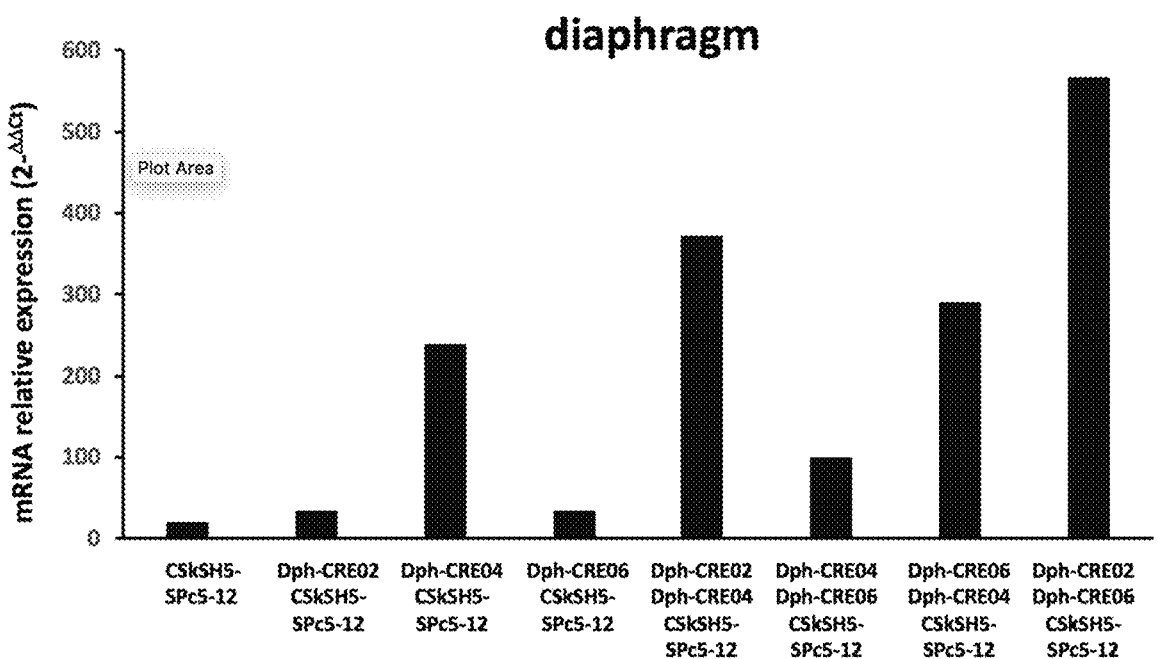
(D)
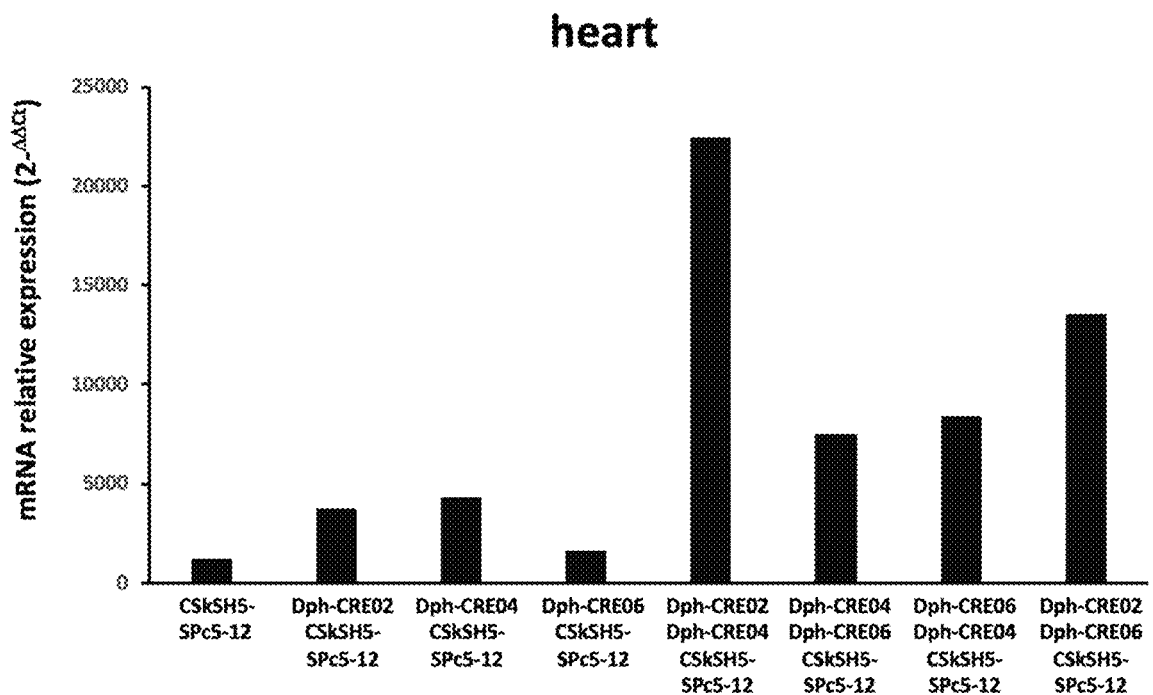

Fig. 5
(A)
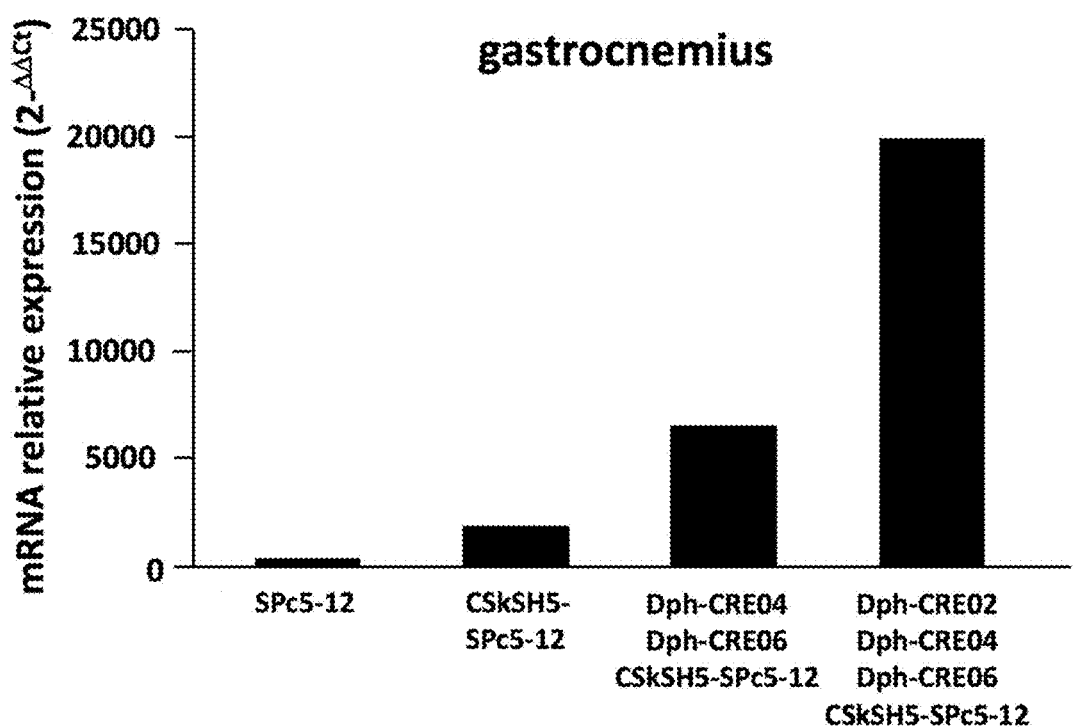
(B)
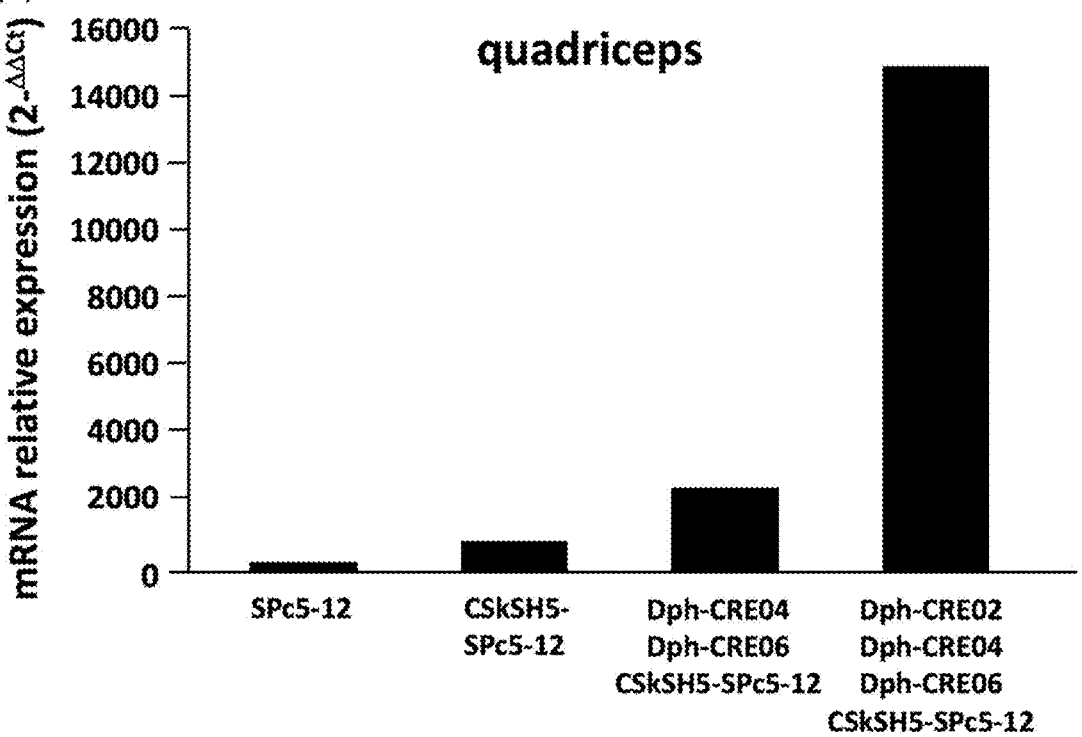

Fig. 5 (cont.)
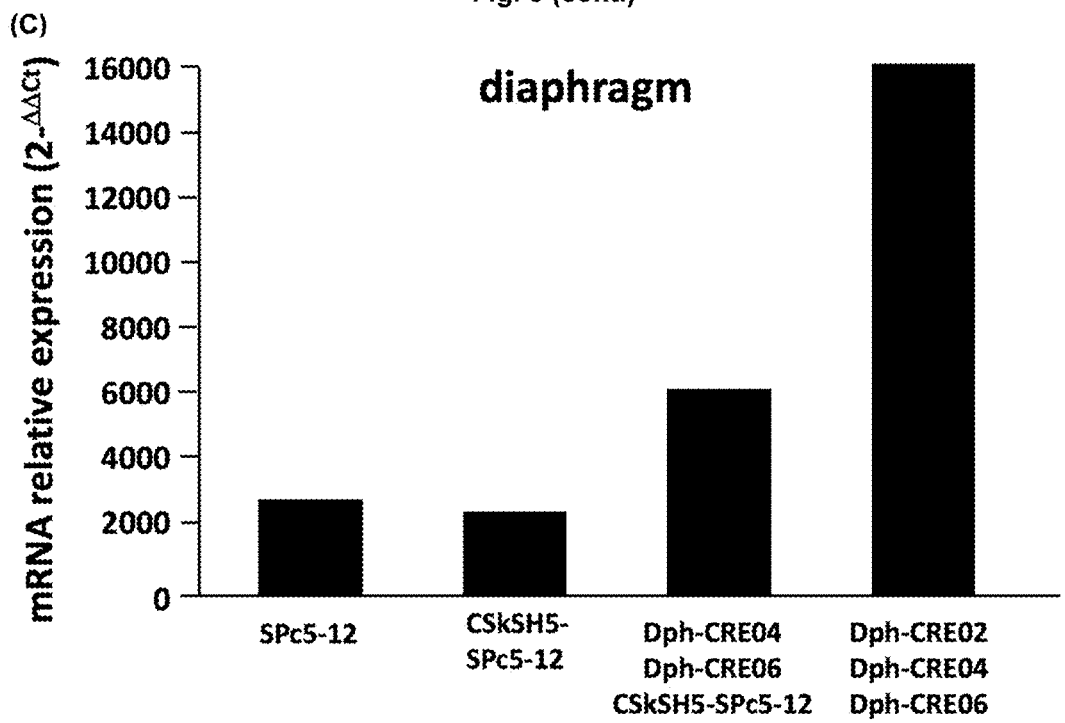
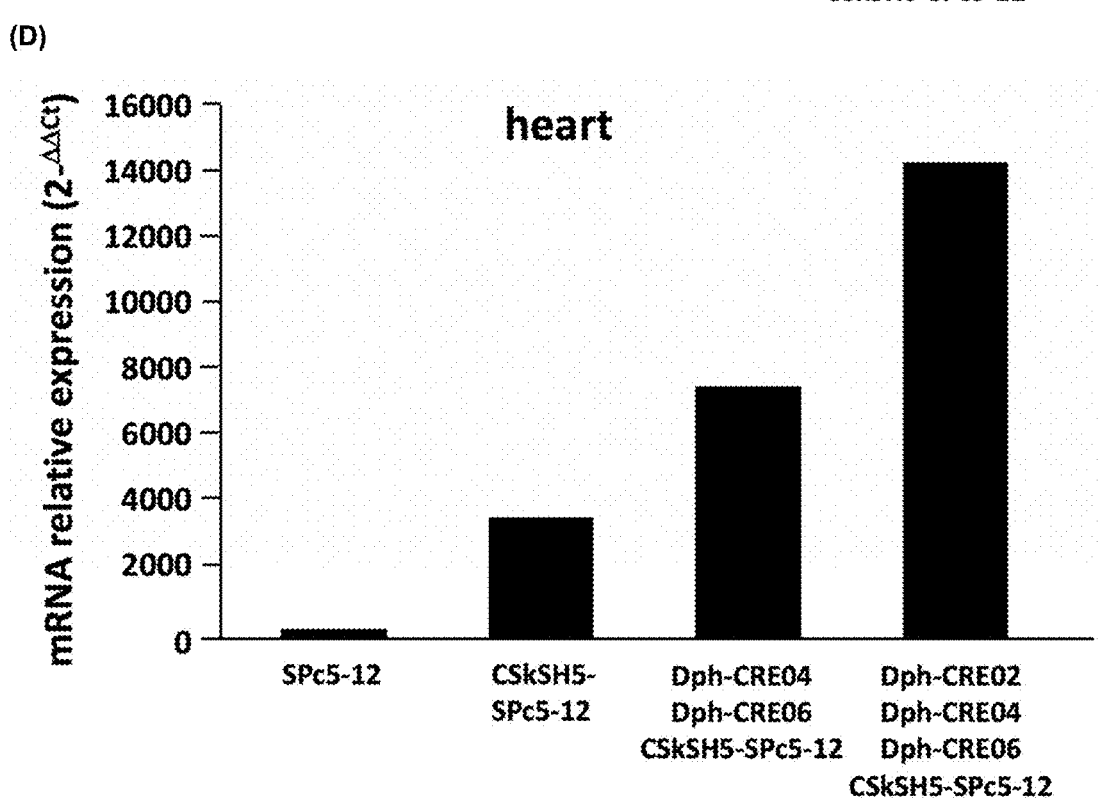

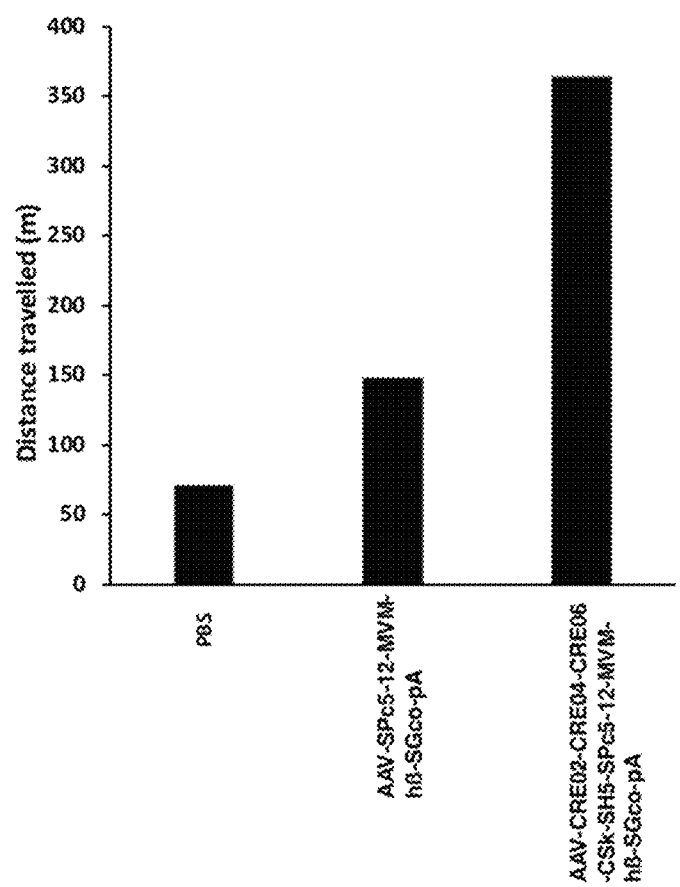

MUSCLE-SPECIFIC NUCLEIC ACID REGULATORY ELEMENTS AND METHODS AND USE THEREOF

CROSS-REFERENCE TO RELATED APPLICATIONS

This application is the U.S. National Phase under 35 U.S.C. § 371 of International Application No. PCT/EP2021/053945, filed Feb. 18, 2021, which claims priority to European Patent Application No. 20158057.8, filed Feb. 18, 2020, the entire content of which is incorporated herein by reference.

SEQUENCE LISTING STATEMENT

The present application contains a Sequence Listing, being submitted via Patent Center on even date herewith. The Sequence Listing is submitted in a file entitled "DECLE69.019APC.txt," which was created on Aug. 8, 2022, and is approximately 251 bytes in size, and further updated by a file entitled "2022-12-01 Sequence Listing—DECLE69.019APC.txt," created on Dec. 1, 2022, which is 246,547 bytes in size. The information in the electronic format of the Sequence Listing is incorporated herein by reference in its entirety.

FIELD

The present invention relates to nucleic acid regulatory elements that are able to enhance muscle-specific expression of genes, methods employing these regulatory elements and use thereof. More particularly, the nucleic acid regulatory elements are able to enhance gene expression in diaphragm, cardiac and skeletal muscle and smooth muscle, preferably in diaphragm, cardiac and skeletal muscle. The invention encompasses expression cassettes, vectors and pharmaceutical compositions comprising these regulatory elements. The present invention is particularly useful for applications using gene therapy, more particularly muscle-directed gene therapy, and for vaccination purposes.

BACKGROUND

There are many hereditary disorders that are due to a gene defect that impairs the function of smooth muscle, skeletal muscle, heart and/or diaphragm (e.g. Pompe disease, muscular dystrophies etc.). This gene defect may ultimately result in severe muscle weakness and paralysis or cardiopulmonary failure with life-threatening consequences. For example, Limb Girdle Muscular Dystrophy Type 2E (LGMD2E) is one of the most severe LGMD disorders with a worldwide incidence of 1 in 200,000 to 350,000. It is a type of autosomal recessive inheritable muscle dystrophy caused by mutation of the β-sarcoglycan (β-sg or βsg) gene, resulting in depletion of the functional β-sarcoglycan protein. Consequently, LGMD2E patients exhibit severe and widespread progressive muscle wasting, pelvic and shoulder girdle weakness, muscle fibrosis and force reduction, cardiomyopathy, joint diseases, and diaphragm dysfunction. Patients often die from cardiopulmonary failure, since standard clinical modalities do not provide a cure to the disease. Hence, developing an effective clinical therapy for LGMD2E represents an urgent unmet medical need.

Gene therapy provides an unprecedented opportunity to simultaneously treat dysfunction and degeneration of the smooth muscle, skeletal muscle, heart and diaphragm, thanks to its ability to deliver therapeutic genes to the affected tissues in order to obtain a lasting therapeutic response. Despite its promise, the drawback is that a relatively high virus vector dose is required to achieve a desirable therapeutic effect, thus impeding possible clinical translation. More particularly, gene therapy to the smooth muscle, skeletal muscle, heart and/or diaphragm, more particularly towards skeletal muscle, heart and/or diaphragm, is relatively inefficient due to limitations in gene delivery and gene expression. Moreover, immune responses specific for the therapeutic gene product curtail the efficiency of gene therapy applications directed towards smooth muscle, skeletal muscle, heart and/or diaphragm, more particularly towards skeletal muscle, heart and/or diaphragm.

The challenges that hamper clinical translation and preclude the development of an effective cure for LGMD2E by gene therapy also relate to: (i) insufficient expression of the therapeutic transgene in the affected skeletal muscles, heart and diaphragm; and (ii) the potential toxicity and untoward immune responses due to very high doses of conventional vectors needed to reach the main muscle groups (i.e. skeletal muscle, heart and diaphragm) affected by this life-threatening disease to effectively treat the different clinical manifestations of this diseases including the skeletal muscle weakness/wasting, cardiomyopathy and diaphragm dysfunction.

Efforts to deliver transgenes to muscle have focused on vectors derived from adenoviruses, retroviruses, lentiviruses, and adeno-associated viruses (AAV), and plasmids. Adeno-associated viral vector (AAV) is by far the most promising gene delivery vehicle for muscle-directed gene therapy. AAV's natural tropism to muscle cells, their long-term persistent transgene expression, their multiple serotypes, as well as their minimal immune response have made AAV vectors well suited for muscle-directed gene therapy. AAV9 is known among the most efficient vectors for cardiac gene delivery (Pacak et al. 2006. Circ Res. 99(4):e3-9; VandenDriessche et al. 2007. J Thromb Haemost. 5(1):16-24; Inagaki et al. 2006. Mol Ther. 2006 14(1):45-53), and is also well suited for skeletal muscle gene delivery. AAV vector can be delivered into skeletal muscle cardiac muscle, smooth muscle and diaphragm by means of local, regional, and systemic administrations.

There remain however concerns regarding the efficacy and safety of some gene delivery approaches. The major limiting factors are: insufficient and/or transient transgene expression levels, and inappropriate expression of the transgene in unwanted cell types. In particular, it has been shown that inadvertent transgene expression in antigen-presenting cells (APCs) increases the risk of untoward immune responses against the gene-modified cells and/or the therapeutic transgene product that consequently curtails long-term gene expression.

This problem has been addressed by boosting gene expression using muscle- and diaphragm-specific cis-regulatory elements (CREs) (also designated as cis-regulatory modules (CRM)). These novel and robust human cis-regulatory elements were obtained via genome-wide data-mining and yielded robust specific transgene expression levels in diaphragm and/or heart and skeletal muscle while avoiding expression in non-target tissues (WO 2015/110449 A1; WO 2018/178067 A1).

However, just expressing the therapeutic protein in the muscle, heart or diaphragm using one of these CRMs may not be sufficient, particularly since there is a need to further diminish the vector doses to levels that do not provoke any unwanted toxicity, such as the well-documented liver toxicity that occurred in most if not all of the gene therapy trials that were based on high vector dose that were systemically administered to the patients.

Thus, there remains a need in the art for safe and efficient gene delivery to muscle. For example, it is imperative to further improve the efficacy and safety of tissue-targeted gene therapy applications for LGMD2E, ideally by developing more robust gene therapy vectors that allow for high and widespread diaphragm, smooth muscle, heart and skeletal muscle-specific expression, preferably diaphragm, heart and skeletal muscle-specific expression, of the therapeutic β-sarcoglycan transgene (β-SG) at lower and thus safer vector doses.

SUMMARY

The present inventors addressed the challenges with current gene therapy applications by developing approaches to maximize expression in muscle cells and tissues such as diaphragm, heart and/or skeletal muscle based on novel combinations of transcriptional cis-regulatory elements or modules (CREs or CRMs) that confer unexpectedly high expression in these specific cells and tissues. To this end, AAV vectors were designed that express human β-sarcoglycan cDNA (hβsg or hβSG) using combinations of CRE elements or modules that direct expression to diaphragm (also referred to herein as Dph-CRE) or heart and skeletal muscle (also referred to herein as CSk(-)CRE or CSk(-)SH(-)CRE or CSk(-)SH or Csk(-)CRE or Csk(-)SH(-)CRE or Csk(-)SH or CSK(-)CRE or CSK(-)SH(-)CRE or CSK(-)SH) in conjunction with a potent muscle-specific promotor as a gene therapy strategy for LGMD2E. These novel regulatory elements were subsequently validated in vivo in mice yielding unexpectedly high and tissue-specific gene expression in heart, smooth muscle, skeletal muscle and diaphragm, preferably in heart, skeletal muscle and diaphragm. This approach hence, allows for the use of lower and thus safer vector doses, while maximizing therapeutic efficacy.

The invention therefore provides the following aspects:

Aspect 1: a nucleic acid regulatory element for enhancing muscle-specific gene expression comprising, consisting essentially of, or consisting of at least two diaphragm-specific regulatory elements selected from a diaphragm-specific regulatory element comprising, consisting essentially of or consisting of a nucleotide sequence having at least 95% identity to the sequence set forth in SEQ ID NO:2, preferably the nucleotide sequence set forth in SEQ ID NO:2 (e.g. Dph-CRE02), or a functional fragment thereof; a diaphragm-specific regulatory element comprising, consisting essentially of or consisting of a nucleotide sequence having at least 95% identity to the sequence set forth in SEQ ID NO:3, preferably the nucleotide sequence set forth in SEQ ID NO:3 (e.g. Dph-CRE04), or a functional fragment thereof; and a diaphragm-specific regulatory element comprising, consisting essentially of or consisting of a nucleotide sequence having at least 95% identity to the sequence set forth in SEQ ID NO:4, preferably the nucleotide sequence set forth in SEQ ID NO:4 (e.g. Dph-CRE06), or a functional fragment thereof; and a heart- and skeletal muscle-specific regulatory element comprising, consisting essentially of or consisting of a nucleotide sequence having at least 95% identity to the sequence set forth in SEQ ID NO:1, preferably the nucleotide sequence set forth in SEQ ID NO:1 (e.g. CSk-SH5), or a functional fragment thereof.

Aspect 2: the nucleic acid regulatory element according to aspect 1 comprising, consisting essentially of or consisting of a diaphragm-specific regulatory element consisting essentially of or consisting of a nucleotide sequence having at least 95% identity to the sequence set forth in SEQ ID NO:2, preferably the diaphragm-specific regulatory element consisting essentially of or consisting of the nucleotide sequence set forth in SEQ ID NO:2 (Dph-CRE02), or a functional fragment thereof; a diaphragm-specific regulatory element consisting essentially of or consisting of a nucleotide sequence having at least 95% identity to the sequence set forth in SEQ ID NO:3, preferably the diaphragm-specific regulatory element consisting essentially of or consisting of the nucleotide sequence set forth in SEQ ID NO:3 (Dph-CRE04), or a functional fragment thereof; and a heart- and skeletal muscle-specific regulatory element consisting essentially of or consisting of a nucleotide sequence having at least 95% identity to the sequence set forth in SEQ ID NO:1, preferably the heart- and skeletal muscle-specific regulatory element consisting essentially of or consisting of the nucleotide sequence set forth in SEQ ID NO:1 (CSk-SH5), or a functional fragment thereof.

Aspect 3: the nucleic acid regulatory element according to aspect 2 comprising, consisting essentially of or consisting of the diaphragm-specific regulatory element consisting essentially of or consisting of the nucleotide sequence set forth in SEQ ID NO:5 (Dph-CRE02-CRE04); and the heart- and skeletal muscle-specific regulatory element consisting essentially of or consisting of the nucleotide sequence set forth in SEQ ID NO:1 (CSk-SH5), or a functional fragment thereof.

Aspect 4: the nucleic acid regulatory element according to aspect 2 or 3, comprising, consisting essentially of or consisting of the nucleotide sequence set forth in SEQ ID NO:10 (Dph-CRE02-Dph-CRE04-CSk-SH5).

Aspect 5: the nucleic acid regulatory element according to any one of aspects 2 to 4, further comprising a diaphragm-specific regulatory element consisting essentially of or consisting of a nucleotide sequence having at least 95% identity to the sequence set forth in SEQ ID NO:4, preferably the diaphragm-specific regulatory element consisting essentially of or consisting of the nucleotide sequence set forth in SEQ ID NO:4 (Dph-CRE06), or a functional fragment thereof.

Aspect 6: the nucleic acid regulatory element according to aspect 1 comprising, consisting essentially of or consisting of a diaphragm-specific regulatory element consisting essentially of or consisting of a nucleotide sequence having at least 95% identity to the sequence set forth in SEQ ID NO:2, preferably the diaphragm-specific regulatory element consisting essentially of or consisting of the nucleotide sequence set forth in SEQ ID NO:2 (Dph-CRE02), or a functional fragment thereof; a diaphragm-specific regulatory element consisting essentially of or consisting of a nucleotide sequence having at least 95% identity to the sequence set forth in SEQ ID NO:4, preferably the diaphragm-specific regulatory element consisting essentially of or consisting of the nucleotide sequence set forth in SEQ ID NO:4 (Dph-CRE06), or a functional fragment thereof; and a heart- and skeletal muscle-specific regulatory element consisting essentially of or consisting of a nucleotide sequence having at least 95% identity to the sequence set forth in SEQ ID NO:1, preferably the heart- and skeletal muscle-specific regulatory element consisting essentially of or consisting of the nucleotide sequence set forth in SEQ ID NO:1 (CSk-SH5), or a functional fragment thereof.

Aspect 7: the nucleic acid regulatory element according to aspect 6 comprising, consisting essentially of or consisting of the diaphragm-specific regulatory element consisting essentially of or consisting of the nucleotide sequence set forth in SEQ ID NO:6 (Dph-CRE02-CRE06) and the heart- and skeletal muscle-specific regulatory element consisting essentially of or consisting of the nucleotide sequence set forth in SEQ ID NO:1 (CSk-SH5) or a functional fragment thereof.

Aspect 8: the nucleic acid regulatory element according to aspect 6 or 7, comprising, consisting essentially of or consisting of the nucleotide sequence set forth in SEQ ID NO:11 (Dph-CRE02-Dph-CRE06-CSk-SH5).

Aspect 9: the nucleic acid regulatory element according to any one of aspects 6 to 8, further comprising a diaphragm-specific regulatory element consisting essentially of or consisting of a nucleotide sequence having at least 95% identity to the sequence set forth in SEQ ID NO:3, preferably the diaphragm-specific regulatory element consisting essentially of or consisting of the nucleotide sequence set forth in SEQ ID NO:3 (Dph-CRE04), or a functional fragment thereof.

Aspect 10: the nucleic acid regulatory element according to aspect 1 comprising, consisting essentially of or consisting of a diaphragm-specific regulatory element consisting essentially of or consisting of a nucleotide sequence having at least 95% identity to the sequence set forth in SEQ ID NO:3, preferably the diaphragm-specific regulatory element consisting essentially of or consisting of the nucleotide sequence set forth in SEQ ID NO:3 (Dph-CRE04), or a functional fragment thereof; a diaphragm-specific regulatory element consisting essentially of or consisting of a nucleotide sequence having at least 95% identity to the sequence set forth in SEQ ID NO:4, preferably the diaphragm-specific regulatory element consisting essentially of or consisting of the nucleotide sequence set forth in SEQ ID NO:4 (Dph-CRE06), or a functional fragment thereof; and a heart- and skeletal muscle-specific regulatory element consisting essentially of or consisting of a nucleotide sequence having at least 95% identity to the sequence set forth in SEQ ID NO:1, preferably the heart- and skeletal muscle-specific regulatory element consisting essentially of or consisting of the nucleotide sequence set forth in SEQ ID NO:1 (CSk-SH5), or a functional fragment thereof.

Aspect 11: the nucleic acid regulatory element according to aspect 10 comprising, consisting essentially of or consisting of the diaphragm-specific regulatory element consisting essentially of or consisting of the nucleotide sequence set forth in SEQ ID NO:7 (Dph-CRE04-CRE06) and the heart- and skeletal muscle-specific regulatory element consisting essentially of or consisting of the nucleotide sequence set forth in SEQ ID NO:1 (CSk-SH5) or a functional fragment thereof.

Aspect 12: the nucleic acid regulatory element according to aspect 10 comprising, consisting essentially of or consisting of the diaphragm-specific regulatory element consisting essentially of or consisting of the nucleotide sequence set forth in SEQ ID NO:8 (Dph-CRE06-CRE04) and the heart- and skeletal muscle-specific regulatory element consisting essentially of or consisting of the nucleotide sequence set forth in SEQ ID NO:1 (CSk-SH5) or a functional fragment thereof.

Aspect 13: the nucleic acid regulatory element according to aspect 10 or 11, comprising, consisting essentially of or consisting of the nucleotide sequence set forth in SEQ ID NO:12 (Dph-CRE04-Dph-CRE06-CSk-SH5).

Aspect 14: the nucleic acid regulatory element according to aspect 10 or 12, comprising, consisting essentially of or consisting of the nucleotide sequence set forth in SEQ ID NO:13 (Dph-CRE06-Dph-CRE04-CSk-SH5).

Aspect 15: the nucleic acid regulatory element according to any one of aspects 10 to 14, further comprising a diaphragm-specific regulatory element consisting essentially of or consisting of a nucleotide sequence having at least 95% identity to the sequence set forth in SEQ ID NO:2, preferably the diaphragm-specific regulatory element consisting essentially of or consisting of the nucleotide sequence set forth in SEQ ID NO:2 (Dph-CRE02), or a functional fragment thereof.

Aspect 16: the nucleic acid regulatory element according to any one of aspects 10, 11, 13 or 15 comprising, consisting essentially of or consisting of the diaphragm-specific regulatory element consisting essentially of or consisting of the nucleotide sequence set forth in SEQ ID NO:9 (Dph-CRE02-CRE04-CRE06); and the heart- and skeletal muscle-specific regulatory element consisting essentially of or consisting of the nucleotide sequence set forth in SEQ ID NO:1 (CSk-SH5), or a functional fragment thereof.

Aspect 17: the nucleic acid regulatory element according to any one of aspects 10, 11, 13, 15 or 16 comprising, consisting essentially of or consisting of the nucleotide sequence set forth in SEQ ID NO:14 (Dph-CRE02-Dph-CRE04-Dph-CRE06-CSk-SH5).

Aspect 18: use, preferably an in vitro or ex vivo use, of the nucleic acid regulatory element according to any one of aspects 1 to 17 for enhancing gene expression in muscle, in particular in diaphragm, smooth muscle, heart and skeletal muscle, more particularly in diaphragm, heart and skeletal muscle.

Aspect 19: a nucleic acid expression cassette comprising a nucleic acid regulatory element according to any one of aspects 1 to 17, operably linked to a promoter.

Aspect 20: the nucleic acid expression cassette according to aspect 19, wherein the nucleic acid regulatory element is operably linked to a promoter and a transgene.

Aspect 21: the nucleic acid expression cassette according to any one of aspects 19 or 20, wherein the promoter is a muscle-specific promoter, such as a muscle-specific promoter selected from the group comprising or consisting of: the desmin (DES) promoter; the synthetic SPc5-12 promoter (SPc5-12); the alpha-actin1 promoter (ACTA1); the Creatine kinase, muscle (CKM) promoter; the Four and a half LIM domains protein 1 (FHL1) promoter; the alpha 2 actinin (ACTN2) promoter; the filamin-C (FLNC) promoter; the sarcoplasmic/endoplasmic reticulum calcium ATPase 1 (ATP2A1) promoter; the Troponin I Type 1 (TNNI1) promoter; the Troponin I Type 2 (TNNI2) promoter; the Troponin T Type 1 (TNNT1) promoter; the Troponin T Type 3 (TNNT3) promoter; the myosin-1 (MYH1) promoter; the myosin-2 (MYH2) promoter; the sarcolipin (SLN) promoter; the Myosin Binding Protein Cl (MYBPC1) promoter; the enolase (EN03) promoter; the Carbonic Anhydrase 3 (CA3) promoter; the phosphorylatable, fast skeletal muscle myosin light chain (MYLPF) promoter; the Tropomyosin 1 (TPM1) promoter; the Tropomyosin 2 (TPM2) promoter; the alpha-3 chain tropomyosin (TPM3) promoter; the ankyrin repeat domain-containing protein 2 (ANKRD2) promoter; the myosin heavy-chain (MHC) promoter; the alpha myosin heavy-chain promoter (ccMHC) promoter; the myosin light-chain (MLC) promoter; the muscle creatine kinase (MCK) promoter; the Myosin, Light Chain 1 (MYL1) promoter; the Myosin, Light Chain 2 (MYL2) promoter; the Myoglobin (MB) promoter; the Troponin T type 2 (TNNT2) promoter; the Troponin C type 2 (TNNC2) promoter; the Troponin C Type 1 (TNNC1) promoter; the Titin-Cap (TCAP) promoter; the Myosin, Heavy Chain 7 (MYH7) promoter; the Aldolase A (ALDOA) promoter; the dMCK promoter, the tMCK promoter; the MHCK7 promoter; the myosin heavy chain 11 (Myh11) promoter; the transgelin (Tagln) promoter and the actin alpha 2 smooth muscle (Acta2) promoter.

Aspect 22: the nucleic acid expression cassette according any one of aspects 19 to 21, wherein the promoter is the SPc5-12 promoter as defined by SEQ ID NO:15.

Aspect 23: the nucleic acid expression cassette according any one of aspects 19 to 21, wherein the promoter is the MHCK7 promoter as defined by SEQ ID NO:56.

Aspect 24: the nucleic acid expression cassette according any one of aspects 19 to 21, wherein the promoter is the desmin promoter as defined by SEQ ID NO:57.

Aspect 25: the nucleic acid expression cassette according to any one of aspects 19 to 24, wherein the transgene encodes a therapeutic protein.

Aspect 26: the nucleic acid expression cassette according to any one of aspects 19 to 25, wherein the transgene encodes a sarcoglycan, preferably β-sarcoglycan, more preferably human β-sarcoglycan (e.g. the transgene set forth in SEQ ID NO:18, preferably the codon-optimized transgene set forth in SEQ ID NO:19).

Aspect 27: the nucleic acid expression cassette according to any one of aspects 19 to 25, wherein the transgene encodes acid α-glucosidase (GAA), preferably human acid α-glucosidase (hGAA) (e.g. the transgene set forth in SEQ ID NO:58, preferably the codon-optimized transgene set forth in SEQ ID NO:59).

Aspect 28: the nucleic acid expression cassette according to any one of aspects 19 to 24, wherein the transgene is a reporter gene such as a luciferase transgene (e.g. the transgene set forth in SEQ ID NO:20).

Aspect 29: the nucleic acid expression cassette according to any one of aspects 19 to 28, wherein the transgene is codon-optimized.

Aspect 30: the nucleic acid expression cassette according to any one of aspects 19 to 29, further comprising an intron, preferably the Minute Virus of Mouse (MVM) intron (as set forth in SEQ ID NO: 16).

Aspect 31: the nucleic acid expression cassette according to any one of aspects 19 to 30, further comprising a polyadenylation signal, preferably a synthetic polyadenylation signal such as the one defined by SEQ ID NO:17.

Aspect 32: a vector comprising the nucleic acid regulatory element according to any one of aspects 1 to 17, or the nucleic acid expression cassette according to any one of aspects 19 to 31.

Aspect 33: the vector according to aspect 32, which is a viral vector, preferably an adeno-associated viral (AAV) vector, more preferably an AAV9 vector or an AAV8 vector.

Aspect 34: a pharmaceutical composition comprising the nucleic acid expression cassette according to any one of aspects 19 to 31, or the vector according to any one of aspects 32 or 33, and a pharmaceutically acceptable carrier.

Aspect 35: the nucleic acid regulatory element according to any one of aspects 1 to 17, the nucleic acid expression cassette according to any one of aspects 19 to 31, the vector according to any one of aspects 32 or 33, or the pharmaceutical composition according to aspect 34 for use in medicine.

Aspect 36: the nucleic acid regulatory element according to any one of aspects 1 to 17, the nucleic acid expression cassette according to any one of aspects 19 to 31, the vector according to any one of aspects 32 or 33, or the pharmaceutical composition according to aspect 34 for use in gene therapy, preferably muscle-directed gene therapy. For example, the gene therapy may be for a disease or disorder selected from lysosomal storage diseases (e.g. Fabry disease) including glycogen storage disorders (e.g. Pompe disease glycogen storage disorder (GSD) type II, Danon disease, GSD type IIb, GSD III or GSD 3 (also known as Cori's disease or Forbes' disease), GSD IV or GSD4 (also known as Andersen disease), GSD V or GSD5 (also known as McArdle disease), GSD VII or GSD7 (also known as Tarui's disease), GSD X or GSD10, GSD XII or GSD 12 (also known as Aldolase A deficiency), GSD XIII or GSD13, GSD XV or GSD15) and mucopolysaccharidosis disorders (e.g. Hunter syndrome, Sanfilippo syndrome, mucopolyssacharidose (MPS) I, MPS II, MPS III, MPS IIIA, MPS IIIB, MPS IIIC, MPS IV, MPS VI, MPS VII, MPS IX); mitochondrial disorders (e.g. Barth syndrome); channelopathy (e.g. Brugada syndrome); metabolic disorders; myotubular myopathy (MTM); muscular dystrophy (e.g. Duchenne muscular dystrophy (DMD), Becker muscular dystrophy (BMD)); myotonic dystrophy; Myotonic Muscular Dystrophy (DM); Miyoshi myopathy; Fukuyama type congenital; dysferlinopathies; neuromuscular disease; motor neuron diseases (MND) (e.g. Charcot-Marie-Tooth disease (CMT)), spinal muscular atrophy (SMA) or amyotrophic lateral sclerosis (ALS)); Emery-Dreifuss muscular dystrophy; facioscapulohumeral muscular dystrophy (FSHD); congenital muscular dystrophies; congenital myopathie; limb girdle muscular dystrophy (e.g. Limb Girdle Muscular Dystrophy type 2E (LGMD2E) Limb Girdle Muscular Dystrophy type 2D (LGMD2D), Limb Girdle Muscular Dystrophy type 2C (LGMD2C), Limb Girdle Muscular Dystrophy type 2B (LGMD2B), Limb Girdle Muscular Dystrophy type 2L (LGMD2L), Limb Girdle Muscular Dystrophy type 2A (LGMD2A)); metabolic myopathies; muscle inflammatory diseases; myasthenia; mitochondrial myopathies; anomalies of ionic channels; nuclear envelop diseases; cardiomyopathies; cardiac hypertrophy; heart failure; distal myopathies, hemophilia (e.g. hemophilia A and B); diabetes; cardiovascular diseases and heart diseases.

Aspect 37: the nucleic acid regulatory element, the nucleic acid expression cassette, the vector, or the pharmaceutical composition for use according to aspect 36, wherein the gene therapy is for treating muscle-related disorders in general, alleviating the symptoms of myopathies in general or restoring the function of muscle cells in general.

Aspect 38: the nucleic acid regulatory element, the nucleic acid expression cassette, the vector, or the pharmaceutical composition for use according to aspect 36, wherein the gene therapy is for treating cardiovascular diseases. Non-limiting examples of cardiovascular diseases include atherosclerosis, arteriosclerosis, coronary heart disease, coronary artery disease, peripheral arterial disease, congenital heart disease, congestive heart failure, heart failure (also known as cardiac insufficiency), myocardial infarction (also known as heart attack), cardiac ischemia, acute coronary syndrome, unstable angina, stable angina, cardiomyopathy, hypertrophic cardiomyopathy, dilated cardiomyopathy, restrictive cardiomyopathy, primary cardiomyopathies caused by genetic mutations such as Brugada syndrome, Pompe disease, Danon disease and Fabry disease, cardiac amyloidosis (also known as stiff heart syndrome), myocarditis (also known as inflammatory cardiomyopathy), valvular heart disease, valvular stenosis, valvular insufficiency, endocarditis, rheumatic heart disease, pericarditis (i.e. a disease caused by an inflammation and/or infection of the pericardium), cardiac tamponade (also known as pericardial tamponade), endocarditis, cardiac arrhythmia, hypertension, hypotension, vessel stenosis, valve stenosis, or restenosis.

Aspect 39: a nucleic acid regulatory element according to any one of aspects 1 to 17, a nucleic acid expression cassette according to any one of aspects 19 to 26 or 29 to 31, a vector according to any one of aspects 32 or 33, or a pharmaceutical composition according to aspect 34 for use in the treatment of limb girdle muscular dystrophy, more preferably limb girdle muscular dystrophy type 2E (LGMD2E).

Aspect 40: a nucleic acid regulatory element according to any one of aspects 1 to 17; a nucleic acid expression cassette according to any one of aspects 19 to 25 or 29 to 31, wherein the transgene encodes a lysosomal protein, preferably a lysosomal protein selected from the group consisting of acid α-galactosidase (GAA), alpha-galactosidase A and LAMP2; a vector according to any one of aspects 32 or 33 comprising said nucleic acid expression cassette; or a pharmaceutical composition according to aspect 34 comprising said nucleic acid expression cassette or said vector, for use in the treatment of a lysosomal storage disease.

Aspect 41: a nucleic acid regulatory element according to any one of aspects 1 to 17, a nucleic acid expression cassette according to any one of aspects 19 to 25, 27, or 29 to 31, a vector according to any one of aspects 32 or 33, or a pharmaceutical composition according to aspect 34 for use in the treatment of Pompe disease.

Aspect 42: A method, preferably an in vitro or ex vivo method, for expressing a transgene product in muscle cells such as diaphragm, smooth muscle, heart and/or skeletal muscle cells, in particular in diaphragm, heart and/or skeletal muscle cells, comprising:

introducing the nucleic acid expression cassette according to any one of aspects 19 to 31, or the vector according to any one of aspects 32 or 33 into the muscle cells;
expressing the transgene product in the muscle cells.

BRIEF DESCRIPTION OF DRAWINGS

FIG. 1: Nucleic acid regulatory elements. (A) CSk-SH5 (SEQ ID NO: 1). (B) Dph-CRE02 (SEQ ID NO:2). (C) Dph-CRE04 (SEQ ID NO:3). (D) Dph-CRE06 (SEQ ID NO:4). (E) Dph-CRE02-CRE04 (SEQ ID NO:5), which is a combination of Dph-CRE02 and Dph-CRE04 connected through a flanking sequence (underlined). (F) Dph-CRE02-CRE06 (SEQ ID NO:6), which is a combination of Dph-CRE02 and Dph-CRE06 connected through a flanking sequence (underlined). (G) Dph-CRE04-CRE06 (SEQ ID NO:7), which is a combination of Dph-CRE04 and Dph-CRE06 connected through a flanking sequence (underlined). (H) Dph-CRE06-CRE04 (SEQ ID NO:8), which is a combination of Dph-CRE06 and Dph-CRE04 connected through a flanking sequence (underlined). (I) Dph-CRE02-CRE04-CRE06 (SEQ ID NO:9), which is a combination of Dph-CRE02, Dph-CRE04 and Dph-CRE06 connected with each other through a flanking sequence (underlined). (J) Dph-CRE02-CRE04-CSk-SH5 (SEQ ID NO:10). (K) Dph-CRE02-CRE06-CSk-SH5 (SEQ ID NO:11). (1) Dph-CRE04-CRE06-CSk-SH5 (SEQ ID NO:12). (M) Dph-CRE06-CRE04-CSk-SH5 (SEQ ID NO:13). (N) Dph-CRE02-CRE04-CRE06-CSk-SH5 (SEQ ID NO:14).

FIG. 2: Design of AAV vectors. AAV vectors were designed to express human β-sarcoglycan (hβsg) or luciferase (Luc). The vectors contain either codon-optimized (hβsgco, SEQ ID NO:19) or non codon-optimized hβsg (SEQ ID NO:18) transgene. The vectors contain a synthetic muscle promoter designated as SPc5-12 (SEQ ID NO:15). The vectors all contain a minute virus of mouse intron (MVM, SEQ ID NO:16) and a synthetic polyadenylation site (pA, SEQ ID NO:17). The vectors are flanked by a 5' and 3' AAV inverted terminal repeat (ITR). The vectors contain a cardiac and skeletal muscle-specific CRE (CSk-SH5) (A, B, A1), in combination with one or more diaphragm-specific CREs (CRE02, CRE04 or CRE06) (C-W), or are devoid of any CRE element (X, Y, Z).

FIG. 4: Effect of CRE combinations on expression of codon-optimized hβsc gene in gastrocnemius (A), quadriceps (B), diaphragm (C) and heart (D). AAV vectors expressing codon-optimized (hβsgco) from the SPc5-12 promoter were injected into CB17-SCID. The vectors contained a heart and skeletal muscle-specific CRE (CSk-SH5), either alone or in combination with one or two diaphragm-specific CREs (Dph-CRE02, Dph-CRE04 and/or Dph-CRE06). Expression of hβsgco gene was determined by quantitative real-time reverse transcriptase PCR (q RT-PCR).

FIG. 5: Effect of CRE combinations on expression of codon-optimized hbsc gene in gastrocnemius (A), quadriceps (B), diaphragm (C) and heart (D). AAV vectors expressing codon-optimized (hβsgco) from the SPc5-12 promoter were injected into CB17-SCID. The vectors contained no CRE element (SPc), a heart and skeletal muscle-specific CRE (CSk-SH5-SPC), a combination of two diaphragm-specific CREs and a heart and skeletal muscle-specific CRE (CRE04-CRE06-CSk-SH5), or a combination of three diaphragm-specific CREs and a heart and skeletal muscle-specific CRE (CRE02-CRE04-CRE06-CSk-SH5). Expression of hβsgco gene was determined by quantitative real-time reverse transcriptase PCR (qRT-PCR).

FIG. 6: Treadmill endurance assay to assess phenotypic correction of gene therapy treated Sgcb-null mice. Three different groups of mice were subjected to a treadmill endurance assay. Sgcb-null mice injected with AAV-SPc5-12-MVM-hβ-SGco-pA, AAV-CRE02-CRE04-CRE06-CSk- SH5-SPc5-12-MVM-hβ-SGco-pA, or PBS as negative control. The average distance run by each mouse group is indicated (n=3).

DESCRIPTION

Figure 3:
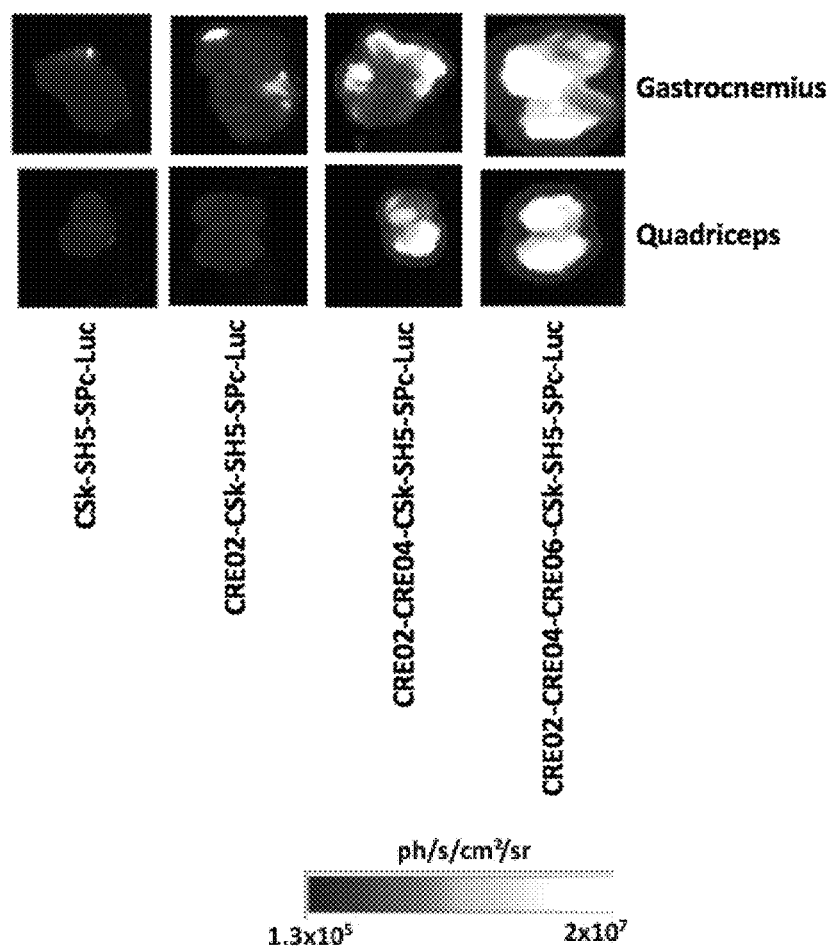
FIG. 3: Effect of CRE combinations on luciferase expression. Bioluminescence analysis (BLI) of gastrocnemius and quadriceps of CB17-SCID mice that were injected with AAV vectors expressing luciferase from a synthetic muscle promoter designated as SPc5-12 (SPc). The vectors contained a cardiac/skeletal muscle CRE (CSk-SH5) alone, or in combination with one or more diaphragm-specific CRE (CRE02, CRE04 and/or CRE06) and/or a cardiac/skeletal muscle CRE (CSk-SH5).

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of", which enjoy well-established meanings in patent terminology.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the terms "one or more" or "at least one", such as one or more members or at least one member of a group of members, is clear per se, by means of further exemplification, the term encompasses inter alia a reference to any one of said members, or to any two or more of said members, such as, e.g., any 3, 4, 5, or etc. of said members, and up to all said members. In another example, "one or more" or "at least one" may refer to 1, 2, 3, 4, 5, 6, 7 or more.

The discussion of the background to the invention herein is included to explain the context of the invention. This is not to be taken as an admission that any of the material referred to was published, known, or part of the common general knowledge in any country as of the priority date of any of the claims.

Throughout this disclosure, various publications, patents and published patent specifications are referenced by an identifying citation. All documents cited in the present specification are hereby incorporated by reference in their entirety. In particular, the teachings or sections of such documents herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the invention. When specific terms are defined in connection with a particular aspect of the invention or a particular embodiment of the invention, such connotation is meant to apply throughout this specification, i.e., also in the context of other aspects or embodiments of the invention, unless otherwise defined.

In the following passages, different aspects or embodiments of the invention are defined in more detail. Each aspect or embodiment so defined may be combined with any other aspect(s) or embodiment(s) unless clearly indicated to the contrary. In particular, any feature indicated as being preferred or advantageous may be combined with any other feature or features indicated as being preferred or advantageous.

Reference throughout this specification to "one embodiment", "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

For general methods relating to the invention, reference is made inter alia to well-known textbooks, including, e.g., "Molecular Cloning: A Laboratory Manual, 4$^{th}$ Ed." (Green and Sambrook, 2012, Cold Spring Harbor Laboratory Press), "Current Protocols in Molecular Biology" (Ausubel et al., 1987).

In an aspect, the invention relates to a nucleic acid regulatory element for enhancing muscle-specific gene expression, in particular for enhancing diaphragm, smooth muscle, cardiac and skeletal muscle-specific gene expression, more particularly for enhancing diaphragm, cardiac and skeletal muscle-specific gene expression comprising, consisting essentially of (i.e., the regulatory element may for instance additionally comprise sequences used for cloning purposes, but the indicated sequences make up the essential part of the regulatory element), or consisting of at least two, such as two, three or more, diaphragm-specific regulatory elements and a heart and skeletal muscle-specific regulatory element, wherein the at least two diaphragm-specific regulatory elements are selected from the group consisting of: a diaphragm-specific regulatory element comprising, consisting essentially of (i.e., the regulatory element may for instance additionally comprise sequences used for cloning purposes, but the indicated sequences make up the essential part of the regulatory element, e.g. they do not form part of a larger regulatory region such as a promoter), or consisting of a nucleotide sequence having at least 95% identity to SEQ ID NO:2, preferably the nucleotide sequence set forth in SEQ ID NO:2 (e.g. Dph-CRE02) or a functional fragment thereof; a diaphragm-specific regulatory element comprising, consisting essentially of, or consisting of a nucleotide sequence having at least 95% identity to SEQ ID NO:3, preferably the nucleotide sequence set forth in SEQ ID NO:3 (e.g. Dph-CRE04), or a functional fragment thereof; and a diaphragm-specific regulatory element comprising, consisting essentially of, or consisting of a nucleotide sequence having at least 95% identity to SEQ ID NO:4, preferably the nucleotide sequence set forth in SEQ ID NO:4 (e.g. Dph-CRE06), or a functional fragment thereof, and wherein the heart and skeletal muscle-specific regulatory element comprises, consists essentially of, or consists of a nucleotide sequence having at least 95% identity to SEQ ID NO:1, preferably the nucleotide sequence set forth in SEQ ID NO:1 (e.g. CSk-SH5), or a functional fragment thereof.

A 'regulatory element' or 'cis-regulatory element (CRE)' or 'cis-regulatory module (CRM)' or "SH" as used herein refers to a transcriptional control element, in particular a non-coding cis-acting transcriptional control element, capable of regulating and/or controlling transcription of a gene, in particular tissue-specific transcription of a gene. Regulatory elements comprise at least one transcription factor binding site (TFBS), more in particular at least one binding site for a tissue-specific transcription factor. Regulatory elements alone are typically not sufficient to initiate transcription, but require a promoter to this end. Typically, regulatory elements as used herein increase or enhance promoter-driven gene expression when compared to the transcription of the gene from the promoter alone, without the regulatory elements. Thus, regulatory elements particularly comprise enhancer sequences, although it is to be understood that the regulatory elements enhancing transcription are not limited to typical far upstream enhancer sequences, but may occur at any distance of the gene they regulate or even within the gene or open reading frame itself. Indeed, it is known in the art that sequences regulating transcription may be situated either upstream (e.g. in the promoter region) or downstream (e.g. in the 3'UTR) of the gene they regulate in vivo, and may be located in the immediate vicinity of the gene or further away. Regulatory elements as disclosed herein encompass naturally occurring sequences, as well as variants thereof and combinations of such regulatory elements or several copies of such a regulatory element, i.e. regulatory elements comprising non-naturally occurring sequences. Regulatory elements as disclosed herein may comprise part of a larger sequence involved in transcriptional control, e.g. part of a promoter sequence. The regulatory elements of the present invention are non-naturally occurring sequences. The regulatory elements disclosed herein are provided as nucleic acid molecules.

The term "nucleic acid" as used herein typically refers to an oligomer or polymer (preferably a linear polymer) of any length composed essentially of nucleotides. A nucleotide unit commonly includes a heterocyclic base, a sugar group, and at least one, e.g. one, two, or three, phosphate groups, including modified or substituted phosphate groups. Heterocyclic bases may include inter alia purine and pyrimidine bases such as adenine (A), guanine (G), cytosine (C), thymine (T) and uracil (U) which are widespread in naturally-occurring nucleic acids, other naturally-occurring bases (e.g., xanthine, inosine, hypoxanthine) as well as chemically or biochemically modified (e.g., methylated), non-natural or derivatised bases. Sugar groups may include inter alia pentose (pentofuranose) groups such as preferably ribose and/or 2-deoxyribose common in naturally-occurring nucleic acids, or arabinose, 2-deoxyarabinose, threose or hexose sugar groups, as well as modified or substituted sugar groups. Nucleic acids as intended herein may include naturally occurring nucleotides, modified nucleotides or mixtures thereof. A modified nucleotide may include a modified heterocyclic base, a modified sugar moiety, a modified phosphate group or a combination thereof. Modifications of phosphate groups or sugars may be introduced to improve stability, resistance to enzymatic degradation, or some other useful property. The term "nucleic acid" further preferably encompasses DNA, RNA and DNA/RNA hybrid molecules, specifically including hnRNA, pre-mRNA, mRNA, cDNA, genomic DNA, amplification products, oligonucleotides, and synthetic (e.g., chemically synthesised) DNA, RNA or DNA/RNA hybrids. A nucleic acid can be naturally occurring, e.g., present in or isolated from nature; or can be non-naturally occurring, e.g., recombinant, i.e., produced by recombinant DNA technology, and/or partly or entirely, chemically or biochemically synthesised. A "nucleic acid" can be double-stranded, partly double stranded, or single-stranded. Where single-stranded, the nucleic acid can be the sense strand or the antisense strand. In addition, nucleic acid can be circular or linear.

As used herein "transcription factor binding site", "transcription factor binding sequence" or "TFBS" refers to a sequence of a nucleic acid region to which transcription factors bind. Non-limiting examples of TFBS include binding sites for transcription factor 3, also known as TCF3 or E2A; binding sites for nuclear factor I, also known as NF1; binding sites for CCAAT-enhancer-binding protein, also known as C/EBP; binding sites for myogenic differentiation, also known as MyoD; binding sites for sterol regulatory element-binding protein, also known as SREBP; binding sites for leukemia/lymphoma-related factor, also known as LRF; binding sites for protein 53, also known as p53; binding sites for hepatocyte nuclear factor 3-alpha, also known as HNF3a; binding sites for hepatocyte nuclear factor 3-beta, also known as HNF3b; binding sites for hepatocyte nuclear factor 4, also known as HNF4; binding sites for myocyte-specific enhancer factor 2A, also known as MEF2A or RSRFC4; binding sites for peroxisome proliferator-activated receptor gamma 1/2, also known as PPAR-gamma1/2; binding sites for serum response factor, also known as SRF; binding sites for transcription activator-like protein 1b, also known as Tal1_b or Tal1-beta; binding sites for enhancer of zeste homolog 2, also known as EZH2; binding sites for Polycom Repressive Complex 2 Subunit, also known as SUZ12; binding sites for TATA-binding protein, also known as TBP; binding sites for folate receptor alpha, also known as FOLR2A; binding sites for RE-1 silencing transcription factor, also known as REST; binding sites for TEA domain transcription factor 4, also known as TEAD4; transcription factor binding sites for Retinablastoma-Binding Protein 5, also known as RBBPS; transcription factor binding sites for Msh Homeobox 1, also known as Msx-1; transcription factor binding sites for SIN3 Transcription Regulator Family Member A, also known as SIN3A; transcription factor binding sites for JunD, also known as JUND; transcription factor binding sites for Zinc Finger ZZ-Type Containing 3, also known as ZZZ3; transcription factor binding sites for Zinc Finger E-Box Binding Homeobox 1, also known as AREB6; transcription factor binding sites for transcription factor E2F; transcription factor binding sites for Transcription Factor 4, also known as ITF2; transcription factor binding sites for estrogen receptor alpha, also known as ER-alpha; Myb-related protein B, also known as MYBL2; forkhead box A1 also known as FOXA1; forkhead box A2, also known as FOXA2; Transcription initiation factor TFIID subunit 7, also known as TAF7; SIN3AK20; MAX transcription factor, also known as MAX; Zinc finger and BTB domain-containing protein 7A, also known as ZBTB7A. Transcription factor binding sites may be found in databases such as Transfac®.

As used herein, the terms "identity" and "identical" and the like refer to the sequence similarity between two polymeric molecules, e.g., between two nucleic acid molecules, e.g., two DNA molecules. Sequence alignments and determination of sequence identity can be done, e.g., using the Basic Local Alignment Search Tool (BLAST) originally described by Altschul et al. 1990 (J Mol Biol 215: 403-10), such as the "Blast 2 sequences" algorithm described by Tatusova and Madden 1999 (FEMS Microbiol Lett 174: 247-250). Typically, the percentage sequence identity is calculated over the entire length of the sequence. As used herein, the term "substantially identical" denotes at least 90%, preferably at least 95%, such as 95%, 96%, 97%, 98% or 99%, sequence identity.

The term "functional fragment" as used in the application with respect to the nucleic acid regulatory elements disclosed herein refers to fragments of said regulatory element sequences that retain the capability of regulating muscle-specific expression, i.e. they can still confer tissue specificity and they are capable of regulating expression of a (trans) gene in the same way (although possibly not to the same extent) as the sequence from which they are derived. Functional fragments may preferably comprise at least 20, at least 25, at least 30, at least 35, at least 40, at least 45, at least 50, at least 60, at least 70, at least 80, at least 90, at least 100, at least 120, at least 150, at least 200, at least 250, at least 300, at least 350, at least 400 or at least 450 contiguous nucleotides from the sequence from which they are derived. Also preferably, functional fragments may comprise at least 1, more preferably at least 2, at least 3, or at least 4, even more preferably at least 5, at least 10, or at least 15, of the transcription factor binding sites (TFBS) that are present in the sequence from which they are derived. Functional fragments as defined herein preferably have at least 50%, at least 60%, at least 70%, at least 80%, at least 90%, at least 95% or about 100% of the nucleic acids regulatory capacities of the regulatory element wherefrom they are derived.

A "cardiac and skeletal muscle-specific regulatory element" or "heart and skeletal muscle-specific regulatory element" as used herein refers to a regulatory element that is capable of enhancing cardiac and skeletal muscle-specific expression. Non-limiting examples of cardiac and skeletal muscle-specific regulatory elements are the regulatory elements denoted as "CSk-SH" in WO 2015/110449. In particular, a cardiac and skeletal muscle-specific regulatory element comprising, consisting essentially of, or consisting of a nucleotide sequence having at least 95% identity to SEQ ID NO:1, preferably the nucleotide sequence set forth in SEQ ID NO:1, or a functional fragment thereof is used herein. In embodiments, the cardiac and skeletal muscle-specific regulatory element consisting essentially of consisting of the nucleotide sequence set forth in SEQ ID NO:1, or a sequence having at least 80%, preferably at least 85%, more preferably at least 90%, even more preferably at least 95%, such as 95%, 96%, 97%, 98%, or 99%, identity to SEQ ID NO:1, also denoted herein as "CSk-SH5" or "CSkSH5" or "Csk-SH5" or "CskSH5" or "CSK-SH5" or "CSKSHS", is used.

As used herein "cardiac and skeletal muscle-specific expression" refers to the preferential or predominant expression of a (trans)gene in heart, in particular heart muscle, and skeletal muscle. At least 50%, more particularly at least 60%, at least 70%, at least 75%, at least 80%, at least 85%, at least 90%, at least 95%, at least 98%, at least 99% or 100% of the (trans)gene expression may occur within heart and skeletal muscle. Less than 50%, less than 40%, less than 30%, less than 20%, less than 10%, less than 5%, less than 2% or even less than 1% of the (trans)gene expression may occur in an organ or tissue other than heart and skeletal muscle. Throughout the application, where cardiac and skeletal muscle-specific is mentioned in the context of expression, cardiomyocyte and skeletal myocyte-specific expression, cardiac myoblast and skeletal myoblast-specific expression or cardiac and muscle stem/progenitor cell or satellite cell-specific expression are also explicitly envisaged.

As used herein, the terms "heart muscle" or "cardiac muscle" refer to the autonomically regulated, striated muscle type found in the heart.

As used herein, the term "skeletal muscle" refers to the voluntarily controlled, striated muscle type that is attached to the skeleton. Non-limiting examples of skeletal muscle include the biceps, the triceps, the quadriceps, the tibialis interior, and the gastrocnemius muscle.

The term "myocyte," as used herein, refers to a cell that has been differentiated from a progenitor muscle stem/progenitor cell, satellite cell or myoblast such that it is capable of expressing muscle-specific phenotype under appropriate conditions. Terminally differentiated myocytes fuse with one another to form myotubes, a major constituent of muscle fibers. The term "myocyte" also refers to myocytes that are de-differentiated. The term includes cells in vivo and cells cultured ex vivo regardless of whether such cells are primary or passaged.

The terms "muscle stem/progenitor cell", "satellite cell" or "myoblast" as used herein, refer to an embryonic cell in the mesoderm that differentiates to give rise to a muscle cell or myocyte. The term includes cells in vivo and cells cultured ex vivo regardless of whether such cells are primary or passaged.

A "diaphragm-specific regulatory element" as used herein refers to a regulatory element that is capable of enhancing diaphragm and skeletal muscle-specific expression. Non-limiting examples of diaphragm-specific regulatory elements are the regulatory elements denoted as Dph-CRE01 to Dph-CRE065 in WO 2018/178067. In particular, a diaphragm-specific regulatory element comprising, consisting essentially of, or consisting of a nucleotide sequence having at least 95% identity to SEQ ID NO:2, preferably the nucleotide sequence set forth in SEQ ID NO:2, or a functional fragment thereof; a diaphragm-specific regulatory element comprising, consisting essentially of, or consisting of a nucleotide sequence having at least 95% identity to SEQ ID NO:3, preferably the nucleotide sequence set forth in SEQ ID NO:3, or a functional fragment thereof; and/or a diaphragm-specific regulatory element comprising, consisting essentially of, or consisting of a nucleotide sequence having at least 95% identity to SEQ ID NO:4, preferably the nucleotide sequence set forth in SEQ ID NO:4, or a functional fragment thereof, is used herein. In embodiments, the diaphragm-specific regulatory element consisting essentially of or consisting of the nucleotide sequence set forth in SEQ ID NO:2 or a sequence having at least 80%, preferably at least 85%, more preferably at least 90%, even more preferably at least 95%, such as 95%, 96%, 97%, 98%, or 99%, identity to SEQ ID NO:2, also denoted herein as "Dph-CRE02" or "CRE-02" or "CRE02", the diaphragm-specific regulatory element consisting essentially of or consisting of the nucleotide sequence set forth in SEQ ID NO:3 or a sequence having at least 80%, preferably at least 85%, more preferably at least 90%, even more preferably at least 95%, such as 95%, 96%, 97%, 98%, or 99%, identity to SEQ ID NO:3, also denoted herein as "Dph-CRE04" or "CRE-04" or "CRE04", and/or the diaphragm-specific regulatory element consisting essentially of or consisting of the nucleotide sequence set forth in SEQ ID NO4 or a sequence having at least 80%, preferably at least 85%, more preferably at least 90%, even more preferably at least 95%, such as 95%, 96%, 97%, 98%, or 99%, identity to SEQ ID NO:4, also denoted herein as "Dph-CRE06" or "CRE-06" or "CRE06", is/are used.

TABLE 1

Nucleic acid regulatory elements

| Sequence | Name | Size (bp) | Conserved TFBS present |
|---|---|---|---|
| SEQ ID NO: 2 | Dph-CRE02 | 452 | EZH2, SUZ12, TBP, FOLR2A, REST TEAD4, RBBP5, Msx-1, SRF, SIN3A |
| SEQ ID NO: 3 | Dph-CRE04 | 509 | JUND, ZZZ3, AREB6, RSRFC4, MEF2A, TBP |
| SEQ ID NO: 4 | Dph-CRE06 | 400 | E2F, ITF2, Tal-1beta, TBP, ER-alpha, PPAR-gamma1, PPAR-gamma-2 |
| SEQ ID NO: 1 | CSk-SH5 | 454 | HNF4, NF1, RSRFC4, CEBP, LRF, MyoD, FOLR2A, MYBL2, HNF4G, FOXA1, HNF4A, FOXA2, MEF2A, TAF7, SIN3A, CEBPB, MAX, ZBTB7 |

In embodiments, the diaphragm-specific regulatory element is a combination of at least 2 diaphragm-specific regulatory elements selected from the group consisting of the diaphragm-specific regulatory element consisting of the nucleotide sequence set forth in SEQ ID NO:2 or a sequence having at least 80%, preferably at least 85%, more preferably at least 90%, even more preferably at least 95%, such as 95%, 96%, 97%, 98%, or 99%, identity to SEQ ID NO:2 (Dph-CRE02), or a functional fragment thereof; the diaphragm-specific regulatory element consisting of the nucleotide sequence set forth in SEQ ID NO:3 or a sequence having at least 80%, preferably at least 85%, more preferably at least 90%, even more preferably at least 95%, such as 95%, 96%, 97%, 98%, or 99%, identity to SEQ ID NO:3 (Dph-CRE04), or a functional fragment thereof; and the diaphragm-specific regulatory element consisting of the nucleotide sequence set forth in SEQ ID NO:4 or a sequence having at least 80%, preferably at least 85%, more preferably at least 90%, even more preferably at least 95%, such as 95%, 96%, 97%, 98%, or 99%, identity to SEQ ID NO:4 (Dph-CRE06), or a functional fragment thereof. More particularly, a diaphragm-specific regulatory element comprising, consisting essentially of, or consisting of the nucleotide sequence set forth in SEQ ID NO:5 or a sequence having at least 80%, preferably at least 85%, more preferably at least 90%, even more preferably at least 95%, such as 95%, 96%, 97%, 98%, or 99%, identity to SEQ ID NO:5 (Dph-CRE02-CRE04), a diaphragm-specific regulatory element comprising, consisting essentially of, or consisting of the nucleotide sequence set forth in SEQ ID NO:6 or a sequence having at least 80%, preferably at least 85%, more preferably at least 90%, even more preferably at least 95%, such as 95%, 96%, 97%, 98%, or 99%, identity to SEQ ID NO:6 (Dph-CRE02-CRE06), a diaphragm-specific regulatory element comprising, consisting essentially of, or consisting of the nucleotide sequence set forth in SEQ ID NO:7 or a sequence having at least 80%, preferably at least 85%, more preferably at least 90%, even more preferably at least 95%, such as 95%, 96%, 97%, 98%, or 99%, identity to SEQ ID NO:7 (Dph-CRE04-CRE06), a diaphragm-specific regulatory element comprising, consisting essentially of, or consisting of the nucleotide sequence set forth in SEQ ID NO:8 or a sequence having at least 80%, preferably at least 85%, more preferably at least 90%, even more preferably at least 95%, such as 95%, 96%, 97%, 98%, or 99%, identity to SEQ ID NO:8 (Dph-CRE06-CRE04) or a diaphragm-specific regulatory element comprising, consisting essentially of, or consisting of the nucleotide sequence set forth in SEQ ID NO:9 or a sequence having at least 80%, preferably at least 85%, more preferably at least 90%, even more preferably at least 95%, such as 95%, 96%, 97%, 98%, or 99%, identity to SEQ ID NO:9 (Dph-CRE02-CRE04-CRE06), is used herein.

"Diaphragm and skeletal muscle-specific expression" as used herein, refers to the preferential or predominant expression of a (trans)gene (as RNA and/or polypeptide) in diaphragm and/or skeletal muscle cells or diaphragm and/or skeletal muscle tissue, as compared to other (i.e. non-diaphragm and skeletal muscle) cells or tissue. At least 50%, more particularly at least 60%, at least 70%, at least 75%, at least 80%, at least 85%, at least 90%, at least 95%, at least 98%, at least 99% or 100% of the (trans)gene expression may occur within diaphragm and/or skeletal muscle cells or tissue. Diaphragm and skeletal muscle specific expression may entail that there is less than 50%, less than 40%, less than 30%, less than 20%, less than 10%, less than 5%, less than 2% or even less than 1% 'leakage' of expressed gene product to other organs or tissue than diaphragm and skeletal muscle, such as lung, liver, brain, kidney and/or spleen.

"Muscle-specific expression" as used herein, refers to the preferential or predominant expression of a (trans)gene (as RNA and/or polypeptide) in muscle cells, as compared to other (i.e. non-muscle) cells or tissue. At least 50%, more particularly at least 60%, at least 70%, at least 75%, at least 80%, at least 85%, at least 90%, at least 95%, at least 98%, at least 99% or 100% of the (trans)gene expression may occur within muscle cells or tissue. Muscle specific expression may entail that there is less than 50%, less than 40%, less than 30%, less than 20%, less than 10%, less than 5%, less than 2% or even less than 1% 'leakage' of expressed gene product to other organs or tissue than muscle, such as lung, liver, brain, kidney and/or spleen.

"Smooth muscle-specific expression" as used in the application, refers to the preferential or predominant expression of a (trans)gene (as RNA and/or polypeptide) in smooth muscle cells and tissue, as compared to other (i.e. non-smooth muscle) cells or tissues. According to particular embodiments, at least 50%, more particularly at least 60%, at least 70%, at least 75%, at least 80%, at least 85%, at least 90%, at least 95%, at least 98%, at least 99% or 100% of the (trans)gene expression occurs within smooth muscle cells or tissue. According to a particular embodiment, smooth muscle specific expression entails that there is less than 50%, less than 40%, less than 30%, less than 20%, less than 10%, less than 5%, less than 2% or even less than 1% "leakage" of expressed gene product to other organs or tissue than smooth muscle.

The nucleic acid regulatory elements of the present invention comprise an artificial sequence by combining two or more diaphragm-specific regulatory elements disclosed herein and a cardiac and skeletal muscle-specific regulatory element disclosed herein. As shown in the experimental section, the combination of two diaphragm-specific regulatory elements disclosed herein and a cardiac and skeletal muscle-specific regulatory element as disclosed herein led to robust transgene expression in diaphragm, smooth muscle, heart and skeletal muscle, more particularly in diaphragm, heart and skeletal muscle. More particularly, the two diaphragm-specific regulatory elements and the cardiac and skeletal muscle-specific regulatory element act synergistically as a new regulatory element for enhancing diaphragm, smooth muscle, cardiac and skeletal muscle-specific transgene expression, more particularly for enhancing diaphragm, cardiac and skeletal muscle-specific transgene expression. It has further been shown that the addition of a third diaphragm-specific regulatory element disclosed herein to this combination could further increase diaphragm, cardiac, smooth muscle and skeletal muscle-specific transgene expression, more particularly diaphragm, cardiac and skeletal muscle-specific transgene expression, in a synergistic way.

As used herein "diaphragm, cardiac, smooth muscle and skeletal muscle-specific expression" refers to the preferential or predominant expression of a (trans)gene in diaphragm, smooth muscle, heart and/or skeletal muscle cells or tissue. According to particular embodiments, at least 50%, more particularly at least 60%, at least 70%, at least 75%, at least 80%, at least 85%, at least 90%, at least 95%, at least 98%, at least 99% or 100% of the (trans)gene expression occurs within diaphragm, smooth muscle, heart and/or skeletal muscle cells and tissue. Thus, according to particular embodiments, less than 50%, less than 40%, less than 30%, less than 20%, less than 10%, less than 5%, less than 2% or even less than 1% of the (trans)gene expression occurs in an organ or tissue other than diaphragm, smooth muscle, heart and skeletal muscle.

As used herein "diaphragm, cardiac and skeletal muscle-specific expression" refers to the preferential or predominant expression of a (trans)gene in diaphragm, heart and/or skeletal muscle cells or tissue. According to particular embodiments, at least 50%, more particularly at least 60%, at least 70%, at least 75%, at least 80%, at least 85%, at least 90%, at least 95%, at least 98%, at least 99% or 100% of the (trans)gene expression occurs within diaphragm, heart and/or skeletal muscle cells and tissue. Thus, according to particular embodiments, less than 50%, less than 40%, less than 30%, less than 20%, less than 10%, less than 5%, less than 2% or even less than 1% of the (trans)gene expression occurs in an organ or tissue other than diaphragm, heart and skeletal muscle.

In embodiments, the invention relates to a nucleic acid regulatory element for enhancing muscle-specific gene expression, in particular diaphragm, smooth muscle, cardiac and skeletal muscle-specific gene expression, more particularly diaphragm, cardiac and skeletal muscle-specific gene expression comprising, consisting essentially of, or consisting of a diaphragm-specific regulatory element comprising, consisting essentially of, or consisting of a nucleotide sequence having at least 95% identity to the nucleotide sequence set forth in SEQ ID NO:2 (e.g. Dph-CRE02), or a functional fragment thereof, a diaphragm-specific regulatory element comprising, consisting essentially of, or consisting of a nucleotide sequence having at least 95% identity to the nucleotide sequence set forth in SEQ ID NO:3 (e.g. Dph-CRE04), or a functional fragment thereof, and a heart and skeletal muscle-specific regulatory element comprising, consisting essentially of, or consisting of a nucleotide sequence having at least 95% identity to the nucleotide sequence set forth in SEQ ID NO:1 (e.g. CSk-SH5), or a functional fragment thereof. In particular embodiments, the invention relates to a nucleic acid regulatory element for enhancing muscle-specific gene expression, in particular diaphragm, smooth muscle, cardiac and skeletal muscle-specific gene expression, more particularly diaphragm, cardiac and skeletal muscle-specific gene expression, comprising, consisting essentially of, or consisting of the diaphragm-specific regulatory element consisting essentially of or consisting of the nucleotide sequence set forth in SEQ ID NO:2 (Dph-CRE02), or a functional fragment thereof, the diaphragm-specific regulatory element consisting essentially of or consisting of the nucleotide sequence set forth in SEQ ID NO:3 (Dph-CRE04), or a functional fragment thereof, and the heart and skeletal muscle-specific regulatory element consisting essentially of or consisting of the nucleotide sequence set forth in SEQ ID NO:1 (CSk-SH5) or a functional fragment thereof. In further embodiments, the nucleic acid regulatory element further comprises a diaphragm-specific regulatory element comprising, consisting essentially of, or consisting of a nucleotide sequence having at least 95% identity to the nucleotide sequence set forth in SEQ ID NO:4 (e.g. Dph-CRE06), or a functional fragment thereof, preferably the diaphragm-specific regulatory element consisting essentially of or consisting of the nucleotide sequence set forth in SEQ ID NO:4 (Dph-CRE06), or a functional fragment thereof.

In embodiments, the invention relates to a nucleic acid regulatory element for enhancing muscle-specific gene expression, in particular diaphragm, smooth muscle, cardiac and skeletal muscle-specific gene expression, more particularly diaphragm, cardiac and skeletal muscle-specific gene expression, comprising, consisting essentially of, or consisting of a diaphragm-specific regulatory element comprising, consisting essentially of, or consisting of a nucleotide sequence having at least 95% identity to the nucleotide sequence set forth in SEQ ID NO:2 (e.g. Dph-CRE02), or a functional fragment thereof; a diaphragm-specific regulatory element comprising, consisting essentially of, or consisting of a nucleotide sequence having at least 95% identity to the nucleotide sequence set forth in SEQ ID NO:4 (e.g. Dph-CRE06), or a functional fragment thereof; and a heart and skeletal muscle-specific regulatory element comprising, consisting essentially of, or consisting of a nucleotide sequence having at least 95% identity to the nucleotide sequence set forth in SEQ ID NO:1 (e.g. CSk-SH5), or a functional fragment thereof. In particular embodiments, the invention relates to a nucleic acid regulatory element for enhancing muscle-specific gene expression, in particular diaphragm, smooth muscle cardiac and skeletal muscle-specific gene expression, more particularly diaphragm, cardiac and skeletal muscle-specific gene expression, comprising, consisting essentially of, or consisting of the diaphragm-specific regulatory element consisting essentially of or consisting of the nucleotide sequence set forth in SEQ ID NO:2 (Dph-CRE02), or a functional fragment thereof; the diaphragm-specific regulatory element consisting essentially of or consisting of the nucleotide sequence set forth in SEQ ID NO:4 (Dph-CRE06), or a functional fragment thereof; and the heart and skeletal muscle-specific regulatory element consisting essentially of or consisting of the nucleotide sequence set forth in SEQ ID NO:1 (CSk-SH5), or a functional fragment thereof. In further embodiments, the nucleic acid regulatory element further comprises a diaphragm-specific regulatory element comprising, consisting essentially of, or consisting of a nucleotide sequence having at least 95% identity to the nucleotide sequence set forth in SEQ ID NO:3 (e.g. Dph-CRE04), or a functional fragment thereof, preferably the diaphragm-specific regulatory element consisting essentially of or consisting of the nucleotide sequence set forth in SEQ ID NO:3 (Dph-CRE04) or a functional fragment thereof.

In embodiments, the invention relates to a nucleic acid regulatory element for enhancing muscle-specific gene expression, in particular diaphragm, smooth muscle, cardiac and skeletal muscle-specific gene expression, more particularly diaphragm, cardiac and skeletal muscle-specific gene expression, comprising, consisting essentially of, or consisting of a diaphragm-specific regulatory element comprising, consisting essentially of, or consisting of a nucleotide sequence having at least 95% identity to the nucleotide sequence set forth in SEQ ID NO:3 (e.g. Dph-CRE04), or a functional fragment thereof; a diaphragm-specific regulatory element comprising, consisting essentially of, or consisting of a nucleotide sequence having at least 95% identity to the nucleotide sequence set forth in SEQ ID NO:4 (e.g. Dph-CRE06), or a functional fragment thereof; and a heart and skeletal muscle-specific regulatory element comprising, consisting essentially of, or consisting of a nucleotide sequence having at least 95% identity to the nucleotide sequence set forth in SEQ ID NO:1 (e.g. CSk-SH5), or a functional fragment thereof. In particular embodiments, the invention relates to a nucleic acid regulatory element for enhancing muscle-specific gene expression, in particular diaphragm, smooth muscle, cardiac and skeletal muscle-specific gene expression, more particularly diaphragm, cardiac and skeletal muscle-specific gene expression, comprising, consisting essentially of, or consisting of the diaphragm-specific regulatory element consisting essentially of or consisting of the nucleotide sequence set forth in SEQ ID NO3 (Dph-CRE04), or a functional fragment thereof; the diaphragm-specific regulatory element consisting essentially of or consisting of the nucleotide sequence set forth in SEQ ID NO:4 (Dph-CREW, or a functional fragment thereof; and the heart and skeletal muscle-specific regulatory element consisting essentially of or consisting of the nucleotide sequence set forth in SEQ ID NO:1 (CSk-SH5), or a functional fragment thereof. In further embodiments, the nucleic acid regulatory element further comprises a diaphragm-specific regulatory element comprising, consisting essentially of, or consisting of a nucleotide sequence having at least 95% identity to the nucleotide sequence set forth in SEQ ID NO:2 (e.g. Dph-CRE02), or a functional fragment thereof, preferably the diaphragm-specific regulatory element consisting essentially of or consisting of the nucleotide sequence set forth in SEQ ID NO:2 (Dph-CRE02) or a functional fragment thereof.

The at least two diaphragm-specific regulatory elements and the cardiac and skeletal muscle-specific regulatory element can be combined in any order in the nucleic acid regulatory elements disclosed herein. The at least two diaphragm-specific regulatory elements and the cardiac and skeletal muscle-specific regulatory element can be combined in tandem or the regulatory elements can be combined with one or more intervening or flanking nucleotides (e.g. nucleotides used for cloning purposes) between one or more of the regulatory elements.

In embodiments, the nucleic acid regulatory element comprises, consists essentially of, or consists of a diaphragm-specific regulatory element comprising, consisting essentially of, or consisting of the nucleotide sequence set forth in SEQ ID NO:5 (e.g. Dph-CRE02-CRE04) and a heart and skeletal muscle-specific regulatory element comprising, consisting essentially of, or consisting of the nucleotide sequence set forth in SEQ ID NO:1 (e.g. CSk-SH5) or a functional fragment thereof. In particular embodiments, the invention relates to a nucleic acid regulatory element for enhancing muscle-specific gene expression, in particular diaphragm, smooth muscle, cardiac and skeletal muscle-specific gene expression, more particularly diaphragm, cardiac and skeletal muscle-specific gene expression, comprising, consisting essentially of, or consisting of the diaphragm-specific regulatory element consisting essentially of or consisting of the nucleotide sequence set forth in SEQ ID NO:5 (Dph-CRE02-CRE04) and the heart and skeletal muscle-specific regulatory element consisting essentially of or consisting of the nucleotide sequence set forth in SEQ ID NO:1 (CSk-SH5) or a functional fragment thereof. In further embodiments, the nucleic acid regulatory element further comprises a diaphragm-specific regulatory element comprising, consisting essentially of, or consisting of a nucleotide sequence having at least 95% identity to the nucleotide sequence set forth in SEQ ID NO:4 (e.g. Dph-CREW, preferably the diaphragm-specific regulatory element consisting essentially of or consisting of the nucleotide sequence set forth in SEQ ID NO:4 (Dph-CRE06), or a functional fragment thereof.

In embodiments, the nucleic acid regulatory element comprises, consists essentially of, or consists of a diaphragm-specific regulatory element comprising, consisting essentially of, or consisting of the nucleotide sequence set forth in SEQ ID NO:6 (e.g. Dph-CRE02-CRE06) and a heart and skeletal muscle-specific regulatory element comprising, consisting essentially of, or consisting of the nucleotide sequence set forth in SEQ ID NO:1 (e.g. CSk-SH5) or a functional fragment thereof. In particular embodiments, the invention relates to a nucleic acid regulatory element for enhancing muscle-specific gene expression, in particular diaphragm, smooth muscle, cardiac and skeletal muscle-specific gene expression, more particularly diaphragm, cardiac and skeletal muscle-specific gene expression, comprising, consisting essentially of, or consisting of the diaphragm-specific regulatory element consisting essentially of or consisting of the nucleotide sequence set forth in SEQ ID NO:6 (Dph-CRE02-CRE06) and the heart and skeletal muscle-specific regulatory element consisting essentially of or consisting of the nucleotide sequence set forth in SEQ ID NO:1 (CSk-SH5) or a functional fragment thereof. In further embodiments, the nucleic acid regulatory element further comprises a diaphragm-specific regulatory element comprising, consisting essentially of, or consisting of a nucleotide sequence having at least 95% identity to the nucleotide sequence set forth in SEQ ID NO:3 (e.g. Dph-CRE04), preferably the diaphragm-specific regulatory element consisting essentially of or consisting of the nucleotide sequence set forth in SEQ ID NO:3 (Dph-CRE04), or a functional fragment thereof.

In embodiments, the nucleic acid regulatory element comprises, consists essentially of, or consists of a diaphragm-specific regulatory element comprising, consisting essentially of, or consisting of the nucleotide sequence set forth in SEQ ID NO:7 (e.g. Dph-CRE04-CRE06) and a heart and skeletal muscle-specific regulatory element comprising, consisting essentially of, or consisting of the nucleotide sequence set forth in SEQ ID NO:1 (e.g. CSk-SH5) or a functional fragment thereof. In particular embodiments, the invention relates to a nucleic acid regulatory element for enhancing muscle-specific gene expression, in particular diaphragm, smooth muscle, cardiac and skeletal muscle-specific gene expression, more particularly diaphragm, cardiac and skeletal muscle-specific gene expression comprising, consisting essentially of, or consisting of the diaphragm-specific regulatory element consisting essentially of or consisting of the nucleotide sequence set forth in SEQ ID NO:7 (Dph-CRE04-CRE06) and the heart and skeletal muscle-specific regulatory element consisting essentially of or consisting of the nucleotide sequence set forth in SEQ ID NO:1 (CSk-SH5) or a functional fragment thereof. In further embodiments, the nucleic acid regulatory element further comprises a diaphragm-specific regulatory element comprising, consisting essentially of, or consisting of a nucleotide sequence having at least 95% identity to the nucleotide sequence set forth in SEQ ID NO:2 (e.g. Dph-CRE02), preferably the diaphragm-specific regulatory element consisting essentially of or consisting of the nucleotide sequence set forth in SEQ ID NO:2 (Dph-CRE02), or a functional fragment thereof. In specific embodiments, the nucleic acid regulatory element comprises, consists essentially of, or consists of a diaphragm-specific regulatory element comprising, consisting essentially of, or consisting of the nucleotide sequence set forth in SEQ ID NO:9 (e.g. Dph-CRE02-CRE04-CRE06) and a heart and skeletal muscle-specific regulatory element comprising, consisting essentially of, or consisting of the nucleotide sequence set forth in SEQ ID NO:1 (e.g. CSk-SH5) or a functional fragment thereof. In particular embodiments, the invention relates to a nucleic acid regulatory element for enhancing muscle-specific gene expression, in particular diaphragm, smooth muscle, cardiac and skeletal muscle-specific gene expression, more particularly diaphragm, cardiac and skeletal muscle-specific gene expression, comprising, consisting essentially of, or consisting of the diaphragm-specific regulatory element consisting essentially of or consisting of the nucleotide sequence set forth in SEQ ID NO:9 (Dph-CRE02-CRE04-CRE06) and the heart and skeletal muscle-specific regulatory element consisting essentially of or consisting of the nucleotide sequence set forth in SEQ ID NO:1 (CSk-SH5) or a functional fragment thereof.

In embodiments, the nucleic acid regulatory element comprises, consists essentially of, or consists of a diaphragm-specific regulatory element comprising, consisting essentially of, or consisting of the nucleotide sequence set forth in SEQ ID NO:8 (e.g. Dph-CRE06-CRE04) and a heart and skeletal muscle-specific regulatory element comprising, consisting essentially of, or consisting of the nucleotide sequence set forth in SEQ ID NO:1 (e.g. CSk-SH5) or a functional fragment thereof. In particular embodiments, the invention relates to a nucleic acid regulatory element for enhancing muscle-specific gene expression, in particular diaphragm, smooth muscle, cardiac and skeletal muscle-specific gene expression, more particularly diaphragm, cardiac and skeletal muscle-specific gene expression, comprising, consisting essentially of, or consisting of the diaphragm-specific regulatory element consisting essentially of or consisting of the nucleotide sequence set forth in SEQ ID NO:8 (Dph-CRE06-CRE04) and the heart and skeletal muscle-specific regulatory element consisting essentially of or consisting of the nucleotide sequence set forth in SEQ ID NO:1 (CSk-SH5) or a functional fragment thereof. In further embodiments, the nucleic acid regulatory element further comprises a diaphragm-specific regulatory element comprising, consisting essentially of, or consisting of a nucleotide sequence having at least 95% identity to the nucleotide sequence set forth in SEQ ID NO:2 (e.g. Dph-CRE02), preferably the diaphragm-specific regulatory element consisting essentially of or consisting of the nucleotide sequence set forth in SEQ ID NO:2 (Dph-CRE02), or a functional fragment thereof.

In specific embodiments, the nucleic acid regulatory element comprises, consists essentially of, or consists of the nucleotide sequence set forth in SEQ ID NO:10 (Dph-CRE02-Dph-CRE04-CSk-SH5). In further embodiments, the nucleic acid regulatory element further comprises a diaphragm-specific regulatory element comprising, consisting essentially of, or consisting of the nucleotide sequence set forth in SEQ ID NO:4 (e.g. Dph-CRE06), preferably the diaphragm-specific regulatory element consisting of the nucleotide sequence set forth in SEQ ID NO:4 (Dph-CRE06), or a functional fragment thereof. In specific embodiments, the nucleic acid regulatory element comprises, consists essentially of, or consists of the nucleotide sequence set forth in SEQ ID NO:11 (Dph-CRE02-Dph-CRE06-CSk-SH5). In further embodiments, the nucleic acid regulatory element further comprises a diaphragm-specific regulatory element comprising, consisting essentially of, or consisting of the nucleotide sequence set forth in SEQ ID NO:3 (e.g. Dph-CRE04), preferably the diaphragm-specific regulatory element consisting of the nucleotide sequence set forth in SEQ ID NO:3 (Dph-CRE04), or a functional fragment thereof.

In specific embodiments, the nucleic acid regulatory element comprises, consists essentially of, or consists of the nucleotide sequence set forth in SEQ ID NO:12 (Dph-CRE04-Dph-CRE06-CSk-SH5). In other specific embodiments, the nucleic acid regulatory element comprises, consists essentially of, or consists of the nucleotide sequence set forth in SEQ ID NO:13 (Dph-CRE06-Dph-CRE04-CSk-SH5). In further embodiments, the nucleic acid regulatory element further comprises a diaphragm-specific regulatory element comprising, consisting essentially of, or consisting of the nucleotide sequence set forth in SEQ ID NO:2 (e.g. Dph-CRE02), preferably the diaphragm-specific regulatory element consisting of the nucleotide sequence set forth in SEQ ID NO:2 (Dph-CRE02), or a functional fragment thereof. In specific embodiments, the nucleic acid regulatory element comprises, consists essentially of, or consists of the nucleotide sequence set forth in SEQ ID NO:14 (Dph-CRE02-Dph-CRE04-Dph-CRE06-CSk-SH5).

The nucleic acid regulatory elements disclosed herein may be used in a nucleic acid expression cassette. Accordingly, in an aspect the invention provides for the use of the nucleic acid regulatory elements as described herein in a nucleic acid expression cassette.

In an aspect the invention provides a nucleic acid expression cassette comprising a nucleic acid regulatory element as described herein, operably linked to a promoter. In embodiments, the nucleic acid expression cassette does not contain a transgene. Such nucleic acid expression cassette may be used to drive expression of an endogenous gene. In preferred embodiments, the nucleic acid expression cassette comprises a nucleic acid regulatory element as described herein, operably linked to a promoter and a transgene.

As used herein, the term 'nucleic acid expression cassette' refers to nucleic acid molecules that include one or more transcriptional control elements (such as, but not limited to promoters, enhancers and/or regulatory elements, polyadenylation sequences, and introns) that direct (trans)gene expression in one or more desired cell types, tissues or organs. Typically, they will also contain a transgene, although it is also envisaged that a nucleic acid expression cassette directs expression of an endogenous gene in a cell into which the nucleic acid cassette is inserted.

The term 'operably linked' as used herein refers to the arrangement of various nucleic acid molecule elements relative to each such that the elements are functionally connected and are able to interact with each other. Such elements may include, without limitation, a promoter, an enhancer and/or a regulatory element, a polyadenylation sequence, one or more introns and/or exons, and a coding sequence of a gene of interest to be expressed (i.e., the transgene). The nucleic acid sequence elements, when properly oriented or operably linked, act together to modulate the activity of one another, and ultimately may affect the level of expression of the transgene. By modulate is meant increasing, decreasing, or maintaining the level of activity of a particular element. The position of each element relative to other elements may be expressed in terms of the 5' terminus and the 3' terminus of each element, and the distance between any particular elements may be referenced by the number of intervening nucleotides, or base pairs, between the elements. As understood by the skilled person, operably linked implies functional activity, and is not necessarily related to a natural positional link. Indeed, when used in nucleic acid expression cassettes, the regulatory elements will typically be located immediately upstream of the promoter (although this is generally the case, it should definitely not be interpreted as a limitation or exclusion of positions within the nucleic acid expression cassette), but this needs not be the case in vivo. E.g., a regulatory element sequence naturally occurring downstream of a gene whose transcription it affects is able to function in the same way when located upstream of the promoter. Hence, according to a specific embodiment, the regulatory or enhancing effect of the regulatory element is position-independent.

As used in the application, the term 'promoter' refers to nucleic acid sequences that regulate, either directly or indirectly, the transcription of corresponding nucleic acid coding sequences to which they are operably linked (e.g. a transgene or endogenous gene). A promoter may function alone to regulate transcription or may act in concert with one or more other regulatory sequences (e.g. enhancers or silencers, or regulatory elements). In the context of the present application, a promoter is typically operably linked to a regulatory element as disclosed herein to regulate transcription of a (trans)gene. When a regulatory element as described herein is operably linked to both a promoter and a transgene, the regulatory element can (1) confer a significant degree of muscle-specific, in particular diaphragm, smooth muscle, cardiac and skeletal muscle-specific more particularly diaphragm, cardiac and skeletal muscle-specific expression in vivo (and/or in myoblasts, myocytes, or muscle-derived cell lines, in particular cardiac and skeletal myoblasts, cardiac and skeletal myocytes, or cardiac and skeletal muscle-derived cell lines in vitro) of the transgene, and/or (2) can increase the level of expression of the transgene in muscle, in particular diaphragm, smooth muscle, cardiac and skeletal muscle, more particularly diaphragm, cardiac and skeletal muscle (and/or in myoblasts, myocytes, or muscle-derived cell lines, in particular smooth, cardiac and skeletal myoblasts, smooth, cardiac and skeletal myocytes, or smooth, cardiac and skeletal muscle-derived cell lines in vitro, more particularly cardiac and skeletal myoblasts, cardiac and skeletal myocytes, or cardiac and skeletal muscle-derived cell lines in vitro).

The promoter may be homologous (i.e. from the same species as the animal, in particular mammal, to be transfected with the nucleic acid expression cassette) or heterologous (i.e. from a source other than the species of the animal, in particular mammal, to be transfected with the expression cassette). As such, the source of the promoter may be any virus (e.g. CMV or cytomegalovirus), any unicellular prokaryotic or eukaryotic organism, any vertebrate or invertebrate organism, or any plant, or may even be a synthetic promoter (i.e. having a non-naturally occurring sequence), provided that the promoter is functional in combination with the regulatory elements described herein. In preferred embodiments, the promoter is a mammalian promoter, in particular a murine or human promoter.

The promoter may be an inducible or constitutive promoter.

The enrichment in muscle-specific TFBS in the nucleic acid regulatory elements disclosed herein in principle allows the regulatory elements to direct muscle-specific expression even from a promoter that itself is not muscle-specific (e.g. CAG promoter, CMV promoter). Hence, the regulatory elements disclosed herein can be used in nucleic acid expression cassettes in conjunction with any promoter, in particular the promoter may either be tissue-specific, e.g. muscle-specific, or ubiquitously expressed. Non-limiting examples of ubiquitously expressed promoters include polymerase II (pol II) promoters, polymerase III (pol III) promoters (e.g. U6) and chimeric pol III promoters. These promoters may be suitable for expressing e.g. non-coding RNAs. Preferably, the nucleic acid expression cassettes disclosed herein comprise a muscle-specific promoter, in particular a diaphragm, smooth muscle, heart, and/or skeletal muscle-specific promoter, more particularly a diaphragm, heart, and/or skeletal muscle-specific promoter, in order to increase muscle-specificity, in particular diaphragm, smooth muscle, heart, and/or skeletal muscle-specificity, more particularly diaphragm, heart, and/or skeletal muscle-specificity, and/or reduce leakage of expression in other tissues.

Non-limiting examples of muscle-specific promoters include the desmin (DES) promoter; the synthetic SPc5-12 promoter (SPc5-12); the alpha-actin1 promoter (ACTA1); the Creatine kinase, muscle (CKM) promoter; the Four and a half LIM domains protein 1 (FHL1) promoter; the alpha 2 actinin (ACTN2) promoter; the filamin-C (FLNC) promoter; the sarcoplasmic/endoplasmic reticulum calcium ATPase 1 (ATP2A1) promoter; the Troponin I type 1 (TNNI1) promoter; the Troponin I type 2 (TNN12) promoter; the Troponin T type 1 (TNNT1) promoter; the Troponin T type 2 (TNNT2) promoter; the Troponin T type 3 (TNNT3) promoter; the myosin-1 (MYH1) promoter; the myosin-2 (MYH2) promoter; the sarcolipin (SLN) promoter; the Myosin Binding Protein Cl (MYBPC1) promoter; the enolase (EN03) promoter; the Carbonic Anhydrase 3 (CA3) promoter; the phosphorylatable, fast skeletal muscle myosin light chain (MYLPF) promoter; the Tropomyosin 1 (TPM1) promoter; the Tropomyosin 2 (TPM2) promoter; the alpha-3 chain tropomyosin (TPM3) promoter; the ankyrin repeat domain-containing protein 2 (ANKRD2) promoter; the myosin heavy-chain (MHC) promoter; the alpha myosin heavy chain promoter (ccMHC) promoter; the myosin light-chain (MLC) promoter; the muscle creatine kinase (MCK) promoter; the Myosin, Light Chain 1 (MYL1) promoter; the Myosin, Light Chain 2 (MYL2) promoter; the Myoglobin (MB) promoter; the Troponin C type 1 (TNNC1) promoter; the Troponin C Type 2 (TNNC2) promoter; the Titin-Cap (TCAP) promoter; the Myosin, Heavy Chain 7 (MYH7) promoter; the Aldolase A (ALDOA) promoter; the myosin heavy chain 11 (Myh11) promoter; the transgelin (Tagln) promoter (also known as SM22α promoter); the actin alpha 2, smooth muscle (Acta2) promoter; synthetic promoters as described in Li et al. (1999, Nat Biotechnol. 17:241-245), such as the SPc5-12 promoter, the dMCK promoter and the tMCK promoter consisting of respectively, a double or triple tandem of the MCK enhancer to the MCK basal promoter as described in Wang et al. (2008, Gene Ther, 15:1489-1499), and the MHCK7 promoter. The MHCK7 promoter is a synthetic skeletal and cardiac muscle-specific promoter and has been described in Salva et al. (2007. Mol Ther 15: 320-9). In preferred embodiments, the promoter is a muscle-specific promoter selected from the group consisting of: the SPc5-12 promoter, the DES promoter and the MHCK7 promoter.

In particularly preferred embodiments, the promoter is a mammalian muscle-specific promoter, in particular a murine or human muscle-specific promoter.

In embodiments, the promoter is the synthetic SPc5-12 promoter. The SPc5-12 promoter is a synthetic muscle-specific promoter and has been described in Li et al. (1999. Nat Biotechnol. 17:241-245). In embodiments, the promoter is the SPc5-12 promoter as defined by SEQ ID NO:15. In embodiments, the promoter is the MHCK7 promoter, preferably the MHCK7 promoter as defined by SEQ ID NO:56. In embodiments, the promoter is the desmin promoter, preferably the desmin promoter as defined by SEQ ID NO:57.

Furthermore, the promoter does not need to be the promoter of the transgene in the nucleic acid expression cassette, although it is possible that the transgene is transcribed from its own promoter.

To minimize the length of the nucleic acid expression cassette, the regulatory elements may be linked to minimal promoters, or shortened versions of the promoters described herein. A 'minimal promoter' (also referred to as basal promoter or core promoter) as used herein is part of a full-size promoter still capable of driving expression, but lacking at least part of the sequence that contributes to regulating (e.g. tissue-specific) expression. This definition covers both promoters from which (tissue-specific) regulatory elements have been deleted—that are capable of driving expression of a gene but have lost their ability to express that gene in a tissue-specific fashion and promoters from which (tissue-specific) regulatory elements have been deleted that are capable of driving (possibly decreased) expression of a gene but have not necessarily lost their ability to express that gene in a tissue-specific fashion.

The term 'transgene' as used herein refers to particular nucleic acid sequences encoding a polypeptide or a portion of a polypeptide to be expressed in a cell into which the nucleic acid sequence is introduced. However, it is also possible that transgenes are expressed as RNA, typically to control (e.g. lower) the amount of a particular polypeptide in a cell into which the nucleic acid sequence is inserted. These RNA molecules include but are not limited to molecules that exert their function through RNA interference (shRNA, RNAi), micro-RNA regulation (miR) (which can be used to control expression of specific genes), non-coding RNA (ncRNA), long non-coding RNA (lncRNA), guide RNA (gRNA), catalytic RNA, antisense RNA, RNA aptamers, etc. How the nucleic acid sequence is introduced into a cell is not essential to the invention, it may for instance be through integration in the genome or as an episomal plasmid. Of note, expression of the transgene may be restricted to a subset of the cells into which the nucleic acid sequence is introduced. The term 'transgene' is meant to include (1) a nucleic acid sequence that is not naturally found in the cell (i.e., a heterologous nucleic acid sequence); (2) a nucleic acid sequence that is a mutant form of a nucleic acid sequence naturally found in the cell into which it has been introduced; (3) a nucleic acid sequence that serves to add additional copies of the same (i.e., homologous) or a similar nucleic acid sequence naturally occurring in the cell into which it has been introduced; or (4) a silent naturally occurring or homologous nucleic acid sequence whose expression is induced in the cell into which it has been introduced.

The transgene may be homologous or heterologous to the promoter (and/or to the animal, in particular mammal, in which it is introduced, e.g. in cases where the nucleic acid expression cassette is used for gene therapy).

The transgene may be a full length cDNA or genomic DNA sequence, or any fragment, subunit or mutant thereof that has at least some biological activity. In particular, the transgene may be a minigene, i.e. a gene sequence lacking part, most or all of its intronic sequences. The transgene thus optionally may contain intron sequences. Optionally, the transgene may be a hybrid nucleic acid sequence, i.e., one constructed from homologous and/or heterologous cDNA and/or genomic DNA fragments. By 'mutant form' is meant a nucleic acid sequence that contains one or more nucleotides that are different from the wild-type or naturally occurring sequence, i.e., the mutant nucleic acid sequence contains one or more nucleotide substitutions, deletions, and/or insertions. The nucleotide substitution, deletion, and/or insertion can give rise to a gene product (i.e. e., protein or nucleic acid) that is different in its amino acid/nucleic acid sequence from the wild type amino acid/nucleic acid sequence. Preparation of such mutants is well known in the art. In some cases, the transgene may also include a sequence encoding a leader peptide or signal sequence such that the transgene product will be secreted from the cell.

In particular embodiments, the transgene is codon-optimized. As used herein the terms "codon-optimization", "codon-optimized" and the like refer to changes in the codon composition of a nucleic acid sequence, in particular a transgene, without altering the amino acid sequence, e.g. for optimal expression in a host cell or organism. As shown in the experimental section, codon-optimization of the transgene can further enhance muscle-specific, in particular diaphragm, smooth muscle, heart and skeletal muscle-specific, more particularly diaphragm, heart and skeletal muscle-specific expression of the transgene.

The transgene that may be contained in the nucleic acid expression cassettes described herein typically encodes a gene product such as RNA or a polypeptide (protein). The transgene may also include members of the CRISPR/Cas system, such as Cas and/or one or more gRNAs.

In embodiments, the transgene encodes a therapeutic protein.

The therapeutic protein may be a secretable protein or a non-secreted protein. Non-limiting examples of secretable proteins, in particular secretable therapeutic proteins, include clotting factors, such as factor VIII or factor IX, insulin, erythropoietin, lipoprotein lipase, antibodies or nanobodies, growth factors, angiogenic factors, cytokines, chemokines, plasma factors, etc. Non-limiting examples of non-secreted proteins include metabolic enzymes (e.g. tafazzin), lysosomal proteins, nuclear proteins, etc. The therapeutic protein may also be a structural protein. Non-limiting examples of structural proteins, in particular structural therapeutic proteins, include dystrophin and sarcoglycans.

A non-exhaustive and non-limiting list of transgenes envisaged in the application includes transgenes encoding angiogenic factors for therapeutic angiogenesis (e.g. VEGF, PlGF, or guidance molecules such as ephrins, semaphorins, Slits and netrins or their cognate receptors); transgenes encoding clotting factors (e.g. factor VIII or factor IX), transgenes encoding insulin, transgenes encodinglipoprotein lipase, transgenes encoding plasma factors, transgenes encoding cytokines, chemokines and/or growth factors (e.g. erythropoietin (EPO), interferon-α, interferon-β, interferon-γ, interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), chemokine (C-X-C motif) ligand 5 (CXCL5), granulocyte-colony stimulating factor (G-CSF), granulocyte-macrophage colony stimulating factor (GM-CSF), macrophage colony stimulating factor (M-CSF), stem cell factor (SCF), keratinocyte growth factor (KGF), monocyte chemoattractant protein-1 (MCP-1) and tumor necrosis factor (TNF)); transgenes encoding proteins involved in calcium handling (e.g. Sarco/Endoplasmic Reticulum Ca2+-ATPase (SERCA), phospholamban, calsequestrin, sodium-calcium exchanger, L-type calcium's channel, ryanodine receptors), transgenes encoding calcineurin; transgenes encoding microdystrophin; transgenes encoding follistatin (FST); transgenes encoding myotubularin 1 (MTM1); transgenes encoding dysferlin; transgenes encoding dystrophin; transgenes encoding metabolic enzymes: transgenes encoding nuclear proteins; transgenes encoding mitochondrial proteins (e.g. tafazzin); transgenes encoding lysosomal proteins (e.g. acid α-glucosidase (GAA) (as a secreted or native form), alpha-galactosidase A, LAMP2); transgenes encoding ion channels (e.g. SCNSA); transgenes encoding enzymes involved in glycogen metabolism (e.g. Glycogen synthase (GYS2), Glycogen debranching enzyme (AGL), Glycogen branching enzyme (GBE1), Muscle glycogen phosphorylase (PYGM), Muscle phosphofructokinase (PKFM), Phosphoglycerate mutase (PGAM2), Aldolase A (ALDOA), β-enolase (ENO3) or Glycogenin-1 (GYG1)); transgenes encoding enzymes deficient in mucopolysaccharidosis (e.g. α-L-iduronidase, Iduronate sulfatase, Heparan sulfamidase, N-acetylglucosaminidase, Heparan-α-glucosaminide N-acetyltransferase, N-acetylglucosamine 6-sulfatase, Galactose-6-sulfate sulfatase, β-galactosidase, N-acetylgalactosamine-4-sulfatase, β-glucuronidase or Hyaluronidase); transgenes encoding sarcoglycan (e.g. alpha-sarcoglycan, beta-sarcoglycan and gamma-sarcoglycan); transgenes encoding anoctamin 5; transgenes encoding calpain 3; transgenes encoding antibodies, transgenes encoding nanobodies, transgenes encoding anti-viral dominant-negative proteins; and transgenes fragments, subunits or mutants thereof.

In particular embodiments, the transgene encodes a sarcoglycan, preferably β-sarcoglycan, more preferably human β-sarcoglycan such as the transgene defined by SEQ ID NO:18. In further embodiments, the transgene encoding human β-sarcoglycan is codon-optimized, such as the transgene defined by SEQ ID NO:19.

In particular embodiments, the transgene encodes a lysosomal protein, preferably the transgene encodes a lysosomal protein selected from the group consisting of acid α-glucosidase (GAA) (e.g. GAA as a secreted or native form), alpha-galactosidase A and LAMP2. In further particular embodiments, the transgene encodes acid α-glucosidase (GAA), preferably human GAA such as the transgene defined by SEQ ID NO:58. In further embodiments, the transgene encoding human GAA is codon-optimized, such as the transgene defined by SEQ ID NO:59. The transgene may also be a reporter gene, i.e. the transgene encodes a reporter such as a luciferase enzyme. In particular embodiments, the transgene encodes a luciferase, e.g. the transgene may have the nucleotide sequence set forth in SEQ ID NO:20.

The transgene may also encode an immunogenic protein. Non-limiting examples of immunogenic proteins include epitopes and antigens derived from a pathogen.

As used herein, the term "immunogenic" refers to a substance or composition capable of eliciting an immune response.

Other sequences may be incorporated in the nucleic acid expression cassette disclosed herein as well, typically to further increase or stabilize the expression of the transgene product (e.g. introns and/or polyadenylation sequences).

Any intron can be utilized in the expression cassettes described herein. The term "intron" encompasses any portion of a whole intron that is large enough to be recognized and spliced by the nuclear splicing apparatus. Typically, short, functional, intron sequences are preferred in order to keep the size of the expression cassette as small as possible which facilitates the construction and manipulation of the expression cassette. In some embodiments, the intron is obtained from a gene that encodes the protein that is encoded by the coding sequence within the expression cassette. The intron can be located 5' to the coding sequence, 3' to the coding sequence, or within the coding sequence. An advantage of locating the intron 5' to the coding sequence is to minimize the chance of the intron interfering with the function of the polyadenylation signal. In embodiments, the nucleic acid expression cassette disclosed herein further comprises an intron. Non-limiting examples of suitable introns are Minute Virus of Mice (MVM) intron, beta-globin intron (betaIVS-II), factor IX (FIX) intron A, Simian virus 40 (SV40) small-t intron, and beta-actin intron. Preferably, the intron is MVM intron (SEQ ID NO:16).

Any polyadenylation signal that directs the synthesis of a polyA tail is useful in the expression cassettes described herein, examples of those are well known to one of skill in the art. Exemplary polyadenylation signals include, but are not limited to, polyA sequences derived from the Simian virus 40 (SV40) late gene, the bovine growth hormone (BGH) polyadenylation signal, the minimal rabbit β-globin (mRBG) gene, and the synthetic polyA site (SPA) site as described in Levitt et al. (1989, Genes Dev 3:1019-1025). Preferably, the polyadenylation signal is the polyadenylation signal defined by SEQ ID NO:17.

In particular embodiments, the invention provides a nucleic acid expression cassette comprising a nucleic acid regulatory element consisting essentially of or consisting of the diaphragm-specific regulatory element consisting essentially of or consisting of the nucleotide sequence set forth in SEQ ID NO:3 (Dph-CRE04) or a functional fragment thereof, the diaphragm-specific regulatory element consisting essentially of or consisting of the nucleotide sequence set forth in SEQ ID NO:4 (Dph-CRE06) or a functional fragment thereof, and the heart- and skeletal muscle-specific regulatory element consisting essentially of or consisting of the nucleotide sequence set forth in SEQ ID NO:1 (CSk-SH5) or a functional fragment thereof, preferably a nucleic acid regulatory element consisting essentially of or consisting of the nucleotide sequence set forth in SEQ ID NO:12 (Dph-CRE04-Dph-CRE06-CSk-SH5), operably linked to a promoter, preferably the SPc5-12 promoter, and a transgene encoding human β-sarcoglycan (e.g. the transgene set forth in SEQ ID NO:18, preferably the codon-optimized transgene set forth in SEQ ID NO:19). In preferred embodiments, the transgene is codon-optimized. In embodiments, the nucleic acid expression cassette further comprises an MVM intron. In embodiments the nucleic acid expression cassette further comprises a polyadenylation signal, preferably a polyadenylation signal defined by SEQ ID NO:17.

In particular embodiments, the invention provides a nucleic acid expression cassette comprising a nucleic acid regulatory element consisting essentially of or consisting of the diaphragm-specific regulatory element consisting of the nucleotide sequence set forth in SEQ ID NO:2 (Dph-CRE02) or a functional fragment thereof, the diaphragm-specific regulatory element consisting of the nucleotide sequence set forth in SEQ ID NO:3 (Dph-CRE04) or a functional fragment thereof, the diaphragm-specific regulatory element consisting of the nucleotide sequence set forth in SEQ ID NO:4 (Dph-CRE06) or a functional fragment thereof, and the heart- and skeletal muscle-specific regulatory element consisting of the nucleotide sequence set forth in SEQ ID NO:1 (CSk-SH5) or a functional fragment thereof, preferably a nucleic acid regulatory element consisting essentially of or consisting of the nucleotide sequence set forth in SEQ ID NO:14 (Dph-CRE02-Dph- CRE04-Dph-CRE06-CSk-SH5), operably linked to a promoter, preferably the SPc5-12 promoter, and a transgene encoding human β-sarcoglycan (e.g. the transgene set forth in SEQ ID NO:18, preferably the codon-optimized transgene set forth in SEQ ID NO:19). In preferred embodiments, the transgene is codon-optimized. In embodiments, the nucleic acid expression cassette further comprises an MVM intron. In embodiments the nucleic acid expression cassette further comprises a polyadenylation signal, preferably a polyadenylation signal defined by SEQ ID NO:17.

The nucleic acid regulatory element and the nucleic acid expression cassette disclosed herein may be used as such, or typically, they may be part of a nucleic acid vector. Accordingly, a further aspect relates to the use of a nucleic acid regulatory element as described herein or a nucleic acid expression cassette as described herein in a vector, in particular a nucleic acid vector.

In an aspect, the invention also provides a vector comprising a nucleic acid regulatory element as disclosed herein. In further embodiments, the vector comprises a nucleic acid expression cassette as disclosed herein.

The term 'vector' as used in the application refers to nucleic acid molecules, e.g. double-stranded DNA, which may have inserted into it another nucleic acid molecule (the insert nucleic acid molecule) such as, but not limited to, a cDNA molecule. The vector is used to transport the insert nucleic acid molecule into a suitable host cell. A vector may contain the necessary elements that permit transcribing the insert nucleic acid molecule, and, optionally, translating the transcript into a polypeptide. The insert nucleic acid molecule may be derived from the host cell, or may be derived from a different cell or organism. Once in the host cell, the vector can replicate independently of, or coincidental with, the host chromosomal DNA, and several copies of the vector and its inserted nucleic acid molecule may be generated. The vectors can be episomal vectors (i.e., that do not integrate into the genome of a host cell), or can be vectors that integrate into the host cell genome. The term 'vector' may thus also be defined as a gene delivery vehicle that facilitates gene transfer into a target cell. This definition includes both non-viral and viral vectors. Non-viral vectors include but are not limited to cationic lipids, liposomes, nanoparticles, PEG, PEI, plasmid vectors (e.g. pUC vectors, bluescript vectors (pBS) and pBR322 or derivatives thereof that are devoid of bacterial sequences (minicircles)) transposons-based vectors (e.g. PiggyBac (PB) vectors or Sleeping Beauty (SB) vectors), etc. Viral vectors are derived from viruses and include but are not limited to retroviral, lentiviral, adeno-associated viral, adenoviral, herpes viral, hepatitis viral vectors or the like. Typically, but not necessarily, viral vectors are replication-deficient as they have lost the ability to propagate in a given cell since viral genes essential for replication have been eliminated from the viral vector. However, some viral vectors can also be adapted to replicate specifically in a given cell, such as e.g. a cancer cell, and are typically used to trigger the (cancer) cell-specific (onco)lysis. Virosomes are a non-limiting example of a vector that comprises both viral and non-viral elements, in particular they combine liposomes with an inactivated HIV or influenza virus (Yamada et al., 2003). Another example encompasses viral vectors mixed with cationic lipids.

In preferred embodiments, the vector is a viral vector, such as a retroviral, lentiviral, adenoviral, or adeno-associated viral (AAV) vector, more preferably an AAV vector. AAV vectors are preferably used as self-complementary, double-stranded AAV vectors (scAAV) in order to overcome one of the limiting steps in AAV transduction (i.e. single-stranded to double-stranded AAV conversion) (McCarty, 2001, 2003; Nathwani et al, 2002, 2006, 2011; Wu et al., 2008), although the use of single-stranded AAV vectors (ssAAV) are also encompassed herein.

In embodiments, the vector is an AAV serotype 9 (AAV9) vector, more particularly a self-complementary AAV9 vector (scAAV9). In embodiments, the vector is an AAV serotype 8 (AAV8) vector such as a self-complementary AAV8 vector (scAAV8) or a single-stranded AAV8 vector (ssAAV8).

The vector may be an AAV vector of which the AAV capsid is engineered to direct the vector specifically to muscle cells. For example, the vector may be a AAVpo1 vector as described in Tulalamba W et al. (Tulalamba W, et al. Distinct transduction of muscle tissue in mice after systemic delivery of AAVpo1 vectors. Gene Ther. (2019) https://doi.org/10.1038/s41434-019-0106-3).

Production of AAV vector particles can be achieved e.g. by transient transfection of suspension-adapted mammalian HEK293 cells, as described (Chahal et al. Production of adeno-associated virus (AAV) serotypes by transient transfection of HEK293 cell suspension cultures for gene delivery, Journal of Virological Methods. 196: 163-173 (2014); Grieger et al., Production of recombinant adeno-associated virus vectors using suspension HEK293 cells and continuous harvest of vector from the culture media for GMP FIX and FLT1 clinical vector. Molecular Therapy. 24: 287-297 (2016); Blessing et al., Scalable Production of AAV Vectors in Orbitally Shaken HEK293 Cells. Molecular Therapy Methods & Clinical Development. 13: 14-26 (2019)), or by infection of *Spodoptera frugiperda* (Sf9) insect cells using the baculovirus expression vector system (BEVS), as described (Kotin et al. Manufacturing Clinical Grade Recombinant Adeno-Associated Virus Using Invertebrate Cell Lines. Human Gene Therapy. 28: 350-360 (2017)), followed by a purification step.

Purification may be based on cesium chloride (CsCl) density gradient ultracentrifugation, as described (Vandendriessche et al., 2007), or using chromatographic techniques or columns or by immunoaffinity as known in the art. The vector can also be a non-viral vector, preferably a plasmid, a minicircle, or a transposon-based vector, such as a Sleeping Beauty (SB)-based vector or piggyBac (PB)-based vector.

The vector may also comprise viral and non-viral elements.

In particular embodiments, the invention provides a vector comprising a nucleic acid expression cassette comprising a nucleic acid regulatory element consisting of the nucleotide sequence set forth in SEQ ID NO:10 (Dph-CRE02-Dph-CRE04-CSk-SH5), a promoter, preferably the SPc5-12 promoter, an MVM intron, a transgene, preferably a transgene encoding human β-sarcoglycan, and a polyadenylation signal, preferably the polyadenylation signal defined by SEQ ID NO:17. In preferred embodiments, the transgene encoding human β-sarcoglycan is codon-optimized such as the transgene set forth in SEQ ID NO:19. In particular embodiments, said vector has SEQ ID NO: 26 or 27.

In particular embodiments, the invention provides a vector comprising a nucleic acid expression cassette comprising a nucleic acid regulatory element consisting of the nucleotide sequence set forth in SEQ ID NO:13 (Dph-CRE06-Dph-CRE04-CSk-SH5), a promoter, preferably the SPc5-12 promoter, an MVM intron, a transgene, preferably a transgene encoding human β-sarcoglycan, and a polyadenylation signal, preferably the polyadenylation signal defined by SEQ ID NO:17. In preferred embodiments, the transgene encoding human β-sarcoglycan is codon-optimized such as the transgene set forth in SEQ ID NO:19. In particular embodiments, said vector has SEQ ID NO: 30 or 31.

In particular embodiments, the invention provides a vector comprising a nucleic acid expression cassette comprising a nucleic acid regulatory element consisting of the nucleotide sequence set forth in SEQ ID NO:11 (Dph-CRE02-Dph-CRE06-CSk-SH5), a promoter, preferably the SPc5-12 promoter, an MVM intron, a transgene, preferably a transgene encoding human β-sarcoglycan, and a polyadenylation signal, preferably the polyadenylation signal defined by SEQ ID NO:17. In preferred embodiments, the transgene encoding human β-sarcoglycan is codon-optimized such as the transgene set forth in SEQ ID NO:19. In particular embodiments, said vector has SEQ ID NO: 32 or 33.

In particular embodiments, the invention provides a vector comprising a nucleic acid expression cassette comprising a nucleic acid regulatory element consisting of the nucleotide sequence set forth in SEQ ID NO:12 (Dph-CRE04-Dph-CRE06-CSk-SH5), a promoter, preferably the SPc5-12 promoter, an MVM intron, a transgene, preferably a transgene encoding human β-sarcoglycan, and a polyadenylation signal, preferably the polyadenylation signal defined by SEQ ID NO:17. In preferred embodiments, the transgene encoding human β-sarcoglycan is codon-optimized such as the transgene set forth in SEQ ID NO:19. In particular embodiments, said vector has SEQ ID NO: 28 or 29.

In particular embodiments, the invention provides a vector comprising a nucleic acid expression cassette comprising a nucleic acid regulatory element consisting of the nucleotide sequence set forth in SEQ ID NO:14 (Dph-CRE02-Dph-CRE04-Dph-CRE06-CSk-SH5), a promoter, preferably the SPc5-12 promoter, an MVM intron, a transgene, preferably a transgene encoding human β-sarcoglycan, and a polyadenylation signal, preferably the polyadenylation signal defined by SEQ ID NO:17. In preferred embodiments, the transgene encoding human β-sarcoglycan is codon-optimized such as the transgene set forth in SEQ ID NO:19. In particular embodiments, said vector has SEQ ID NO: 34 or 35.

The nucleic acid expression cassettes and vectors disclosed herein may be used, for example, to express proteins that are normally expressed and utilized in muscle (i.e. structural proteins), or to express proteins that are expressed in muscle and that are then exported to the blood stream for transport to other portions of the body (i.e. secretable proteins). For example, the expression cassettes and vectors disclosed herein may be used to express a therapeutic amount of a gene product (such as a polypeptide, in particular a therapeutic protein, or RNA) for therapeutic purposes, in particular for gene therapy. Typically, the gene product is encoded by the transgene within the expression cassette or vector, although in principle it is also possible to increase expression of an endogenous gene for therapeutic purposes. In an alternative example, the expression cassettes and vectors disclosed herein may be used to express an immunological amount of a gene product (such as a polypeptide, in particular an immunogenic protein, or RNA) for vaccination purposes.

The nucleic acid expression cassettes and vectors as taught herein may be formulated in a pharmaceutical composition with a pharmaceutically acceptable excipient, i.e., one or more pharmaceutically acceptable carrier substances and/or additives, e.g., buffers, carriers, excipients, stabilisers, etc. The pharmaceutical composition may be provided in the form of a kit.

The term "pharmaceutically acceptable" as used herein is consistent with the art and means compatible with the other ingredients of the pharmaceutical composition and not deleterious to the recipient thereof.

Accordingly, a further aspect of the invention relates to a pharmaceutical composition comprising a nucleic acid expression cassette or a vector described herein.

The use of nucleic acid regulatory elements and vectors described herein for the manufacture of these pharmaceutical compositions is also disclosed herein.

For example, the pharmaceutical composition may be a vaccine. The vaccine may further comprise one or more adjuvants for enhancing the immune response. Suitable adjuvants include, for example, but without limitation, saponin, mineral gels such as aluminium hydroxide, surface active substances such as lysolecithin, pluronic polyols, polyanions, peptides, oil or hydrocarbon emulsions, bacilli Calmette-Guerin (BCG), *Corynebacterium parvum*, and the synthetic adjuvant QS-21. Optionally, the vaccine may further comprise one or more immunostimulatory molecules. Non-limiting examples of immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc.

In a further aspect, the invention relates to the nucleic acid regulatory elements, the nucleic acid expression cassettes, the vectors, or the pharmaceutical compositions described herein for use in medicine.

As used herein, the terms "treat" or "treatment" refer to both therapeutic treatment and prophylactic or preventative measures. Beneficial or desired clinical results include, but are not limited to, prevention of an undesired clinical state or disorder, reducing the incidence of a disorder, alleviation of symptoms associated with a disorder, diminishment of extent of a disorder, stabilized (i.e., not worsening) state of a disorder, delay or slowing of progression of a disorder, amelioration or palliation of the state of a disorder, remission (whether partial or total), whether detectable or undetectable, or combinations thereof. "Treatment" can also mean prolonging survival as compared to expected survival if not receiving treatment.

As used herein, the terms "therapeutic treatment" or "therapy" and the like, refer to treatments wherein the object is to bring a subjects body or an element thereof from an undesired physiological change or disorder to a desired state, such as a less severe or unpleasant state (e.g., alleviation of symptoms, amelioration of the condition or palliation), or back to its normal, healthy state (e.g., restoring the health, the physical integrity and the physical well-being of a subject), to keep it at said undesired physiological change or disorder (e.g., stabilization, or not worsening), or to prevent or slow down progression to a more severe or worse state compared to said undesired physiological change or disorder.

As used herein the terms "prevention", "preventive treatment" or "prophylactic treatment" and the like encompass preventing the onset of a disease or disorder, including reducing the severity of a disease or disorder or symptoms associated therewith prior to affliction with said disease or disorder. Such prevention or reduction prior to affliction refers to administration of the nucleic acid regulatory elements, the nucleic acid expression cassettes, the vectors, or the pharmaceutical compositions described herein to a patient that is not at the time of administration afflicted with clear symptoms of the disease or disorder. "Preventing" also encompasses preventing the recurrence or relapse-prevention of a disease or disorder for instance after a period of improvement.

In embodiments, the nucleic acid regulatory elements, the nucleic acid expression cassettes, the vectors, or the pharmaceutical compositions described herein may be for use in gene therapy, in particular muscle-directed gene therapy, in particular diaphragm-, smooth muscle-, heart- and skeletal muscle-directed gene therapy, more particularly diaphragm-, heart- and skeletal muscle-directed gene therapy.

Also disclosed herein is the use of the nucleic acid regulatory elements, the nucleic acid expression cassettes, the vectors, or the pharmaceutical compositions described herein for the manufacture of a medicament for gene therapy, in particular muscle-directed gene therapy, in particular diaphragm-, smooth muscle-, heart- and skeletal muscle-directed gene therapy, more particularly diaphragm-, heart- and skeletal muscle-directed gene therapy.

Also disclosed herein is a method for gene therapy, in particular muscle-directed gene therapy, in particular diaphragm-, smooth muscle-, heart- and skeletal muscle-directed gene therapy, more particularly diaphragm-, heart- and skeletal muscle-directed gene therapy, in a subject in need of said gene therapy comprising:

introducing in the subject, in particular in muscle tissue or cells of the subject, in particular in diaphragm, smooth muscle, heart, and/or skeletal muscle tissue or cells, more particularly in diaphragm, heart, and/or skeletal muscle tissue or cells of the subject, a nucleic acid expression cassette, a vector or a pharmaceutical composition described herein, wherein the nucleic acid expression cassette, the vector or the pharmaceutical composition comprises a nucleic acid regulatory element described herein, operably linked to a promoter and a transgene; and expressing a therapeutically effective amount of the transgene product in the subject, in particular in muscle cells or tissue of the subject, in particular in diaphragm, smooth muscle, heart and/or skeletal muscle cells or tissue, more particularly in diaphragm, heart and/or skeletal muscle cells or tissue of the subject.

The transgene product may be a polypeptide, in particular a structural protein such as, e.g., dystrophin or a sarcoglycan; a secretable protein such as, e.g., a clotting factor, e.g., factor IX or factor VIII, a cytokine, a growth factor, an antibody or nanobody, a chemokine, a plasma factor, insulin, erythropoietin, lipoprotein lipase; or a non-secreted protein such as a nuclear protein, metabolic enzyme or a lysosomal protein. Further, non-limiting examples of transgene products have been disclosed above in connection with the transgene and include, without limitation, angiogenic factors; cytokines and/or growth factors; proteins involved in calcium handling; lysosomal proteins; ion channels antibodies, nanobodies, anti-viral dominant-negative proteins, and fragments, subunits or mutants thereof; and enzymes (e.g. enzymes involved in glycogen metabolism and enzymes deficient in mucopolysaccharidosis). In particular embodiments, the transgene product is a sarcoglycan, preferably β-sarcoglycan. In particular embodiments, the transgene product is a lysosomal protein, preferably acid α-glucosidase (GAA) (e.g. GAA as a secreted or native form), alpha-galactosidase A or LAMP2, more preferably acid alpha-glucosidase (GAA). Alternatively, the transgene product may be RNA, such as siRNA or non-coding RNA (ncRNA).

Exemplary diseases and disorders that may benefit from gene therapy using the nucleic acid regulatory elements, the nucleic acid expression cassettes, the vectors, or the pharmaceutical compositions described herein include:

lysosomal storage diseases (e.g. Fabry disease) including glycogen storage disorders (e.g. Pompe disease glycogen storage disorder (GSD) type II, Danon disease, glycogen storage disorder (GSD) type IIb, GSD III or GSD 3 (also known as Cori's disease or Forbes' disease), GSD IV or GSD4 (also known as Andersen disease), GSD V or GSD5 (also known as McArdle disease), GSD VII or GSD7 (also known as Tarui's disease), GSD X or GSD10, GSD XII or GSD 12 (also known as Aldolase A deficiency), GSD XIII or GSD13, GSD XV or GSD15) and mucopolysaccharidosis disorders (e.g. Hunter syndrome, Sanfilippo syndrome, mucopolyssacharidose (MPS) I, MPS II, MPS III, MPS IIIA, MPS IIIB, MPS IIIC, MPS IV, MPS VI, MPS VII, MPS IX);

mitochondrial disorders (e.g. Barth syndrome);
channelopathy (e.g. Brugada syndrome);
metabolic disorders;
myotubular myopathy (MTM);
muscular dystrophy (e.g. Duchenne muscular dystrophy (DMD), Becker muscular dystrophy (BMD));
myotonic dystrophy;
Myotonic Muscular Dystrophy (DM);
Miyoshi myopathy;
Fukuyama type congenital;
dysferlinopathies;
neuromuscular disease;
motor neuron diseases (MND) (e.g. Charcot-Marie-Tooth disease (CMT), spinal muscular atrophy (SMA) or amyotrophic lateral sclerosis (ALS));
Emery-Dreifuss muscular dystrophy;
facioscapulohumeral muscular dystrophy (FSHD);
congenital muscular dystrophies;
congenital myopathies;
limb girdle muscular dystrophy (e.g. Limb Girdle Muscular Dystrophy type 2E (LGMD2E), Limb Girdle Muscular Dystrophy type 2D (LGMD2D), Limb Girdle Muscular Dystrophy type 2C (LGMD2C), Limb Girdle Muscular Dystrophy type 2B (LGMD2B), Limb Girdle Muscular Dystrophy type 2L (LGMD2L), Limb Girdle Muscular Dystrophy type 2A (LGMD2A));
metabolic myopathies;
muscle inflammatory diseases;
myasthenia;
mitochondrial myopathies;
anomalies of ionic channels;
nuclear envelop diseases;
cardiomyopathies;
cardiac hypertrophy;
heart failure;
distal myopathies;
hemophilia (e.g. hemophilia A and B);
diabetes; and
cardiovascular diseases and heart diseases (e.g. atherosclerosis, arteriosclerosis, coronary heart disease, coronary artery disease, peripheral arterial disease, congenital heart disease, congestive heart failure, heart failure (also known as cardiac insufficiency), myocardial infarction (also known as heart attack), cardiac ischemia, acute coronary syndrome, unstable angina, stable angina, cardiomyopathy, hypertrophic cardiomyopathy, dilated cardiomyopathy, restrictive cardiomyopathy, primary cardiomyopathies caused by genetic mutations such as Brugada syndrome, Pompe disease, Danon disease and Fabry disease, cardiac amyloidosis (also known as stiff heart syndrome), myocarditis (also known as inflammatory cardiomyopathy), valvular heart disease, valvular stenosis, valvular insufficiency, endocarditis, rheumatic heart disease, pericarditis (i.e. a disease caused by an inflammation and/or infection of the pericardium), cardiac tamponade (also known as pericardial tamponade), endocarditis, cardiac arrhythmia, hypertension, hypotension, vessel stenosis, valve stenosis, or restenosis).

In addition, many neuromuscular disorders affect respiratory function due to weakening of the diaphragm and respiratory muscles (www.medscape.com/viewarticle/805299_3) Semin Respir Crit Care Med. 2002 June; 23(3): 191-200). Causes of diseases of the diaphragm vary, but they can be due to gene defects that influence diaphragm function directly. In particular, there are multiple genetic disorders that are due to mutations in genes that affect the function of the diaphragm, often in combination with abnormalities at the level of skeletal muscles and/or heart. For example, myotubular myopathy (MTM) is due to mutations in the myotubularin gene and affects the skeletal muscle and diaphragm. Patients suffering from MTM typically present with hypotonia, generalized muscle weakness and respiratory failure at birth. Survival beyond the postnatal period requires intensive support, often including gastrostomy feeding and mechanical ventilation. Because of their severe breathing problems, patients suffering from MTM typically do not live past age 2. For MTM, muscle-directed gene therapy is currently the only clinically relevant option. Alternatively, Pompe's disease (also referred to as glycogen storage disorder type II or GSD II) mainly affects skeletal muscle, diaphragm and heart. GSD II results in deficiency of the lysosomal enzyme acid α-glucosidase (GAA) that leads to a lysosomal storage defect. In GSD II patients, glycogen cannot be broken down effectively into glucose. The accumulation of glycogen in GSD II patients causes myopathy with progressive muscle weakness. Without medical intervention, patients suffering from the most severe form of GSD II die because of respiratory failure within the first year of life. Other muscle diseases such as Duchenne muscular dystrophy (DMD) afflicts approximately one in 3500 live male births. The disease leads to a progressive destruction of skeletal muscles, including the diaphragm, the most affected individuals die of ventilatory failure in the third decade of life. Many other myopathies also affect pulmonary function, including—but not limited to—polymyositis/dermatomyositis, hereditary channel disorders, mitochondrial encephalomyopathies, acid maltase deficiency, and congenital myopathy, disuse atrophy. Other diseases affecting diaphragm include Congenital Muscular Dystrophy (CMD), Becker Muscular Dystrophy (BMD), Facioscapulohumeral Muscular Dystrophy (FSHD), Limb Girdle Muscular Dystrophy (LGMD), Myotonic Muscular Dystrophy (DM), Miyoshi myopathy, Fukuyama type congenital muscular dystrophy, dysferlinopathies. Also many neuropathic disorders weaken the diaphragm and respiratory muscles. This includes amyotrophic lateral sclerosis, poliomyelitis, postpolio syndrome, Kennedy syndrome, stroke, multiple sclerosis, spinal muscular atrophy, syringomyelia, neuralgic neuropathy, and motor neuron diseases. Brachial plexitis and isolated unilateral or bilateral phrenic neuropathies can also weaken the diaphragm significantly. Peripheral neuropathies affecting respiration are primarily acute disorders such as Guillain-Barré syndrome, porphyria, and critical illness neuropathy, but chronic diseases such as chronic inflammatory demyelinating polyneuropathy (CIDP) and Charcot-Marie-Tooth disease (CMT) can also cause respiratory insufficiency. Disorders of neuromuscular transmission such as Lambert-Eaton syndrome, and myasthenia gravis often affect respiration. Alternatively, diaphragm dysfunction can be the result of congenital defects resulting in anatomical abnormalities (e.g. Arnold-Chiari malformation) or acquired defects, which occur as the result of an injury, trauma, infection (e.g. West Nile virus, botulism), exposure to, organophosphates, radiation therapy, malnutrition, tumour compression or surgery. Cold cardioplegia used in cardiac surgery is another common cause of phrenic nerve injury. In addition, radiation therapy can affect the phrenic nerve resulting in diaphragmatic dysfunction. Obstructive airway diseases that affect the lungs, such as chronic obstructive pulmonary disease (COPD) and asthma, can result in significant hyperinflation resulting in diaphragmatic disadvantage and weakness. Finally, it is known that lupus and thyroid disorders can also contribute to diaphragm dysfunction.

In embodiments, the nucleic acid expression cassettes, the vectors, or the pharmaceutical compositions described herein are for use in the treatment of Limb Girdle Muscular Dystrophy, in particular Limb Girdle Muscular Dystrophy type 2E (LGMD2E), wherein the nucleic acid expression cassette, the vector or the pharmaceutical composition comprises a nucleic acid regulatory element described herein operably linked to a promoter and a transgene encoding β-sarcoglycan, preferably human β-sarcoglycan (e.g. the transgene set forth in SEQ ID NO:18, preferably the codon-optimized transgene set forth in SEQ ID NO:19).

Also disclosed herein is the use of the nucleic acid expression cassettes, the vectors, or the pharmaceutical compositions described herein for the manufacture of a medicament for the treatment of Limb Girdle Muscular Dystrophy, in particular Limb Girdle Muscular Dystrophy type 2E (LGMD2E), wherein the nucleic acid expression cassette, the vector or the pharmaceutical composition comprises a nucleic acid regulatory element described herein operably linked to a promoter and a transgene encoding β-sarcoglycan, preferably human β-sarcoglycan (e.g. the transgene set forth in SEQ ID NO:18, preferably the codon-optimized transgene set forth in SEQ ID NO:19).

Also disclosed herein is a method for treating Limb Girdle Muscular Dystrophy, in particular Limb Girdle Muscular Dystrophy type 2E (LGMD2E), in a subject comprising:
  introducing in the subject, in particular in muscle tissue or cells of the subject, preferably in diaphragm, smooth muscle, skeletal muscle, and heart tissue or cells of the subject, more preferably in diaphragm, skeletal muscle- and heart tissue or cells of the subject, a nucleic acid expression cassettes, a vector, or a pharmaceutical compositions described herein, wherein the nucleic acid expression cassette, the vector or the pharmaceutical composition comprises a nucleic acid regulatory element described herein operably linked to a promoter and a transgene encoding β-sarcoglycan, preferably human β-sarcoglycan (e.g. the transgene set forth in SEQ ID NO:18, preferably the codon-optimized transgene set forth in SEQ ID NO:19); and
  expressing a therapeutically effective amount of β-sarcoglycan, preferably human β-sarcoglycan, in the subject, in particular in the muscle tissue or cells of the subject, preferably in the diaphragm, skeletal muscle, smooth muscle and heart tissue or cells of the subject, more preferably in the diaphragm-, skeletal muscle- and heart tissue or cells of the subject.

In particular embodiments, the invention relates to a nucleic acid expression cassette comprising a regulatory element consisting essentially of or consisting of the nucleotide sequence set forth in SEQ ID NO:12 (Dph-CRE04-Dph-CRE06-CSk-SH5), operably linked to a promoter, preferably a promoter selected from the group consisting the SPc5-12 promoter, the MHCK7 promoter and the desmin promoter, and a transgene encoding human β-sarcoglycan (e.g. the transgene set forth in SEQ ID NO:18, preferably the codon-optimized transgene set forth in SEQ ID NO:19), a vector comprising said nucleic acid expression cassette, or a pharmaceutical composition comprising said nucleic acid expression cassette or said vector, for use in the treatment of Limb Girdle Muscular Dystrophy, preferably Limb Girdle Muscular Dystrophy type 2E (LGMD2E). In particular embodiments, the invention provides a nucleic acid expression cassette comprising a regulatory element consisting essentially of or consisting of the nucleotide sequence set forth in SEQ ID NO:14 (Dph-CRE02-Dph-CRE04-Dph-CRE06-CSk-SH5), operably linked to a promoter, preferably a promoter selected from the group consisting the SPc5-12 promoter, the MHCK7 promoter and the desmin promoter, and a transgene encoding human β-sarcoglycan (e.g. the transgene set forth in SEQ ID NO:18, preferably the codon-optimized transgene set forth in SEQ ID NO:19), a vector comprising said nucleic acid expression cassette, or a pharmaceutical composition comprising said nucleic acid expression cassette or said vector, for use in the treatment of Limb Girdle Muscular Dystrophy type 2E (LGMD2E). In particular embodiments, the invention relates to a nucleic acid expression cassette comprising a regulatory element consisting essentially of or consisting of the nucleotide sequence set forth in SEQ ID NO:11 (Dph-CRE02-Dph-CRE06-CSk-SH5), operably linked to a promoter, preferably a promoter selected from the group consisting the SPc5-12 promoter, the MHCK7 promoter and the desmin promoter, and a transgene encoding human β-sarcoglycan (e.g. the transgene set forth in SEQ ID NO:18, preferably the codon-optimized transgene set forth in SEQ ID NO:19), a vector comprising said nucleic acid expression cassette, or a pharmaceutical composition comprising said nucleic acid expression cassette or said vector, for use in the treatment of Limb Girdle Muscular Dystrophy type 2E (LGMD2E). In particular embodiments, the invention relates to a nucleic acid expression cassette comprising a regulatory element consisting essentially of or consisting of the nucleotide sequence set forth in SEQ ID NO:13 (Dph-CRE06-Dph-CRE04 CSk-SH5), operably linked to a promoter, preferably a promoter selected from the group consisting the SPc5-12 promoter, the MHCK7 promoter and the desmin promoter, and a transgene encoding human β-sarcoglycan (e.g. the transgene set forth in SEQ ID NO:18, preferably the codon-optimized transgene set forth in SEQ ID NO:19), a vector comprising said nucleic acid expression cassette, or a pharmaceutical composition comprising said nucleic acid expression cassette or said vector, for use in the treatment of Limb Girdle Muscular Dystrophy type 2E (LGMD2E). In particular embodiments, the invention relates to a nucleic acid expression cassette comprising a regulatory element consisting essentially of or consisting of the nucleotide sequence set forth in SEQ ID NO:10 (Dph-CRE02-Dph-CRE04-CSk-SH5), operably linked to a promoter, preferably a promoter selected from the group consisting the SPc5-12 promoter, the MHCK7 promoter and the desmin promoter, and a transgene encoding human β-sarcoglycan (e.g. the transgene set forth in SEQ ID NO:18, preferably the codon-optimized transgene set forth in SEQ ID NO:19), a vector comprising said nucleic acid expression cassette, or a pharmaceutical composition comprising said nucleic acid expression cassette or said vector, for use in the treatment of Limb Girdle Muscular Dystrophy, preferably Limb Girdle Muscular Dystrophy type 2E (LGMD2E).

In further embodiments of the nucleic acid expression cassette, the vector or the pharmaceutical composition for use in the treatment of Limb Girdle Muscular Dystrophy, preferably Limb Girdle Muscular Dystrophy type 2E (LGMD2E) as disclosed herein, the transgene is codon-optimized. In embodiments, the nucleic acid expression cassette further comprises an MVM intron. In embodiments the nucleic acid expression cassette further comprises a polyadenylation signal, preferably a polyadenylation signal defined by SEQ ID NO:17.

Also disclosed herein is a nucleic acid expression cassette, a vector, or a pharmaceutical compositions described herein for use in treating Pompe disease, wherein the nucleic acid expression cassette, the vector or the pharmaceutical composition comprises a nucleic acid regulatory element described herein operably linked to a promoter and a transgene encoding acid α-glucosidase (GAA), preferably human acid α-glucosidase (hGAA) (e.g. the transgene set forth in SEQ ID NO:58, preferably the codon-optimized transgene set forth in SEQ ID NO:59).

Also disclosed herein is the use of a nucleic acid expression cassette, a vector, or a pharmaceutical compositions described herein, wherein the nucleic acid expression cassette, the vector or the pharmaceutical composition comprises a nucleic acid regulatory element described herein operably linked to a promoter and a transgene encoding acid α-glucosidase (GAA), preferably human acid α-glucosidase (hGAA) (e.g. the transgene set forth in SEQ ID NO:58, preferably the codon-optimized transgene set forth in SEQ ID NO:59), for the manufacture of a medicament for treating Pompe disease.

Also disclosed herein is a method for treating Pompe disease in a subject comprising:
   introducing in the subject, in particular in muscle tissue or cells of the subject, preferably in diaphragm, skeletal muscle, smooth muscle and heart tissue or cells of the subject, more preferably in diaphragm-, skeletal muscle- and heart tissue or cells of the subject, a nucleic acid expression cassette, a vector, or a pharmaceutical compositions described herein, wherein the nucleic acid expression cassette, the vector or the pharmaceutical composition comprises a nucleic acid regulatory element described herein operably linked to a promoter and a transgene encoding acid α-glucosidase (GAA), preferably human acid α-glucosidase (hGAA) (e.g. the transgene set forth in SEQ ID NO:58, preferably the codon-optimized transgene set forth in SEQ ID NO:59); and
   expressing a therapeutically effective amount of GAA, preferably hGAA, in the subject, in particular in the muscle tissue or cells of the subject, preferably in the diaphragm, skeletal muscle, smooth muscle and heart tissue or cells of the subject, more preferably in the diaphragm-, skeletal muscle- and heart tissue or cells of the subject.

Gene therapy protocols have been extensively described in the art. These include, but are not limited to, intramuscular injection of plasmid (naked or in liposomes), hydrodynamic gene delivery in various tissues, including muscle, interstitial injection, instillation in airways, application to endothelium, intra-hepatic parenchyme, and intravenous or intra-arterial administration. Various devices have been developed for enhancing the availability of DNA to the target cell. A simple approach is to contact the target cell physically with catheters or implantable materials containing DNA. Another approach is to utilize needle-free, jet injection devices which project a column of liquid directly into the target tissue under high pressure. These delivery paradigms can also be used to deliver vectors. Another approach to targeted gene delivery is the use of molecular conjugates, which consist of protein or synthetic ligands to which a nucleic acid- or DNA-binding agent has been attached for the specific targeting of nucleic acids to cells (Cristiano et al., 1993).

The nucleic acid regulatory elements, the nucleic acid expression cassettes, the vectors, or the pharmaceutical compositions described herein may also be for use as a vaccine, more particularly for use as a prophylactic vaccine.

Also disclosed herein is the use of the nucleic acid regulatory elements, the nucleic acid expression cassettes, the vectors, or the pharmaceutical compositions described herein for the manufacture of a vaccine, in particular for the manufacture of a prophylactic vaccine.

Also disclosed herein is a method of vaccination, in particular prophylactic vaccination, of a subject in need of said vaccination comprising:

introducing in the subject, in particular in muscle of the subject, more particularly in diaphragm, smooth muscle, heart and/or skeletal muscle tissue or cells, even more particularly in diaphragm, heart and/or skeletal muscle tissue or cells of the subject, a nucleic acid expression cassette, a vector or a pharmaceutical composition described herein, wherein the nucleic acid expression cassette, the vector or the pharmaceutical composition comprises a nucleic acid regulatory element described herein operably linked to a promoter and a transgene; and expressing an immunologically effective amount of the transgene product in the subject, in particular in muscle of the subject, more particularly in diaphragm, smooth muscle, heart and/or skeletal muscle tissue or cells, even more particularly in diaphragm, heart and/or skeletal muscle cells or tissue of the subject.

As used herein, a phrase such as "a subject in need of treatment" includes subjects that would benefit from treatment of a recited disease or disorder. Such subjects may include, without limitation, those that have been diagnosed with said disease or disorder, those prone to contract or develop said disease or disorder and/or those in whom said disease or disorder is to be prevented.

The terms "subject" and "patient" are used interchangeably herein and refer to animals, preferably vertebrates, more preferably mammals, and specifically include human patients and non-human mammals. "Mammalian" subjects include, but are not limited to, humans, domestic animals, commercial animals, farm animals, zoo animals, sport animals, pet and experimental animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. Preferred patients or subjects are human subjects.

A 'therapeutic amount' or 'therapeutically effective amount' as used herein refers to the amount of gene product effective to treat a disease or disorder in a subject, i.e., to obtain a desired local or systemic effect. The term thus refers to the quantity of gene product that elicits the biological or medicinal response in a tissue, system, animal, or human that is being sought by a researcher, veterinarian, medical doctor or other clinician. Such amount will typically depend on the gene product and the severity of the disease, but can be decided by the skilled person, possibly through routine experimentation.

An "immunologically effective amount" as used herein refers to the amount of (trans)gene product effective to enhance the immune response of a subject against a subsequent exposure to the immunogen encoded by the (trans) gene. Levels of induced immunity can be determined, e.g. by measuring amounts of neutralizing secretory and/or serum antibodies, e.g., by plaque neutralization, complement fixation, enzyme-linked immunosorbent, or microneutralization assay.

Typically, the amount of (trans)gene product expressed when using an expression cassette or vector as described herein (i.e., with at least one muscle-specific nucleic acid regulatory element) are higher than when an identical expression cassette or vector is used but without a nucleic acid regulatory element therein. More particularly, the expression is at least double as high, at least five times as high, at least ten times as high, at least 20 times as high, at least 30 times as high, at least 40 times as high, at least 50 times as high, or even at least 60 times as high as when compared to the same nucleic acid expression cassette or vector without nucleic acid regulatory element. Moreover, the higher expression remains specific to muscle, in particular diaphragm, smooth muscle, heart and skeletal muscle tissues or cells, more particularly diaphragm, heart and skeletal muscle tissues or cells. Furthermore, the expression cassettes and vectors described herein direct the expression of a therapeutic amount of the gene product for an extended period. Typically, therapeutic expression is envisaged to last at least 20 days, at least 50 days, at least 100 days, at least 200 days, or at least 300 days or more such as at least 1 year, at least 2 years, at least 3 years, at least 5 years, at least 6 years, at least 7 years, at least 8 years, at least 9 years, or even at least 10 years or more. Expression of the gene product (e.g. polypeptide) can be measured by any art-recognized means, such as by antibody-based assays, e.g. a Western Blot or an ELISA assay, for instance to evaluate whether therapeutic expression of the gene product is achieved. Expression of the gene product may also be measured in a bioassay that detects an enzymatic or biological activity of the gene product.

Also disclosed herein is the use of the nucleic acid regulatory elements, the nucleic acid expression cassettes, or the vectors disclosed herein for transfecting or transducing muscle cells, preferably diaphragm, smooth muscle, heart and/or skeletal muscle cells, more preferably diaphragm, heart and/or skeletal muscle cells.

Further disclosed herein is the use of the nucleic acid expression cassettes or the vectors disclosed herein for expressing a transgene product in muscle cells, preferably diaphragm, smooth muscle, heart and/or skeletal muscle cells, more preferably diaphragm, heart and/or skeletal muscle cells, wherein the nucleic acid expression cassette or the vector comprises a nucleic acid regulatory element disclosed herein operably linked to a promoter and a transgene.

Further disclosed herein is a method for expressing a transgene product in muscle cells, preferably diaphragm, smooth muscle, heart and/or skeletal muscle cells, more preferably diaphragm, heart and/or skeletal muscle cells, comprising:

transfecting or transducing the muscle cells with a nucleic acid expression cassette or a vector disclosed herein, wherein the nucleic acid expression cassette or the vector comprises a nucleic acid regulatory element disclosed herein operably linked to a promoter and a transgene; and expressing the transgene product in the muscle cells.

Non-viral transfection or viral vector-mediated transduction of muscle cells may be performed by in vitro, ex vivo or in vivo procedures. The in vitro approach requires the in vitro transfection or transduction of muscle cells, e.g. muscle cells previously harvested from a subject, muscle cell lines or muscle cells differentiated from e.g. induced pluripotent stem cells or embryonic cells. The ex vivo approach requires harvesting of the muscle cells from a subject, in vitro transfection or transduction, and optionally re-introduction of the transfected muscle cells into the subject. The in vivo approach requires the administration of the nucleic acid expression cassette or the vector disclosed herein into a subject. In preferred embodiments, the transfection of the muscle cells is performed in vitro or ex vivo.

It is understood by the skilled person that the use of the nucleic acid regulatory elements, the nucleic acid expression cassettes and vectors disclosed herein has implications beyond gene therapy, e.g. coaxed differentiation of stem cells into diaphragm, smooth muscle, heart and skeletal muscle cells, transgenic models for over-expression of proteins in muscle cells or tissue such as in diaphragm, smooth muscle heart and/or skeletal muscle cells and/or tissue, etc.

The invention is further explained by the following non-limiting examples.

EXAMPLES

Example 1: Design and Construction of Novel AAV Vectors Containing De Novo Computationally-Designed Regulatory Elements (CREs)

AAV9 vectors were designed that express either a codon-optimized transgene encoding human β-sacoglycan (hβ-sgco or hβsgco) (SEQ ID NO: 19) or the wild type hβ-sg (wt) gene (SEQ ID NO:18), or a luciferase reporter gene (Luc) (SEQ ID NO:20) from a synthetic SPc5-12 promoter (SEQ ID NO:15) combined with (combinations of) CRE elements. The individual CRE elements are known to mediate high transgene expression in diaphragm and skeletal muscle (denoted as Dph-CRE herein) or in heart and skeletal muscle (denoted as CSk-CRE or CSk-SH herein). The vectors also contained a Minute Virus of Mouse (MVM) intron (SEQ ID NO: 16) and a synthetic polyadenylation site (pA) (SEQ ID NO:17).

AAV vectors devoid of any CRE element were constructed as control (designated herein as AAV-SPc5-12-MVM-hβsgco-pA and AAV-SPc5-12-MVM-hβsg-pA).

FIG. 2 depicts the different AAV vectors that were designed and constructed. The vectors were constructed by conventional cloning.

Briefly, the wild-type human beta-sarcoglycan gene (hβsg) (SEQ ID NO: 18), the codon-optimized hβsgco gene (SEQ ID NO: 19), or a luciferase encoding reporter gene (SEQ ID NO:20), all flanked by Hind III and BstBI restriction sites at the 5' and 3' ends, were cloned downstream from the SPc5-12 promoter, which was operably linked to the regulatory element CSk-SH5 (SEQ ID NO: 1). The human beta-sarcoglycan gene (hβsg) gene was codon-optimized using the Gene optimizer (GeneArt, Life technologies, Germany).

The CSk-SH5 regulatory element (SEQ ID NO: 1) operably linked to the SPc5-12 promoter (SEQ ID NO:15), were cloned upstream of the MVM intron (SEQ ID NO:16) in the context of a single stranded adeno-associated viral vector (AAVss) backbone. The vector also contained a 49 bp synthetic polyadenylation site (Levitt N et al, 1989) (SEQ ID NO:17).

The vectors depicted in FIG. 2A (AAV-CSk-SH5-SPc5-12-MVM-hβsgco-pA), FIG. 2B (AAV-CSk-SH5-SPc5-12-MVM-hβsg-pA) and FIG. 2A1 (AAV-CSk-SH5-SPc5-12-MVM-Luc-pA) served as a backbone for cloning the different Dph-CREs.

One, two or three diaphragm CREs (Dph-CRE) were cloned upstream of the CSk-SH5 CRE to generate constructs expressing hβsgco gene (one CRE: FIG. 2C (AAV-CRE02-CSk-SH5-SPc5-12-MVM-hβsgco-pA), FIG. 2D (AAV-CRE04-CSk-SH5-SPc5-12-MVM-hβsgco-pA), FIG. 2E (AAV-CRE06-CSk-SH5-SPc5-12-MVM-hβsgco-pA); two CREs: FIG. 2F (AAV-CRE02-CRE04-CSk-SH5-SPc5-12-MVM-hβsgco-pA), FIG. 2H (AAV-CRE04-CRE06-CSk-SH5-SPc5-12-MVM-hβsgco-pA), FIG. 2J (AAV-CRE06-CRE04-CSk-SH5-SPc5-12-MVM-hβsgco-pA), FIG. 2L (AAV-CRE02-CRE06-CSk-SH5-SPc5-12-MVM-hβsgco-pA); and three CREs: FIG. 2N (AAV-CRE02-CRE04-CRE06-CSk-SH5-SPc5-12-MVM-hβsgco-pA)).

Similarly, two or three diaphragm CREs were cloned upstream of the CSk-SH5 CRE to generate constructs expressing the wild type hβsg gene (two CREs: FIG. 2G (AAV-CRE02-CRE04-CSk-SH5-SPc5-12-MVM-hβsg-pA), FIG. 2I (AAV-CRE04-CRE06-CSk-SH5-SPc5-12-MVM-hβsg-pA), FIG. 2K (AAV-CRE06-CRE04-CSk-SH5-SPc5-12-MVM-hβsg-pA), FIG. 2M (AAV-CRE02-CRE06-CSk-SH5-SPc5-12-MVM-hβsg-pA); and three CREs: FIG. 2O (AAV-CRE02-CRE04-CRE06-CSk-SH5-SPc5-12-MVM-hβsg-pA)).

In addition, two or three diaphragm CREs were cloned upstream of the CSk-SH5 CRE to generate constructs expressing Luc reporter gene (one CRE: FIG. 2R (AAV-CRE02-CSk-SH5-SPc5-12-MVM-Luc-pA), FIG. 2Q (AAV-CRE04-CSk-SH5-SPc5-12-MVM-Luc-pA), FIG. 2P (AAV-CRE06-CSk-SH5-SPc5-12-MVM-Luc-pA); two CREs: FIG. 2S (AAV-CRE06-CRE04-CSk-SH5-SPc5-12-MVM-Luc-pA, FIG. 2T (AAV-CRE04-CRE06-CSk-SH5-SPc5-12-MVM-Luc-pA), FIG. 2U (AAV-CRE02-CRE06-CSk-SH5-SPc5-12-MVM-Luc-pA), FIG. 2V (AAV-CRE02-CRE04-CSk-SH5-SPc5-12-MVM-Luc-pA); and three CREs: FIG. 2W (AAV-CRE02-CRE04-CRE06-CSk-SH5-SPc5-12-MVM-Luc-pA)).

Lastly, three control vectors devoid of CRE were generated namely, AAV-SPc5-12-MVM-hβsgco-pA (FIG. 2Y), AAV-SPc5-12-MVM-hβsg-pA (FIG. 2X) and AAV-SPc5-12-MVM-Luc-pA (FIG. 2Z).

Example 2: In Vivo Validation of the Regulatory Elements Via a Reporter Gene

To evaluate which CRE combinations were most potent, AAV vectors expressing luciferase gene (Luc) from the Spc5-12 promoter and containing different CRE combinations were injected into CB17-SCID mice for comparative analysis. Different CRE combinations were tested for their ability to augment luciferase gene expression. More particularly, the following vectors were injected:

AAV-SPc5-12-MVM-Luc-pA (FIG. 2Z, SEQ ID NO: 46)

AAV-CSk-SH5-SPc5-12-MVM-Luc-pA (FIG. 2A1, SEQ ID NO: 47)

AAV-CRE06-CSk-SH5-SPc5-12-MVM-Luc-pA (FIG. 2P, SEQ ID NO: 36)

AAV-CRE04-CSk-SH5-SPc5-12-MVM-Luc-pA (FIG. 2Q, SEQ ID NO: 37)

AAV-CRE02-CSk-SH5-SPc5-12-MVM-Luc-pA (FIG. 2R, SEQ ID NO: 38)

AAV-CRE06-CRE04-CSk-SH5-SPc5-12-MVM-Luc-pA (FIG. 2S, SEQ ID NO: 39)

AAV-CRE04-CRE06-CSk-SH5-SPc5-12-MVM-Luc-pA (FIG. 2T, SEQ ID NO: 40)

AAV-CRE02-CRE06-CSk-SH5-SPc5-12-MVM-Luc-pA (FIG. 2U, SEQ ID NO: 41)

AAV-CRE02-CRE04-CSk-SH5-SPc5-12-MVM-Luc-pA (FIG. 2V, SEQ ID NO: 42)

AAV-CRE02-CRE04-CRE06-CSk-SH5-SPc5-12-MVM-Luc-pA (FIG. 2W, SEQ ID NO: 43)

Experimental Procedures

AAV Vector Production and Purification

AAV9 vectors were produced by calcium phosphate (Invitrogen Corp, Carlsbad, CA) co-transfection of 293T human embryonic kidney cells with the pAAV plasmid of interest, an adenoviral helper plasmid and a chimeric packaging construct that delivers the AAV2 rep gene together with the AAV9 cap gene, as described in Vandendriessche et al. (2007. J Thromb Haemost 5:16-24), which is specifically incorporated by reference herein.

Briefly, two days post transfection, cells were harvested and vector particles were purified using isopycnic centrifugation methods. Harvested cells were lysed by successive freeze/thaw cycles and sonication, treated with benzonase (Novagen, Madison, WI) and deoxycholic acid (Sigma-Aldrich, St. Louis, MO) and subsequently subjected to 3 successive rounds of cesium chloride (Invitrogen Corp, Carlsbad, CA) density gradient ultracentrifugation. Fractions containing the AAV vector were collected, concentrated in 1 mM $MgCl_2$ in Dulbecco's phosphate buffered saline (PBS) (Gibco, BRL) and stored at −80° C.

Vector titers (in viral genomes (vg)/ml) were determined by quantitative real-time PCR using SYBR Green mix (which included SYBR Green dye, Taqman polymerase, ROX and dNTP's all in one) and luciferase specific primers on an ABI 7500 Real-Time PCR System (Applied Biosystem, Foster city, CA, USA). The forward and reverse primers used were 5'-CCCACCGTCGTATTCGTGAG-3' (SEQ ID NO: 48) and 5'-TCAGGGCGATGGTTTTGTCCC-3' (SEQ ID NO: 49), respectively.

Known copy numbers ($10^2$-$10^7$) of the respective vector plasmids used to generate the corresponding AAV vectors, carrying the appropriate cDNAs, were used to generate the standard curves.

Animal Studies

Adult 4-5 weeks old CB17-SCID mice were intravenously injected with a dose of $10^{11}$ vg per mouse. Luciferase activity was assessed by whole body bioluminescence analysis (BLI), 7 or 10 days post-injection. 15 weeks post-injection, one mouse per cohort was sacrificed and individual organ BLI was performed to quantify the level of luciferase expression in each individual organ. FIG. 3 shows the fold difference of the luciferase expression in gastrocnemius and quadriceps of the constructs tested.

Results

Whole body bioluminescence analysis revealed that the combination of the CSk-Sh5-CRE, and the dual Dph-CRE combinations CRE02 and CRE04, CRE04 and CRE06, in any order, and CRE02 and CRE06, or the triple Dph-CRE combination CRE02, CRE04 and CRE06 resulted in an unexpected and disproportionate increase in luciferase expression, compared to the control Spc5-12 promoter devoid of any CRE (data not shown). The combination of CRE elements increased the expression of the luciferase reporter gene to a higher level compared to the individual CRE elements. In addition, we dissected out the gastrocnemius and quadriceps of the injected mice upon euthanasia and examined the bioluminescence activity using BLI. These results confirmed the whole body BLI results by showing an unexpected increase upon combining the CSk-SH5-CRE with one Dph-CRE (i.e. CRE-02), two Dph-CREs (i.e. CRE-02+CRE-04) or three Dph-CREs (i.e. CRE-02+CRE-04+CRE-06) (FIG. 3).

Example 3: In Vivo Validation of the Regulatory Elements Via a Therapeutic Transgene To determine which CRE combinations were most potent, AAV vectors containing different CRE combinations were injected into CB17-SCID mice for comparative analysis. Different CRE combinations were evaluated for codon-optimized hβsg gene expression. More particularly, the following vectors were injected:

AAV-CSk-SH5-SPc5-12-MVM-hβ-SGco-pA (FIG. 2A, SEQ ID NO: 21)

AAV-CRE02-CSk-SH5-SPc5-12-MVM-hβ-SGco-pA (FIG. 2C, SEQ ID NO: 23)

AAV-CRE04-CSk-SH5-SPc5-12-MVM-hβ-SGco-pA (FIG. 2D, SEQ ID NO: 24)

AAV-CRE06-CSk-SH5-SPc5-12-MVM-hβ-SGco-pA (FIG. 2E, SEQ ID NO: 25)

AAV-CRE02-CRE04-CSk-SH5-SPc5-12-MVM-hβ-SGco-pA (FIG. 2F, SEQ ID NO: 26)

AAV-CRE04-CRE06-CSk-SH5-SPc5-12-MVM-hβ-SGco-pA (FIG. 2H, SEQ ID NO: 28)

AAV-CRE06-CRE04-CSk-SH5-SPc5-12-MVM-hβ-SGco-pA (FIG. 2J, SEQ ID NO: 30)

AAV-CRE02-CRE06-CSk-SH5-SPc5-12-MVM-hβ-SGco-pA (FIG. 2L, SEQ ID NO: 32)

Experimental Procedures

AAV Vector Production and Purification

AAV vector production and purification was conducted as described in Example 2. The forward and reverse primers used to determine the vector titers by quantitative real-time PCR were 5'-AGGGATGGTTGGTTGGTGG-3' (SEQ ID NO: 50) and 5'-GGCAGGTGCTCCAGGTAAT-3' (SEQ ID NO: 51), respectively.

Animal Studies

Adult 4-5 week old CB17-SCID mice were intravenously injected with a dose of $3 \times 10^{11}$ vg per mouse. 2-3 mice were injected per cohort. 26 days post-injection, one mouse per cohort was sacrificed and different organs were isolated from the sacrificed mice (isolation of muscles such as quadriceps, gastrocnemius, tibialis, triceps, biceps, diaphragm, heart, as well as non-muscle such as liver, kidney, brain, spleen). Q-RT-PCR was performed to quantify hβsgco gene expression.

mRNA Analysis

Total RNA was extracted from different organs of the mice by a silica-membrane based purification kit according to the manufacturer's instructions (Invitrogen Corp, Carlsbad, CA, USA). Subsequently, 200 ng of total RNA from each sample was subjected to reverse transcription (RT) using a cDNA synthesis kit (Invitrogen Corp, Carlsbad, CA, USA). Next, a cDNA amount corresponding to 10 ng of total RNA was amplified by quantitative(q) PCR on an ABI 7700 (Applied Biosystems, Foster City, CA, USA), using 5'-CATCACAAGTGACATCGGCA-3' (SEQ ID NO: 52) as a forward primer and 5'-TGGCAGCCCATGTTCTGGC-3' (SEQ ID NO: 53) as reverse primer (amplicon 217 bp). The hβsgco mRNA levels were normalized to mRNA levels of the endogenous murine glyceraldehyde-3-phosphate dehydrogenase (mGAPDH) gene, using 5'-TGTGTCCGTCGTGGATCTGA-3' (SEQ ID NO:54) as forward primer and 5'-GCCTGCTTCACCACCTTCTTGA-3' (SEQ ID NO:55) as the reverse primer (amplicon 82 bp). RNA samples were amplified with and without reverse transcriptase to exclude DNA amplification. The size of the amplified PCR fragments was verified on a 1.8% agarose gel.

Results

The combination of the CSk-SH5-CRE with the dual Dph-CRE combinations CRE02 and CRE04, CRE04 and CRE06, in any order, and CRE02 and CRE06, or the tripe Dph-CRE combination CRE02, CRE04 and CRE06 resulted in an unexpected and disproportionate increase in hβsgco gene expression, compared to the CSk-SH5-CRE alone, or the combination of CSk-SH5-CRE with a single Dph-CRE (FIG. 4). Certain CRE combinations are more potent than others for enhancing hβsgco gene expression.

Example 4: In Vivo Validation of the Regulatory Elements Via a Therapeutic Transgene To determine which CRE combinations were most potent, AAV vectors containing different CRE combinations were injected into CB17-SCID mice for comparative analysis of hβsgco gene expression. The following vectors were injected:

```
                                    (FIG. 2Y, SEQ ID NO: 45)
-AAV-SPc5-12-MVM-hβ-SGco-pA (SPC5-12)

(FIG. 2A, SEQ ID NO: 21)
-AAV-CSk-SH5-SPc5-12-MVM-hβ-SGco-pA (CSkSH5-
SPc5-12)

(FIG. 2H, SEQ ID NO: 28)
-AAV-CRE04-CRE06-CSk-SH5-SPc5-12-MVM-hβ-SGco-pA
(Dph-CRE04-Dph-CRE06-CSkSH5-SpC5-12)

(FIG. 2N, SEQ ID NO: 34)
-AAV-CRE02-CRE04-CRE06-CSk-SH5-SPc5-12-MVM-hβ-
SGco-pA (Dph-CRE02-Dph-CRE04-Dph-CRE06-CSkSH5-
SpC5-12)
```

Experimental Procedures

The experimental procedures are the same as described in Example 3 with some modification in the animal study design. Briefly, adult 4-5 week old CB17-SCID mice were intravenously injected with a dose of $3 \times 10^{11}$ vg per mouse. 4-5 mice were injected per cohort. Two months post-injection, one mouse per cohort was sacrificed and different organs were isolated from the sacrificed mice (isolation of muscles such as quadriceps, gastrocnemius, tibialis, triceps, biceps, diaphragm, heart, as well as non-muscle such as liver, kidney, brain, spleen). Q-RT-PCR was performed to quantify hβsgco gene expression.

Results

Tables 2-4 show hβSGco expression in gastrocnemius, quadriceps and heart of the tested vectors relative to each other. Relative hβSGco expression is shown as fold difference.

TABLE 2

Relative hβSGco expression in gastrocnemius.

| | SPc5-12 | CSkSH5-SPc5-12 | Dph-CRE04-Dph-CRE06-CSkSH5-SpC5-12 | Dph-CRE02-Dph-CRE04-Dph-CRE06-CSkSH5-SpC5-12 |
|---|---|---|---|---|
| SPc5-12 | 1.0 | — | — | — |
| CSkSH5-SPc5-12 | 9.1 | 1.0 | — | — |
| Dph-CRE04-Dph-CRE06-CSkSH5-SpC5-12 | 33.3 | 3.7 | 1.0 | — |
| Dph-CRE02-Dph-CRE04-Dph-CRE06-CSkSH5-SpC5-12 | 105.6 | 11.6 | 3.2 | 1.0 |

TABLE 3

Relative hβSGco expression in quadriceps.

| | SPc5-12 | CSkSH5-Spc5-12 | Dph-CRE04-Dph-CRE06-CSkSH5-SpC5-12 | Dph-CRE02-Dph-CRE04-Dph-CRE06-CSkSH5-SpC5-12 |
|---|---|---|---|---|
| SPc5-12 | 1.0 | — | — | — |
| CSkSH5-SPc5-12 | 3.4 | 1.0 | — | — |
| Dph-CRE04-Dph-CRE06-CSkSH5-SpC5-12 | 9.8 | 2.9 | 1.0 | — |
| Dph-CRE02-Dph-CRE04-Dph-CRE06-CSkSH5-SpC5-12 | 58.2 | 17.0 | 5.9 | 1.0 |

TABLE 4

Relative hβSGco expression in heart.

| | SPc5-12 | CSkSH5-SPc5-12 | Dph-CRE04-Dph-CRE06-CSkSH5-SpC5-12 | Dph-CRE02-Dph-CRE04-Dph-CRE06-CSkSH5-SpC5-12 |
|---|---|---|---|---|
| SPc5-12 | 1.0 | — | — | — |
| CSkSH5-SPc5-12 | 7.4 | 1.0 | — | — |
| Dph-CRE04-Dph-CRE06-CSkSH5-SpC5-12 | 16.0 | 2.2 | 1.0 | — |

TABLE 4-continued

Relative hβSGco expression in heart.

| | SPc5-12 | CSkSH5-SPc5-12 | Dph-CRE04-Dph-CRE06-CSkSH5-SpC5-12 | Dph-CRE02-Dph-CRE04-Dph-CRE06-CSkSH5-SpC5-12 |
|---|---|---|---|---|
| Dph-CRE02-Dph-CRE04-Dph-CRE06-CSkSH5-SpC5-12 | 30.7 | 4.2 | 1.9 | 1.0 |

The results shown in FIG. 5 and Tables 2-4 show a significant increase in skeletal muscle or heart-specific mRNA expression of the hβsgco gene, whenever the vectors contained a CRE compared to the control vector (devoid of any CRE, designated as SPc5-12 in FIG. 5 and Tables 1-3). Most importantly, the combination of the CSk-SH5-CRE and the dual Dph-CRE combination CRE04 and CRE06 or the triple Dph-CRE combination CRE02, CRE04 and CRE06 resulted in an unexpected and disproportionate increase in hβsgco mRNA expression levels, up to approximately 100-fold or 30-fold in skeletal muscle and heart, respectively, compared to the control Spc5-12 promoter devoid of any CRE.

Example 5: In Vivo Evaluation of Effect of Codon-Optimization of the Transgene To determine if codon-optimization of the hβsg gene can further increase hβsg protein levels when compared to the non-codon-optimized gene, three pairs of AAV vectors containing either codon-optimized or wild type hβsg gene are compared side by side. The three pairs of vectors are:

i)
```
                              (FIG. 2X, SEQ ID NO: 44)
pAAV-SPc5-12-MVM-hβ-SGwt-SynthpA
```
versus
```
                              (FIG. 2Y; SEQ ID NO: 45)
pAAV-SPc5-12-MVM-hβ-SGco-SynthpA
```
ii)
```
                              (FIG. 2B, SEQ ID NO: 22)
pAAV-CSk-SH5-SPc5-12-MVM-hβ-SGwt-SynthpA
```
versus
```
                              (FIG. 2A, SEQ ID NO: 21)
pAAV-CSk-SH5-SPc5-12-MVM-hβ-SGco-SynthpA
```
iii)
```
                              (FIG. 2H, SEQ ID NO: 28)
pAAV-CRE04-CRE06-CSk-SH5-SPc5-12-MVM-hβ-SGwt-SynthpA
```
versus
```
                              (FIG. 2I, SEQ ID NO: 29)
pAAV-CRE04-CRE06-CSk-SH5-SPc5-12-MVM-hβ-SGco-SynthpA
```

The AAV vectors are produced, titered and injected into 4-5 weeks old male CB17 mice as described in Example 3. Each mouse is injected with a dose of $3\times10^{11}$ vg; 4 to 5 mice are injected per cohort. Two months post injection, mice are sacrificed and different organs are isolated from the sacrificed mice (isolation of muscles such as quadriceps, gastrocnemius, tibialis, triceps, biceps, diaphragm, heart, as wells as non-muscle tissues such as liver, kidney, brain, spleen). A Western blot is performed on the different isolated tissues of mice injected with AAV vectors encoding either wt or codon-optimized hβsg gene.

Example 6: In Vivo Evaluation of the Regulatory Elements in SGCB Null Mice

Therapeutic efficacy of the CRE combination Dph-CRE02-Dph-CRE04-Dph-CRE06-CSkSH5 (SEQ ID NO:14) was evaluated in homozygous sarcoglycan, beta (dystrophin-associated glycoprotein) (Sgcb) targeted mutant mice by gene therapy using a vector comprising β-sarcoglycan-encoding transgene. Sgcb-null mice, with knocked-out β-sarcoglycan, develop severe muscular dystrophy as in type 2E human limb girdle muscular dystrophy.

2-3 days old neonatal Sgcb-null male mice were injected with experimental vector AAV-CRE02-CRE04-CRE06-CSk-SH5-SPc5-12-MVM-hβ-SGco-pA (FIG. 2N, SEQ ID NO: 34) or the control vector AAV-SPc5-12-MVM-hβ-SGco-pA devoid of CRE (FIG. 2Y, SEQ ID NO: 45) at a vector dose of $1\times10^{11}$ vg with 3 mice per cohort.

6 months post vector injection, mice were subjected to a treadmill endurance assay to monitor muscle performance. Phosphate-buffered saline (PBS)-injected Sgcb-null mice were used as controls that were not treated by gene therapy. The running distance was determined using a Bioseb (France) treadmill using the TREAD SOFTWARE. Results are shown in FIG. 6.

Mice injected with the experimental vector AAV-CRE02-CRE04-CRE06-CSk-SH5-SPc5-12-MVM-hβ-SGco-pA run a longer distance (average distance 364 meter) as compared to mice injected with the control vector devoid of CREs (designated as AAV-SPc5-12-MVM-hβ-SGco-pA) (average distance 148 meter). Mice injected with the experimental vector also run a 5 times longer distance than control mice that were injected with PBS (average distance 71 meter).

These results show that the gene therapy was efficient in Sgcb-null mice, and that the CRE combination increased therapeutic efficacy.

The invention claimed is:

1. A nucleic acid regulatory element for enhancing muscle-specific gene expression comprising the nucleotide sequence set forth in SEQ ID NO: 14 (Dph-CRE02-Dph-CRE04-Dph-CRE06-CSk-SH5).

2. A nucleic acid expression cassette comprising the nucleic acid regulatory element according to claim 1 operably linked to a promoter and a transgene.

3. The nucleic acid expression cassette according to claim 2, wherein the promoter is a muscle-specific promoter.

4. The nucleic acid expression cassette according to claim 2, wherein the transgene encodes a sarcoglycan.

5. The nucleic acid expression cassette according to claim 2, wherein the promoter is the Spc5-12 promoter as defined by SEQ ID NO:15, and wherein the transgene encodes β-sarcoglycan.

6. A pharmaceutical composition comprising the nucleic acid expression cassette according to claim 2 and a pharmaceutically acceptable carrier.

7. A vector comprising the nucleic acid regulatory element according to claim 1.

8. A method of enhancing expression of a gene in muscle cells or tissue, comprising operably linking the nucleic acid regulatory element according to claim 1 to the gene.

9. A method of treating limb girdle muscular dystrophy in a subject in need thereof, comprising introducing the nucleic acid regulatory element according to claim 1 into muscle tissue or cells of the subject.

10. A method for expressing a transgene product in muscle cells comprising:
- introducing the nucleic acid expression cassette according to claim 2 into said muscle cells; and
- expressing the transgene product in the muscle cells.

* * * * *

SEQUENCE LISTING

<160> NUMBER OF SEQ ID NOS: 59

<210> SEQ ID NO 1
<211> LENGTH: 454
<212> TYPE: DNA
<213> ORGANISM: Artificial Sequence
<220> FEATURE:
<223> OTHER INFORMATION: CSk-SH5

<400> SEQUENCE: 1

```
cagtttactc accagggatt cagaggcagc actgctgaac cctgagccct tggcacatca    60
ggttggctgt cagaagtcgg cctttgtaca tacacagttc ccttgtgagg cccagctgcg   120
tgtcctagga gcggggcctc tctccacagc agagctcagc ctctcaagtg tatggacagc   180
acgggtgcct gatgggtgga tttagccatg agttgaaggt ggcttgggga gaatgagagt   240
tctagagata gggagaaggg gttgccaata ggagagtgga attcctgagc acctcgtcac   300
aggcagccga cagaacatga gccgcagggc ccaggctatt tatacctcgc ctgtcactat   360
cagggtcccc acagctcccc ccacctccag ccacacacag caggtccttt tgctctttct   420
ggtcccttct ctactcctcc ccctccctac ctaa                               454
```

<210> SEQ ID NO 2
<211> LENGTH: 452
<212> TYPE: DNA
<213> ORGANISM: Artificial Sequence
<220> FEATURE:
<223> OTHER INFORMATION: Dph-CRE02

<400> SEQUENCE: 2

```
gacaggtgcg gttcccggag cgcaggcgca cacatgcacc caccggcgaa cgcggtgacc    60
ctcgccccac cccatcccct ccggcgggca actgggtcgg gtcaggaggg gcaaacccgc   120
tagggagaca ctccatatac ggcccggccc gcgttacctg ggaccgggcc aacccgctcc   180
ttctttggtc aacgcagggg acccgggcgg gggcccaggc cgcgaaccgg ccgagggagg   240
gggctctagt gcccaacacc caaatatggc tcgagaaggg cagcgacatt cctgcggggt   300
ggcgcggagg gaatgcccgc gggctatata aaacctgagc agagggacaa gcggccaccg   360
cagcggacag cgccaagtga agcctcgctt cccctccgcg gcgaccaggg cccgagccga   420
gagtagcagt tgtagctacc cgcccaggta gg                                 452
```

<210> SEQ ID NO 3
<211> LENGTH: 509
<212> TYPE: DNA
<213> ORGANISM: Artificial Sequence
<220> FEATURE:
<223> OTHER INFORMATION: Dph-CRE04

<400> SEQUENCE: 3

```
cctttagag aatccacacc tgtcccagtt gctgggttcc actaccaaaa gtgaattgca    60
actattttag gagcacttaa gcacatccga aaaatgagtg attctgttct ggcccacacc   120
acatcactga tgtaccccct taaagcatgt ccctgagttc atcacagaag actgctcctc   180
ctgtgccctc cacaaggtta gaactgtcct tgtcttaggg aaaaaggaga gagagagaga   240
gagagagaga gagagagaga gagagagaga gagagaggga caggcaccaa ctgggtaacc   300
tctgctgacc cccactctac tttaccataa gtagctccaa atccttctag aaaatctgaa   360
aggcatagcc ccatatatca gtgatataaa tagaacctgc agcaggctct ggtaaatgat   420
gactacaagg tggactggga ggcagcccgg ccttggcagg catcatcctc taaatataaa   480
gatgagtttg ttcagccttt gcagaagga                                     509
```

<210> SEQ ID NO 4
<211> LENGTH: 400
<212> TYPE: DNA
<213> ORGANISM: Artificial Sequence
<220> FEATURE:
<223> OTHER INFORMATION: Dph-CRE06

<400> SEQUENCE: 4

```
gggccagggg acggtggctt ctacgtgctt gggacgttcc cagccaccgt cccatgttcc    60
cggcgggggg ccagctgtcc ccaccgccag cccaactcag cacttggtca gggtatcagc   120
ttggtggggg ggcgtgagcc cagcccctgg ggcggctcag cccatacaag gccatggggc   180
tgggcgcaaa gcatgcctgg gttcaggggtg gtatggtgc gggagcaggg aggtgagagg   240
ctcagctgcc ctccagaact cctccctggg acaacccct cccagccaat agcacagcct   300
aggtccccct atataaggcc acggctgctg gcccttcctt tgggtcagtg tcacctccag   360
gatacagaca gccccccttc agcccagccc agccaggtac                         400
```

<210> SEQ ID NO 5
<211> LENGTH: 981
<212> TYPE: DNA
<213> ORGANISM: Artificial Sequence
<220> FEATURE:
<223> OTHER INFORMATION: Dph-CRE02-CRE04

<400> SEQUENCE: 5

```
gacaggtgcg gttcccggag cgcaggcgca cacatgcacc caccggcgaa cgcggtgacc    60
ctcgccccac cccatcccct ccggcgggca actgggtcgg gtcaggaggg gcaaacccgc   120
tagggagaca ctccatatac ggcccggccc gcgttacctg ggaccgggcc aacccgctcc   180
ttctttggtc aacgcagggg acccgggcgg gggcccaggc cgcgaaccgg ccgagggagg   240
gggctctagt gcccaacacc caaatatggc tcgagaaggg cagcgacatt cctgcggggt   300
ggcgcggagg gaatgcccgc gggctatata aacctgagc agagggacaa gcggccaccg   360
cagcggacag cgccaagtga agcctcgctt cccctccgcg gcgaccaggg cccgagccga   420
gagtagcagt tgtagctacc cgcccaggta ggggcgcgcc gtcgacggat ccccttttag   480
agaatccaca cctgtcccag ttgctgggtt ccactaccaa aagtgaattg caactatttt   540
aggagcactt aagcacatcc gaaaaatgag tgattctgtt ctggcccaca ccacatcact   600
gatgtacccc cttaaagcat gtccctgagt tcatcacaga agactgctcc tcctgtgccc   660
tccacaaggt tagaactgtc cttgtcttag ggaaaaagga gagagagaga gagagagaga   720
gagagagaga gagagagaga gagagagagg gacaggcacc aactgggtaa cctctgctga   780
cccccactct actttaccat aagtagctcc aaatccttct agaaaatctg aaaggcatag   840
ccccatatat cagtgatata aatagaacct gcagcaggct ctggtaaatg atgactacaa   900
ggtggactgg gaggcagccc ggccttggca ggcatcatcc tctaaatata aagatgagtt   960
tgttcagcct ttgcagaagg a                                             981
```

<210> SEQ ID NO 6
<211> LENGTH: 872
<212> TYPE: DNA
<213> ORGANISM: Artificial Sequence
<220> FEATURE:
<223> OTHER INFORMATION: Dph-CRE02-CRE06

<400> SEQUENCE: 6

```
gacaggtgcg gttcccggag cgcaggcgca cacatgcacc caccggcgaa cgcggtgacc    60
ctcgccccac cccatcccct ccggcgggca actgggtcgg gtcaggaggg gcaaacccgc   120
tagggagaca ctccatatac ggcccggccc gcgttacctg ggaccgggcc aacccgctcc   180
ttctttggtc aacgcagggg acccgggcgg gggcccaggc cgcgaaccgg ccgagggagg   240
```

| | |
|---|---|
| gggctctagt gcccaacacc caaatatggc tcgagaaggg cagcgacatt cctgcggggt | 300 |
| ggcgcggagg gaatgcccgc gggctatata aaacctgagc agagggacaa gcggccaccg | 360 |
| cagcggacag cgccaagtga agcctcgctt cccctccgcg gcgaccaggg cccgagccga | 420 |
| gagtagcagt tgtagctacc cgcccaggta ggggcgcgcc gtcgacggat ccgggccagg | 480 |
| ggacggtggc ttctacgtgc ttgggacgtt cccagccacc gtccatgttc ccggcgggg | 540 |
| ggccagctgt ccccaccgcc agcccaactc agcacttggt cagggtatca gcttggtggg | 600 |
| ggggcgtgag cccagcccct ggggcggctc agcccataca aggccatggg gctgggcgca | 660 |
| aagcatgcct gggttcaggg tgggtatggt gcgggagcag ggaggtgaga ggctcagctg | 720 |
| ccctccagaa ctcctccctg gggacaaccc ctcccagcca atagcacagc ctaggtcccc | 780 |
| ctatataagg ccacggctgc tggcccttcc tttgggtcag tgtcacctcc aggatacaga | 840 |
| cagcccccct tcagcccagc ccagccaggt ac | 872 |

<210> SEQ ID NO 7
<211> LENGTH: 929
<212> TYPE: DNA
<213> ORGANISM: Artificial Sequence
<220> FEATURE:
<223> OTHER INFORMATION: Dph-CRE04-CRE06

<400> SEQUENCE: 7

| | |
|---|---|
| cctttagag aatccacacc tgtcccagtt gctgggttcc actaccaaaa gtgaattgca | 60 |
| actattttag gagcacttaa gcacatccga aaaatgagtg attctgttct ggcccacacc | 120 |
| acatcactga tgtaccccct aaagcatgt ccctgagttc atcacagaag actgctcctc | 180 |
| ctgtgccctc cacaaggtta gaactgtcct tgtcttaggg aaaaaggaga gagagagaga | 240 |
| gagagagaga gagagagaga gagagagaga gagagaggga caggcaccaa ctgggtaacc | 300 |
| tctgctgacc cccactctac tttaccataa gtagctccaa atccttctag aaaatctgaa | 360 |
| aggcatagcc ccatatatca gtgatataaa tagaacctgc agcaggctct ggtaaatgat | 420 |
| gactacaagg tggactggga ggcagcccgg ccttggcagg catcatcctc taaatataaa | 480 |
| gatgagtttg ttcagccttt gcagaaggag gcgcgccgtc gacggatccg gccaggga | 540 |
| cggtggcttc tacgtgcttg gacgttccc agccaccgtc ccatgttccc ggcgggggc | 600 |
| cagctgtccc caccgccagc ccaactcagc acttggtcag ggtatcagct tggtgggggg | 660 |
| gcgtgagccc agcccctggg gcggctcagc ccatacaagg ccatgggct gggcgcaaag | 720 |
| catgcctggg ttcagggtgg gtatggtgcg ggagcaggga ggtgagaggc tcagctgccc | 780 |
| tccagaactc ctccctgggg acaacccctc ccagccaata gcacagccta ggtccccta | 840 |
| tataaggcca cggctgctgg cccttccttt gggtcagtgt cacctccagg atacagacag | 900 |
| cccccttca gcccagccca gccaggtac | 929 |

<210> SEQ ID NO 8
<211> LENGTH: 929
<212> TYPE: DNA
<213> ORGANISM: Artificial Sequence
<220> FEATURE:
<223> OTHER INFORMATION: Dph-CRE06-CRE04

<400> SEQUENCE: 8

| | |
|---|---|
| gggccagggg acggtggctt ctacgtgctt gggacgttcc cagccaccgt cccatgttcc | 60 |
| cggcgggggc ccagctgtcc ccaccgccag cccaactcag cacttggtca gggtatcagc | 120 |
| ttggtggggg ggcgtgagcc cagcccctgg ggcggctcag cccatacaag gccatgggc | 180 |

| | |
|---|---|
| tgggcgcaaa gcatgcctgg gttcagggtg ggtatggtgc gggagcaggg aggtgagagg | 240 |
| ctcagctgcc ctccagaact cctccctggg acaaccccct cccagccaat agcacagcct | 300 |
| aggtccccct atataaggcc acggctgctg gcccttcctt tgggtcagtg tcacctccag | 360 |
| gatacagaca gccccccttc agcccagccc agccaggtac ggcgcgccgt cgacggatcc | 420 |
| cctttagag aatccacacc tgtcccagtt gctgggttcc actaccaaaa gtgaattgca | 480 |
| actatttag gagcacttaa gcacatccga aaaatgagtg attctgttct ggcccacacc | 540 |
| acatcactga tgtaccccct aaagcatgt ccctgagttc atcacagaag actgctcctc | 600 |
| ctgtgccctc cacaaggtta gaactgtcct tgtcttaggg aaaaaggaga gagagagaga | 660 |
| gagagagaga gagagagaga gagagagaga gagagaggga caggcaccaa ctgggtaacc | 720 |
| tctgctgacc cccactctac tttaccataa gtagctccaa atccttctag aaaatctgaa | 780 |
| aggcatagcc ccatatatca gtgatataaa tagaacctgc agcaggctct ggtaaatgat | 840 |
| gactacaagg tggactggga ggcagcccgg ccttggcagg catcatcctc taaatataaa | 900 |
| gatgagtttg ttcagccttt gcagaagga | 929 |

<210> SEQ ID NO 9
<211> LENGTH: 1407
<212> TYPE: DNA
<213> ORGANISM: Artificial Sequence
<220> FEATURE:
<223> OTHER INFORMATION: Dph-CRE02-CRE04-CRE06

<400> SEQUENCE: 9

| | |
|---|---|
| gacaggtgcg gttcccggag cgcaggcgca cacatgcacc caccggcgaa cgcggtgacc | 60 |
| ctcgccccac cccatcccct ccggcgggca actgggtcgg gtcaggaggg gcaaacccgc | 120 |
| tagggagaca ctccatatac ggcccggccc gcgttacctg ggaccgggcc aacccgctcc | 180 |
| ttctttggtc aacgcagggg acccgggcgg gggcccaggc cgcgaaccgg ccagagggagg | 240 |
| gggctctagt gcccaacacc caaatatggc tcgagaaggg cagcgacatt cctgcggggt | 300 |
| ggcgcggagg gaatgcccgc gggctatata aaacctgagc agaggacaa gcggccaccg | 360 |
| cagcggacag cgccaagtga agcctcgctt ccctccgcg cgaccaggg cccgagccga | 420 |
| gagtagcagt tgtagctacc cgcccaggta ggggcgcgcc cgtacggtcg acggatcccc | 480 |
| ttttagagaa tccacacctg tcccagttgc tgggttccac taccaaaagt gaattgcaac | 540 |
| tattttagga gcacttaagc acatccgaaa aatgagtgat tctgttctgg cccacaccac | 600 |
| atcactgatg taccccctta aagcatgtcc ctgagttcat cacagaagac tgctcctcct | 660 |
| gtgccctcca caaggttaga actgtccttg tcttagggaa aaaggagaga gagagagaga | 720 |
| gagagagaga gagagagaga gagagagaga gagagggaca ggcaccaact gggtaacctc | 780 |
| tgctgacccc cactctactt taccataagt agctccaaat ccttctagaa atctgaaag | 840 |
| gcatagcccc atatatcagt gatataaata gaacctgcag caggctctgg taaatgatga | 900 |
| ctacaaggtg gactgggagg cagcccggcc ttggcaggca tcatcctcta aatataaaga | 960 |
| tgagtttgtt cagcctttgc agaaggaggc gcgccgtcga cggatccggg ccaggggacg | 1020 |
| gtggcttcta cgtgctggg acgttccag ccaccgtccc atgttcccgg cgggggggcca | 1080 |
| gctgtccca ccgccagccc aactcagcac ttggtcaggg tatcagcttg gtggggggc | 1140 |
| gtgagcccag cccctgggc ggctcagccc atacaaggcc atgggctgg gcgcaaagca | 1200 |
| tgcctgggtt cagggtgggt atggtgcggg agcagggagg tgagaggctc agctgccctc | 1260 |

| cagaactcct ccctggggac aaccoctccc agccaatagc acagcctagg tccccctata | 1320 |
| taaggccacg gctgctggcc cttcctttgg gtcagtgtca cctccaggat acagacagcc | 1380 |
| ccccttcagc ccagcccagc caggtac | 1407 |

<210> SEQ ID NO 10
<211> LENGTH: 1461
<212> TYPE: DNA
<213> ORGANISM: Artificial Sequence
<220> FEATURE:
<223> OTHER INFORMATION: Dph-CRE02-CRE04-CSk-SH5

<400> SEQUENCE: 10

| gacaggtgcg gttcccggag cgcaggcgca cacatgcacc caccggcgaa cgcggtgacc | 60 |
| ctcgccccac cccatcccct ccggcgggca actgggtcgg gtcaggaggg gcaaacccgc | 120 |
| tagggagaca ctccatatac ggcccggccc gcgttacctg ggaccgggcc aacccgctcc | 180 |
| ttctttggtc aacgcagggg acccggggcgg gggcccaggc cgcgaaccgg ccgagggagg | 240 |
| gggctctagt gcccaacacc caaatatggc tcgagaaggg cagcgacatt cctgcggggt | 300 |
| ggcgcggagg gaatgcccgc gggctatata aaacctgagc agagggacaa gcggccaccg | 360 |
| cagcggacag cgccaagtga agcctcgctt ccoctccgcg gcgaccaggg cccgagccga | 420 |
| gagtagcagt tgtagctacc cgcccaggta ggggcgcgcc gtcgacggat cccctttag | 480 |
| agaatccaca cctgtcccag ttgctgggtt ccactaccaa aagtgaattg caactatttt | 540 |
| aggagcactt aagcacatcc gaaaaatgag tgattctgtt ctggcccaca ccacatcact | 600 |
| gatgtacccc cttaaagcat gtccctgagt tcatcacaga agactgctcc tcctgtgccc | 660 |
| tccacaaggt tagaactgtc cttgtcttag ggaaaaagga gagagagaga gagagagaga | 720 |
| gagagagaga gagagagaga gagagagagg gacaggcacc aactgggtaa cctctgctga | 780 |
| cccccactct actttaccat aagtagctcc aaatccttct agaaaatctg aaaggcatag | 840 |
| ccccatatat cagtgatata aatagaacct gcagcaggct ctggtaaatg atgactacaa | 900 |
| ggtggactgg gaggcagccc ggccttggca ggcatcatcc tctaaatata aagatgagtt | 960 |
| tgttcagcct ttgcagaagg aggatccgtc gacggcgcgc cacgcgtcag tttactcacc | 1020 |
| agggattcag aggcagcact gctgaaccct gagcccttgg cacatcaggt tggctgtcag | 1080 |
| aagtcggcct ttgtacatac acagttccct tgtgaggccc agctgcgtgt cctaggagcg | 1140 |
| gggcctctct ccacagcaga gctcagcctc tcaagtgtat ggacagcacg ggtgcctgat | 1200 |
| gggtggattt agccatgagt tgaaggtggc ttggggagaa tgagagttct agagataggg | 1260 |
| agaaggggtt gccaatagga gagtggaatt cctgagcacc tcgtcacagg cagccgacag | 1320 |
| aacatgagcc gcagggccca ggctatttat acctcgcctg tcactatcag ggtccccaca | 1380 |
| gctcccccca cctccagcca cacacagcag gtccttttgc tctttctggt cccttctcta | 1440 |
| ctcctccccc tccctaccta a | 1461 |

<210> SEQ ID NO 11
<211> LENGTH: 1352
<212> TYPE: DNA
<213> ORGANISM: Artificial Sequence
<220> FEATURE:
<223> OTHER INFORMATION: Dph-CRE02-CRE06-Csk-SH5

<400> SEQUENCE: 11

| gacaggtgcg gttcccggag cgcaggcgca cacatgcacc caccggcgaa cgcggtgacc | 60 |
| ctcgccccac cccatcccct ccggcgggca actgggtcgg gtcaggaggg gcaaacccgc | 120 |

```
tagggagaca ctccatatac ggcccggccc gcgttacctg ggaccgggcc aacccgctcc    180
ttctttggtc aacgcagggg acccgggcgg gggcccaggc cgcgaaccgg ccgagggagg    240
gggctctagt gcccaacacc caaatatggc tcgagaaggg cagcgacatt cctgcggggt    300
ggcgcggagg aatgcccgc gggctatata aacctgagc agaggacaa gcggccaccg       360 cagcggacag cgccaagtga agcctcgctt ccctccgcg gcgaccaggg cccgagccga     420
gagtagcagt tgtagctacc cgcccaggta ggggcgcgcc gtcgacggat ccgggccagg    480
ggacggtggc ttctacgtgc ttgggacgtt cccagccacc gtcccatgtt cccggcgggg   540
ggccagctgt ccccaccgcc agcccaactc agcacttggt cagggtatca gcttggtggg    600
ggggcgtgag cccagcccct ggggcggctc agcccataca aggccatggg gctgggcgca    660
aagcatgcct gggttcaggg tgggtatggt gcggagcag gaggtgaga ggctcagctg     720 ccctccagaa ctcctccctg ggacaaccc ctcccagcca atagcacagc taggtcccc    780 ctatataagg ccacggctgc tggcccttcc tttgggtcag tgtcacctcc aggatacaga   840 cagccccct tcagcccagc ccagccaggt acggatccgt cgacggcgcg ccacgcgtca    900
gtttactcac cagggattca gaggcagcac tgctgaaccc tgagcccttg gcacatcagg   960
ttggctgtca gaagtcggcc tttgtacata cacagttccc ttgtgaggcc cagctgcgtg   1020
tcctaggagc ggggcctctc tccacagcag agctcagcct ctcaagtgta tggacagcac  1080
gggtgcctga tgggtggatt tagccatgag ttgaaggtgg cttggggaga atgagagttc   1140
tagagatagg gagaagggt tgccaatagg agagtggaat tcctgagcac ctcgtcacag    1200
gcagccgaca gaacatgagc cgcagggccc aggctattta tacctcgcct gtcactatca   1260
gggtccccac agctccccc acctccagcc acacacagca ggtccttttg ctctttctgg    1320
tcccttctct actcctcccc ctccctacct aa                                 1352
```

<210> SEQ ID NO 12
<211> LENGTH: 1409
<212> TYPE: DNA
<213> ORGANISM: Artificial Sequence
<220> FEATURE:
<223> OTHER INFORMATION: Dph-CRE04-CRE06-Csk-SH5

<400> SEQUENCE: 12

```
ccttttagag aatccacacc tgtcccagtt gctgggttcc actaccaaaa gtgaattgca     60
actattttag gagcacttaa gcacatccga aaaatgagtg attctgttct ggcccacacc    120
acatcactga tgtaccccct taaagcatgt ccctgagttc atcacagaag actgctcctc   180
ctgtgccctc cacaaggtta gaactgtcct tgtcttaggg aaaaggaga gagagagaga    240 gagagagaga gagagagaga gagagagaga gagagaggga caggcaccaa ctgggtaacc   300
tctgctgacc cccactctac tttaccataa gtagctccaa atccttctag aaaatctgaa    360
aggcatagcc ccatatatca gtgatataaa tagaacctgc agcaggctct ggtaaatgat   420
gactacaagg tggactggga ggcagcccgg ccttggcagg catcatcctc taaatataaa   480
gatgagtttg ttcagccttt gcagaaggag gcgcgccgtc gacggatccg gccaggggga   540
cggtggcttc tacgtgcttg gacgttccc agccaccgtc catgttccc ggcggggggc    600 cagctgtccc caccgccagc ccaactcagc acttggtcag ggtatcagct tggtgggggg   660
gcgtgagccc agcccctggg gcggctcagc ccatacaagg ccatgggct gggcgcaaag    720 catgcctggg ttcagggtgg gtatggtgcg ggagcaggga ggtgagaggc tcagctgccc   780
```

| | |
|---|---|
| tccagaactc ctccctgggg acaacccctc ccagccaata gcacagccta ggtccccta | 840 |
| tataaggcca cggctgctgg cccttccttt gggtcagtgt cacctccagg atacagacag | 900 |
| ccccccttca gcccagccca gccaggtacg gatccgtcga cggcgcgcca cgcgtcagtt | 960 |
| tactcaccag ggattcagag gcagcactgc tgaaccctga gcccttggca catcaggttg | 1020 |
| gctgtcagaa gtcggccttt gtacatacac agttcccttg tgaggcccag ctgcgtgtcc | 1080 |
| taggagcggg gcctctctcc acagcagagc tcagcctctc aagtgtatgg acagcacggg | 1140 |
| tgcctgatgg gtggatttag ccatgagttg aaggtggctt ggggagaatg agagttctag | 1200 |
| agatagggag aaggggttgc aataggaga gtggaattcc tgagcacctc gtcacaggca | 1260 |
| gccgacagaa catgagccgc agggcccagg ctatttatac ctcgcctgtc actatcaggg | 1320 |
| tccccacagc tccccccacc tccagccaca cacagcaggt ccttttgctc tttctggtcc | 1380 |
| cttctctact cctccccctc cctacctaa | 1409 |

<210> SEQ ID NO 13
<211> LENGTH: 1409
<212> TYPE: DNA
<213> ORGANISM: Artificial Sequence
<220> FEATURE:
<223> OTHER INFORMATION: Dph-CRE06-CRE04-Csk-SH5

<400> SEQUENCE: 13

| | |
|---|---|
| gggccagggg acggtggctt ctacgtgctt gggacgttcc cagccaccgt cccatgttcc | 60 |
| cggcgggggg ccagctgtcc ccaccgccag cccaactcag cacttggtca gggtatcagc | 120 |
| ttggtggggg ggcgtgagcc cagccctgg ggcggctcag cccatacaag gccatggggc | 180 |
| tgggcgcaaa gcatgcctgg gttcaggtg ggtatggtgc gggagcaggg aggtgagagg | 240 |
| ctcagctgcc ctccagaact cctccctggg gacaacccct cccagccaat agcacagcct | 300 |
| aggtcccct atataaggcc acggctgctg gcccttcctt tgggtcagtg tcacctccag | 360 |
| gatacagaca gccccccttc agcccagccc agccaggtac ggcgcgccgt cgacggatcc | 420 |
| ccttttagag aatccacacc tgtcccagtt gctgggttcc actaccaaaa gtgaattgca | 480 |
| actattttag gagcacttaa gcacatccga aaaatgagtg attctgttct ggcccacacc | 540 |
| acatcactga tgtacccct taaagcatgt ccctgagttc atcacagaag actgctcctc | 600 |
| ctgtgccctc cacaaggtta gaactgtcct tgtcttaggg aaaaaggaga gagagagaga | 660 |
| gagagagaga gagagagaga gagagagaga gagagaggga caggcaccaa ctgggtaacc | 720 |
| tctgctgacc cccactctac tttaccataa gtagctccaa atccttctag aaaatctgaa | 780 |
| aggcatagcc ccatatatca gtgatataaa tagaacctgc agcaggctct ggtaaatgat | 840 |
| gactacaagg tggactggga ggcagccggg ccttggcagg catcatcctc taaatataaa | 900 |
| gatgagtttg ttcagccttt gcagaaggag gatccgtcga cggcgcgcca cgcgtcagtt | 960 |
| tactcaccag ggattcagag gcagcactgc tgaaccctga gcccttggca catcaggttg | 1020 |
| gctgtcagaa gtcggccttt gtacatacac agttcccttg tgaggcccag ctgcgtgtcc | 1080 |
| taggagcggg gcctctctcc acagcagagc tcagcctctc aagtgtatgg acagcacggg | 1140 |
| tgcctgatgg gtggatttag ccatgagttg aaggtggctt ggggagaatg agagttctag | 1200 |
| agatagggag aaggggttgc aataggaga gtggaattcc tgagcacctc gtcacaggca | 1260 |
| gccgacagaa catgagccgc agggcccagg ctatttatac ctcgcctgtc actatcaggg | 1320 |
| tccccacagc tccccccacc tccagccaca cacagcaggt ccttttgctc tttctggtcc | 1380 |
| cttctctact cctccccctc cctacctaa | 1409 |

<210> SEQ ID NO 14
<211> LENGTH: 1893
<212> TYPE: DNA
<213> ORGANISM: Artificial Sequence
<220> FEATURE:
<223> OTHER INFORMATION: Dph-CRE02-CRE04-CRE06-Csk-SH5

<400> SEQUENCE: 14

```
gacaggtgcg gttcccggag cgcaggcgca cacatgcacc caccggcgaa cgcggtgacc      60
ctcgccccac cccatcccct ccggcgggca actgggtcgg gtcaggaggg gcaaacccgc     120
tagggagaca ctccatatac ggcccggccc gcgttacctg ggaccgggcc aacccgctcc     180
ttctttggtc aacgcagggg acccgggcgg gggcccaggc cgcgaaccgg ccgagggagg     240
gggctctagt gcccaacacc caaatatggc tcgagaaggg cagcgacatt cctgcgtggt     300
ggcgcggagg gaatgcccgc gggctatata aacctgagc agagggacaa gcggccaccg     360
cagcggacag cgccaagtga agcctcgctt ccctccgcg cgaccaggg cccgagccga     420
gagtagcagt tgtagctacc cgcccaggta ggggcgcgcc cgtacggtcg acggatcccc     480
ttttagagaa tccacacctg tcccagttgc tgggttccac taccaaaagt gaattgcaac     540
tattttagga gcacttaagc acatccgaaa aatgagtgat tctgttctgg cccacaccac     600
atcactgatg tacccccta aagcatgtcc ctgagttcat cacagaagac tgctcctcct     660
gtgccctcca caaggttaga actgtccttg tcttagggaa aaaggagaga gagagagaga     720
gagagagaga gagagagaga gagagagaga gagagggaca ggcaccaact gggtaacctc     780
tgctgacccc cactctactt taccataagt agctccaaat ccttctagaa aatctgaaag     840
gcatagcccc atatatcagt gatataaata gaacctgcag caggctctgg taaatgatga     900
ctacaaggtg gactgggagg cagcccggcc ttggcaggca tcatcctcta aatataaaga     960
tgagtttgtt cagcctttgc agaaggaggc gcgccgtcga cggatccggg ccaggggacg    1020
gtggcttcta cgtgcttggg acgttcccag ccaccgtccc atgttcccgg cggggggcca    1080
gctgtcccca ccgccagccc aactcagcac ttggtcaggg tatcagcttg gtgggggggc    1140
gtgagcccag cccctggggc ggctcagccc atacaaggcc atggggctgg gcgcaaagca    1200
tgcctgggtt cagggtgggt atggtgcggg agcaggagg tgagaggctc agctgccctc    1260
cagaactcct ccctggggac aacccctccc agccaatagc acagcctagg tccccctata    1320
taaggccacg gctgctggcc cttcctttgg gtcagtgtca cctccaggat acagacagcc    1380
cccttcagc ccagcccagc caggtacgga tccgtcgacc gtacgggcgc gccacgcgtc    1440
agtttactca ccagggattc agaggcagca ctgctgaacc ctgagcccttt ggcacatcag    1500
gttggctgtc agaagtcggc ctttgtacat acacagttcc cttgtgaggc ccagctgcgt    1560
gtcctaggag cggggcctct ctccacagca gagctcagcc tctcaagtgt atggacagca    1620
cgggtgcctg atgggtggat ttagccatga gttgaaggtg gcttggggag aatgagagtt    1680
ctagagatag ggagaagggg ttgccaatag gagagtggaa ttcctgagca cctcgtcaca    1740
ggcagccgac agaacatgag ccgcagggcc caggctattt atacctcgcc tgtcactatc    1800
agggtcccca cagctccccc cacctccagc cacacacagc aggtccttt gctctttctg    1860
gtccctttctc tactcctccc cctccctacc taa                               1893
```

<210> SEQ ID NO 15
<211> LENGTH: 334
<212> TYPE: DNA

<213> ORGANISM: Artificial Sequence
<220> FEATURE:
<223> OTHER INFORMATION: Spc5-12 promoter

<400> SEQUENCE: 15

| tggccaccgc | cttcggcacc | atcctcacga | cacccaaata | tggcgacggg | tgaggaatgg | 60 |
| tggggagtta | ttttagagc | ggtgaggaag | gtgggcaggc | agcaggtgtt | ggcgctctaa | 120 |
| aaataactcc | cggagttat | ttttagagcg | gaggaatggt | ggacacccaa | atatggcgac | 180 |
| ggttcctcac | ccgtcgccat | atttgggtgt | ccgccctcgg | ccggggccgc | attcctgggg | 240 |
| gccgggcggt | gctcccgccc | gcctcgataa | aaggctccgg | gccggcggc | ggcccacgag | 300 |
| ctacccggag | gagcgggagg | cgccaagctc | taga | | | 334 |

<210> SEQ ID NO 16
<211> LENGTH: 92
<212> TYPE: DNA
<213> ORGANISM: Artificial Sequence
<220> FEATURE:
<223> OTHER INFORMATION: MVM intron

<400> SEQUENCE: 16

| aagaggtaag | ggtttaaggg | atggttggtt | ggtggggtat | taatgtttaa | ttacctggag | 60 |
| cacctgcctg | aaatcacttt | ttttcaggtt | gg | | | 92 |

<210> SEQ ID NO 17
<211> LENGTH: 49
<212> TYPE: DNA
<213> ORGANISM: Artificial Sequence
<220> FEATURE:
<223> OTHER INFORMATION: pA signal

<400> SEQUENCE: 17

| aataaaagat | ctttattttc | attagatctg | tgtgttggtt | ttttgtgtg | | 49 |

<210> SEQ ID NO 18
<211> LENGTH: 957
<212> TYPE: DNA
<213> ORGANISM: Homo sapiens

<400> SEQUENCE: 18

| atggcggcag | cggcggcggc | ggctgcagaa | cagcaaagtt | ccaatggtcc | tgtaaagaag | 60 |
| tccatgcgtg | agaaggctgt | tgagagaagg | agtgtcaata | aagagcacaa | cagtaacttt | 120 |
| aaagctggat | acattccgat | tgatgaagat | cgtctccaca | aaacagggtt | gagaggaaga | 180 |
| aagggcaatt | tagccatctg | tgtgattatc | ctcttgttta | tcctggctgt | catcaattta | 240 |
| ataataacac | ttgttatttg | ggccgtgatt | cgcattggac | aaatggctg | tgatagtatg | 300 |
| gagtttcatg | aaagtggcct | gcttcgattt | aagcaagtat | ctgacatggg | agtgatccac | 360 |
| cctctttata | aaagcacagt | aggaggaagg | cgaaatgaaa | atttggtcat | cactggcaac | 420 |
| aaccagccta | ttgtttttca | gcaagggaca | acaaagctca | gtgtagaaaa | caacaaaact | 480 |
| tctattacaa | gtgacatcgg | catgcagttt | tttgacccga | ggactcaaaa | tatcttattc | 540 |
| agcacagact | atgaaactca | tgagtttcat | ttgccaagtg | gagtgaaaag | tttgaatgtt | 600 |
| caaaaggcat | ctactgaaag | gattaccagc | aatgctacca | gtgatttaaa | tataaaagtt | 660 |
| gatgggcgtg | ctattgtgcg | tggaaatgaa | ggtgtattca | ttatgggcaa | aaccattgaa | 720 |
| tttcacatgg | gtggtaatat | ggagttaaag | gcggaaaaca | gtatcatcct | aaatggatct | 780 |
| gtgatggtca | gcaccacccg | cctacccagt | tcctccagtg | gagaccagtt | gggtagtggt | 840 |

```
gactgggtac gctacaagct ctgcatgtgt gctgatggga cgctcttcaa ggtgcaagta    900
accagccaga acatgggctg ccaaatctca gacaacccct gtggaaacac tcattaa      957
```

<210> SEQ ID NO 19
<211> LENGTH: 957
<212> TYPE: DNA
<213> ORGANISM: Artificial Sequence
<220> FEATURE:
<223> OTHER INFORMATION: codon-optimized beta-sarcoglycan gene

<400> SEQUENCE: 19

```
atggctgctg ccgctgctgc tgcagctgaa cagcaatcta gcaacggccc cgtgaagaaa    60
tccatgcgcg agaaggccgt cgagcggaga tctgtgaaca agagcacaa cagcaacttc    120 aaggccggct acatccccat cgacgaggac agactgcaca agacaggcct gagaggcaga    180
aagggcaatc tggccatctg cgtgatcatc ctgctgttca tcctggccgt gatcaacctg    240
atcatcaccc tggtcatctg ggccgtgatt agaatcggcc caacggctg cgacagcatg    300 gaatttcacg agagcggcct gctgcggttc aaacaggtgt ccgatatggg cgtgatccat    360
ccactgtaca gagcaccgt tggcggcaga agaaacgaga tctggtcat caccggcaac    420 aaccagccta tcgtgtttca gcagggcacc accaagctga gcgtggaaaa caacaagacc    480
agcatcacca gcgacatcgg catgcagttc ttcgacccca gaacacagaa catcctgttc    540
agcaccgact acgagacaca cgagttccat ctgcctagcg gcgtgaagtc cctgaatgtg    600
cagaaggcca gcaccgagag aatcaccagc aatgccacct ccgacctgaa catcaaagtg    660
gacggcagag ccatcgtgcg gggaaatgag ggcgtgttca tcatgggcaa gaccatcgag    720
ttccacatgg cggcaacat ggaactgaag gccgagaaca gcatcatcct gaacggcagc    780
gtgatggtgt ccaccacaag actgccaagc agcagctctg gcgatcagct tggatctggc    840
gactgggtcc gatacaagct gtgtatgtgt gccgacggca cctgttcaa ggtgcaagtg    900 acaagccaga acatgggctg ccagatcagc gacaacccctt gcggcaatac ccactga     957
```

<210> SEQ ID NO 20
<211> LENGTH: 1653
<212> TYPE: DNA
<213> ORGANISM: Artificial Sequence
<220> FEATURE:
<223> OTHER INFORMATION: luciferase gene

<400> SEQUENCE: 20

```
atggaagatg ccaaaaacat taagaagggc ccagcgccat tctacccact cgaagacggg    60
accgccggcg agcagctgca caaagccatg aagcgctacg ccctggtgcc cggcaccatc    120
gcctttaccg acgcacatat cgaggtggac attacctacg ccgagtactt cgagatgagc    180
gttcggctgg cagaagctat gaagcgctat gggctgaata caaaccatcg gatcgtggtg    240
tgcagcgaga atagcttgca gttcttcatg cccgtgttgg tgccctgttt catcggtgtg    300
gctgtggccc cagctaacga catctacaac gagcgcgagc tgctgaacag catgggcatc    360
agccagccca ccgtcgtatt cgtgagcaag aaagggctgc aaaagatcct caacgtgcaa    420
aagaagctac cgatcataca aaagatcatc atcatggata gcaagaccga ctaccagggc    480
ttccaaagca tgtacacctt cgtgacttcc catttgccac ccggcttcaa cgagtacgac    540
ttcgtgcccg agagcttcga ccgggacaaa accatcgccc tgatcatgaa cagtagtggc    600
agtaccggat tgcccaaggg cgtagcccta ccgcaccgca ccgcttgtgt ccgattcagt    660
```

| | | |
|---|---|---|
| catgcccgcg acccatctt cggcaaccag atcatcccg acaccgctat cctcagcgtg | 720 | |
| gtgccatttc accacggctt cggcatgttc accacgctgg gctacttgat ctgcggcttt | 780 | |
| cgggtcgtgc tcatgtaccg cttcgaggag gagctattct tgcgcagctt gcaagactat | 840 | |
| aagattcaat ctgccctgct ggtgcccaca ctatttagct tcttcgctaa gagcactctc | 900 | |
| atcgacaagt acgacctaag caacttgcac gagatcgcca gcggcggggc gccgctcagc | 960 | |
| aaggaggtag gtgaggccgt ggccaaacgc ttccacctac caggcatccg ccagggctac | 1020 | |
| ggcctgacag aaacaaccag cgccattctg atcacccccg aaggggacga caagcctggc | 1080 | |
| gcagtaggca aggtggtgcc cttcttcgag gctaaggtgg tggacttgga caccggtaag | 1140 | |
| acactgggtg tgaaccagcg cggcgagctg tgcgtccgtg gccccatgat catgagcggc | 1200 | |
| tacgttaaca accccgaggc tacaaacgct ctcatcgaca aggacggctg gctgcacagc | 1260 | |
| ggcgacatcg cctactggga cgaggacgag cacttcttca tcgtggaccg gctgaagagc | 1320 | |
| ctgatcaaat acaagggcta ccaggtagcc cagccgaac tggagagcat cctgctgcaa | 1380 | |
| caccccaaca tcttcgacgc cggggtcgcc ggcctgcccg acgacgatgc cggcgagctg | 1440 | |
| cccgccgcag tcgtcgtgct ggaacacggt aaaaccatga ccgagaagga gatcgtggac | 1500 | |
| tatgtggcca gccaggttac aaccgccaag aagctgcgcg tggtgttgt gttcgtggac | 1560 | |
| gaggtgccta aaggactgac cggcaagttg gacgcccgca gatccgcga gattctcatt | 1620 | |
| aaggccaaga agggcggcaa gatcgccgtg taa | 1653 | |

<210> SEQ ID NO 21
<211> LENGTH: 4882
<212> TYPE: DNA
<213> ORGANISM: Artificial Sequence
<220> FEATURE:
<223> OTHER INFORMATION: AAV-CSK-SH5-SPc5-12-MVM-hB-SGco-pA

<400> SEQUENCE: 21

| | | |
|---|---|---|
| acatgtcctg caggcagctg cgcgctcgct cgctcactga ggccgcccgg gcaaagcccg | 60 | |
| ggcgtcgggc gacctttggt cgcccggcct cagtgagcga gcgagcgcgc agagagggag | 120 | |
| tggccaactc catcactagg ggttcctgcg gccggcgcgc cacgcgtcag tttactcacc | 180 | |
| agggattcag aggcagcact gctgaaccct gagcccttgg cacatcaggt tggctgtcag | 240 | |
| aagtcggcct ttgtacatac acagttccct tgtgaggccc agctgcgtgt cctaggagcg | 300 | |
| gggcctctct ccacagcaga gctcagcctc tcaagtgtat ggacagcacg ggtgcctgat | 360 | |
| gggtggattt agccatgagt tgaaggtggc ttggggagaa tgagagttct agagataggg | 420 | |
| agaaggggtt gccaatagga gagtggaatt cctgagcacc tcgtcacagg cagccgacag | 480 | |
| aacatgagcc gcagggccca ggctatttat acctcgcctg tcactatcag ggtccccaca | 540 | |
| gctcccccca cctccagcca cacacagcag gtccttttgc tctttctggt cccttctcta | 600 | |
| ctcctcccc tccctaccta aggtacccaa cgcgttacgt ggccaccgcc ttcggcacca | 660 | |
| tcctcacgac acccaaatat ggcgacgggt gaggaatggt ggggagttat ttttagagcg | 720 | |
| gtgaggaagg tgggcaggca gcaggtgttg gcgctctaaa aataactccc gggagttatt | 780 | |
| tttagagcgg aggaatggtg gacacccaaa tatggcgacg ttcctcacc cgtcgccata | 840 | |
| tttgggtgtc cgccctcggc cggggccgca ttcctggggg ccgggcggtg ctcccgcccg | 900 | |
| cctcgataaa aggctccggg gccgcggcg gccacgagc tacccggagg agcgggaggc | 960 | |
| gccaagctct agatctagaa agaggtaagg gtttaaggga tggttggttg gtggggtatt | 1020 | |
| aatgtttaat tacctggagc acctgcctga aatcactttt tttcaggttg gaagcttgcc | 1080 | |

```
accatggctg ctgccgctgc tgctgcagct gaacagcaat ctagcaacgg ccccgtgaag   1140
aaatccatgc gcgagaaggc cgtcgagcgg agatctgtga acaaagagca caacagcaac   1200
ttcaaggccg gctacatccc catcgacgag gacagactgc acaagacagg cctgagaggc   1260
agaaagggca atctgccat ctgcgtgatc atcctgctgt tcatcctggc cgtgatcaac    1320
ctgatcatca ccctggtcat ctgggccgtg attagaatcg ccccaacgg ctgcgacagc    1380 atggaatttc acgagagcgg cctgctgcgg ttcaaacagg tgtccgatat gggcgtgatc   1440
catccactgt acaagagcac cgttggcggc agaagaaacg agaatctggt catcaccggc   1500
aacaaccagc ctatcgtgtt tcagcagggc accaccaagc tgagcgtgga aaacaacaag   1560
accagcatca ccagcgacat cggcatgcag ttcttcgacc ccagaacaca gaacatcctg   1620
ttcagcaccg actacgagac acacgagttc catctgccta gcggcgtgaa gtccctgaat   1680
gtgcagaagg ccagcaccga gagaatcacc agcaatgcca cctccgacct gaacatcaaa   1740
gtggacggca gagccatcgt gcggggaaat gagggcgtgt tcatcatggg caagaccatc   1800
gagttccaca tgggcggcaa catggaactg aaggccgaga acagcatcat cctgaacggc   1860
agcgtgatga tgtccaccac aagactgcca agcagcagct ctggcgatca gcttggatct   1920
ggcgactggg tccgatacaa gctgtgtatg tgtgccgacg gcaccctgtt caaggtgcaa   1980
gtgacaagcc agaacatggg ctgccagatc agcgacaacc cttgcggcaa tacccactga   2040
ttcgaaacgt tcggtccatc ttgagcatct gacttctggc taaataaaag atctttattt   2100
tcattagatc tgtgtgttgg tttttgtgt gcgtcgagat ccacggccgc aggaacccct    2160
agtgatggag ttggccactc cctctctgcg cgctcgctcg ctcactgagg ccgggcgacc   2220
aaaggtcgcc cgacgcccgg gctttgcccg ggcggcctca gtgagcgagc gagcgcgcag   2280
ctgcctgcag gggcgcctga tgcggtattt tctccttacg catctgtgcg gtatttcaca   2340
ccgcatacgt caaagcaacc atagtacgcg ccctgtagcg cgcattaag cgcggcgggt    2400 gtggtggtta cgcgcagcgt gaccgctaca cttgccagcg ccctagcgcc cgctcctttc   2460
gctttcttcc cttcctttct cgccacgttc gccggctttc cccgtcaagc tctaaatcgg   2520
gggctcccct tagggttccg atttagtgct ttacggcacc tcgaccccaa aaaacttgat   2580
ttgggtgatg gttcacgtag tgggccatcg ccctgataga cggttttcg ccctttgacg    2640 ttggagtcca cgttctttaa tagtggactc ttgttccaaa ctggaacaac actcaaccct   2700
atctcgggct attcttttga tttataaggg attttgccga tttcggccta ttggttaaaa   2760
aatgagctga tttaacaaaa atttaacgcg aattttaaca aaatattaac gtttacaatt   2820
ttatggtgca ctctcagtac aatctgctct gatgccgcat agttaagcca gccccgacac   2880
ccgccaacac ccgctgacgc gccctgacgg gcttgtctgc tcccggcatc cgcttacaga   2940
caagctgtga ccgtctccgg gagctgcatg tgtcagaggt tttcaccgtc atcaccgaaa   3000
cgcgcgagac gaaagggcct cgtgatacgc ctatttttat aggttaatgt catgataata   3060
atggtttctt agacgtcagg tggcacttt cggggaaatg tgcgcggaac ccctatttgt    3120
ttatttttct aaatacattc aaatatgtat ccgctcatga gacaataacc ctgataaatg   3180
cttcaataat attgaaaaag gaagagtatg agtattcaac atttccgtgt cgcccttatt   3240 ccctttttg cggcattttg ccttcctgtt tttgctcacc cagaaacgct ggtgaaagta    3300
aaagatgctg aagatcagtt gggtgcacga gtgggttaca tcgaactgga tctcaacagc   3360
ggtaagatcc ttgagagttt tcgccccgaa gaacgttttc caatgatgag cacttttaaa   3420
```

```
gttctgctat gtggcgcggt attatcccgt attgacgccg gcaagagca actcggtcgc   3480
cgcatacact attctcagaa tgacttggtt gagtactcac cagtcacaga aaagcatctt   3540
acggatggca tgacagtaag agaattatgc agtgctgcca taaccatgag tgataacact   3600
gcggccaact tacttctgac aacgatcgga ggaccgaagg agctaaccgc ttttttgcac   3660
aacatggggg atcatgtaac tcgccttgat cgttgggaac cggagctgaa tgaagccata   3720
ccaaacgacg agcgtgacac cacgatgcct gtagcaatgg caacaacgtt gcgcaaacta   3780
ttaactggcg aactacttac tctagcttcc cggcaacaat taatagactg gatggaggcg   3840
gataaagttg caggaccact tctgcgctcg gcccttccgg ctggctggtt tattgctgat   3900
aaatctggag ccggtgagcg tgggtctcgc ggtatcattg cagcactggg gccagatggt   3960
aagccctccc gtatcgtagt tatctacacg acggggagtc aggcaactat ggatgaacga   4020
aatagacaga tcgctgagat aggtgcctca ctgattaagc attggtaact gtcagaccaa   4080
gtttactcat atatacttta gattgattta aaacttcatt tttaatttaa aaggatctag   4140
gtgaagatcc ttttttgataa tctcatgacc aaaatccctt aacgtgagtt ttcgttccac   4200
tgagcgtcag accccgtaga aaagatcaaa ggatcttctt gagatccttt ttttctgcgc   4260
gtaatctgct gcttgcaaac aaaaaaacca ccgctaccag cggtggtttg tttgccggat   4320
caagagctac caactctttt tccgaaggta actggcttca gcagagcgca gataccaaat   4380
actgtccttc tagtgtagcc gtagttaggc caccacttca agaactctgt agcaccgcct   4440
acatacctcg ctctgctaat cctgttacca gtggctgctg ccagtggcga taagtcgtgt   4500
cttaccgggt tggactcaag acgatagtta ccggataagg cgcagcggtc gggctgaacg   4560
gggggttcgt gcacacagcc cagcttggag cgaacgacct acaccgaact gagatacta   4620
cagcgtgagc tatgagaaag cgccacgctt cccgaaggga gaaaggcgga caggtatccg   4680
gtaagcggca gggtcggaac aggagagcgc acgagggagc ttccaggggg aaacgcctgg   4740
tatctttata gtcctgtcgg gtttcgccac ctctgacttg agcgtcgatt tttgtgatgc   4800
tcgtcagggg ggcggagcct atggaaaaac gccagcaacg cggcctttt acggttcctg   4860
gccttttgct ggccttttgc tc                                          4882
```

<210> SEQ ID NO 22
<211> LENGTH: 4882
<212> TYPE: DNA
<213> ORGANISM: Artificial Sequence
<220> FEATURE:
<223> OTHER INFORMATION: AAV-CSK-SH5-SPc5-12-MVM-hB-SG-pA

<400> SEQUENCE: 22

```
acatgtcctg caggcagctg cgcgctcgct cgctcactga ggccgcccgg gcaaagcccg    60
ggcgtcgggc gacctttggt cgcccggcct cagtgagcga gcgagcgcgc agagagggag   120
tggccaactc catcactagg ggttcctgcg gccggcgcgc cacgcgtcag tttactcacc   180
agggattcag aggcagcact gctgaaccct gagcccttgg cacatcaggt tggctgtcag   240
aagtcggcct ttgtacatac acagttccct tgtgaggccc agctgcgtgt cctaggagcg   300
gggcctctct ccacagcaga gctcagcctc tcaagtgtat ggacagcacg ggtgcctgat   360
gggtggattt agccatgagt tgaaggtggc ttggggagaa tgagagttct agagataggg   420
agaaggggtt gccaatagga gagtggaatt cctgagcacc tcgtcacagg cagccgacag   480
aacatgagcc gcagggccca ggctatttat acctcgcctg tcactatcag ggtccccaca   540
gctccccccca cctccagcca cacacagcag gtccttttgc tctttctggt cccttctcta   600
```

```
ctcctccccc tccctaccta aggtacccaa cgcgttacgt ggccaccgcc ttcggcacca      660
tcctcacgac acccaaatat ggcgacgggt gaggaatggt ggggagttat ttttagagcg      720
gtgaggaagg tgggcaggca gcaggtgttg gcgctctaaa ataactccc gggagttatt      780 tttagagcgg aggaatggtg gacacccaaa tatggcgacg gttcctcacc cgtcgccata      840
tttgggtgtc cgccctcggc cggggccgca ttcctggggg ccgggcggtg ctcccgcccg      900
cctcgataaa aggctccggg gccggcgcg gcccacgagc tacccggagg agcgggaggc      960
gccaagctct agatctagaa agaggtaagg gtttaaggga tggttggttg gtgggtatt     1020 aatgttttaat tacctggagc acctgcctga aatcactttt tttcaggttg gaagcttgcc    1080
accatggcgg cagcggcggc ggcggctgca gaacagcaaa gttccaatgg tcctgtaaag    1140
aagtccatgc gtgagaaggc tgttgagaga aggagtgtca ataaagagca caacagtaac    1200
tttaaagctg gatacattcc gattgatgaa gatcgtctcc acaaacagg gttgagagga     1260 agaagggca atttagccat ctgtgtgatt atcctcttgt ttatcctggc tgtcatcaat     1320
ttaataataa cacttgttat ttgggccgtg attcgcattg gaccaaatgg ctgtgatagt    1380
atggagtttc atgaaagtgg cctgcttcga tttaagcaag tatctgacat gggagtgatc    1440
caccctcttt ataaaagcac agtaggagga aggcgaaatg aaaatttggt catcactggc   1500
aacaaccagc ctattgtttt tcagcaaggg acaacaaagc tcagtgtaga aaacaacaaa   1560
acttctatta caagtgacat cggcatgcag tttttgacc cgaggactca aaatatctta    1620
ttcagcacag actatgaaac tcatgagttt catttgccaa gtggagtgaa agtttgaat    1680 gttcaaaagg catctactga aaggattacc agcaatgcta ccagtgatt aaatataaaa    1740 gttgatgggc gtgctattgt gcgtggaaat aaggtgtat tcattatggg caaaaccatt    1800
gaatttcaca tgggtggtaa tatggagtta aaggcggaaa acagtatcat cctaaatgga   1860
tctgtgatgg tcagcaccac ccgcctaccc agttcctcca gtggagacca gttgggtagt   1920
ggtgactggg tacgctacaa gctctgcatg tgtgctgatg ggacgctctt caaggtgcaa   1980
gtaaccagcc agaacatggg ctgccaaatc tcagacaacc cctgtggaaa cactcattaa   2040
ttcgaaacgt tcggtccatc ttgagcatct gacttctggc taaataaaag atctttattt   2100
tcattagatc tgtgtgttgg ttttttgtgt gcgtcgagat ccacggccgc aggaacccct   2160
agtgatggag ttggccactc cctctctgcg cgctcgctcg ctcactgagg ccgggcgacc   2220
aaaggtcgcc cgacgcccgg gctttgcccg ggcggcctca gtgagcgagc gagcgcgcag   2280
ctgcctgcag gggcgcctga tgcggtattt tctccttacg catctgtgcg gtatttcaca   2340
ccgcatacgt caaagcaacc atagtacgcg ccctgtagcg gcgcattaag cgcggcgggt   2400
gtggtggtta cgcgcagcgt gaccgctaca cttgccagcg ccctagcgcc cgctcctttc   2460
gctttcttcc cttcctttct cgccacgttc gccggctttc cccgtcaagc tctaaatcgg   2520
gggctccctt tagggttccg atttagtgct ttacggcacc tcgaccccaa aaaacttgat   2580
ttgggtgatg gttcacgtag tgggccatcg ccctgataga cggttttcg ccctttgacg    2640 ttggagtcca cgttctttaa tagtggactc ttgttccaaa ctggaacaac actcaaccct    2700
atctcgggct attcttttga tttataaggg attttgccga tttcggccta ttggttaaaa    2760
aatgagctga tttaacaaaa atttaacgcg aattttaaca aaatattaac gtttacaatt    2820
ttatggtgca ctctcagtac aatctgctct gatgccgcat agttaagcca gccccgacac    2880
ccgccaacac ccgctgacgc gccctgacgg gcttgtctgc tcccggcatc cgcttacaga    2940
```

| | |
|---|---|
| caagctgtga ccgtctccgg agctgcatg tgtcagaggt tttcaccgtc atcaccgaaa | 3000 |
| cgcgcgagac gaaagggcct cgtgatacgc ctatttttat aggttaatgt catgataata | 3060 |
| atggtttctt agacgtcagg tggcactttt cggggaaatg tgcgcggaac ccctatttgt | 3120 |
| ttatttttct aaatacattc aaatatgtat ccgctcatga caataaacc ctgataaatg | 3180 |
| cttcaataat attgaaaaag gaagagtatg agtattcaac atttccgtgt cgcccttatt | 3240 |
| cccttttttg cggcattttg ccttcctgtt tttgctcacc cagaaacgct ggtgaaagta | 3300 |
| aaagatgctg aagatcagtt gggtgcacga gtgggttaca tcgaactgga tctcaacagc | 3360 |
| ggtaagatcc ttgagagttt tcgccccgaa gaacgttttc caatgatgag cacttttaaa | 3420 |
| gttctgctat gtggcgcggt attatcccgt attgacgccg ggcaagagca actcggtcgc | 3480 |
| cgcatacact attctcagaa tgacttggtt gagtactcac cagtcacaga aaagcatctt | 3540 |
| acggatggca tgacagtaag agaattatgc agtgctgcca taaccatgag tgataacact | 3600 |
| gcggccaact tacttctgac aacgatcgga ggaccgaagg agctaaccgc ttttttgcac | 3660 |
| aacatggggg atcatgtaac tcgccttgat cgttgggaac cggagctgaa tgaagccata | 3720 |
| ccaaacgacg agcgtgacac cacgatgcct gtagcaatgg caacaacgtt gcgcaaacta | 3780 |
| ttaactggcg aactacttac tctagcttcc cggcaacaat taatagactg gatggaggcg | 3840 |
| gataaagttg caggaccact tctgcgctcg gcccttccgg ctggctggtt tattgctgat | 3900 |
| aaatctggag ccggtgagcg tgggtctcgc ggtatcattg cagcactggg gccagatggt | 3960 |
| aagccctccc gtatcgtagt tatctacacg acggggagtc aggcaactat ggatgaacga | 4020 |
| aatagacaga tcgctgagat aggtgcctca ctgattaagc attggtaact gtcagaccaa | 4080 |
| gtttactcat atatacttta gattgattta aaacttcatt tttaatttaa aaggatctag | 4140 |
| gtgaagatcc tttttgataa tctcatgacc aaaatccctt aacgtgagtt ttcgttccac | 4200 |
| tgagcgtcag accccgtaga aaagatcaaa ggatcttctt gagatccttt ttttctgcgc | 4260 |
| gtaatctgct gcttgcaaac aaaaaaacca ccgctaccag cggtggtttg tttgccggat | 4320 |
| caagagctac caactctttt tccgaaggta actggcttca gcagagcgca gataccaaat | 4380 |
| actgtccttc tagtgtagcc gtagttaggc caccacttca agaactctgt agcaccgcct | 4440 |
| acatacctcg ctctgctaat cctgttacca gtggctgctg ccagtggcga taagtcgtgt | 4500 |
| cttaccgggt tggactcaag acgatagtta ccggataagg cgcagcggtc gggctgaacg | 4560 |
| gggggttcgt gcacacagcc cagcttggag cgaacgacct acaccgaact gagataccta | 4620 |
| cagcgtgagc tatgagaaag cgccacgctt cccgaaggga gaaaggcgga caggtatccg | 4680 |
| gtaagcggca gggtcggaac aggagagcgc acgagggagc ttccagggga aaacgcctgg | 4740 |
| tatctttata gtcctgtcgg gtttcgccac ctctgacttg agcgtcgatt tttgtgatgc | 4800 |
| tcgtcagggg ggcggagcct atggaaaaac gccagcaacg cggccttttt acggttcctg | 4860 |
| gccttttgct ggccttttgc tc | 4882 |

<210> SEQ ID NO 23
<211> LENGTH: 5323
<212> TYPE: DNA
<213> ORGANISM: Artificial Sequence
<220> FEATURE:
<223> OTHER INFORMATION: AAV-CRE02-CSK-SH5-SPc5-12-MVM-hB-SGco-pA

<400> SEQUENCE: 23

| | |
|---|---|
| cctgcaggca gctgcgcgct cgctcgctca ctgaggccgc ccgggcgtcg ggcgaccttt | 60 |
| ggtcgcccgg cctcagtgag cgagcgagcg cgcagagagg gagtggccaa ctccatcact | 120 |

```
aggggttcct gcggccgaca ggtgcggttc ccggagcgca ggcgcacaca tgcacccacc      180
ggcgaacgcg gtgaccctcg ccccacccca tccccctccgg cgggcaactg ggtcgggtca     240 ggagggggcaa acccgctagg gagacactcc atatacggcc cggcccgcgt tacctgggac    300
cgggccaacc cgctccttct ttggtcaacg caggggaccc gggcggggc ccaggccgcg       360 aaccggccga gggagggggc tctagtgccc aacacccaaa tatggctcga agggcagc        420 gacattcctg cggggtggcg cggagggaat gcccgcgggc tatataaaac ctgagcagag     480
ggacaagcgg ccaccgcagc ggacagcgcc aagtgaagcc tcgcttcccc tccgcggcga     540
ccagggcccg agccgagagt agcagttgta gctacccgcc caggtagggg cgcgccacgc     600
gtcagtttac tcaccaggga ttcagaggca gcactgctga accctgagcc cttggcacat    660
caggttggct gtcagaagtc ggcctttgta catacacagt tcccttgtga ggcccagctg     720
cgtgtcctag gagcggggcc tctctccaca gcagagctca gcctctcaag tgtatggaca    780
gcacgggtgc ctgatgggtg gatttagcca tgagttgaag gtggcttggg gagaatgaga    840
gttctagaga tagggagaag gggttgccaa taggagagtg gaattcctga gcacctcgtc    900
acaggcagcc gacagaacat gagccgcagg gcccaggcta tttataccctc gcctgtcact    960 atcagggtcc ccacagctcc ccccaccctcc agccacacac agcaggtcct tttgctcttt   1020 ctggtcccctt ctctactcct cccctccct acctaaggta cccaacgcgt tacgtggcca   1080
ccgccttcgg caccatcctc acgacaccca aatatggcga cgggtgagga atggtgggga    1140 gttatttta gagcggtgag gaaggtgggc aggcagcagg tgttggcgct ctaaaaataa      1200
ctcccgggag ttattttag agcggaggaa tggtggacac ccaaatatgg cgacggttcc    1260
tcacccgtcg ccatatttgg gtgtccgccc tcggccgggg ccgcattcct ggggccggg    1320 cggtgctccc gcccgcctcg ataaaaggct ccggggccgg cggcggccca cgagctaccc   1380
ggaggagcgg gaggcgccaa gctctagatc tagaaagagg taagggttta agggatggtt   1440
ggttggtggg gtattaatgt ttaattacct ggagcacctg cctgaaatca cttttttttca  1500 ggttggaagc ttgccaccat ggctgctgcc gctgctgctg cagctgaaca gcaatctagc    1560
aacggccccg tgaagaaatc catgcgcgag aaggccgtcg agcggagatc tgtgaacaaa    1620
gagcacaaca gcaacttcaa ggccggctac atccccatcg acgaggacag actgcacaag   1680
acaggcctga gaggcagaaa gggcaatctg gccatctgcg tgatcatcct gctgttcatc   1740
ctggccgtga tcaacctgat catcaccctg gtcatctggg ccgtgattag aatcggcccc   1800
aacggctgcg acagcatgga atttcacgag agcggcctgc tgcggttcaa acaggtgtcc   1860
gatatgggcg tgatccatcc actgtacaag agcaccgttg gcggcagaag aaacgagaat   1920
ctggtcatca ccggcaacaa ccagcctatc gtgtttcagc agggcaccac caagctgagc   1980
gtggaaaaca acaagaccag catcaccagc gacatcggca tgcagttctt cgaccccaga   2040
acacagaaca tcctgttcag caccgactac gagacacacg agttccatct gcctagcggc   2100
gtgaagtccc tgaatgtgca gaaggccagc accgagagaa tcaccagcaa tgccacctcc   2160
gacctgaaca tcaaagtgga cggcagagcc atcgtgcggg gaaatgaggg cgtgttcatc   2220
atgggcaaga ccatcgagtt ccacatgggc ggcaacatgg aactgaaggc cgagaacagc   2280
atcatcctga acggcagcgt gatggtgtcc accacaagac tgccaagcag cagctctggc   2340
gatcagcttg gatctggcga ctgggtccga tacaagctgt gtatgtgtgc cgacggcacc   2400
ctgttcaagg tgcaagtgac aagccagaac atgggctgcc agatcagcga caacccttgc   2460
```

-continued

```
ggcaataccc actgattcga aacgtcaagt ccatcttgag catctgactt ctggctaaat    2520
aaaagatctt tattttcatt agatctgtgt gttggttttt tgtgtgcgtc gagatccacg    2580
gccgcaggaa cccctagtga tggagttggc cactccctct ctgcgcgctc gctcgctcac    2640
tgaggccggg cgaccaaagg tcgcccgacg cccgggcttt gccgggcgg cctcagtgag     2700 cgagcgagcg cgcagctgcc tgcaggggcg cctgatgcgg tattttctcc ttacgcatct    2760
gtgcggtatt tcacaccgca tacgtcaaag caaccatagt acgcgccctg tagcggcgca    2820
ttaagcgcgg cgggtgtggt ggttacgcgc agcgtgaccg ctacacttgc cagcgcccta    2880
gcgcccgctc ctttcgcttt cttcccttcc tttctcgcca cgttcgccgg ctttccccgt    2940
caagctctaa atcgggggct ccctttaggg ttccgattta gtgctttacg gcacctcgac    3000
cccaaaaaac ttgatttggg tgatggttca cgtagtgggc catcgccctg atagacggtt    3060
tttcgccctt tgacgttgga gtccacgttc tttaatagtg actcttgtt ccaaactgga     3120 acaacactca accctatctc gggctattct tttgatttat aagggatttt gccgatttcg    3180
gcctattggt taaaaatga gctgatttaa caaaaattta acgcgaattt taacaaaata     3240
ttaacgttta caattttatg gtgcactctc agtacaatct gctctgatgc cgcatagtta    3300
agccagcccc gacacccgcc aacacccgct gacgcgccct gacgggcttg tctgctcccg    3360
gcatccgctt acagacaagc tgtgaccgtc tccgggagct gcatgtgtca gaggttttca    3420
ccgtcatcac cgaaacgcgc gagacgaaag ggcctcgtga tacgcctatt tttataggtt    3480
aatgtcatga taataatggt ttcttagacg tcaggtggca cttttcgggg aaatgtgcgc    3540 ggaacccta tttgtttatt tttctaaata cattcaaata tgtatccgct catgagacaa     3600
taaccctgat aaatgcttca ataatattga aaaggaaga gtatgagtat caacatttc      3660 cgtgtcgccc ttattccctt ttttgcggca ttttgccttc ctgtttttgc tcacccagaa    3720
acgctggtga agtaaaaga tgctgaagat cagttgggtg cacgagtggg ttacatcgaa     3780
ctggatctca acagcggtaa gatccttgag agttttcgcc ccgaagaacg ttttccaatg    3840
atgagcactt ttaaagttct gctatgtggc gcggtattat cccgtattga cgccgggcaa    3900
gagcaactcg gtcgccgcat acactattct cagaatgact tggttgagta ctcaccagtc    3960
acagaaaagc atcttacgga tggcatgaca gtaagagaat tatgcagtgc tgccataacc    4020
atgagtgata acactgcggc caacttactt ctgacaacga tcggaggacc gaaggagcta    4080
accgcttttt tgcacaacat gggggatcat gtaactcgcc ttgatcgttg ggaaccggag    4140
ctgaatgaag ccataccaaa cgacgagcgt gacaccacga tgcctgtagc aatggcaaca    4200
acgttgcgca aactattaac tggcgaacta cttactctag cttcccggca acaattaata    4260
gactggatgg aggcggataa agttgcagga ccacttctgc gctcggccct tccggctggc    4320
tggtttattg ctgataaatc tggagccggt gagcgtgggt ctcgcggtat cattgcagca    4380
ctggggccag atggtaagcc ctcccgtatc gtagttatct acacgacggg gagtcaggca    4440
actatggatg aacgaaatag acagatcgct gagataggtg cctcactgat taagcattgg    4500
taactgtcag accaagttta ctcatatata ctttagattg atttaaaact tcatttttaa    4560
tttaaaagga tctaggtgaa gatcctttt gataatctca tgaccaaaat cccttaacgt     4620
gagttttcgt tccactgagc gtcagacccc gtagaaaaga tcaaaggatc ttcttgagat    4680
cctttttttc tgcgcgtaat ctgctgcttg caaacaaaaa aaccaccgct accagcggtg    4740
gtttgtttgc cggatcaaga gctaccaact ctttttccga aggtaactgg cttcagcaga    4800
gcgcagatac caaatactgt ccttctagtg tagccgtagt taggccacca cttcaagaac    4860
```

```
tctgtagcac cgcctacata cctcgctctg ctaatcctgt taccagtggc tgctgccagt    4920
ggcgataagt cgtgtcttac cgggttggac tcaagacgat agttaccgga taaggcgcag    4980
cggtcgggct gaacgggggg ttcgtgcaca cagcccagct tggagcgaac gacctacacc    5040
gaactgagat acctcagcg tgagctatga aaagcgcca cgcttcccga agggagaaag     5100
```

```
gaactgagat acctcagcg tgagctatga aaagcgcca cgcttcccga agggagaaag     5100
gcggacaggt atccggtaag cggcagggtc ggaacaggag agcgcacgag ggagcttcca    5160
gggggaaacg cctggtatct ttatagtcct gtcgggtttc gccacctctg acttgagcgt    5220 cgattttgt gatgctcgtc agggggggcgg agcctatgga aaaacgccag caacgcggcc    5280
tttttacggt tcctggcctt ttgctggcct tttgctcaca tgt                     5323

<210> SEQ ID NO 24
<211> LENGTH: 5391
<212> TYPE: DNA
<213> ORGANISM: Artificial Sequence
<220> FEATURE:
<223> OTHER INFORMATION: AAV-CRE04-CSK-SH5-SPc5-12-MVM-hB-SGco-pA

<400> SEQUENCE: 24
acatgtcctg caggcagctg cgcgctcgct cgctcactga ggccgcccgg gcaaagcccg      60
ggcgtcgggc gacctttggt cgcccggcct cagtgagcga gcgagcgcgc agagagggag     120
tggccaactc catcactagg ggttcctgcg gcccctttta gagaatccac acctgtccca    180
gttgctgggt tccactacca aaagtgaatt gcaactattt taggagcact taagcacatc    240
cgaaaaatga gtgattctgt tctggcccac accacatcac tgatgtaccc ccttaaagca    300
tgtccctgag ttcatcacag aagactgctc ctcctgtgcc ctccacaagg ttagaactgt    360
ccttgtctta gggaaaaagg agagagagag agagagagag agagagagag agagagagag    420
agagagagag ggacaggcac caactgggta acctctgctg accccccactc tactttacca   480 taagtagctc caaatccttc tagaaaatct gaaaggcata gccccatata tcagtgatat    540
aaatagaacc tgcagcaggc tctggtaaat gatgactaca aggtggactg ggaggcagcc    600
cggccttggc aggcatcatc ctctaaatat aaagatgagt ttgttcagcc tttgcagaag    660
gaggcgcgcc acgcgtcagt ttactcacca gggattcaga ggcagcactg ctgaaccctg    720
agcccttggc acatcaggtt ggctgtcaga agtcggcctt tgtacataca cagttccctt    780
gtgaggccca gctgcgtgtc ctaggagcgg ggcctctctc cacagcagag ctcagcctct    840
caagtgtatg gacagcacgg gtgcctgatg ggtggattta gccatgagtt gaaggtggct    900
tggggagaat gagagttcta gagatagga gaaggggttg caataggag agtggaattc     960 ctgagcacct cgtcacaggc agccgacaga acatgagccg cagggcccag gctatttata   1020
cctcgcctgt cactatcagg gtccccacag ctcccccac ctccagccac acacagcagg   1080
tccttttgct ctttctggtc ccttctctac tcctcccccct ccctacctaa ggtacccaac   1140
gcgttacgtg gccaccgcct tcggcaccat cctcacgaca cccaaatatg cgacgggtg    1200 aggaatggtg gggagttatt tttagagcgg tgaggaaggt gggcaggcag caggtgttgg   1260
cgctctaaaa ataactcccg ggagttattt ttagagcgga ggaatggtgg acacccaaat   1320
atggcgacgg ttcctcaccc gtcgccatat ttgggtgtcc gccctcggcc ggggccgcat   1380 tcctggggc cggcggtgc tcccgcccgc ctcgataaaa ggctccgggg ccggcggcgg     1440
cccacgagct acccggagga gcggaggcg ccaagctcta gatctagaaa gaggtaaggg    1500
tttaagggat ggttggttgg tggggtatta atgtttaatt acctggagca cctgcctgaa   1560
```

```
atcactttttt ttcaggttgg aagcttgcca ccatggctgc tgccgctgct gctgcagctg    1620
aacagcaatc tagcaacggc cccgtgaaga atccatgcg cgagaaggcc gtcgagcgga     1680
gatctgtgaa caaagagcac aacagcaact tcaaggccgg ctacatcccc atcgacgagg    1740
acagactgca caagacaggc ctgagaggca gaaagggcaa tctggccatc tgcgtgatca    1800
tcctgctgtt catcctggcc gtgatcaacc tgatcatcac cctggtcatc tgggccgtga    1860
ttagaatcgg ccccaacggc tgcgacagca tggaatttca cgagagcggc ctgctgcggt    1920
tcaaacaggt gtccgatatg ggcgtgatcc atccactgta caagagcacc gttggcggca    1980
gaagaaacga gaatctggtc atcaccggca caaccagcc tatcgtgttt cagcagggca    2040
ccaccaagct gagcgtggaa acaacaaga ccagcatcac cagcgacatc ggcatgcagt     2100
tcttcgaccc cagaacacag aacatcctgt tcagcaccga ctacgagaca cacgagttcc    2160
atctgcctag cggcgtgaag tccctgaatg tgcagaaggc cagcaccgag agaatcacca    2220
gcaatgccac ctccgacctg aacatcaaag tggacggcag agccatcgtg cggggaaatg    2280
agggcgtgtt catcatgggc aagaccatcg agttccacat gggcggcaac atggaactga    2340
aggccgagaa cagcatcatc ctgaacggca gcgtgatggt gtccaccaca agactgccaa    2400
gcagcagctc tggcgatcag cttggatctg cgactgggc ccgatacaag ctgtgtatgt     2460
gtgccgacgg caccctgttc aaggtgcaag tgacaagcca gaacatgggc tgccagatca    2520
gcgacaaccc ttgcggcaat acccactgat tcgaaacgtc acgtccatct tgagcatctg    2580
acttctggct aaataaaaga tctttatttt cattagatct gtgtgttggt tttttgtgtg    2640
cgtcgagatc cacggccgca ggaacccta gtgatggagt tggccactcc ctctctgcgc     2700
gctcgctcgc tcactgaggc cgggcgacca aggtcgccc gacgcccggg ctttgcccgg     2760
gcggcctcag tgagcgagcg agcgcgcagc tgcctgcagg ggcgcctgat gcggtatttt    2820
ctccttacgc atctgtgcgg tatttcacac cgcatacgtc aaagcaacca tagtacgcgc    2880
cctgtagcgc gcattaagc gcggcgggtg tggtggttac gcgcagcgtg accgctacac     2940
ttgccagcgc cctagcgccc gctcctttcg ctttcttccc ttcctttctc gccacgttcg    3000
ccggctttcc ccgtcaagct ctaaatcggg ggctcccttt agggttccga tttagtgctt    3060
tacggcacct cgaccccaaa aaacttgatt tgggtgatgg ttcacgtagt gggccatcgc    3120
cctgatagac ggttttttcgc cctttgacgt tggagtccac gttctttaat agtggactct    3180
tgttccaaac tggaacaaca ctcaaccta tctcgggcta ttcttttgat ttataaggga     3240
ttttgccgat ttcggcctat tggttaaaaa atgagctgat ttaacaaaaa tttaacgcga    3300
attttaacaa aatattaacg tttacaattt tatggtgcac tctcagtaca atctgctctg    3360
atgccgcata gttaagccag ccccgacacc cgccaacacc cgctgacgcg ccctgacggg    3420
cttgtctgct cccggcatcc gcttacagac aagctgtgac cgtctccggg agctgcatgt    3480
gtcagaggtt ttcaccgtca tcaccgaaac gcgcgagacg aaagggcctc gtgatacgcc    3540
tatttttata ggttaatgtc atgataataa tggtttctta gacgtcaggt ggcacttttc    3600
ggggaaatgt gcgcggaacc cctatttgtt tattttccta atacattca aatatgtatc     3660 cgctcatgag acaataaccc tgataaatgc ttcaataata ttgaaaaagg aagagtatga    3720
gtattcaaca tttccgtgtc gcccttattc ccttttttgc ggcattttgc cttcctgttt    3780
ttgctcaccc agaaacgctg gtgaaagtaa aagatgctga agatcagttg ggtgcacgag    3840
tgggttacat cgaactggat ctcaacagcg gtaagatcct tgagagtttt cgccccgaag    3900
aacgttttcc aatgatgagc acttttaaag ttctgctatg tggcgcggta ttatcccgta    3960
```

```
ttgacgccgg gcaagagcaa ctcggtcgcc gcatacacta ttctcagaat gacttggttg     4020
agtactcacc agtcacagaa aagcatctta cggatggcat gacagtaaga gaattatgca     4080
gtgctgccat aaccatgagt gataacactg cggccaactt acttctgaca acgatcggag     4140
gaccgaagga gctaaccgct tttttgcaca acatggggga tcatgtaact cgccttgatc     4200
gttgggaacc ggagctgaat gaagccatac caaacgacga gcgtgacacc acgatgcctg     4260
tagcaatggc aacaacgttg cgcaaactat taactggcga actacttact ctagcttccc     4320
ggcaacaatt aatagactgg atggaggcgg ataaagttgc aggaccactt ctgcgctcgg     4380
cccttccggc tggctggttt attgctgata atctggagc cggtgagcgt gggtctcgcg      4440
gtatcattgc agcactgggg ccagatggta agccctcccg tatcgtagtt atctacacga     4500
cggggagtca ggcaactatg gatgaacgaa atagacagat cgctgagata ggtgcctcac     4560
tgattaagca ttggtaactg tcagaccaag tttactcata tatactttag attgatttaa     4620
aacttcattt ttaatttaaa aggatctagg tgaagatcct ttttgataat ctcatgacca     4680
aaatccctta acgtgagttt tcgttccact gagcgtcaga ccccgtagaa aagatcaaag     4740
gatcttcttg agatcctttt tttctgcgcg taatctgctg cttgcaaaca aaaaaaccac     4800
cgctaccagc ggtggtttgt ttgccggatc aagagctacc aactcttttt ccgaaggtaa     4860
ctggcttcag cagagcgcag ataccaaata ctgtccttct agtgtagccg tagttaggcc     4920
accacttcaa gaactctgta gcaccgccta catacctcgc tctgctaatc ctgttaccag     4980
tggctgctgc cagtggcgat aagtcgtgtc ttaccgggtt ggactcaaga cgatagttac     5040
cggataaggc gcagcggtcg ggctgaacgg ggggttcgtg cacacagccc agcttggagc     5100
gaacgaccta caccgaactg agatacctac agcgtgagct atgagaaagc gccacgcttc     5160
ccgaagggag aaaggcggac aggtatccgg taagcggcag gtcggaaca ggagagcgca      5220 cgagggagct ccaggggga aacgcctggt atctttatag tcctgtcggg tttcgccacc      5280
tctgacttga gcgtcgattt tgtgatgct cgtcagggg gcggagccta tggaaaaacg       5340
ccagcaacgc ggcctttta cggttcctgg ccttttgctg ccttttgct c                5391
```

<210> SEQ ID NO 25
<211> LENGTH: 5271
<212> TYPE: DNA
<213> ORGANISM: Artificial Sequence
<220> FEATURE:
<223> OTHER INFORMATION: AAV-CRE06-CSK-SH5-SPc5-12-MVM-hB-SGco-pA

<400> SEQUENCE: 25

```
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact    120 agggggttcct gcggccgggc caggggacgg tggcttctac gtgcttggga cgttcccagc   180
caccgtccca tgttcccggc gggggccag ctgtccccac cgccagccca actcagcact    240
tggtcagggt atcagcttgg tggggggcg tgagcccagc cctggggcg gctcagccca    300 tacaaggcca tggggctggg cgcaaagcat gcctgggttc aggtgggta tggtgcggga    360 gcagggaggt gagaggctca gctgccctcc agaactcctc cctggggaca accctccca    420 gccaatagca cagcctaggt cccctatat aaggccacgg ctgctggcc ttcctttggg      480 tcagtgtcac ctccaggata cagacagccc ccttcagcc cagcccagcc aggtacggcg    540
cgccacgcgt cagtttactc accagggatt cagaggcagc actgctgaac cctgagccct   600
```

```
tggcacatca ggttggctgt cagaagtcgg cctttgtaca tacacagttc ccttgtgagg    660
cccagctgcg tgtcctagga gcggggcctc tctccacagc agagctcagc ctctcaagtg    720
tatggacagc acgggtgcct gatgggtgga tttagccatg agttgaaggt ggcttgggga    780
gaatgagagt tctagagata gggagaaggg gttgccaata ggagagtgga attcctgagc    840
acctcgtcac aggcagccga cagaacatga ccgcagggc ccaggctatt tatacctcgc    900
ctgtcactat cagggtcccc acagctcccc ccacctccag ccacacacag caggtccttt    960
tgctctttct ggtcccttct ctactcctcc ccctccctac ctaaggtacc caacgcgtta   1020
cgtggccacc gccttcggca ccatcctcac gacacccaaa tatggcgacg ggtgaggaat   1080
ggtggggagt tattttttaga gcggtgagga aggtgggcag cagcaggtg ttggcgctct    1140 aaaaataact cccgggagtt attttttagag cggaggaatg gtggacaccc aaatatggcg   1200
acggttcctc acccgtcgcc atatttgggt gtccgccctc ggccggggcc gcattcctgg   1260
gggccgggcg tgctcccgc ccgcctcgat aaaaggctcc ggggccggcg gcggcccacg    1320
agctacccgg aggagcggga ggcgccaagc tctagatcta gaaagaggta agggtttaag   1380
ggatggttgg ttggtggggt attaatgttt aattacctgg agcacctgcc tgaaatcact   1440 tttttttcagg ttggaagctt gccaccatgg ctgctgccgc tgctgctgca gctgaacagc   1500
aatctagcaa cggccccgtg aagaaatcca tgcgcgagaa ggccgtcgag cggagatctg   1560
tgaacaaaga gcaacagc aacttcaagg ccggctacat ccccatcgac gaggacagac    1620
tgcacaagac aggcctgaga ggcagaaagg gcaatctggc catctgcgtg atcatcctgc   1680
tgttcatcct ggccgtgatc aacctgatca tcacctggt catctgggcc gtgattagaa   1740
tcggccccaa cggctgcgac agcatggaat tcacgagag cggcctgctg cggttcaaac   1800
aggtgtccga tatgggcgtg atccatccac tgtacaagag caccgttggc ggcagaagaa   1860
acgagaatct ggtcatcacc ggcaacaacc agcctatcgt gtttcagcag ggcaccacca   1920
agctgagcgt ggaaaacaac aagaccagca tcaccagcga tcggcatg cagttcttcg    1980 accccagaac acagaacatc ctgttcagca ccgactacga gacacacgag ttccatctgc   2040
ctagcggcgt gaagtccctg aatgtgcaga aggccagcac cgagagaatc accagcaatg   2100
ccacctccga cctgaacatc aaagtggacg gcagagccat cgtgcgggga aatgagggcg   2160
tgttcatcat gggcaagacc atcgagttcc acatgggcgg caacatggaa ctgaaggccg   2220
agaacagcat catcctgaac ggcagcgtga tggtgtccac cacaagactg ccaagcagca   2280
gctctggcga tcagcttgga tctggcgact gggtccgata caagctgtgt atgtgtgccg   2340
acggcaccct gttcaaggtg caagtgacaa gccagaacat gggctgccag atcagcgaca   2400
acccttgcgg caataccac tgattcgaaa cgtctagtcc atcttgagca tctgacttct    2460
ggctaaataa aagatcttta ttttcattag atctgtgtgt tggttttttg tgtgcgtcga   2520 gatcacggc cgcaggaacc cctagtgatg gagttggcca ctccctctct gcgcgctcgc    2580
tcgctcactg aggccgggcg accaaaggtc gcccgacgcc cgggctttgc ccgggcggcc   2640
tcagtgagcg agcgagcgcg cagctgcctg caggggcgcc tgatgcggta ttttctcctt   2700
acgcatctgt gcggtatttc acaccgcata cgtcaaagca accatagtac gcgccctgta   2760
gcggcgcatt aagcgcggcg ggtgtggtgg ttacgcgcag cgtgaccgct acacttgcca   2820
gcgccctagc gcccgctcct ttcgctttct tcccttcctt tctcgccacg ttcgccggct   2880
ttccccgtca gctctaaat cggggcgtcc ctttagggtt ccgatttagt gctttacggc    2940
acctcgaccc caaaaaactt gatttgggtg atggttcacg tagtgggcca tcgccctgat   3000
```

-continued

```
agacggtttt tcgcccttgg acgttggagt ccacgttctt taatagtgga ctcttgttcc    3060
aaactggaac aacactcaac cctatctcgg gctattcttt tgatttataa gggattttgc    3120
cgatttcggc ctattggtta aaaatgagc tgatttaaca aaatttaac gcgaatttta    3180
acaaatatt aacgtttaca attttatggt gcactctcag tacaatctgc tctgatgccg    3240
catagttaag ccagccccga cacccgccaa cacccgctga cgcgccctga cgggcttgtc    3300
tgctcccggc atccgcttac agacaagctg tgaccgtctc cgggagctgc atgtgtcaga    3360
ggttttcacc gtcatcaccg aaacgcgcga gacgaaaggg cctcgtgata cgcctatttt    3420
tataggttaa tgtcatgata ataatggttt cttagacgtc aggtggcact tttcggggaa    3480
atgtgcgcgg aaccccctatt tgtttatttt tctaaataca ttcaaatatg tatccgctca    3540
tgagacaata accctgataa atgcttcaat aatattgaaa aaggaagagt atgagtattc    3600
aacatttccg tgtcgccctt attcccttt ttgcggcatt ttgccttcct gttttgctc    3660
acccagaaac gctggtgaaa gtaaaagatg ctgaagatca gttgggtgca cgagtgggtt    3720
acatcgaact ggatctcaac agcggtaaga tccttgagag ttttcgcccc gaagaacgtt    3780
ttccaatgat gagcactttt aaagttctgc tatgtggcgc ggtattatcc cgtattgacg    3840
ccgggcaaga gcaactcggt cgccgcatac actattctca gaatgacttg gttgagtact    3900
caccagtcac agaaaagcat cttacggatg gcatgacagt aagagaatta tgcagtgctg    3960
ccataaccat gagtgataac actgcggcca acttacttct gacaacgatc ggaggaccga    4020
aggagctaac cgcttttttg cacaacatgg gggatcatgt aactcgcctt gatcgttggg    4080
aaccggagct gaatgaagcc ataccaaacg acgagcgtga ccacgatgg cctgtagcaa    4140
tggcaacaac gttgcgcaaa ctattaactg gcgaactact tactctagct tcccggcaac    4200
aattaataga ctggatggag gcggataaag ttgcaggacc acttctgcgc tcggcccttc    4260
cggctggctg gtttattgct gataaatctg gagccggtga gcgtgggtct cgcggtatca    4320
ttgcagcact ggggccagat ggtaagccct cccgtatcgt agttatctac acgacgggga    4380
gtcaggcaac tatggatgaa cgaaatagac agatcgctga gataggtgcc tcactgatta    4440
agcattggta actgtcagac caagtttact catatatact ttagattgat ttaaaacttc    4500
atttttaatt taaaaggatc taggtgaaga tcctttttga taatctcatg accaaaatcc    4560
cttaacgtga gttttcgttc cactgagcgt cagaccccgt agaaaagatc aaaggatctt    4620
cttgagatcc ttttttttctg cgcgtaatct gctgcttgca acaaaaaaa ccaccgctac    4680
cagcggtggt ttgtttgccg gatcaagagc taccaactct ttttccgaag gtaactggct    4740
tcagcagagc gcagatacca atactgtcc ttctagtgta gccgtagtta ggccaccact    4800
tcaagaactc tgtagcaccg cctacatacc tcgctctgct aatcctgtta ccagtggctg    4860
ctgccagtgg cgataagtcg tgtcttaccg ggttggactc aagacgatag ttaccggata    4920
aggcgcagcg gtcgggctga acggggggtt cgtgcacaca gcccagcttg gagcgaacga    4980
cctacaccga actgagatac ctacagcgtg agctatgaga aagcgccacg cttcccgaag    5040
ggagaaaggc ggacaggtat ccggtaagcg gcagggtcgg aacaggagag cgcacgaggg    5100
agcttccagg gggaaacgcc tggtatcttt atagtcctgt cgggtttcgc cacctctgac    5160
ttgagcgtcg atttttgtga tgctcgtcag ggggcggag cctatggaaa aacgccagca    5220
acgcggcctt tttacggttc ctggcctttt gctggccttt tgctcacatg t             5271
```

<210> SEQ ID NO 26

<211> LENGTH: 5864
<212> TYPE: DNA
<213> ORGANISM: Artificial Sequence
<220> FEATURE:
<223> OTHER INFORMATION: AAV-CRE02-CRE04-CSK-SH5-SPc5-12-MVM-hB-SGco-pA

<400> SEQUENCE: 26

```
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggccgaca ggtgcggttc ccggagcgca ggcgcacaca tgcacccacc     180
ggcgaacgcg gtgaccctcg ccccacccca tccctccgg cgggcaactg gtcgggtca      240
ggagggcaa acccgctagg gagacactcc atatacggcc cggcccgcgt tacctgggac     300
cgggccaacc cgctccttct ttggtcaacg caggggaccc gggcggggc ccaggccgcg      360
aaccggccga gggagggggc tctagtgccc aacacccaaa tatggctcga aagggcagc     420
gacattcctg cggggtggcg cggagggaat gcccgcgggc tatataaaac ctgagcagag     480
ggacaagcgg ccaccgcagc ggacagcgcc aagtgaagcc tcgcttcccc tccgcggcga     540
ccagggcccg agccgagagt agcagttgta gctacccgcc caggtagggg cgcgccgtcg     600
acggatcccc ttttagagaa tccacacctg tcccagttgc tgggttccac taccaaaagt     660
gaattgcaac tattttagga gcacttaagc acatccgaaa aatgagtgat tctgttctgg     720
cccacaccac atcactgatg taccccctta agcatgtcc ctgagttcat cacagaagac      780
tgctcctcct gtgccctcca caaggttaga actgtccttg tcttagggaa aaaggagaga     840
gagagagaga gagagagaga gagagagaga gagagagaga gagagggaca ggcaccaact     900
gggtaacctc tgctgacccc cactctactt taccataagt agctccaaat ccttctagaa     960
aatctgaaag gcatagcccc atatatcagt gatataaata gaacctgcag caggctctgg    1020
taaatgatga ctacaaggtg gactgggagg cagcccggcc ttggcaggca tcatcctcta    1080
aatataaaga tgagttttgtt cagcctttgc agaaggagga tccgtcgacg gcgcgccacg    1140
cgtcagttta ctcaccaggg attcagaggc agcactgctg aaccctgagc ccttggcaca    1200
tcaggttggc tgtcagaagt cggcctttgt acatacacag ttcccttgtg aggcccagct    1260
gcgtgtccta ggagcggggc ctctctccac agcagagctc agcctctcaa gtgtatggac    1320
agcacgggtg cctgatgggt ggatttagcc atgagttgaa ggtggcttgg ggagaatgag    1380
agttctagag atagggagaa ggggttgcca ataggagagt ggaattcctg agcacctcgt    1440
cacaggcagc cgacagaaca tgagccgcag ggcccaggct atttatacct cgcctgtcac    1500
tatcagggtc cccacagctc cccccacctc cagccacaca cagcaggtcc ttttgctctt    1560
tctggtccct tctctactcc tccccctccc tacctaaggt acccaacgcg ttacgtggcc    1620
accgccttcg gcaccatcct cacgacaccc aaatatggcg acgggtgagg aatggtgggg    1680
agttattttt agagcggtga ggaaggtggg caggcagcag gtgttggcgc tctaaaaata    1740
actcccggga gttatttta gagcggagga atggtggaca cccaaatatg gcgacggttc    1800
ctcacccgtc gccatatttg ggtgtccgcc ctcggccggg gccgcattcc tggggccgg     1860
gcggtgctcc cgcccgcctc gataaaaggc tccggggccg gcggcggccc acgagctacc    1920
cggaggagcg ggaggcgcca agctctagat ctagaaagag gtaagggttt aagggatggt    1980
tggttggtgg ggtattaatg tttaattacc tggagcacct gcctgaaatc acttttttc     2040
aggttggaag cttgccacca tggctgctgc cgctgctgct gcagctgaac agcaatctag    2100
caacggcccc gtgaagaaat ccatgcgcga gaaggccgtc gagcggagat ctgtgaacaa    2160
```

```
agagcacaac agcaacttca aggccggcta catccccatc gacgaggaca gactgcacaa    2220
gacaggcctg agaggcagaa agggcaatct ggccatctgc gtgatcatcc tgctgttcat    2280
cctggccgtg atcaacctga tcatcaccct ggtcatctgg gccgtgatta gaatcggccc    2340
caacggctgc gacagcatgg aatttcacga gagcggcctg ctgcggttca acaggtgtc     2400 cgatatgggc gtgatccatc cactgtacaa gagcaccgtt ggcggcagaa gaaacgagaa    2460
tctggtcatc accggcaaca accagcctat cgtgtttcag cagggcacca ccaagctgag    2520
cgtggaaaac aacaagacca gcatcaccag cgacatcggc atgcagttct tcgaccccag    2580
aacacagaac atcctgttca gcaccgacta cgagacacac gagttccatc tgcctagcgg    2640
cgtgaagtcc ctgaatgtgc agaaggccag caccgagaga atcaccagca atgccacctc    2700
cgacctgaac atcaaagtgg acggcagagc catcgtgcgg ggaaatgagg gcgtgttcat    2760
catgggcaag accatcgagt tccacatggg cggcaacatg gaactgaagg ccgagaacag    2820
catcatcctg aacggcagcg tgatggtgtc caccacaaga ctgccaagca gcagctctgg    2880
cgatcagctt ggatctggcg actgggtccg atacaagctg tgtatgtgtg ccgacggcac    2940
cctgttcaag gtgcaagtga caagccagaa catgggctgc cagatcagcg acaacccttg    3000
cggcaatacc cactgattcg aaacgtcaag tccatcttga gcatctgact tctggctaaa    3060
taaaagatct ttattttcat tagatctgtg tgttggtttt ttgtgtgcgt cgagatccac    3120
ggccgcagga accccctagtg atggagttgg ccactccctc tctgcgcgct cgctcgctca   3180
ctgaggccgg gcgaccaaag gtcgcccgac gcccgggctt gcccgggcg gcctcagtga    3240 gcgagcgagc gcgcagctgc ctgcaggggc gcctgatgcg gtattttctc cttacgcatc    3300
tgtgcggtat ttcacaccgc atacgtcaaa gcaaccatag tacgcgccct gtagcggcgc    3360
attaagcgcg gcgggtgtgg tggttacgcg cagcgtgacc gctacacttg ccagcgccct    3420
agcgcccgct cctttcgctt tcttcccttc ctttctcgcc acgttcgccg ctttccccg     3480 tcaagctcta atcgggggc tccctttagg gttccgattt agtgctttac ggcacctcga    3540
ccccaaaaaa cttgatttgg gtgatggttc acgtagtggg ccatcgccct gatagacggt    3600
ttttcgccct ttgacgttgg agtccacgtt ctttaatagt ggactcttgt tccaaactgg    3660
aacaacactc aacccctatct cgggctattc ttttgattta taaggattt tgccgatttc    3720 ggcctattgg ttaaaaaatg agctgattta acaaaaattt aacgcgaatt ttaacaaaat    3780
attaacgttt acaatttat ggtgcactct cagtacaatc tgctctgatg ccgcatagtt     3840
aagccagccc cgacacccgc caacacccgc tgacgcgccc tgacgggctt gtctgctccc    3900
ggcatccgct tacagacaag ctgtgaccgt ctccgggagc tgcatgtgtc agaggttttc    3960
accgtcatca ccgaaacgcg cgagacgaaa gggcctcgtg atacgcctat ttttataggt    4020
taatgtcatg ataataatgg tttcttagac gtcaggtggc acttttcggg gaaatgtgcg    4080
cggaacccct atttgtttat ttttctaaat acattcaaat atgtatccgc tcatgagaca    4140
ataaccctga taaatgcttc aataatattg aaaaggaag agtatgagta ttcaacattt     4200
ccgtgtcgcc cttattccct tttttgcggc attttgcctt cctgttttg ctcacccaga     4260 aacgctggtg aaagtaaaag atgctgaaga tcagttgggt gcacgagtgg gttacatcga    4320
actggatctc aacagcggta agatccttga gagttttcgc cccgaagaac gttttccaat    4380
gatgagcact tttaaagttc tgctatgtgg cgcggtatta tcccgtattg acgccgggca    4440
agagcaactc ggtcgccgca tacactattc tcagaatgac ttggttgagt actcaccagt    4500
```

| | | | | |
|---|---|---|---|---|
| cacagaaaag | catcttacgg | atggcatgac | agtaagagaa | ttatgcagtg | ctgccataac | 4560 |
| catgagtgat | aacactgcgg | ccaacttact | tctgacaacg | atcggaggac | cgaaggagct | 4620 |
| aaccgctttt | ttgcacaaca | tgggggatca | tgtaactcgc | cttgatcgtt | gggaaccgga | 4680 |
| gctgaatgaa | gccataccaa | acgacgagcg | tgacaccacg | atgcctgtag | caatggcaac | 4740 |
| aacgttgcgc | aaactattaa | ctggcgaact | acttactcta | gcttcccggc | aacaattaat | 4800 |
| agactggatg | gaggcggata | aagttgcagg | accacttctg | cgctcggccc | ttccggctgg | 4860 |
| ctggtttatt | gctgataaat | ctggagccgg | tgagcgtggg | tctcgcggta | tcattgcagc | 4920 |
| actggggcca | gatggtaagc | cctcccgtat | cgtagttatc | tacacgacgg | ggagtcaggc | 4980 |
| aactatggat | gaacgaaata | gacagatcgc | tgagataggt | gcctcactga | ttaagcattg | 5040 |
| gtaactgtca | gaccaagttt | actcatatat | actttagatt | gatttaaaac | ttcattttta | 5100 |
| atttaaaagg | atctaggtga | agatcctttt | tgataatctc | atgaccaaaa | tcccttaacg | 5160 |
| tgagttttcg | ttccactgag | cgtcagaccc | cgtagaaaag | atcaaaggat | cttcttgaga | 5220 |
| tccttttttt | ctgcgcgtaa | tctgctgctt | gcaaacaaaa | aaaccaccgc | taccagcggt | 5280 |
| ggtttgtttg | ccggatcaag | agctaccaac | tcttttccg | aaggtaactg | gcttcagcag | 5340 |
| agcgcagata | ccaaatactg | tccttctagt | gtagccgtag | ttaggccacc | acttcaagaa | 5400 |
| ctctgtagca | ccgcctacat | acctcgctct | gctaatcctg | ttaccagtgg | ctgctgccag | 5460 |
| tggcgataag | tcgtgtctta | ccgggttgga | ctcaagacga | tagttaccgg | ataaggcgca | 5520 |
| gcggtcgggc | tgaacggggg | gttcgtgcac | acagcccagc | ttggagcgaa | cgacctacac | 5580 |
| cgaactgaga | tacctacagc | gtgagctatg | agaaagcgcc | acgcttcccg | aagggagaaa | 5640 |
| ggcggacagg | tatccggtaa | gcggcagggt | cggaacagga | gagcgcacga | gggagcttcc | 5700 |
| agggggaaac | gcctggtatc | tttatagtcc | tgtcgggttt | cgccacctct | gacttgagcg | 5760 |
| tcgatttttg | tgatgctcgt | caggggggcg | gagcctatgg | aaaaacgcca | gcaacgcggc | 5820 |
| cttttacgg | ttcctggcct | tttgctggcc | ttttgctcac | atgt | | 5864 |

<210> SEQ ID NO 27
<211> LENGTH: 5864
<212> TYPE: DNA
<213> ORGANISM: Artificial Sequence
<220> FEATURE:
<223> OTHER INFORMATION: AAV-CRE02-CRE04-CSK-SH5-SPc5-12-MVM-hB-SG-pA

<400> SEQUENCE: 27

| | | | | |
|---|---|---|---|---|
| cctgcaggca | gctgcgcgct | cgctcgctca | ctgaggccgc | ccgggcgtcg | ggcgaccttt | 60 |
| ggtcgcccgg | cctcagtgag | cgagcgagcg | cgcagagagg | gagtggccaa | ctccatcact | 120 |
| aggggttcct | gcggccgaca | ggtgcggttc | ccggagcgca | ggcgcacaca | tgcacccacc | 180 |
| ggcgaacgcg | gtgaccctcg | ccccacccca | tcccctccgg | cgggcaactg | ggtcgggtca | 240 |
| ggaggggcaa | acccgctagg | gagacactcc | atatacggcc | cggcccgcgt | tacctgggac | 300 |
| cgggccaacc | cgctccttct | ttggtcaacg | caggggaccc | gggcggggc | ccaggccgcg | 360 |
| aaccggccga | gggagggggc | tctagtgccc | aacacccaaa | tatggctcga | aagggcagc | 420 |
| gacattcctg | cggggtggcg | cggagggaat | gcccgcgggc | tatataaaac | ctgagcagag | 480 |
| ggacaagcgg | ccaccgcagc | ggacagcgcc | aagtgaagcc | tcgcttcccc | tccgcggcga | 540 |
| ccagggcccc | agccgagagt | agcagttgta | gctaccgcc | caggtagggg | cgcgccgtcg | 600 |
| acggatccct | ttttagagaa | tccacacctg | tcccagttgc | tgggttccac | taccaaaagt | 660 |
| gaattgcaac | tattttagga | gcacttaagc | acatccgaaa | aatgagtgat | tctgttctgg | 720 |

-continued

```
cccacaccac atcactgatg taccccctta aagcatgtcc ctgagttcat cacagaagac     780
tgctcctcct gtgccctcca caaggttaga actgtccttg tcttagggaa aaaggagaga     840
gagagagaga gagagagaga gagagagaga gagagagaga gagagggaca ggcaccaact     900
gggtaacctc tgctgacccc cactctactt taccataagt agctccaaat ccttctagaa     960
aatctgaaag gcatagcccc atatatcagt gatataaata gaacctgcag caggctctgg    1020
taaatgatga ctacaaggtg gactgggagg cagcccggcc ttggcaggca tcatcctcta    1080
aatataaaga tgagtttgtt cagcctttgc agaaggagga tccgtcgacg gcgcgccacg    1140
cgtcagttta ctcaccaggg attcagaggc agcactgctg aaccctgagc ccttggcaca    1200
tcaggttggc tgtcagaagt cggcctttgt acatacacag ttcccttgtg aggcccagct    1260
gcgtgtccta ggagcggggc ctctctccac agcagagctc agcctctcaa gtgtatggac    1320
agcacgggtg cctgatgggt ggatttagcc atgagttgaa ggtggcttgg ggagaatgag    1380
agttctagag atagggagaa ggggttgcca ataggagagt ggaattcctg agcacctcgt    1440
cacaggcagc cgacagaaca tgagccgcag ggcccaggct atttatacct cgcctgtcac    1500
tatcagggtc cccacagctc cccccacctc cagccacaca cagcaggtcc ttttgctctt    1560
tctggtccct tctctactcc tccccctccc tacctaaggt acccaacgcg ttacgtggcc    1620
accgccttcg gcaccatcct cacgacaccc aaatatggcg acgggtgagg aatggtgggg    1680
agttattttt agagcggtga ggaaggtggg caggcagcag gtgttggcgc tctaaaaata    1740
actcccggga gttattttta gagcggagga atggtggaca cccaaatatg gcgacggttc    1800
ctcacccgtc gccatatttg ggtgtccgcc ctcggccggg gccgcattcc tgggggccgg    1860
gcggtgctcc cgcccgcctc gataaaaggc tccggggccg gcggcggccc acgagctacc    1920
cggaggagcg ggaggcgcca agctctagat ctagaaagag gtaagggttt aagggatggt    1980
tggttggtgg ggtattaatg tttaattacc tggagcacct gcctgaaatc actttttttc    2040
aggttggaag cttgccacca tggcggcagc ggcggcggcg gctgcagaac agcaaagttc    2100
caatggtcct gtaaagaagt ccatgcgtga gaaggctgtt gagagaagga gtgtcaataa    2160
agagcacaac agtaacttta aagctggata cattccgatt gatgaagatc gtctccacaa    2220
aacagggttg agaggaagaa agggcaattt agccatctgt gtgattatcc tcttgtttat    2280
cctggctgtc atcaatttaa taataacact tgttatttgg gccgtgattc gcattggacc    2340
aaatggctgt gatagtatgg agtttcatga aagtggcctg cttcgattta agcaagtatc    2400
tgacatggga gtgatccacc ctctttataa agcacagta ggaggaaggc gaaatgaaaa    2460

tttggtcatc actggcaaca accagcctat tgtttttcag caagggacaa caaagctcag    2520
tgtagaaaac aacaaaactt ctattacaag tgacatcggc atgcagtttt ttgacccgag    2580
gactcaaaat atcttattca gcacagacta tgaaactcat gagtttcatt tgccaagtgg    2640
agtgaaaagt ttgaatgttc aaaaggcatc tactgaaagg attaccagca atgctaccag    2700 tgatтттaaat ataaagttg atgggcgtgc tattgtgcgt ggaaatgaag gtgtattcat    2760
tatgggcaaa accattgaat tcacatggg tggtaatatg gagttaaagg cggaaaacag    2820
tatcatccta aatggatctg tgatggtcag caccacccgc ctacccagtt cctccagtgg    2880
agaccagttg ggtagtggtg actgggtacg ctacaagctc tgcatgtgtg ctgatgggac    2940
gctcttcaag gtgcaagtaa ccagccagaa catgggctgc caaatctcag acaaccctg    3000 tggaaacact cattaattcg aaacgtcaag tccatcttga gcatctgact tctggctaaa    3060
```

```
taaaagatct ttattttcat tagatctgtg tgttggtttt ttgtgtgcgt cgagatccac    3120
ggccgcagga accctagtg atggagttgg ccactccctc tctgcgcgct cgctcgctca    3180
ctgaggccgg gcgaccaaag gtcgcccgac gcccgggctt tgcccgggcg gcctcagtga    3240
gcgagcgagc gcgcagctgc ctgcaggggc gcctgatgcg gtattttctc cttacgcatc    3300
tgtgcggtat ttcacaccgc atacgtcaaa gcaaccatag tacgcgccct gtagcggcgc    3360
attaagcgcg gcgggtgtgg tggttacgcg cagcgtgacc gctacacttg ccagcgccct    3420
agcgcccgct cctttcgctt tcttcccttc ctttctcgcc acgttcgccg gctttccccg    3480
tcaagctcta atcgggggc tcccttagg gttccgattt agtgctttac ggcacctcga    3540
ccccaaaaaa cttgatttgg gtgatggttc acgtagtggg ccatcgccct gatagacggt    3600
ttttcgccct ttgacgttgg agtccacgtt ctttaatagt ggactcttgt tccaaactgg    3660
aacaacactc aaccctatct cgggctattc ttttgattta aagggatttt gccgatttc    3720 ggcctattgg ttaaaaaatg agctgattta acaaaaattt aacgcgaatt ttaacaaaat    3780
attaacgttt acaattttat ggtgcactct cagtacaatc tgctctgatg ccgcatagtt    3840
aagccagccc cgacacccgc caacacccgc tgacgcgccc tgacgggctt gtctgctccc    3900
ggcatccgct tacagacaag ctgtgaccgt ctccgggagc tgcatgtgtc agaggttttc    3960
accgtcatca ccgaaacgcg cgagacgaaa gggcctcgtg atacgcctat ttttataggt    4020
taatgtcatg ataataatgg tttcttagac gtcaggtggc acttttcggg gaaatgtgcg    4080
cggaacccct atttgtttat ttttctaaat acattcaaat atgtatccgc tcatgagaca    4140
ataaccctga taaatgcttc aataatattg aaaaaggaag agtatgagta ttcaacattt    4200
ccgtgtcgcc cttattccct tttttgcggc attttgcctt cctgtttttg ctcacccaga    4260
aacgctggtg aaagtaaaag atgctgaaga tcagttgggt gcacgagtgg gttacatcga    4320
actggatctc aacagcggta agatccttga gagttttcgc cccgaagaac gttttccaat    4380
gatgagcact tttaaagttc tgctatgtgg cgcggtatta tcccgtattg acgccgggca    4440
agagcaactc ggtcgccgca tacactattc tcagaatgac ttggttgagt actcaccagt    4500
cacagaaaag catcttacgg atggcatgac agtaagagaa ttatgcagtg ctgccataac    4560
catgagtgat aacactgcgg ccaacttact tctgacaacg atcggaggac cgaaggagct    4620
aaccgctttt ttgcacaaca tgggggatca tgtaactcgc cttgatcgtt gggaaccgga    4680
gctgaatgaa gccataccaa acgacgagcg tgacaccacg atgcctgtag caatggcaac    4740
aacgttgcgc aaactattaa ctggcgaact acttactcta gcttcccggc aacaattaat    4800
agactggatg gaggcggata agttgcagg accacttctg cgctcggccc ttccggctgg    4860
ctggtttatt gctgataaat ctggagccgg tgagcgtggg tctcgcggta tcattgcagc    4920
actggggcca gatggtaagc cctcccgtat cgtagttatc tacacgacgg ggagtcaggc    4980
aactatggat gaacgaaata gacagatcgc tgagataggt gcctcactga ttaagcattg    5040
gtaactgtca gaccaagttt actcatatat actttagatt gatttaaaac ttcatttta    5100 atttaaaagg atctaggtga agatcctttt tgataatctc atgaccaaaa tcccttaacg    5160
tgagttttcg ttccactgag cgtcagaccc cgtagaaaag atcaaggat cttcttgaga    5220 tcctttttt ctgcgcgtaa tctgctgctt gcaaacaaaa aaaccaccgc taccagcggt    5280
ggtttgtttg ccggatcaag agctaccaac tcttttccg aaggtaactg gcttcagcag    5340
agcgcagata ccaaatactg tccttctagt gtagccgtag ttaggccacc acttcaagaa    5400
ctctgtagca ccgcctacat acctcgctct gctaatcctg ttaccagtgg ctgctgccag    5460
```

```
tggcgataag tcgtgtctta ccgggttgga ctcaagacga tagttaccgg ataaggcgca    5520
gcggtcgggc tgaacggggg gttcgtgcac acagcccagc ttggagcgaa cgacctacac    5580
cgaactgaga tacctacagc gtgagctatg agaaagcgcc acgcttcccg aagggagaaa    5640
ggcggacagg tatccggtaa gcggcagggt cggaacagga gagcgcacga gggagcttcc    5700
agggggaaac gcctggtatc tttatagtcc tgtcgggttt cgccacctct gacttgagcg    5760
tcgatttttg tgatgctcgt caggggggcg agcctatgg aaaaacgcca gcaacgcggc    5820 cttttttacgg ttcctggcct tttgctggcc ttttgctcac atgt              5864
```

```
<210> SEQ ID NO 28
<211> LENGTH: 5823
<212> TYPE: DNA
<213> ORGANISM: Artificial Sequence
<220> FEATURE:
<223> OTHER INFORMATION: AAV-CRE04-CRE06-CSK-SH5-SPc5-12-MVM-hB-SGco-pA

<400> SEQUENCE: 28
```

```
acatgtcctg caggcagctg cgcgctcgct cgctcactga ggccgcccgg gcaaagcccg      60
ggcgtcgggc gacctttggt cgcccggcct cagtgagcga gcgagcgcgc agagagggag     120
tggccaactc catcactagg ggttcctgcg gccccttta gagaatccac acctgtccca     180
gttgctgggt tccactacca aaagtgaatt gcaactattt taggagcact taagcacatc     240
cgaaaaatga gtgattctgt tctggcccac accacatcac tgatgtaccc ccttaaagca     300
tgtccctgag ttcatcacag aagactgctc ctcctgtgcc ctccacaagg ttagaactgt     360
ccttgtctta gggaaaaagg agagagagag agagagagag agagagagag agagagagag     420
agagagagag ggacaggcac caactgggta acctctgctg accccactc tactttacca     480 taagtagctc caaatccttc tagaaaatct gaaaggcata gccccatata tcagtgatat     540
aaatagaacc tgcagcaggc tctggtaaat gatgactaca aggtggactg ggaggcagcc     600
cggccttggc aggcatcatc tctaaatat aaagatgagt ttgttcagcc tttgcagaag     660
gaggcgcgcc gtcgacggat ccgggccagg ggacggtggc ttctacgtgc ttgggacgtt     720
cccagccacc gtcccatgtt cccggcgggg ggccagctgt ccccaccgcc agcccaactc     780
agcacttggt cagggtatca gcttggtggg ggggcgtgag cccagcccct ggggcggctc     840
agcccataca aggccatggg gctgggcgca aagcatgcct gggttcaggg tgggtatggt     900
gcgggagcag ggaggtgaga ggctcagctg ccctccagaa ctcctccctg gggacaaccc     960
ctcccagcca atagcacagc ctaggtcccc ctatataagg ccacggctgc tggcccttcc    1020
tttgggtcag tgtcacctcc aggatacaga cagcccccct tcagcccagc ccagccaggt    1080
acggatccgt cgacggcgcg ccacgcgtca gtttactcac cagggattca gaggcagcac    1140
tgctgaaccc tgagcccttg gcacatcagg ttggctgtca gaagtcggcc tttgtacata    1200
cacagttccc ttgtgaggcc cagctgcgtg tcctaggagc ggggcctctc tccacagcag    1260
agctcagcct ctcaagtgta tggacagcac gggtgcctga tgggtggatt tagccatgag    1320
ttgaaggtgg cttggggaga atgagagttc tagagatagg gagaagggt tgccaatagg    1380 agagtggaat tcctgagcac ctcgtcacag gcagccgaca gaacatgagc cgcagggccc    1440
aggctattta tacctcgcct gtcactatca gggtccccac agctccccc acctccagcc    1500 acacacagca ggtcctttg ctctttctgg tccttctct actcctcccc ctccctacct    1560
aaggtaccca acgcgttacg tggccaccgc cttcggcacc atcctcacga cacccaaata    1620
```

```
tggcgacggg tgaggaatgg tggggagtta tttttagagc ggtgaggaag gtgggcaggc    1680
agcaggtgtt ggcgctctaa aaataactcc cgggagttat ttttagagcg gaggaatggt    1740
ggacacccaa atatggcgac ggttcctcac ccgtcgccat atttgggtgt ccgccctcgg    1800
ccggggccgc attcctgggg gccgggcggt gctcccgccc gcctcgataa aaggctccgg    1860
ggccggcggc ggcccacgag ctacccggag gagcgggagg cgccaagctc tagatctaga    1920
aagaggtaag ggtttaaggg atggttggtt ggtggggtat taatgtttaa ttacctggag    1980
cacctgcctg aaatcacttt ttttcaggtt ggaagcttgc caccatggct gctgccgctg    2040
ctgctgcagc tgaacagcaa tctagcaacg gccccgtgaa gaaatccatg cgcgagaagg    2100
ccgtcgagcg gagatctgtg aacaaagagc acaacagcaa cttcaaggcc ggctacatcc    2160
ccatcgacga ggacagactg cacaagacag gcctgagagg cagaaagggc aatctggcca    2220
tctgcgtgat catcctgctg ttcatcctgg ccgtgatcaa cctgatcatc accctggtca    2280
tctgggccgt gattagaatc ggccccaacg gctgcgacag catggaattt cacgagagcg    2340
gcctgctgcg gttcaaacag gtgtccgata tgggcgtgat ccatccactg tacaagagca    2400
ccgttggcgg cagaagaaac gagaatctgg tcatcaccgg caacaaccag cctatcgtgt    2460
ttcagcaggg caccaccaag ctgagcgtgg aaaacaacaa gaccagcatc accagcgaca    2520
tcggcatgca gttcttcgac cccagaacac agaacatcct gttcagcacc gactacgaga    2580
cacacgagtt ccatctgcct agcggcgtga agtccctgaa tgtgcagaag gccagcaccg    2640
agagaatcac cagcaatgcc acctccgacc tgaacatcaa agtggacggc agagccatcg    2700
tgcggggaaa tgagggcgtg ttcatcatgg caagaccat cgagttccac atgggcggca    2760
acatggaact gaaggccgag aacagcatca tcctgaacgg cagcgtgatg gtgtccacca    2820
caagactgcc aagcagcagc tctggcgatc agcttggatc tggcgactgg gtccgataca    2880
agctgtgtat gtgtgccgac ggcaccctgt tcaaggtgca agtgacaagc cagaacatgg    2940
gctgccagat cagcgacaac ccttgcggca atacccactg attcgaaacg tcacgtccat    3000
cttgagcatc tgacttctgg ctaaataaaa gatctttatt ttcattagat ctgtgtgttg    3060
gttttttgtg tgcgtcgaga tccacggccg caggaacccc tagtgatgga gttggccact    3120
ccctctctgc gcgctcgctc gctcactgag gccgggcgac caaaggtcgc ccgacgcccg    3180
ggctttgccc gggcggcctc agtgagcgag cgagcgcgca gctgcctgca ggggcgcctg    3240
atgcggtatt ttctccttac gcatctgtgc ggtatttcac accgcatacg tcaaagcaac    3300
catagtacgc gccctgtagc ggcgcattaa gcgcggcggg tgtggtggtt acgcgcagcg    3360
tgaccgctac acttgccagc gccctagcgc ccgctccttt cgctttcttc ccttcctttc    3420
tcgccacgtt cgccggcttt ccccgtcaag ctctaaatcg gggctccct ttagggttcc    3480 gatttagtgc tttacggcac ctcgacccca aaaaacttga tttgggtgat ggttcacgta    3540
gtgggccatc gccctgatag acggtttttc gccctttgac gttggagtcc acgttcttta    3600
atagtggact cttgttccaa actggaacaa cactcaaccc tatctcgggc tattcttttg    3660
atttataagg gattttgccg atttcggcct attggttaaa aaatgagctg atttaacaaa    3720
aatttaacgc gaattttaac aaaatattaa cgtttacaat tttatggtgc actctcagta    3780
caatctgctc tgatgccgca tagttaagcc agccccgaca cccgccaaca cccgctgacg    3840
cgccctgacg ggcttgtctg ctcccggcat ccgcttacag acaagctgtg accgtctccg    3900
ggagctgcat gtgtcagagg ttttcaccgt catcaccgaa acgcgcgaga cgaaagggcc    3960
tcgtgatacg cctatttta taggttaatg tcatgataat aatggtttct tagacgtcag    4020
```

```
gtggcacttt tcggggaaat gtgcgcggaa cccctatttg tttattttttc taaatacatt    4080 caaatatgta tccgctcatg agacaataac cctgataaat gcttcaataa tattgaaaaa    4140
ggaagagtat gagtattcaa catttccgtg tcgcccttat tcccttttttt gcggcatttt    4200 gccttcctgt ttttgctcac ccagaaacgc tggtgaaagt aaaagatgct gaagatcagt    4260
tgggtgcacg agtgggttac atcgaactgg atctcaacag cggtaagatc cttgagagtt    4320
ttcgccccga agaacgtttt ccaatgatga gcacttttaa agttctgcta tgtggcgcgg    4380
tattatcccg tattgacgcc gggcaagagc aactcggtcg ccgcatacac tattctcaga    4440
atgacttggt tgagtactca ccagtcacag aaaagcatct tacgatggc atgacagtaa     4500 gagaattatg cagtgctgcc ataaccatga gtgataacac tgcggccaac ttacttctga    4560
caacgatcgg aggaccgaag gagctaaccg cttttttgca acatggggga tcatgtaa     4620 ctcgccttga tcgttgggaa ccggagctga atgaagccat accaaacgac gagcgtgaca    4680
ccacgatgcc tgtagcaatg gcaacaacgt tgcgcaaact attaactggc gaactactta    4740
ctctagcttc ccggcaacaa ttaatagact ggatggaggc ggataaagtt gcaggaccac    4800
ttctgcgctc ggcccttccg gctggctggt ttattgctga taaatctgga gccggtgagc    4860
gtgggtctcg cggtatcatt gcagcactgg ggccagatgg taagccctcc cgtatcgtag    4920
ttatctacac gacggggagt caggcaacta tggatgaacg aaatagacag atcgctgaga    4980
taggtgcctc actgattaag cattggtaac tgtcagacca agtttactca tatatacttt    5040
agattgattt aaaacttcat ttttaattta aaaggatcta ggtgaagatc ctttttgata    5100
atctcatgac caaaatccct aacgtgagt tttcgttcca ctgagcgtca gaccccgtag     5160
aaaagatcaa aggatcttct tgagatcctt ttttctgcg cgtaatctgc tgcttgcaaa     5220
caaaaaaacc accgctacca gcggtggttt gtttgccgga tcaagagcta ccaactcttt    5280
ttccgaaggt aactggcttc agcagagcgc agataccaaa tactgtcctt ctagtgtagc    5340
cgtagttagg ccaccacttc aagaactctg tagcaccgcc tacatacctc gctctgctaa    5400
tcctgttacc agtggctgct gccagtggcg ataagtcgtg tcttaccggg ttggactcaa    5460
gacgatagtt accggataag cgcagcggt cgggctgaac gggggggttcg tgcacacagc    5520 ccagcttgga gcgaacgacc tacaccgaac tgagatacct acagcgtgag ctatgagaaa    5580
gcgccacgct tcccgaaggg agaaaggcgg acaggtatcc ggtaagcggc agggtcggaa    5640
caggagagcg cacgagggag cttccagggg gaaacgcctg gtatctttat agtcctgtcg    5700
ggtttcgcca cctctgactt gagcgtcgat ttttgtgatg ctcgtcaggg gggcggagcc    5760
tatggaaaaa cgccagcaac gcggcctttt tacggttcct ggccttttgc tggccttttg    5820
ctc                                                                  5823
```

<210> SEQ ID NO 29
<211> LENGTH: 5823
<212> TYPE: DNA
<213> ORGANISM: Artificial Sequence
<220> FEATURE:
<223> OTHER INFORMATION: AAV-CRE04-CRE06-CSK-SH5-SPc5-12-MVM-hB-SG-pA

<400> SEQUENCE: 29

```
acatgtcctg caggcagctg cgcgctcgct cgctcactga ggccgcccgg gcaaagcccg     60
ggcgtcgggc gacctttggt cgcccggcct cagtgagcga gcgagcgcgc agagagggag    120
tggccaactc catcactagg ggttcctgcg gccccttttta gagaatccac acctgtccca    180
```

```
gttgctgggt tccactacca aaagtgaatt gcaactattt taggagcact taagcacatc      240
cgaaaaatga gtgattctgt tctggcccac accacatcac tgatgtaccc ccttaaagca      300
tgtccctgag ttcatcacag aagactgctc ctcctgtgcc ctccacaagg ttagaactgt      360
ccttgtctta gggaaaaagg agagagagag agagagagag agagagagag agagagagag      420
agagagagag ggacaggcac caactgggta acctctgctg accccactc tactttacca       480
taagtagctc caaatccttc tagaaaatct gaaaggcata gccccatata tcagtgatat      540
aaatagaacc tgcagcaggc tctggtaaat gatgactaca aggtggactg ggaggcagcc      600
cggccttggc aggcatcatc ctctaaatat aaagatgagt ttgttcagcc tttgcagaag      660
gaggcgcgcc gtcgacggat ccgggccagg ggacggtggc ttctacgtgc ttgggacgtt      720
cccagccacc gtcccatgtt cccggcgggg ggccagctgt ccccaccgcc agcccaactc      780
agcacttggt cagggtatca gcttggtggg ggggcgtgag cccagcccct ggggcggctc      840
agcccataca aggccatggg gctgggcgca aagcatgcct gggttcaggg tgggtatggt      900
gcgggagcag ggaggtgaga ggctcagctg ccctccagaa ctcctccctg gggacaaccc      960
ctcccagcca atagcacagc ctaggtcccc ctatataagg ccacggctgc tggcccttcc     1020
tttgggtcag tgtcacctcc aggatacaga cagcccccct tcagcccagc ccagccaggt     1080
acggatccgt cgacgcgcg ccacgcgtca gtttactcac cagggattca gaggcagcac      1140
tgctgaaccc tgagcccttg gcacatcagg ttggctgtca gaagtcggcc tttgtacata     1200
cacagttccc ttgtgaggcc cagctgcgtg tcctaggagc ggggcctctc tccacagcag     1260
agctcagcct ctcaagtgta tggacagcac gggtgcctga tgggtggatt tagccatgag     1320
ttgaaggtgg cttggggaga atgagagttc tagagatagg gagaaggggt tgccaatagg     1380
agagtggaat tcctgagcac ctcgtcacag gcagccgaca gaacatgagc cgcagggccc     1440
aggctattta tacctcgcct gtcactatca gggtccccac agctccccc acctccagcc     1500
acacacagca ggtcctttg ctctttctgg tcccttctct actcctcccc ctccctacct      1560
aaggtaccca acgcgttacg tggccaccgc cttcggcacc atcctcacga cacccaaata     1620
tggcgacggg tgaggaatgg tggggagtta ttttttagagc ggtgaggaag gtgggcaggc     1680
agcaggtgtt ggcgctctaa aaataactcc cgggagttat ttttagagcg gaggaatggt     1740
ggacacccaa atatggcgac ggttcctcac ccgtcgccat atttgggtgt ccgccctcgg     1800
ccggggccgc attcctgggg gccgggcggt gctcccgccc gcctcgataa aaggctccgg     1860
ggccggcggc ggcccacgag ctacccggag gagcgggagg cgccaagctc tagatctaga     1920
aagaggtaag ggtttaaggg atggttggtt ggtggggtat taatgtttaa ttacctggag     1980
cacctgcctg aaatcacttt ttttcaggtt ggaagcttgc caccatggcg gcagcggcgg     2040
cggcggctgc agaacagcaa agttccaatg gtcctgtaaa gaagtccatg cgtgagaagg     2100
ctgttgagag aaggagtgtc aataaagagc acaacagtaa ctttaaagct ggatacattc     2160
cgattgatga agatcgtctc cacaaaacag ggttgagagg aagaaagggc aatttagcca     2220
tctgtgtgat tatcctcttg tttatcctgg ctgtcatcaa tttaataata acacttgtta     2280
tttgggccgt gattcgcatt ggaccaaatg gctgtgatag tatggagttt catgaaagtg     2340
gcctgcttcg atttaagcaa gtatctgaca tgggagtgat ccaccctctt tataaaagca     2400
cagtaggagg aaggcgaaat gaaaatttgg tcatcactgg caacaaccag cctattgttt     2460
ttcagcaagg acaacaaag ctcagtgtag aaaacaacaa aacttctatt acaagtgaca     2520
tcggcatgca gttttttgac ccgaggactc aaaatatctt attcagcaca gactatgaaa     2580
```

| | |
|---|---|
| ctcatgagtt tcatttgcca agtggagtga aaagtttgaa tgttcaaaag gcatctactg | 2640 |
| aaaggattac cagcaatgct accagtgatt taaatataaa agttgatggg cgtgctattg | 2700 |
| tgcgtggaaa tgaaggtgta ttcattatgg gcaaaaccat tgaatttcac atgggtggta | 2760 |
| atatggagtt aaaggcggaa aacagtatca tcctaaatgg atctgtgatg gtcagcacca | 2820 |
| cccgcctacc cagttcctcc agtggagacc agttgggtag tggtgactgg gtacgctaca | 2880 |
| agctctgcat gtgtgctgat gggacgctct caaggtgca agtaaccagc cagaacatgg | 2940 |
| gctgccaaat ctcagacaac ccctgtggaa acactcatta attcgaaacg tcacgtccat | 3000 |
| cttgagcatc tgacttctgg ctaaataaaa gatctttatt ttcattagat ctgtgtgttg | 3060 |
| gttttttgtg tgcgtcgaga tccacggccg caggaacccc tagtgatgga gttggccact | 3120 |
| ccctctctgc gcgctcgctc gctcactgag gccgggcgac caaaggtcgc ccgacgcccg | 3180 |
| ggctttgccc gggcggcctc agtgagcgag cgagcgcgca gctgcctgca ggggcgcctg | 3240 |
| atgcggtatt ttctccttac gcatctgtgc ggtatttcac accgcatacg tcaaagcaac | 3300 |
| catagtacgc gccctgtagc ggcgcattaa gcgcggcggg tgtggtggtt acgcgcagcg | 3360 |
| tgaccgctac acttgccagc gccctagcgc ccgctccttt cgctttcttc ccttcctttc | 3420 |
| tcgccacgtt cgccggcttt ccccgtcaag ctctaaatcg gggctccct ttagggttcc | 3480 |
| gatttagtgc tttacggcac ctcgacccca aaaaacttga tttgggtgat ggttcacgta | 3540 |
| gtgggccatc gccctgatag acggtttttc gccctttgac gttggagtcc acgttcttta | 3600 |
| atagtggact cttgttccaa actgaacaa cactcaaccc tatctcgggc tattcttttg | 3660 |
| atttataagg gattttgccg atttcggcct attggttaaa aaatgagctg atttaacaaa | 3720 |
| aatttaacgc gaattttaac aaaatattaa cgtttacaat tttatggtgc actctcagta | 3780 |
| caatctgctc tgatgccgca tagttaagcc agccccgaca cccgccaaca cccgctgacg | 3840 |
| cgccctgacg ggcttgtctg ctcccggcat ccgcttacag acaagctgtg accgtctccg | 3900 |
| ggagctgcat gtgtcagagg ttttcaccgt catcaccgaa acgcgcgaga cgaaagggcc | 3960 |
| tcgtgatacg cctatttta taggttaatg tcatgataat aatggtttct tagacgtcag | 4020 |
| gtggcacttt tcggggaaat gtgcgcggaa ccccctatttg tttatttttc taaatacatt | 4080 |
| caaatatgta tccgctcatg agacaataac cctgataaat gcttcaataa tattgaaaaa | 4140 |
| ggaagagtat gagtattcaa catttccgtg tcgcccttat tcccttttt gcggcatttt | 4200 |
| gccttcctgt ttttgctcac ccagaaacgc tggtgaaagt aaaagatgct gaagatcagt | 4260 |
| tgggtgcacg agtgggttac atcgaactgg atctcaacag cggtaagatc cttgagagtt | 4320 |
| ttcgccccga agaacgtttt ccaatgatga gcacttttaa agttctgcta tgtggcgcgg | 4380 |
| tattatcccg tattgacgcc gggcaagagc aactcggtcg ccgcatacac tattctcaga | 4440 |
| atgacttggt tgagtactca ccagtcacag aaaagcatct tacggatggc atgacagtaa | 4500 |
| gagaattatg cagtgctgcc ataaccatga gtgataacac tgcggccaac ttacttctga | 4560 |
| caacgatcgg aggaccgaag gagctaaccg cttttttgca acatggggg atcatgtaa | 4620 |
| ctcgccttga tcgttgggaa ccggagctga atgaagccat accaaacgac gagcgtgaca | 4680 |
| ccacgatgcc tgtagcaatg gcaacaacgt tgcgcaaact attaactggc gaactactta | 4740 |
| ctctagcttc ccggcaacaa ttaatagact ggatggaggc ggataaagtt gcaggaccac | 4800 |
| ttctgcgctc ggcccttccg gctggctggt ttattgctga taaatctgga gccggtgagc | 4860 |
| gtgggtctcg cggtatcatt gcagcactgg ggccagatgg taagccctcc cgtatcgtag | 4920 |

-continued

| | |
|---|---|
| ttatctacac gacgggagt caggcaacta tggatgaacg aaatagacag atcgctgaga | 4980 |
| taggtgcctc actgattaag cattggtaac tgtcagacca agtttactca tatatacttt | 5040 |
| agattgattt aaaacttcat ttttaattta aaaggatcta ggtgaagatc cttttgata | 5100 |
| atctcatgac caaaatccct taacgtgagt tttcgttcca ctgagcgtca gaccccgtag | 5160 |
| aaaagatcaa aggatcttct tgagatcctt ttttctgcg cgtaatctgc tgcttgcaaa | 5220 |
| caaaaaaacc accgctacca gcggtggttt gtttgccgga tcaagagcta ccaactcttt | 5280 |
| ttccgaaggt aactggcttc agcagagcgc agataccaaa tactgtcctt ctagtgtagc | 5340 |
| cgtagttagg ccaccacttc aagaactctg tagcaccgcc tacatacctc gctctgctaa | 5400 |
| tcctgttacc agtggctgct gccagtggcg ataagtcgtg tcttaccggg ttggactcaa | 5460 |
| gacgatagtt accggataag cgcagcggt cgggctgaac ggggggttcg tgcacacagc | 5520 |
| ccagcttgga gcgaacgacc tacaccgaac tgagatacct acagcgtgag ctatgagaaa | 5580 |
| gcgccacgct tcccgaaggg agaaaggcgg acaggtatcc ggtaagcggc agggtcggaa | 5640 |
| caggagagcg cacgagggag cttccagggg gaaacgcctg gtatctttat agtcctgtcg | 5700 |
| ggtttcgcca cctctgactt gagcgtcgat ttttgtgatg ctcgtcaggg gggcggagcc | 5760 |
| tatggaaaaa cgccagcaac gcggcctttt tacggttcct ggccttttgc tggccttttg | 5820 |
| ctc | 5823 |

<210> SEQ ID NO 30
<211> LENGTH: 5812
<212> TYPE: DNA
<213> ORGANISM: Artificial Sequence
<220> FEATURE:
<223> OTHER INFORMATION: AAV-CRE06-CRE04-CSK-SH5-SPc5-12-MVM-hB-SGco-pA

<400> SEQUENCE: 30

| | |
|---|---|
| cctgcaggca gctgcgcgct cgctcgctca ctgaggccgc ccgggcgtcg ggcgaccttt | 60 |
| ggtcgcccgg cctcagtgag cgagcagcgc gcagagagg gagtggccaa ctccatcact | 120 |
| aggggttcct gcggccgggc caggggacgg tggcttctac gtgcttggga cgttcccagc | 180 |
| caccgtccca tgttcccggc gggggccag ctgtccccac cgccagccca actcagcact | 240 |
| tggtcagggt atcagcttgg tggggggcg tgagcccagc ccctggggcg gctcagccca | 300 |
| tacaaggcca tggggctggg cgcaaagcat gcctgggttc aggtgggta tggtgcggga | 360 |
| gcagggaggt gagaggctca gctgccctcc agaactcctc cctggggaca accctccca | 420 |
| gccaatagca cagcctaggt ccccctatat aaggccacgg ctgctggccc ttcctttggg | 480 |
| tcagtgtcac ctccaggata cagacagccc ccttcagcc cagcccagcc aggtacggcg | 540 |
| cgccgtcgac ggatcccctt ttagagaatc cacacctgtc ccagttgctg ggttccacta | 600 |
| ccaaaagtga attgcaacta ttttaggagc acttaagcac atccgaaaaa tgagtgattc | 660 |
| tgttctggcc cacaccacat cactgatgta cccccttaaa gcatgtccct gagttcatca | 720 |
| cagaagactg ctcctcctgt gccctccaca aggttagaac tgtccttgtc ttagggaaaa | 780 |
| aggagagaga gagagagaga gagagagaga gagagagaga gagagagaga gagggacagg | 840 |
| caccaactgg gtaacctctg ctgaccccca ctctacttta ccataagtag ctccaaatcc | 900 |
| ttctagaaaa tctgaaaggc atagccccat atatcagtga tataaataga acctgcagca | 960 |
| ggctctggta aatgatgact acaaggtgga ctgggaggca gcccggcctt ggcaggcatc | 1020 |
| atcctctaaa tataaagatg agtttgttca gcctttgcag aaggaggatc cgtcgacggc | 1080 |
| gcgccacgcg tcagtttact caccagggat tcagaggcag cactgctgaa ccctgagccc | 1140 |

```
ttggcacatc aggttggctg tcagaagtcg gcctttgtac atacacagtt cccttgtgag    1200
gcccagctgc gtgtcctagg agcggggcct ctctccacag cagagctcag cctctcaagt    1260
gtatggacag cacgggtgcc tgatgggtgg atttagccat gagttgaagg tggcttgggg    1320
agaatgagag ttctagagat agggagaagg ggttgccaat aggagagtgg aattcctgag    1380
cacctcgtca caggcagccg acagaacatg agccgcaggg cccaggctat ttatacctcg    1440
cctgtcacta tcagggtccc cacagctccc cccacctcca gccacacaca gcaggtcctt    1500
ttgctctttc tggtcccttc tctactcctc cccctcccta cctaaggtac caacgcgtt     1560 acgtggccac cgccttcggc accatcctca cgacacccaa atatgcgac gggtgaggaa     1620 tggtggggag ttatttttag agcggtgagg aaggtgggca ggcagcaggt gttggcgctc    1680
taaaaataac tcccgggagt tattttttaga gcggaggaat ggtggacacc caaatatggc   1740
gacggttcct cacccgtcgc catatttggg tgtccgccct cggccggggc cgcattcctg    1800
ggggccgggc ggtgctcccg cccgcctcga taaaaggctc cggggccggc ggcggcccac    1860
gagctacccg gaggagcggg aggcgccaag ctctagatct agaaagaggt aagggtttaa    1920
gggatggttg gttggtgggg tattaatgtt taattacctg gagcacctgc ctgaaatcac    1980 ttttttttcag gttggaagct tgccaccatg gctgctgccg ctgctgctgc agctgaacag   2040
caatctagca acgccccgt gaagaaatcc atgcgcgaga aggccgtcga gcggagatct     2100
gtgaacaaag agcacaacag caacttcaag gccggctaca tccccatcga cgaggacaga    2160
ctgcacaaga caggcctgag aggcagaaag ggcaatctgg ccatctgcgt gatcatcctg    2220
ctgttcatcc tggccgtgat caacctgatc atcccctgg tcatctgggc cgtgattaga     2280
atcggcccca acggctgcga cagcatgaa tttcacgaga gcggcctgct gcggttcaaa     2340
caggtgtccg atatgggcgt gatccatcca ctgtacaaga gcaccgttgg cggcagaaga   2400
aacgagaatc tggtcatcac cggcaacaac cagcctatcg tgtttcagca gggcaccacc   2460
aagctgagcg tggaaaacaa caagaccagc atcaccagcg acatcggcat gcagttcttc   2520
gaccccagaa cacagaacat cctgttcagc accgactacg agacacacga gttccatctg   2580
cctagcggcg tgaagtccct gaatgtgcag aaggccagca ccgagagaat caccagcaat   2640
gccacctccg acctgaacat caaagtggac ggcagagcca tcgtgcgggg aaatgagggc   2700
gtgttcatca tgggcaagac catcgagttc cacatgggcg gcaacatgga actgaaggcc   2760
gagaacagca tcatcctgaa cggcagcgtg atggtgtcca ccacaagact gccaagcagc   2820
agctctggcg atcagcttgg atctggcgac tgggtccgat acaagctgtg tatgtgtgcc   2880
gacggcaccc tgttcaaggt gcaagtgaca agccagaaca tgggctgcca gatcagcgac   2940
aacccttgcg gcaatacca ctgattcgaa acgtctagtc catcttgagc atctgacttc    3000
tggctaaata aaagatcttt attttcatta gatctgtgtg ttggtttttt gtgtgcgtcg   3060
agatccacgg ccgcaggaac ccctagtgat ggagttggcc actccctctc tgcgcgctcg   3120
ctcgctcact gaggccgggc gaccaaaggt cgcccgacgc ccgggctttg cccgggcggc    3180
ctcagtgagc gagcgagcgc gcagctgcct gcagggcgc ctgatgcggt attttctcct    3240
tacgcatctg tgcggtattt cacaccgcat acgtcaaagc aaccatagta cgcgccctgt   3300
agcggcgcat taagcgcggc gggtgtggtg gttacgcgca gcgtgaccgc tacacttgcc   3360
agcgccctag cgcccgctcc tttcgctttc ttcccttcct ttctcgccac gttcgccggc   3420
tttccccgtc aagctctaaa tcgggggctc cctttagggt tccgatttag tgctttacgg   3480
```

```
cacctcgacc ccaaaaaact tgatttgggt gatggttcac gtagtgggcc atcgccctga    3540
tagacggttt ttcgcccttt gacgttggag tccacgttct ttaatagtgg actcttgttc    3600
caaactggaa caacactcaa ccctatctcg ggctattctt ttgatttata agggattttg    3660
ccgatttcgg cctattggtt aaaaaatgag ctgatttaac aaaaatttaa cgcgaatttt    3720
aacaaaatat taacgtttac aattttatgg tgcactctca gtacaatctg ctctgatgcc    3780
gcatagttaa gccagcccg acacccgcca cacccgctg acgcgccctg acgggcttgt     3840
ctgctcccgg catccgctta cagacaagct gtgaccgtct ccgggagctg catgtgtcag    3900
aggttttcac cgtcatcacc gaaacgcgcg agacgaaagg ccctcgtgat acgcctattt    3960
ttataggtta atgtcatgat aataatggtt tcttagacgt caggtggcac ttttcgggga   4020
aatgtgcgcg gaaccctat ttgtttattt tctaaatac attcaaatat gtatccgctc      4080
atgagacaat aaccctgata aatgcttcaa taatattgaa aaggaagag tatgagtatt    4140
caacatttcc gtgtcgccct tattcccttt tttgcggcat tttgccttcc tgttttgct    4200
cacccagaaa cgctggtgaa agtaaaagat gctgaagatc agttgggtgc acgagtggg    4260
tacatcgaac tggatctcaa cagcggtaag atccttgaga gttttcgccc cgaagaacgt   4320
tttccaatga tgagcacttt taaagttctg ctatgtggcg cggtattatc ccgtattgac   4380
gccgggcaag agcaactcgg tcgccgcata cactattctc agaatgactt ggttgagtac   4440
tcaccagtca cagaaaagca tcttacggat ggcatgacag taagagaatt atgcagtgct   4500
gccataacca tgagtgataa cactgcggcc aacttacttc tgacaacgat cggaggaccg   4560
aaggagctaa ccgcttttt gcacaacatg ggggatcatg taactcgcct tgatcgttgg    4620
gaaccggagc tgaatgaagc cataccaaac gacgagcgtg acaccacgat gcctgtagca   4680
atggcaacaa cgttgcgcaa actattaact ggcgaactac ttactctagc ttcccggcaa   4740
caattaatag actggatgga ggcggataaa gttgcaggac cacttctgcg ctcggccctt   4800
ccggctggct ggtttattgc tgataaatct ggagccggtg agcgtgggtc tcgcggtatc   4860
attgcagcac tggggccaga tggtaagccc tcccgtatcg tagttatcta cacgacgggg   4920
agtcaggcaa ctatggatga acgaaataga cagatcgctg agataggtgc ctcactgatt   4980
aagcattggt aactgtcaga ccaagtttac tcatatatac tttagattga tttaaaactt   5040
catttttaat ttaaaaggat ctaggtgaag atcctttttg ataatctcat gaccaaaatc   5100
ccttaacgtg agttttcgtt ccactgagcg tcagaccccg tagaaaagat caaaggatct   5160
tcttgagatc ctttttttct gcgcgtaatc tgctgcttgc aaacaaaaaa accaccgcta   5220
ccagcggtgg tttgtttgcc ggatcaagag ctaccaactc tttttccgaa ggtaactggc   5280
ttcagcagag cgcagatacc aaatactgtc cttctagtgt agccgtagtt aggccaccac   5340
ttcaagaact ctgtagcacc gcctacatac ctcgctctgc taatcctgtt accagtggct   5400
gctgccagtg gcgataagtc gtgtcttacc gggttggact caagacgata gttaccggat   5460
aaggcgcagc ggtcgggctg aacggggggt tcgtgcacac agcccagctt ggagcgaacg   5520
acctacaccg aactgagata cctacagcgt gagctatgag aaagcgccac gcttcccgaa   5580
gggagaaagg cggacaggta tccggtaagc ggcagggtcg gaacaggaga gcgcacgagg   5640
gagcttccag ggggaaacgc ctggtatctt tatagtcctg tcgggtttcg ccacctctga   5700
cttgagcgtc gatttttgtg atgctcgtca gggggcgga gcctatggaa aaacgccagc    5760
aacgcggcct ttttacggtt cctggccttt tgctggcctt tgctcacat gt             5812
```

<210> SEQ ID NO 31
<211> LENGTH: 5812
<212> TYPE: DNA
<213> ORGANISM: Artificial Sequence
<220> FEATURE:
<223> OTHER INFORMATION: AAV-CRE06-CRE04-CSK-SH5-SPc5-12-MVM-hB-SG-pA

<400> SEQUENCE: 31

```
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggccgggc caggggacgg tggcttctac gtgcttggga cgttcccagc     180
caccgtccca tgttcccggc gggggccag ctgtccccac cgccagccca actcagcact      240
tggtcagggt atcagcttgg tggggggcg tgagcccagc ccctggggcg gctcagccca      300
tacaaggcca tggggctggg cgcaaagcat gcctgggttc aggtgggta tggtgcggga      360
gcagggaggt gagaggctca gctgccctcc agaactcctc cctgggaca accccctccca     420
gccaatagca cagcctaggt cccccctata aaggccacgg ctgctggccc ttcctttggg     480
tcagtgtcac ctccaggata cagacagccc cccttcagcc cagcccagcc aggtacggcg     540
cgccgtcgac ggatcccctt ttagagaatc cacacctgtc ccagttgctg gttccacta      600
ccaaaagtga attgcaacta ttttaggagc acttaagcac atccgaaaaa tgagtgattc      660
tgttctggcc cacaccacat cactgatgta ccccccttaaa gcatgtccct gagttcatca    720
cagaagactg ctcctcctgt gccctccaca aggttagaac tgtccttgtc ttagggaaaa     780
aggagagaga gagagagaga gagagagaga gagagagaga gagagagaga gagggacagg     840
caccaactgg gtaacctctg ctgacccca ctctacttta ccataagtag ctccaaatcc      900
ttctagaaaa tctgaaaggc atagccccat atatcagtga tataaataga acctgcagca    960
ggctctggta aatgatgact acaaggtgga ctggaggca gccggccttt ggcaggcatc    1020
atcctctaaa tataaagatg agtttgttca gcctttgcag aaggaggatc cgtcgacggc    1080
gcgccacgcg tcagtttact caccagggat tcagaggcag cactgctgaa ccctgagccc    1140
ttggcacatc aggttggctg tcagaagtcg gcctttgtac atacacagtt cccttgtgag    1200
gcccagctgc gtgtcctagg agcggggcct ctctccacag cagagctcag cctctcaagt    1260
gtatggacag cacgggtgcc tgatgggtgg atttagccat gagttgaagg tggcttgggg    1320
agaatgagag ttctagagat agggagaagg ggttgccaat aggagagtgg aattcctgag    1380
cacctcgtca caggcagccg acagaacatg agccgcaggg cccaggctat ttatacctcg    1440
cctgtcacta tcagggtccc cacagctccc cccacctcca gccacacaca gcaggtcctt    1500
ttgctctttc tggtcccttc tctactcctc cccctcccta cctaaggtac ccaacgcgtt    1560
acgtggccac cgccttcggc accatcctca cgacacccaa atatgcgac gggtgaggaa     1620
tggtggggag ttattttag agcggtgagg aaggtgggca ggcagcaggt gttggcgctc    1680
taaaaataac tcccgggagt tatttttaga gcggaggaat ggtggacacc caaatatggc    1740
gacggttcct cacccgtcgc catatttggg tgtccgccct cggccggggc gcattcctg    1800
ggggccgggc ggtgctcccg cccgcctcga taaaaggctc cggggccggc ggcggcccac    1860
gagctacccg gaggagcggg aggcgccaag ctctagatct agaaagaggt aagggtttaa    1920
gggatggttg gttggtgggg tattaatgtt taattacctg gagcacctgc ctgaaatcac    1980
tttttttcag gttggaagct tgccaccatg gcggcagcgg cggcggcggc tgcagaacag    2040
caaagttcca atggtcctgt aaagaagtcc atgcgtgaga aggctgttga gagaaggagt    2100
```

```
gtcaataaag agcacaacag taactttaaa gctggataca ttccgattga tgaagatcgt    2160
ctccacaaaa cagggttgag aggaagaaag ggcaatttag ccatctgtgt gattatcctc    2220
ttgtttatcc tggctgtcat caatttaata ataacacttg ttatttgggc cgtgattcgc    2280
attggaccaa atggctgtga tagtatggag tttcatgaaa gtggcctgct tcgatttaag    2340
caagtatctg acatgggagt gatccaccct ctttataaaa gcacagtagg aggaaggcga    2400
aatgaaaatt tggtcatcac tggcaacaac cagcctattg tttttcagca agggacaaca    2460
aagctcagtg tagaaaacaa caaaacttct attacaagtg acatcggcat gcagtttttt    2520
gacccgagga ctcaaaatat cttattcagc acagactatg aaactcatga gtttcatttg    2580
ccaagtggag tgaaaagttt gaatgttcaa aaggcatcta ctgaaaggat taccagcaat    2640
gctaccagtg atttaaatat aaaagttgat gggcgtgcta ttgtgcgtgg aaatgaaggt    2700
gtattcatta tgggcaaaac cattgaattt cacatgggtg gtaatatgga gttaaaggcg    2760
gaaaacagta tcatcctaaa tggatctgtg atggtcagca ccacccgcct acccagttcc    2820
tccagtggag accagttggg tagtggtgac tgggtacgct acaagctctg catgtgtgct    2880
gatgggacgc tcttcaaggt gcaagtaacc agccagaaca tgggctgcca aatctcagac    2940
aacccctgtg gaaacactca ttaattcgaa acgtctagtc catcttgagc atctgacttc    3000
tggctaaata aaagatcttt attttcatta gatctgtgtg ttggttttt gtgtgcgtcg    3060
agatccacgc ccgcaggaac ccctagtgat ggagttggcc actccctctc tgcgcgctcg    3120
ctcgctcact gaggccgggc gaccaaaggt cgcccgacgc ccgggctttg cccgggcggc    3180
ctcagtgagc gagcgagcgc gcagctgcct gcaggggcgc ctgatgcggt attttctcct    3240
tacgcatctg tgcggtattt cacaccgcat acgtcaaagc aaccatagta cgcgccctgt    3300
agcggcgcat taagcgcggc gggtgtggtg gttacgcgca gcgtgaccgc tacacttgcc    3360
agcgccctag cgcccgctcc tttcgctttc ttcccttcct ttctcgccac gttcgccggc    3420
tttccccgtc aagctctaaa tcgggggctc cctttagggt tccgatttag tgctttacgg    3480
cacctcgacc ccaaaaaact tgatttgggt gatggttcac gtagtgggcc atcgccctga    3540
tagacggttt ttcgcccttt gacgttggag tccacgttct ttaatagtgg actcttgttc    3600
caaactggaa caacactcaa ccctatctcg ggctattctt ttgatttata agggattttg    3660
ccgatttcgg cctattggtt aaaaaatgag ctgatttaac aaaaatttaa cgcgaatttt    3720
aacaaaatat taacgtttac aatttatgg tgcactctca gtacaatctg ctctgatgcc    3780
gcatagttaa gccagccccg acacccgcca cacccgctg acgcgccctg acgggcttgt    3840
ctgctcccgg catccgctta cagacaagct gtgaccgtct ccgggagctg catgtgtcag    3900
aggttttcac cgtcatcacc gaaacgcgcg agacgaaagg gcctcgtgat acgcctattt    3960
ttataggtta atgtcatgat aataatggtt tcttagacgt caggtggcac ttttcgggga    4020
aatgtgcgcg gaacccctat tgttttattt tctaaataca attcaaatat gtatccgctc    4080
atgagacaat aaccctgata aatgcttcaa taatattgaa aaggaagag tatgagtatt    4140
caacatttcc gtgtcgccct tattcccttt tttgcggcat tttgccttcc tgttttgct    4200
cacccagaaa cgctggtgaa agtaaaagat gctgaagatc agttgggtgc acgagtgggt    4260
tacatcgaac tggatctcaa cagcggtaag atccttgaga gttttcgccc cgaagaacgt    4320
tttccaatga tgagcacttt taaagttctg ctatgtggcg cggtattatc ccgtattgac    4380
gccgggcaag agcaactcgg tcgccgcata cactattctc agaatgactt ggttgagtac    4440
tcaccagtca cagaaaagca tcttacggat ggcatgacag taagagaatt atgcagtgct    4500
```

```
gccataacca tgagtgataa cactgcggcc aacttacttc tgacaacgat cggaggaccg    4560
aaggagctaa ccgcttttt  gcacaacatg ggggatcatg taactcgcct tgatcgttgg    4620
gaaccggagc tgaatgaagc cataccaaac gacgagcgtg acaccacgat gcctgtagca    4680
atggcaacaa cgttgcgcaa actattaact ggcgaactac ttactctagc ttcccggcaa    4740
caattaatag actggatgga ggcggataaa gttgcaggac cacttctgcg ctcggccctt    4800
ccggctggct ggtttattgc tgataaatct ggagccggtg agcgtgggtc tcgcggtatc    4860
attgcagcac tggggccaga tggtaagccc tcccgtatcg tagttatcta cacgacgggg    4920
agtcaggcaa ctatggatga acgaaataga cagatcgctg agataggtgc ctcactgatt    4980
aagcattggt aactgtcaga ccaagtttac tcatatatac tttagattga tttaaaactt    5040
catttttaat ttaaaaggat ctaggtgaag atccttttg  ataatctcat gaccaaaatc    5100
ccttaacgtg agttttcgtt ccactgagcg tcagaccccg tagaaaagat caaaggatct    5160
tcttgagatc ctttttttct gcgcgtaatc tgctgcttgc aaacaaaaaa accaccgcta    5220
ccagcggtgg tttgtttgcc ggatcaagag ctaccaactc ttttccgaa  ggtaactggc    5280 ttcagcagag cgcagatacc aaatactgtc cttctagtgt agccgtagtt aggccaccac    5340
ttcaagaact ctgtagcacc gcctacatac ctcgctctgc taatcctgtt accagtggct    5400
gctgccagtg gcgataagtc gtgtcttacc gggttggact caagacgata gttaccggat    5460
aaggcgcagc ggtcgggctg aacggggggt tcgtgcacac agcccagctt ggagcgaacg    5520
acctacaccg aactgagata cctacagcgt gagctatgag aaagcgccac gcttcccgaa    5580
gggagaaagg cggacaggta tccggtaagc ggcagggtcg gaacaggaga gcgcacgagg    5640
gagcttccag ggggaaacgc ctggtatctt tatagtcctg tcgggtttcg ccacctctga    5700
cttgagcgtc gatttttgtg atgctcgtca ggggggcgga gcctatggaa aaacgccagc    5760
aacgcggcct ttttacggtt cctggccttt tgctggcctt ttgctcacat gt            5812
```

<210> SEQ ID NO 32
<211> LENGTH: 5755
<212> TYPE: DNA
<213> ORGANISM: Artificial Sequence
<220> FEATURE:
<223> OTHER INFORMATION: AAV-CRE02-CRE06-CSK-SH5-SPc5-12-MVM-hB-SGco-pA

<400> SEQUENCE: 32

```
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggccgaca ggtgcggttc ccggagcgca ggcgcacaca tgcacccacc    180
ggcgaacgcg gtgaccctcg ccccacccca tccctccgg  cgggcaactg gtcgggtca     240 ggaggggcaa acccgctagg gagacactcc atatacggcc cggcccgcgt tacctgggac    300
cgggccaacc cgctccttct ttggtcaacg caggggaccc gggcggggc  ccaggccgcg    360 aaccggccga gggaggggggc tctagtgccc aacacccaaa tatggctcga aagggcagc    420 gacattcctg cggggtggcg cggagggaat gcccgcgggc tatataaaac ctgagcagag    480
ggacaagcgc ccaccgcagc ggacagcgcc aagtgaagcc tcgcttcccc tccgcggcga    540
ccagggcccg agccgagagt agcagttgta gctacccgcc caggtagggg cgcgccgtcg    600
acggatccgg gccaggggac ggtggcttct acgtgcttgg gacgttccca gccaccgtcc    660
catgttcccg gcggggggcc agctgtcccc accgccagcc caactcagca cttggtcagg    720
```

```
gtatcagctt ggtgggggg cgtgagccca gccctgggg cggctcagcc catacaaggc      780 catgggctg ggcgcaaagc atgcctgggt tcagggtggg tatggtgcgg gagcagggag      840
gtgagaggct cagctgccct ccagaactcc tccctgggga caacccctcc cagccaatag     900
cacagcctag gtcccctat ataaggccac ggctgctggc ccttcctttg gtcagtgtc       960 acctccagga tacagacagc ccccttcag cccagcccag ccaggtacgg atccgtcgac      1020
ggcgcgccac gcgtcagttt actcaccagg gattcagagg cagcactgct gaaccctgag    1080
cccttggcac atcaggttgg ctgtcagaag tcggcctttg tacatacaca gttcccttgt    1140
gaggcccagc tgcgtgtcct aggagcgggg cctctctcca cagcagagct cagcctctca    1200
agtgtatgga cagcacgggt gcctgatggg tggatttagc catgagttga aggtggcttg    1260
gggagaatga gagttctaga gatagggaga aggggttgcc aataggagag tggaattcct    1320
gagcacctcg tcacaggcag ccgacagaac atgagccgca gggcccaggc tatttatacc    1380
tcgcctgtca ctatcagggt ccccacagct ccccccacct ccagccacac acagcaggtc    1440
cttttgctct ttctggtccc ttctctactc ctccccctcc ctacctaagg tacccaacgc    1500
gttacgtggc caccgccttc ggcaccatcc tcacgacacc caaatatggc gacgggtgag    1560
gaatggtggg gagttatttt tagagcggtg aggaaggtgg gcaggcagca ggtgttggcg    1620
ctctaaaaat aactcccggg agttattttt agagcggagg aatggtggac acccaaatat    1680
ggcgacggtt cctcacccgt cgccatattt gggtgtccgc cctcggccgg ggccgcattc    1740
ctgggggccg ggcggtgctc ccgcccgcct cgataaaagg ctccggggcc ggcggcggcc    1800
cacgagctac ccggaggagc gggaggcgcc aagctctaga tctagaaaga ggtaagggtt    1860
taagggatgg ttggttggtg gggtattaat gtttaattac ctggagcacc tgcctgaaat    1920
cacttttttt caggttggaa gcttgccacc atggctgctg ccgctgctgc tgcagctgaa    1980
cagcaatcta gcaacggccc cgtgaagaaa tccatgcgcg agaaggccgt cgagcggaga    2040
tctgtgaaca aagagcacaa cagcaacttc aaggccggct acatccccat cgacgaggac    2100
agactgcaca agacaggcct gagaggcaga aagggcaatc tggccatctg cgtgatcatc    2160
ctgctgttca tcctggccgt gatcaacctg atcatcaccc tggtcatctg ggccgtgatt    2220
agaatcggcc ccaacggctg cgacagcatg gaatttcacg agagcggcct gctgcggttc    2280
aaacaggtgt ccgatatggg cgtgatccat ccactgtaca agagcaccgt ggcggcagaa    2340
agaaacgaga atctggtcat caccggcaac aaccagccta tcgtgtttca gcagggcacc    2400
accaagctga gcgtggaaaa caacaagacc agcatcacca gcgacatcgg catgcagttc    2460
ttcgacccca gaacacagaa catcctgttc agcaccgact acgagacaca cgagttccat    2520
ctgcctagcg gcgtgaagtc cctgaatgtg cagaaggcca gcaccgagag aatcaccagc    2580
aatgccacct ccgacctgaa catcaaagtg gacggcagag ccatcgtgcg gggaaatgag    2640
ggcgtgttca tcatgggcaa gaccatcgag ttccacatgg gcggcaacat ggaactgaag    2700
gccgagaaca gcatcatcct gaacggcagc gtgatggtgt ccaccacaag actgccaagc    2760
agcagctctg cgatcagct tggatctggc gactgggtcc gatacaagct gtgtatgtgt    2820
gccgacggca cctgttcaa ggtgcaagtg acaagccaga acatgggctg ccagatcagc    2880 gacaacccctt gcggcaatac ccactgattc gaaacgtcaa gtccatcttg agcatctgac    2940
ttctggctaa ataaaagatc tttatttttca ttagatctgt gtgttggttt tttgtgtgcg    3000
tcgagatcca cggccgcagg aaccctagt gatggagttg ccactccct ctctgcgcgc     3060 tcgctcgctc actgaggccg ggcgaccaaa ggtcgcccga cgcccgggct tgcccgggc    3120
```

```
ggcctcagtg agcgagcgag cgcgcagctg cctgcagggg cgcctgatgc ggtattttct    3180
ccttacgcat ctgtgcggta tttcacaccg catacgtcaa agcaaccata gtacgcgccc    3240
tgtagcggcg cattaagcgc ggcgggtgtg gtggttacgc gcagcgtgac cgctacactt    3300
gccagcgccc tagcgcccgc tcctttcgct ttcttccctt cctttctcgc cacgttcgcc    3360
ggctttcccc gtcaagctct aaatcggggg ctcccttag ggttccgatt tagtgcttta    3420
cggcacctcg accccaaaaa acttgatttg ggtgatggtt cacgtagtgg gccatcgccc    3480
tgatagacgg ttttcgccc tttgacgttg gagtccacgt tctttaatag tggactcttg    3540
ttccaaactg gaacaacact caaccctatc tcgggctatt cttttgattt ataagggatt    3600
ttgccgattt cggcctattg gttaaaaaat gagctgattt aacaaaaatt taacgcgaat    3660
tttaacaaaa tattaacgtt tacaatttta tggtgcactc tcagtacaat ctgctctgat    3720
gccgcatagt taagccagcc ccgacacccg ccaacacccg ctgacgcgcc ctgacgggct    3780
tgtctgctcc cggcatccgc ttacagacaa gctgtgaccg tctccgggag ctgcatgtgt    3840
cagaggtttt caccgtcatc accgaaacgc gcgagacgaa agggcctcgt gatacgccta    3900
tttttatagg ttaatgtcat gataataatg gtttcttaga cgtcaggtgg cacttttcgg    3960
ggaaatgtgc gcggaacccc tatttgttta ttttctaaa tacattcaaa tatgtatccg    4020
ctcatgagac aataaccctg ataaatgctt caataatatt gaaaaaggaa gagtatgagt    4080
attcaacatt tccgtgtcgc ccttattccc ttttttgcgg cattttgcct tcctgttttt    4140
gctcacccag aaacgctggt gaaagtaaaa gatgctgaag atcagttggg tgcacgagtg    4200
ggttacatcg aactggatct caacagcggt aagatccttg agagttttcg ccccgaagaa    4260
cgttttccaa tgatgagcac ttttaaagtt ctgctatgtg gcgcggtatt atcccgtatt    4320
gacgccgggc aagagcaact cggtcgccgc atacactatt ctcagaatga cttggttgag    4380
tactcaccag tcacagaaaa gcatcttacg gatggcatga cagtaagaga attatgcagt    4440
gctgccataa ccatgagtga taacactgcg gccaacttac ttctgacaac gatcggagga    4500
ccgaaggagc taaccgcttt tttgcacaac atggggatc atgtaactcg ccttgatcgt    4560
tgggaaccgg agctgaatga agccatacca aacgacgagc gtgacaccac gatgcctgta    4620
gcaatggcaa caacgttgcg caaactatta actggcgaac tacttactct agcttcccgg    4680
caacaattaa tagactggat ggaggcggat aaagttgcag gaccacttct gcgctcggcc    4740
cttccggctg gctggtttat tgctgataaa tctggagccg gtgagcgtgg gtctcgcggt    4800
atcattgcag cactggggcc agatggtaag ccctcccgta tcgtagttat ctacacgacg    4860
gggagtcagg caactatgga tgaacgaaat agacagatcg ctgagatagg tgcctcactg    4920
attaagcatt ggtaactgtc agaccaagtt tactcatata tactttagat tgatttaaaa    4980
cttcattttt aatttaaaag gatctaggtg aagatccttt ttgataatct catgaccaaa    5040
atcccttaac gtgagttttc gttccactga gcgtcagacc ccgtagaaaa gatcaaagga    5100
tcttcttgag atccttttt tctgcgcgta atctgctgct tgcaaacaaa aaaaccaccg    5160
ctaccagcgg tggtttgttt gccggatcaa gagctaccaa ctcttttcc gaaggtaact    5220 ggcttcagca gagcgcagat accaaatact gtccttctag tgtagccgta gttaggccac    5280
cacttcaaga actctgtagc accgcctaca tacctcgctc tgctaatcct gttaccagtg    5340
gctgctgcca gtggcgataa gtcgtgtctt accgggttgg actcaagacg atagttaccg    5400
gataaggcgc agcggtcggg ctgaacgggg ggttcgtgca cacagcccag cttggagcga    5460
```

```
acgacctaca ccgaactgag atacctacag cgtgagctat gagaaagcgc cacgcttccc    5520
gaagggagaa aggcggacag gtatccggta agcggcaggg tcggaacagg agagcgcacg    5580
agggagcttc caggggggaaa cgcctggtat ctttatagtc ctgtcgggtt tcgccacctc    5640
tgacttgagc gtcgattttt gtgatgctcg tcagggggc ggagcctatg gaaaaacgcc    5700
agcaacgcgg cctttttacg gttcctggcc ttttgctggc cttttgctca catgt         5755

<210> SEQ ID NO 33
<211> LENGTH: 5755
<212> TYPE: DNA
<213> ORGANISM: Artificial Sequence
<220> FEATURE:
<223> OTHER INFORMATION: AAV-CRE02-CRE06-CSK-SH5-SPc5-12-MVM-hB-SG-pA

<400> SEQUENCE: 33
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggccgaca ggtgcggttc ccggagcgca ggcgcacaca tgcacccacc     180
ggcgaacgcg gtgaccctcg ccccacccca tcccctccgg cgggcaactg ggtcgggtca     240
ggaggggcaa acccgctagg gagacactcc atatacggcc cggcccgcgt tacctgggac     300
cgggccaacc cgctccttct ttggtcaacg caggggaccc gggcggggc ccaggccgcg      360 aaccggccga gggaggggc tctagtgccc aacacccaaa tatggctcga agggcagc       420 gacattcctg cggggtggcg cggagggaat gcccgcgggc tatataaaac ctgagcagag     480
ggacaagcgc ccaccgcagc ggacagcgcc aagtgaagcc tcgcttcccc tccgcggcga     540
ccagggcccg agccgagagt agcagttgta gctacccgcc caggtagggg cgcgccgtcg     600
acggatccgg gccaggggac ggtggcttct acgtgcttgg gacgttccca gccaccgtcc     660
catgttcccg gcggggggcc agctgtcccc accgccagcc caactcagca cttggtcagg    720
gtatcagctt ggtggggggg cgtgagccca gcccctgggg cggctcagcc catacaaggc     780
catggggctg ggcgcaaagc atgcctgggt tcagggtggg tatggtgcgg gagcagggag     840
gtgagaggct cagctgccct ccagaactcc tccctgggga caacccctcc cagccaatag    900
cacagcctag gtcccccctat ataaggccac ggctgctggc ccttccttttg ggtcagtgtc    960 acctccagga tacagacagc ccccttcag cccagcccag ccaggtacgg atccgtcgac    1020
ggcgcgccac gcgtcagttt actcaccagg gattcagagg cagcactgct gaaccctgag    1080
cccttggcac atcaggttgg ctgtcagaag tcggcctttg tacatacaca gttcccttgt    1140
gaggcccagc tgcgtgtcct aggagcgggg cctctctcca cagcagagct cagcctctca    1200
agtgtatgga cagcacgggt gcctgatggg tggatttagc catgagttga aggtggcttg    1260
gggagaatga gagttctaga gatagggaga aggggttgcc aataggagag tggaattcct    1320
gagcacctcg tcacaggcag ccgacagaac atgagccgca gggcccaggc tatttatacc    1380
tcgcctgtca ctatcagggt ccccacagct ccccccacct ccagccacac acagcaggtc    1440
cttttgctct ttctggtccc ttctctactc ctccccctcc ctacctaagg tacccaacgc    1500
gttacgtggc caccgccttc ggcaccatcc tcacgacacc caaatatggc gacgggtgag    1560
gaatggtggg gagttatttt tagagcggtg aggaaggtgg gcaggcagca ggtgttggcg    1620
ctctaaaaat aactcccggg agttattttt agagcggagg aatggtggac acccaaatat     1680
ggcgacggtt cctcacccgt cgccatattt gggtgtccgc cctcggccgg ggccgcattc    1740 ctggggggccg ggcggtgctc ccgcccgcct cgataaaagg ctccggggcc ggcggcggcc    1800
```

```
cacgagctac ccggaggagc gggaggcgcc aagctctaga tctagaaaga ggtaagggtt    1860
taagggatgg ttggttggtg gggtattaat gtttaattac ctggagcacc tgcctgaaat    1920
cacttttttt caggttggaa gcttgccacc atggcggcag cggcggcggc ggctgcagaa    1980
cagcaaagtt ccaatggtcc tgtaaagaag tccatgcgtg agaaggctgt tgagagaagg    2040
agtgtcaata aagagcacaa cagtaacttt aaagctggat acattccgat tgatgaagat    2100
cgtctccaca aaacagggtt gagaggaaga aagggcaatt tagccatctg tgtgattatc    2160
ctcttgttta tcctggctgt catcaattta ataataacac ttgttatttg ggccgtgatt    2220
cgcattggac caaatggctg tgatagtatg gagtttcatg aaagtggcct gcttcgattt    2280
aagcaagtat ctgacatggg agtgatccac cctctttata aaagcacagt aggaggaagg    2340
cgaaatgaaa atttggtcat cactggcaac aaccagccta ttgttttttca gcaagggaca    2400 acaaagctca gtgtagaaaa caacaaaact tctattacaa gtgacatcgg catgcagttt    2460
tttgacccga ggactcaaaa tatcttattc agcacagact atgaaactca tgagtttcat    2520
ttgccaagtg gagtgaaaag tttgaatgtt caaaaggcat ctactgaaag gattaccagc    2580
aatgctacca gtgatttaaa tataaaagtt gatgggcgtg ctattgtgcg tggaaatgaa    2640
ggtgtattca ttatgggcaa aaccattgaa tttcacatgg gtggtaatat ggagttaaag    2700
gcggaaaaca gtatcatcct aaatggatct gtgatggtca gcaccacccg cctacccagt    2760
tcctccagtg agaccagttt gggtagtggt gactgggtac gctacaagct ctgcatgtgt    2820
gctgatggga cgctcttcaa ggtgcaagta accagccaga acatgggctg ccaaatctca    2880
gacaacccct gtggaaacac tcattaattc gaaacgtcaa gtccatcttg agcatctgac    2940
ttctggctaa ataaaagatc tttattttca ttagatctgt gtgttggttt tttgtgtgcg    3000
tcgagatcca cggccgcagg aaccctagt gatggagttg gccactccct ctctgcgcgc    3060
tcgctcgctc actgaggccg ggcgaccaaa ggtcgcccga cgcccgggct ttgcccgggc    3120
ggcctcagtg agcgagcgag cgcgcagctg cctgcagggg cgcctgatgc ggtattttct    3180
ccttacgcat ctgtgcggta tttcacaccg catacgtcaa agcaaccata gtacgcgccc    3240
tgtagcggcg cattaagcgc ggcgggtgtg gtggttacgc gcagcgtgac cgctacactt    3300
gccagcgccc tagcgcccgc tcctttcgct ttcttccctt cctttctcgc cacgttcgcc    3360
ggctttcccc gtcaagctct aaatcggggg ctccctttag ggttccgatt tagtgcttta    3420
cggcacctcg accccaaaaa acttgatttg ggtgatggtt cacgtagtgg gccatcgccc    3480
tgatagacgg ttttctcgcc tttgacgttg gagtccacgt tctttaatag tggactcttg    3540
ttccaaactg gaacaacact caaccctatc tcgggctatt cttttgattt ataagggatt    3600
ttgccgattt cggcctattg gttaaaaaat gagctgattt aacaaaaatt taacgcgaat    3660
tttaacaaaa tattaacgtt tacaattta tggtgcactc tcagtacaat ctgctctgat    3720
gccgcatagt taagccagcc ccgacacccg ccaacacccg ctgacgcgcc ctgacgggct    3780
tgtctgctcc cggcatccgc ttacagacaa gctgtgaccg tctccgggag ctgcatgtgt    3840
cagaggtttt caccgtcatc accgaaacgc gcgagacgaa agggcctcgt gatacgccta    3900
tttttatagg ttaatgtcat gataataatg gtttcttaga cgtcaggtgg cacttttcgg    3960
ggaaatgtgc gcggaacccc tatttgttta ttttctaaa tacattcaaa tatgtatccg    4020
ctcatgagac aataaccctg ataaatgctt caataatatt gaaaaggaa gagtatgagt    4080 attcaacatt tccgtgtcgc ccttattccc ttttttgcgg cattttgcct tcctgttttt    4140
```

-continued

```
gctcacccag aaacgctggt gaaagtaaaa gatgctgaag atcagttggg tgcacgagtg    4200
ggttacatcg aactggatct caacagcggt aagatccttg agttttcg ccccgaagaa     4260
cgttttccaa tgatgagcac ttttaaagtt ctgctatgtg gcgcggtatt atcccgtatt   4320
gacgccgggc aagagcaact cggtcgccgc atacactatt ctcagaatga cttggttgag   4380
tactcaccag tcacagaaaa gcatcttacg gatggcatga cagtaagaga attatgcagt   4440
gctgccataa ccatgagtga taacactgcg gccaacttac ttctgacaac gatcggagga   4500
ccgaaggagc taaccgcttt tttgcacaac atggggatc atgtaactcg ccttgatcgt    4560
tgggaaccgg agctgaatga agccatacca aacgacgagc gtgacaccac gatgcctgta   4620
gcaatggcaa caacgttgcg caaactatta actggcgaac tacttactct agcttcccgg   4680
caacaattaa tagactggat ggaggcggat aaagttgcag gaccacttct gcgctcggcc   4740
cttccggctg gctggtttat tgctgataaa tctggagccg gtgagcgtgg gtctcgcggt   4800
atcattgcag cactggggcc agatggtaag ccctcccgta tcgtagttat ctacacgacg   4860
gggagtcagg caactatgga tgaacgaaat agacagatcg ctgagatagg tgcctcactg   4920
attaagcatt ggtaactgtc agaccaagtt tactcatata ctttagat tgatttaaaa    4980
cttcattttt aatttaaaag gatctaggtg aagatccttt tgataatct catgaccaaa    5040
atcccttaac gtgagttttc gttccactga gcgtcagacc ccgtagaaaa gatcaaagga   5100
tcttcttgag atcctttttt tctgcgcgta atctgctgct tgcaaacaaa aaaaccaccg   5160
ctaccagcgg tggtttgttt gccggatcaa gagctaccaa ctctttttcc gaaggtaact   5220
ggcttcagca gagcgcagat accaaatact gtccttctag tgtagccgta gttaggccac   5280
cacttcaaga actctgtagc accgcctaca tacctcgctc tgctaatcct gttaccagtg   5340
gctgctgcca gtggcgataa gtcgtgtctt accgggttgg actcaagacg atagttaccg   5400
gataaggcgc agcggtcggg ctgaacgggg ggttcgtgca cacagcccag cttggagcga   5460
acgacctaca ccgaactgag atacctacag cgtgagctat gagaaagcgc cacgcttccc   5520
gaagggagaa aggcggacag gtatccggta agcggcaggg tcggaacagg agagcgcacg   5580
agggagcttc caggggggaaa cgcctggtat ctttatagtc ctgtcgggtt tcgccacctc   5640
tgacttgagc gtcgattttt gtgatgctcg tcaggggggc ggagcctatg gaaaaacgcc   5700
agcaacgcgg cctttttacg gttcctggcc ttttgctggc cttttgctca catgt         5755
```

<210> SEQ ID NO 34
<211> LENGTH: 6296
<212> TYPE: DNA
<213> ORGANISM: Artificial Sequence
<220> FEATURE:
<223> OTHER INFORMATION: AAV-CRE02-CRE04-CRE06-CSK-SH5-SPc5-12-MVM-hB-
    SGco-pA

<400> SEQUENCE: 34

```
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcact   120
agggggttcct gcggccgaca ggtgcggttc ccggagcgca ggcgcacaca tgcacccacc   180
ggcgaacgcg gtgaccctcg ccccacccca tcccctccgg cgggcaactg ggtcgggtca   240
ggaggggcaa accgctagg gagacactcc atatacggcc cggcccgcgt tacctgggac    300
cgggccaacc cgctccttct ttggtcaacg caggggaccc gggcgggggc ccaggccgcg   360
aaccggccga gggaggggggc tctagtgccc aacacccaaa tatggctcga aagggcagc    420
```

```
gacattcctg cggggtggcg cggagggaat gcccgcgggc tatataaaac ctgagcagag    480
ggacaagcgg ccaccgcagc ggacagcgcc aagtgaagcc tcgcttcccc tccgcggcga    540
ccagggcccg agccgagagt agcagttgta gctacccgcc caggtagggg cgcgcccgta    600
cggtcgacgg atccccttttt agagaatcca cacctgtccc agttgctggg ttccactacc    660
aaaagtgaat tgcaactatt ttaggagcac ttaagcacat ccgaaaaatg agtgattctg    720
ttctggccca caccacatca ctgatgtacc cccttaaagc atgtccctga gttcatcaca    780
gaagactgct cctcctgtgc cctccacaag gttagaactg tccttgtctt agggaaaaag    840
gagagagaga gagagagaga gagagagaga gagagagaga gagagagaga gggacaggca    900
ccaactgggt aacctctgct gacccccact ctactttacc ataagtagct ccaaatcctt    960
ctagaaaatc tgaaaggcat agccccatat atcagtgata taaatagaac ctgcagcagg   1020
ctctggtaaa tgatgactac aaggtggact gggaggcagc ccggccttgg caggcatcat   1080
cctctaaata taaagatgag tttgttcagc ctttgcagaa ggaggcgcgc cgtcgacgga   1140
tccgggccag gggacggtgg cttctacgtg cttgggacgt tcccagccac cgtcccatgt   1200
tcccggcggg gggccagctg tccccaccgc agcccaact cagcacttgg tcagggtatc   1260
agcttggtgg gggggcgtga gcccagcccc tggggcggct cagcccatac aaggccatgg   1320
ggctgggcgc aaagcatgcc tgggttcagg gtgggtatgg tgcgggagca gggaggtgag   1380
aggctcagct gccctccaga actcctccct ggggacaacc cctcccagcc aatagcacag   1440
cctaggtccc cctatataag gccacggctg ctggcccttc ctttgggtca gtgtcacctc   1500
caggatacag acagcccccc ttcagcccag cccagccagg tacggatccg tcgaccgtac   1560
gggcgcgcca cgcgtcagtt tactcaccag ggattcagag gcagcactgc tgaaccctga   1620
gcccttggca catcaggttg gctgtcagaa gtcggccttt gtacatacac agttcccttg   1680
tgaggcccag ctgcgtgtcc taggagcggg gcctctctcc acagcagagc tcagcctctc   1740
aagtgtatgg acagcacggg tgcctgatgg gtggatttag ccatgagttg aaggtggctt   1800
ggggagaatg agagttctag agatagggag aaggggttgc aataggaga gtggaattcc   1860
tgagcacctc gtcacaggca gccgacagaa catgagccgc agggcccagg ctatttatac   1920
ctcgcctgtc actatcaggg tccccacagc tcccccacc tccagccaca cacagcaggt   1980
cctttttgctc tttctggtcc cttctctact cctcccccct cctacctaag gtacccaacg   2040
cgttacgtgg ccaccgcctt cggcaccatc ctcacgacac ccaaatatgg cgacgggtga   2100
ggaatggtgg ggagttattt ttagagcggt gaggaaggtg ggcaggcagc aggtgttggc   2160
gctctaaaaa taactcccgg gagttatttt tagagcggag gaatggtgga cacccaaata   2220
tggcgacggt tcctcacccg tcgccatatt tgggtgtccg ccctcggccg gggccgcatt   2280
cctgggggcc gggcggtgct cccgcccgcc tcgataaaag gctccggggc cggcggcggc   2340
ccacgagcta cccggaggag cgggaggcgc caagctctag atctagaaag aggtaagggt   2400
ttaagggatg gttggttggt ggggtattaa tgtttaatta cctggagcac ctgcctgaaa   2460
tcactttttt tcaggttgga agcttgccac catggctgct gccgctgctg ctgcagctga   2520
acagcaatct agcaacggcc ccgtgaagaa atccatgcgc gagaaggccg tcgagcggag   2580
atctgtgaac aaagagcaca acagcaactt caaggccggc tacatcccca tcgacgagga   2640
cagactgcac aagacaggcc tgagaggcag aaagggcaat ctggccatct gcgtgatcat   2700
cctgctgttc atcctggccg tgatcaacct gatcatcacc ctggtcatct gggccgtgat   2760
tagaatcggc cccaacggct gcgacagcat ggaatttcac gagagcggcc tgctgcggtt   2820
```

```
caaacaggtg tccgatatgg gcgtgatcca tccactgtac aagagcaccg ttggcggcag    2880
aagaaacgag aatctggtca tcaccggcaa caaccagcct atcgtgtttc agcagggcac    2940
caccaagctg agcgtggaaa acaacaagac cagcatcacc agcgacatcg gcatgcagtt    3000
cttcgacccc agaacacaga acatcctgtt cagcaccgac tacgagacac acgagttcca    3060
tctgcctagc ggcgtgaagt ccctgaatgt gcagaaggcc agcaccgaga gaatcaccag    3120
caatgccacc tccgacctga acatcaaagt ggacggcaga gccatcgtgc ggggaaatga    3180
gggcgtgttc atcatgggca agaccatcga gttccacatg ggcggcaaca tggaactgaa    3240
ggccgagaac agcatcatcc tgaacggcag cgtgatggtg tccaccacaa gactgccaag    3300
cagcagctct ggcgatcagc ttggatctgg cgactgggtc cgatacaagc tgtgtatgtg    3360
tgccgacggc accctgttca aggtgcaagt gacaagccag aacatgggct gccagatcag    3420
cgacaaccct tgcggcaata cccactgatt cgaaacgtca agtccatctt gagcatctga    3480
cttctggcta aataaaagat ctttatttc attagatctg tgtgttggtt ttttgtgtgc     3540
gtcgagatcc acggccgcag gaacccctag tgatggagtt ggccactccc tctctgcgcg    3600
ctcgctcgct cactgaggcc gggcgaccaa aggtcgcccg acgcccgggc tttgcccggg    3660
cggcctcagt gagcgagcga gcgcgcagct gcctgcaggg gcgcctgatg cggtattttc    3720
tccttacgca tctgtgcggt atttcacacc gcatacgtca aagcaaccat agtacgcgcc    3780
ctgtagcggc gcattaagcg cggcgggtgt ggtggttacg cgcagcgtga ccgctacact    3840
tgccagcgcc ctagcgcccg ctcctttcgc tttcttccct cctttctcg ccacgttcgc     3900 cggctttccc cgtcaagctc taaatcgggg ctcccttta gggttccgat ttagtgcttt     3960
acggcacctc gaccccaaaa aacttgattt gggtgatggt tcacgtagtg gccatcgcc     4020 ctgatagacg gtttttcgcc ctttgacgtt ggagtccacg ttctttaata gtggactctt    4080
gttccaaact ggaacaacac tcaaccctat ctcgggctat tcttttgatt tataagggat    4140
tttgccgatt tcggcctatt ggttaaaaaa tgagctgatt taacaaaaat ttaacgcgaa    4200
ttttaacaaa atattaacgt ttacaatttt atggtgcact ctcagtacaa tctgctctga    4260
tgccgcatag ttaagccagc cccgacaccc gccaacaccc gctgacgcgc cctgacgggc    4320
ttgtctgctc ccggcatccg cttacagaca agctgtgacc gtctccggga gctgcatgtg    4380
tcagaggttt tcaccgtcat caccgaaacg cgcgagacga agggcctcg tgatacgcct     4440 atttttatag gttaatgtca tgataataat ggtttcttag acgtcaggtg gcacttttcg    4500
gggaaatgtg cgcggaaccc ctatttgttt attttctaa atacattcaa atatgtatcc     4560
gctcatgaga caataaccct gataaatgct tcaataatat tgaaaaagga agagtatgag    4620
tattcaacat ttccgtgtcg cccttattcc cttttttgcg gcattttgcc ttcctgtttt    4680
tgctcaccca gaaacgctgg tgaaagtaaa agatgctgaa gatcagttgg gtgcacgagt    4740
gggttacatc gaactggatc tcaacagcgg taagatcctt gagagttttc gccccgaaga    4800
acgttttcca atgatgagca cttttaaagt tctgctatgt ggcgcggtat tatcccgtat    4860
tgacgccggg caagagcaac tcggtcgccg catacactat tctcagaatg acttggttga    4920
gtactcacca gtcacagaaa agcatcttac ggatggcatg acagtaagag aattatgcag    4980
tgctgccata accatgagtg ataacactgc ggccaactta cttctgacaa cgatcggagg    5040
accgaaggag ctaaccgctt ttttgcacaa catgggggat catgtaactc gccttgatcg    5100
ttgggaaccg gagctgaatg aagccatacc aaacgacgag cgtgacacca cgatgcctgt    5160
```

| | |
|---|---|
| agcaatggca acaacgttgc gcaaactatt aactggcgaa ctacttactc tagcttcccg | 5220 |
| gcaacaatta atagactgga tggaggcgga taaagttgca ggaccacttc tgcgctcggc | 5280 |
| ccttccggct ggctggttta ttgctgataa atctggagcc ggtgagcgtg ggtctcgcgg | 5340 |
| tatcattgca gcactggggc cagatggtaa gccctcccgt atcgtagtta tctacacgac | 5400 |
| ggggagtcag gcaactatgg atgaacgaaa tagacagatc gctgagatag gtgcctcact | 5460 |
| gattaagcat tggtaactgt cagaccaagt ttactcatat atactttaga ttgatttaaa | 5520 |
| acttcatttt taatttaaaa ggatctaggt gaagatcctt tttgataatc tcatgaccaa | 5580 |
| aatcccttaa cgtgagtttt cgttccactg agcgtcagac cccgtagaaa agatcaaagg | 5640 |
| atcttcttga tccttttttt ttctgcgcgt aatctgctgc ttgcaaacaa aaaaaccacc | 5700 |
| gctaccagcg gtggtttgtt tgccggatca agagctacca actctttttc cgaaggtaac | 5760 |
| tggcttcagc agagcgcaga taccaaatac tgtccttcta gtgtagccgt agttaggcca | 5820 |
| ccacttcaag aactctgtag caccgcctac atacctcgct ctgctaatcc tgttaccagt | 5880 |
| ggctgctgcc agtggcgata agtcgtgtct taccgggttg gactcaagac gatagttacc | 5940 |
| ggataaggcg cagcggtcgg gctgaacggg gggttcgtgc acacagccca gcttggagcg | 6000 |
| aacgacctac accgaactga gatacctaca gcgtgagcta tgagaaagcg ccacgcttcc | 6060 |
| cgaagggaga aaggcggaca ggtatccggt aagcggcagg gtcggaacag gagagcgcac | 6120 |
| gagggagctt ccagggggaa acgcctggta tctttatagt cctgtcgggt ttcgccacct | 6180 |
| ctgacttgag cgtcgatttt tgtgatgctc gtcaggggg cggagcctat ggaaaaacgc | 6240 |
| cagcaacgcg gcctttttac ggttcctggc cttttgctgg ccttttgctc acatgt | 6296 |

<210> SEQ ID NO 35
<211> LENGTH: 6296
<212> TYPE: DNA
<213> ORGANISM: Artificial Sequence
<220> FEATURE:
<223> OTHER INFORMATION: AAV-CRE02-CRE04-CRE06-CSK-SH5-SPc5-12-MVM-hB-
    SG-pA

<400> SEQUENCE: 35

| | |
|---|---|
| cctgcaggca gctgcgcgct cgctcgctca ctgaggccgc ccgggcgtcg ggcgaccttt | 60 |
| ggtcgcccgg cctcagtgag cgagcgagcg cgcagagagg gagtggccaa ctccatcact | 120 |
| aggggttcct gcggccgaca ggtgcggttc ccggagcgca ggcgcacaca tgcacccacc | 180 |
| ggcgaacgcg gtgaccctcg ccccacccca tccctccgg cgggcaactg ggtcgggtca | 240 |
| ggaggggcaa acccgctagg gagacactcc atatacggcc cggcccgcgt tacctgggac | 300 |
| cgggccaacc cgctccttct ttggtcaacg caggggaccc gggcgggggc ccaggccgcg | 360 |
| aaccggccga gggaggggc tctagtgccc aacacccaaa tatggctcga aagggcagc | 420 |
| gacattcctg cggggtggcg cggagggaat gcccgcgggc tatataaaac ctgagcagag | 480 |
| ggacaagcgc ccaccgcagc ggacagcgcc aagtgaagcc tcgcttcccc tccgcggcga | 540 |
| ccagggcccg agccgagagt agcagttgta gctacccgcc caggtagggg cgcgcccgta | 600 |
| cggtcgacgg atccccttt agagaatcca cacctgtccc agttgctggg ttccactacc | 660 |
| aaaagtgaat tgcaactatt ttaggagcac ttaagcacat ccgaaaaatg agtgattctg | 720 |
| ttctggccca caccacatca ctgatgtacc cccttaaagc atgtccctga gttcatcaca | 780 |
| gaagactgct cctcctgtgc cctccacaag gttagaactg tccttgtctt agggaaaaag | 840 |
| gagagagaga gagagagaga gagagagaga gagagagaga gagagagaga gggacaggca | 900 |

```
ccaactgggt aacctctgct gacccccact ctactttacc ataagtagct ccaaatcctt      960
ctagaaaatc tgaaaggcat agccccatat atcagtgata taaatagaac ctgcagcagg     1020
ctctggtaaa tgatgactac aaggtggact gggaggcagc ccggccttgg caggcatcat     1080
cctctaaata taaagatgag tttgttcagc ctttgcagaa ggaggcgcgc cgtcgacgga     1140
tccgggccag gggacggtgg cttctacgtg cttgggacgt tcccagccac cgtcccatgt     1200
tcccggcggg gggccagctg tccccaccgc cagcccaact cagcacttgg tcagggtatc     1260
agcttggtgg gggggcgtga gcccagcccc tggggcggct cagcccatac aaggccatgg     1320
ggctgggcgc aaagcatgcc tgggttcagg gtgggtatgg tgcgggagca gggaggtgag     1380
aggctcagct gccctccaga actcctccct ggggacaacc cctcccagcc aatagcacag     1440
cctaggtccc cctatataag gccacggctg ctggcccttc ctttgggtca gtgtcacctc     1500
caggatacag acagcccccc ttcagcccag cccagccagg tacggatccg tcgaccgtac     1560
gggcgcgcca cgcgtcagtt tactcaccag ggattcagag gcagcactgc tgaaccctga     1620
gcccttggca catcaggttg gctgtcagaa gtcggccttt gtacatacac agttcccttg     1680
tgaggcccag ctgcgtgtcc taggagcggg gcctctctcc acagcagagc tcagcctctc     1740
aagtgtatgg acagcacggg tgcctgatgg gtggatttag ccatgagttg aaggtggctt     1800
ggggagaatg agagttctag atatagggag aaggggttgc aataggagaa gtggaattcc     1860
tgagcacctc gtcacaggca gccgacagaa catgagccgc agggcccagg ctatttatac     1920
ctcgcctgtc actatcaggg tccccacagc tccccccacc tccagccaca cacagcaggt     1980
cctttgctc ttttctggtcc cttctctact cctcccctc cctacctaag gtacccaacg       2040
cgttacgtgg ccaccgcctt cggcaccatc ctcacgacac ccaaatatgg cgacgggtga     2100
ggaatggtgg ggagttattt ttagagcggt gaggaaggtg ggcaggcagc aggtgttggc      2160
gctctaaaaa taactcccgg gagttatttt tagagcggag aatggtgga cacccaaata      2220
tggcgacggt tcctcacccg tcgccatatt tgggtgtccg ccctcggccg gggccgcatt     2280
cctgggggcc gggcggtgct cccgcccgcc tcgataaaag gctccggggc cggcggcggc     2340
ccacgagcta cccggaggag cgggaggcgc caagctctag atctagaaag aggtaagggt     2400
ttaagggatg gttggttggt ggggtattaa tgtttaatta cctggagcac ctgcctgaaa     2460
tcactttttt tcaggttgga agcttgccac catggcggca gcggcggcgg cggctgcaga     2520
acagcaaagt tccaatggtc ctgtaaagaa gtccatgcgt gagaaggctg ttgagagaag     2580
gagtgtcaat aaagagcaca acagtaactt taaagctgga tacattccga ttgatgaaga     2640
tcgtctccac aaaacagggt tgagaggaag aaagggcaat ttagccatct gtgtgattat     2700
cctcttgttt atcctggctg tcatcaattt aataataaca cttgttattt gggccgtgat     2760
tcgcattgga ccaaatggct gtgatagtat ggagtttcat gaaagtggcc tgcttcgatt     2820
taagcaagta tctgacatgg gagtgatcca ccctcttttat aaaagcacag taggaggaag     2880
gcgaaatgaa aatttggtca tcactggcaa caaccagcct attgttttc agcaagggac     2940
aacaaagctc agtgtagaaa acaacaaaac ttctattaca agtgacatcg gcatgcagtt     3000
ttttgacccg aggactcaaa atatcttatt cagcacagac tatgaaactc atgagtttca     3060
tttgccaagt ggagtgaaaa gtttgaatgt tcaaaaggca tctactgaaa ggattaccag     3120
caatgctacc agtgatttaa atataaaagt tgatggcgt gctattgtgc gtggaaatga     3180
aggtgtattc attatgggca aaaccattga atttcacatg ggtggtaata tggagttaaa     3240
ggcggaaaac agtatcatcc taaatggatc tgtgatggtc agcaccaccc gcctacccag     3300
```

```
ttcctccagt ggagaccagt tgggtagtgg tgactgggta cgctacaagc tctgcatgtg    3360
tgctgatggg acgctcttca aggtgcaagt aaccagccag aacatgggct gccaaatctc    3420
agacaacccc tgtggaaaca ctcattaatt cgaaacgtca agtccatctt gagcatctga    3480
cttctggcta aataaaagat ctttattttc attagatctg tgtgttggtt ttttgtgtgc    3540
gtcgagatcc acggccgcag gaaccccctag tgatggagtt ggccactccc tctctgcgcg    3600
ctcgctcgct cactgaggcc gggcgaccaa aggtcgcccg acgcccgggc tttgcccggg    3660
cggcctcagt gagcgagcga gcgcgcagct gcctgcaggg gcgcctgatg cggtattttc    3720
tccttacgca tctgtgcggt atttcacacc gcatacgtca aagcaaccat agtacgcgcc    3780
ctgtagcggc gcattaagcg cggcgggtgt ggtggttacg cgcagcgtga ccgctacact    3840
tgccagcgcc ctagcgcccg ctcctttcgc tttcttccct ccttctcg ccacgttcgc    3900
cggctttccc cgtcaagctc taaatcgggg gctcccttta gggttccgat ttagtgcttt    3960
acggcacctc gaccccaaaa aacttgattt gggtgatggt tcacgtagtg gccatcgcc    4020
ctgatagacg gttttcgcc ctttgacgtt ggagtccacg ttctttaata gtggactctt    4080
gttccaaact ggaacaacac tcaaccctat ctcgggctat tcttttgatt tataagggat    4140
tttgccgatt tcggcctatt ggttaaaaaa tgagctgatt taacaaaaat ttaacgcgaa    4200
ttttaacaaa atattaacgt ttacaatttt atggtgcact ctcagtacaa tctgctctga    4260
tgccgcatag ttaagccagc cccgacaccc gccaacaccc gctgacgcgc cctgacgggc    4320
ttgtctgctc ccggcatccg cttacagaca agctgtgacc gtctccggga gctgcatgtg    4380
tcagaggttt tcaccgtcat caccgaaacg cgcgagacga aagggcctcg tgatacgcct    4440
attttatag gttaatgtca tgataataat ggtttcttag acgtcaggtg cacttttcg    4500
gggaaatgtg cgcggaaccc ctatttgttt attttctaa atacattcaa atatgtatcc    4560
gctcatgaga caataaccct gataaatgct tcaataatat tgaaaaagga agagtatgag    4620
tattcaacat ttccgtgtcg cccttattcc cttttttgcg gcattttgcc ttcctgtttt    4680
tgctcaccca gaaacgctgg tgaaagtaaa agatgctgaa gatcagttgg gtgcacgagt    4740
gggttacatc gaactggatc tcaacagcgg taagatcctt gagagttttc gccccgaaga    4800
acgttttcca atgatgagca cttttaaagt tctgctatgt ggcgcggtat tatcccgtat    4860
tgacgccggg caagagcaac tcggtcgccg catacactat tctcagaatg acttggttga    4920
gtactcacca gtcacagaaa agcatcttac ggatggcatg acagtaagag aattatgcag    4980
tgctgccata accatgagtg ataacactgc ggccaactta cttctgacaa cgatcggagg    5040
accgaaggag ctaaccgctt ttttgcacaa catgggggat catgtaactc gccttgatcg    5100
ttgggaaccg gagctgaatg aagccatacc aaacgacgag cgtgacacca cgatgcctgt    5160
agcaatggca acaacgttgc gcaaactatt aactggcgaa ctacttactc tagcttcccg    5220
gcaacaatta atagactgga tggaggcgga taaagttgca ggaccacttc tgcgctcggc    5280
ccttccggct ggctggttta ttgctgataa atctggagcc ggtgagcgtg ggtctcgcgg    5340
tatcattgca gcactggggc cagatggtaa gccctcccgt atcgtagtta tctacacgac    5400
ggggagtcag gcaactatgg atgaacgaaa tagacagatc gctgagatag gtgcctcact    5460
gattaagcat tggtaactgt cagaccaagt ttactcatat atactttaga ttgatttaaa    5520
acttcatttt taatttaaaa ggatctaggt gaagatcctt tttgataatc tcatgaccaa    5580
aatcccttaa cgtgagtttt cgttccactg agcgtcagac cccgtagaaa agatcaaagg    5640
```

| atcttcttga | gatcctttt | ttctgcgcgt | aatctgctgc | ttgcaaacaa | aaaaaccacc | 5700 |
| gctaccagcg | gtggtttgtt | tgccggatca | agagctacca | actcttttc | cgaaggtaac | 5760 |
| tggcttcagc | agagcgcaga | taccaaatac | tgtccttcta | gtgtagccgt | agttaggcca | 5820 |
| ccacttcaag | aactctgtag | caccgcctac | atacctcgct | ctgctaatcc | tgttaccagt | 5880 |
| ggctgctgcc | agtggcgata | agtcgtgtct | taccgggttg | gactcaagac | gatagttacc | 5940 |
| ggataaggcg | cagcggtcgg | gctgaacggg | gggttcgtgc | acacagccca | gcttggagcg | 6000 |
| aacgacctac | accgaactga | gatacctaca | gcgtgagcta | tgagaaagcg | ccacgcttcc | 6060 |
| cgaagggaga | aaggcggaca | ggtatccggt | aagcggcagg | gtcggaacag | gagagcgcac | 6120 |
| gagggagctt | ccaggggggaa | acgcctggta | tctttatagt | cctgtcgggt | ttcgccacct | 6180 |
| ctgacttgag | cgtcgatttt | tgtgatgctc | gtcaggggg | cggagcctat | ggaaaaacgc | 6240 |
| cagcaacgcg | gcctttttac | ggttcctggc | cttttgctgg | cttttgctc | acatgt | 6296 |

<210> SEQ ID NO 36
<211> LENGTH: 5961
<212> TYPE: DNA
<213> ORGANISM: Artificial Sequence
<220> FEATURE:
<223> OTHER INFORMATION: AAV-CRE06-CSK-SH5-SPc5-12-MVM-Luc-pA

<400> SEQUENCE: 36

| cctgcaggca | gctgcgcgct | cgctcgctca | ctgaggccgc | ccgggcgtcg | ggcgaccttt | 60 |
| ggtcgcccgg | cctcagtgag | cgagcgagcg | cgcagagagg | gagtggccaa | ctccatcact | 120 |
| aggggttcct | gcggccgggc | cagggacgg | tggcttctac | gtgcttggga | cgttcccagc | 180 |
| caccgtccca | tgttcccggc | gggggggccag | ctgtccccac | cgccagccca | actcagcact | 240 |
| tggtcagggt | atcagcttgg | tgggggggcg | tgagcccagc | ccctggggcg | gctcagccca | 300 |
| tacaaggcca | tggggctggg | cgcaaagcat | gcctgggttc | agggtgggta | tggtgcggga | 360 |
| gcagggaggt | gagaggctca | gctgccctcc | agaactcctc | cctggggaca | ccctcccca | 420 |
| gccaatagca | cagcctaggt | ccccctatat | aaggccacgg | ctgctggccc | ttcctttggg | 480 |
| tcagtgtcac | ctccaggata | cagacagccc | cccttcagcc | cagcccagcc | aggtacggcg | 540 |
| cgccacgcgt | cagtttactc | accagggatt | cagaggcagc | actgctgaac | cctgagccct | 600 |
| tggcacatca | ggtggctgt | cagaagtcgg | cctttgtaca | tacacagttc | ccttgtgagg | 660 |
| cccagctgcg | tgtcctagga | gcggggcctc | tctccacagc | agagctcagc | ctctcaagtg | 720 |
| tatggacagc | acgggtgcct | gatggtggga | tttagccatg | agttgaaggt | ggcttgggga | 780 |
| gaatgagagt | tctagagata | gggagaaggg | gttgccaata | ggagagtgga | attcctgagc | 840 |
| acctcgtcac | aggcagccga | cagaacatga | gccgcagggc | ccaggctatt | tatacctcgc | 900 |
| ctgtcactat | cagggtcccc | acagctcccc | ccacctccag | ccacacacag | caggtccttt | 960 |
| tgctctttct | ggtcccttct | ctactcctcc | cctccctac | ctaaggtacc | caacgcgtta | 1020 |
| cgtggccacc | gccttcggca | ccatcctcac | gacacccaaa | tatggcgacg | ggtgaggaat | 1080 |
| ggtggggagt | tattttaga | gcggtgagga | aggtgggcag | gcagcaggtg | ttggcgctct | 1140 |
| aaaaataact | cccgggagtt | attttagag | cggaggaatg | gtggacaccc | aaatatggcg | 1200 |
| acggttcctc | accegtcgcc | atatttgggt | gtccgccctc | ggccggggcc | gcattcctgg | 1260 |
| gggccgggcg | gtgctcccgc | ccgcctcgat | aaaaggctcc | ggggccggcg | gcggcccacg | 1320 |
| agctaccegg | aggagcggga | ggcgccaagc | tctagatcta | gaaagaggta | agggtttaag | 1380 |
| ggatggttgg | ttggtgggggt | attaatgttt | aattacctgg | agcacctgcc | tgaaatcact | 1440 |

```
tttttttcagg ttggaagctt atggaagatg ccaaaaacat taagaagggc ccagcgccat    1500
tctacccact cgaggacggg accgccggcg agcagctgca caaagccatg aagcgctacg    1560
ccctggtgcc cggcaccatc gcctttaccg acgcacatat cgaggtggac attacctacg    1620
ccgagtactt cgagatgagc gttcggctgg cagaagctat gaagcgctat gggctgaata    1680
caaaccatcg gatcgtggtg tgcagcgaga atagcttgca gttcttcatg cccgtgttgg    1740
gtgccctgtt catcggtgtg gctgtggccc agctaacga catctacaac gagcgcgagc    1800
tgctgaacag catgggcatc agccagccca ccgtcgtatt cgtgagcaag aaagggctgc    1860
aaaagatcct caacgtgcaa aagaagctac cgatcataca aaagatcatc atcatggata    1920
gcaagaccga ctaccagggc ttccaaagca tgtacacctt cgtgacttcc catttgccac    1980
ccggcttcaa cgagtacgac ttcgtgcccg agagcttcga ccgggacaaa accatcgccc    2040
tgatcatgaa cagtagtggc agtaccggat tgcccaaggg cgtagcccta ccgcaccgca    2100
ccgcttgtgt ccgattcagt catgcccgcg accccatctt cggcaaccag atcatccccg    2160
acaccgctat cctcagcgtg gtgccatttc accacggctt cggcatgttc accacgctgg    2220
gctacttgat ctgcggcttt cgggtcgtgc tcatgtaccg cttcgaggag gagctattct    2280
tgcgcagctt gcaagactat aagattcaat ctgccctgct ggtgcccaca ctatttagct    2340
tcttcgctaa gagcactctc atcgacaagt acgacctaag caacttgcac gagatcgcca    2400 gcggcgggc gccgctcagc aaggaggtag gtgaggccgt ggccaaacgc ttccacctac    2460
caggcatccg ccagggctac ggcctgacag aaacaaccag cgccattctg atcaccccg    2520 aaggggacga caagcctggc gcagtaggca aggtggtgcc cttcttcgag gctaaggtgg    2580
tggacttgga caccggtaag acactgggtg tgaaccagcg cggcgagctg tgcgtccgtg    2640 gcccccatgat catgagcggc tacgttaaca accccgaggc tacaaacgct ctcatcgaca    2700 aggacgctg gctgcacagc ggcgacatcg cctactggga cgaggacgag cacttcttca    2760
tcgtggaccg gctgaagagc ctgatcaaat acaagggcta ccaggtagcc ccagccgaac    2820
tggagagcat cctgctgcaa cacccccaaca tcttcgacgc cggggtcgcc ggcctgcccg    2880
acgacgatgc cggcgagctg cccgccgcag tcgtcgtgct ggaacacggt aaaaccatga    2940
ccgagaagga gatcgtggac tatgtggcca gccaggttac aaccgccaag aagctgcgcg    3000
gtggtgttgt gttcgtggac gaggtgccta aaggactgac cggcaagttg gacgcccgca    3060
agatccgcga gattctcatt aaggccaaga agggcggcaa gatcgccgtg taattcgaaa    3120
cgtctagtcc atcttgagca tctgacttct ggctaaataa aagatcttta ttttcattag    3180
atctgtgtgt tggttttttg tgtgcgtcga gatccacggc cgcaggaacc cctagtgatg    3240
gagttggcca ctccctctct gcgcgctcgc tcgctcactg aggccgggcg accaaaggtc    3300
gcccgacgcc cgggctttgc ccgggcggcc tcagtgagcg agcgagcgcg cagctgcctg    3360
caggggcgcc tgatgcggta ttttctcctt acgcatctgt gcggtatttc acaccgcata    3420
cgtcaaagca accatagtac gcgccctgta gcggcgcatt aagcgcggcg ggtgtggtgg    3480
ttacgcgcag cgtgaccgct acacttgcca gcgccctagc gcccgctcct ttcgctttct    3540
tcccttcctt tctcgccacg ttcgccggct ttccccgtca gctctaaat cggggctcc    3600 ctttagggtt ccgatttagt gctttacggc acctcgaccc caaaaaactt gatttgggtg    3660
atggttcacg tagtgggcca tcgccctgat agacggtttt tcgccctttg acgttggagt    3720
ccacgttctt taatagtgga ctcttgttcc aaactggaac aacactcaac cctatctcgg    3780
```

-continued

```
gctattctttt  tgatttataa  gggattttgc  cgatttcggc  ctattggtta  aaaaatgagc   3840
tgatttaaca   aaaatttaac  gcgaatttta  acaaaatatt  aacgtttaca  attttatggt   3900
gcactctcag   tacaatctgc  tctgatgccg  catagttaag  ccagcccga   cacccgccaa   3960
cacccgctga   cgcgcccctga cgggcttgtc  tgctcccggc  atccgcttac  agacaagctg   4020
tgaccgtctc   cgggagctgc  atgtgtcaga  ggttttcacc  gtcatcaccg  aaacgcgcga   4080
gacgaaaggg   cctcgtgata  cgcctatttt  tataggttaa  tgtcatgata  ataatggttt   4140
cttagacgtc   aggtggcact  tttcggggaa  atgtgcgcgg  aaccctatt   tgtttatttt   4200
tctaaataca   ttcaaatatg  tatccgctca  tgagacaata  accctgataa  atgcttcaat   4260
aatattgaaa   aggaagagt   atgagtattc  aacatttccg  tgtcgccctt  attccctttt   4320
ttgcggcatt   ttgccttcct  gttttttgctc acccagaaac  gctggtgaaa  gtaaaagatg   4380
ctgaagatca   gttgggtgca  cgagtgggtt  acatcgaact  ggatctcaac  agcggtaaga   4440
tccttgagag   ttttcgcccc  gaagaacgtt  ttccaatgat  gagcactttt  aaagttctgc   4500
tatgtggcgc   ggtattatcc  cgtattgacg  ccgggcaaga  gcaactcggt  cgccgcatac   4560
actattctca   gaatgacttg  gttgagtact  caccagtcac  agaaaagcat  cttacggatg   4620
gcatgacagt   aagagaatta  tgcagtgctg  ccataaccat  gagtgataac  actgcggcca   4680
acttacttct   gacaacgatc  ggaggaccga  aggagctaac  cgcttttttg  cacaacatgg   4740
gggatcatgt   aactcgcctt  gatcgttggg  aaccggagct  gaatgaagcc  ataccaaacg   4800
acgagcgtga   caccacgatg  cctgtagcaa  tggcaacaac  gttgcgcaaa  ctattaactg   4860
gcgaactact   tactctagct  tcccggcaac  aattaataga  ctggatggag  gcggataaag   4920
ttgcaggacc   acttctgcgc  tcggcccttc  cggctggctg  gtttattgct  gataaatctg   4980
gagccggtga   gcgtgggtct  cgcggtatca  ttgcagcact  ggggccagat  ggtaagccct   5040
cccgtatcgt   agttatctac  acgacgggga  gtcaggcaac  tatggatgaa  cgaaatagac   5100
agatcgctga   gataggtgcc  tcactgatta  agcattggta  actgtcagac  caagtttact   5160
catatatact   ttagattgat  ttaaaacttc  attttttaatt taaaaggatc  taggtgaaga   5220
tccttttttga  taatctcatg  accaaaatcc  cttaacgtga  gttttcgttc  cactgagcgt   5280
cagaccccgt   agaaaagatc  aaaggatctt  cttgagatcc  ttttttttctg  cgcgtaatct   5340
gctgcttgca   acaaaaaaa   ccaccgctac  cagcggtggt  ttgtttgccg  gatcaagagc   5400
taccaactct   ttttccgaag  gtaactggct  tcagcagagc  gcagatacca  aatactgtcc   5460
ttctagtgta   gccgtagtta  ggccaccact  tcaagaactc  tgtagcaccg  cctacatacc   5520
tcgctctgct   aatcctgtta  ccagtggctg  ctgccagtgg  cgataagtcg  tgtcttaccg   5580
ggttggactc   aagacgatag  ttaccggata  aggcgcagcg  gtcgggctga  acggggggtt   5640
cgtgcacaca   gcccagcttg  gagcgaacga  cctacaccga  actgagatac  ctacagcgtg   5700
agctatgaga   aagcgccacg  cttcccgaag  ggagaaaggc  ggacaggtat  ccggtaagcg   5760
gcagggtcgg   aacaggagag  cgcacgaggg  agcttccagg  gggaaacgcc  tggtatcttt   5820
atagtcctgt   cgggtttcgc  cacctctgac  ttgagcgtcg  atttttgtga  tgctcgtcag   5880
ggggcggag    cctatggaaa  aacgccagca  acgcggcctt  tttacggttc  ctggccttt    5940
gctggccttt   tgctcacatg  t                                               5961
```

<210> SEQ ID NO 37
<211> LENGTH: 6081
<212> TYPE: DNA
<213> ORGANISM: Artificial Sequence
<220> FEATURE:
<223> OTHER INFORMATION: AAV-CRE04-CSK-SH5-SPc5-12-MVM-Luc-pA

<400> SEQUENCE: 37

| | | | | |
|---|---|---|---|---|
| acatgtcctg | caggcagctg | cgcgctcgct | cgctcactga | ggccgcccgg | gcaaagcccg | 60 |
| ggcgtcgggc | gacctttggt | cgcccggcct | cagtgagcga | gcgagcgcgc | agagagggag | 120 |
| tggccaactc | catcactagg | ggttcctgcg | gcccttttta | gagaatccac | acctgtccca | 180 |
| gttgctgggt | tccactacca | aaagtgaatt | gcaactattt | taggagcact | taagcacatc | 240 |
| cgaaaaatga | gtgattctgt | tctggcccac | accacatcac | tgatgtaccc | ccttaaagca | 300 |
| tgtccctgag | ttcatcacag | aagactgctc | ctcctgtgcc | ctccacaagg | ttagaactgt | 360 |
| ccttgtctta | gggaaaaagg | agagagagag | agagagagag | agagagagag | agagagagag | 420 |
| agagagagag | ggacaggcac | caactgggta | acctctgctg | accccactc | tactttacca | 480 |
| taagtagctc | caaatccttc | tagaaaatct | gaaaggcata | gccccatata | tcagtgatat | 540 |
| aaatagaacc | tgcagcaggc | tctggtaaat | gatgactaca | aggtggactg | ggaggcagcc | 600 |
| cggccttggc | aggcatcatc | ctctaaatat | aaagatgagt | tgttcagcc | tttgcagaag | 660 |
| gaggcgcgcc | acgcgtcagt | ttactcacca | gggattcaga | ggcagcactg | ctgaaccctg | 720 |
| agcccttggc | acatcaggtt | ggctgtcaga | agtcggcctt | tgtacataca | cagttccctt | 780 |
| gtgaggccca | gctgcgtgtc | ctaggagcgg | ggcctctctc | cacagcagag | ctcagcctct | 840 |
| caagtgtatg | gacagcacgg | gtgcctgatg | ggtggattta | gccatgagtt | gaaggtggct | 900 |
| tggggagaat | gagagttcta | gagataggga | gaagggttg | ccaataggag | agtggaattc | 960 |
| ctgagcacct | cgtcacaggc | agccgacaga | acatgagccg | cagggcccag | gctatttata | 1020 |
| cctcgcctgt | cactatcagg | gtccccacag | ctcccccac | ctccagccac | acacagcagg | 1080 |
| tcctttgct | ctttctggtc | ccttctctac | tcctccccct | ccctacctaa | ggtacccaac | 1140 |
| gcgttacgtg | gccaccgcct | tcggcaccat | cctcacgaca | cccaaatatg | gcgacgggtg | 1200 |
| aggaatggtg | gggagttatt | tttagagcgg | tgaggaaggt | gggcaggcag | caggtgttgg | 1260 |
| cgctctaaaa | ataactcccg | ggagttattt | ttagagcgga | ggaatggtgg | acacccaaat | 1320 |
| atggcgacgg | ttcctcaccc | gtcgccatat | ttgggtgtcc | gccctcggcc | ggggccgcat | 1380 |
| tcctgggggc | cggcggtgc | tcccgcccgc | ctcgataaaa | ggctccgggg | ccggcggcgg | 1440 |
| cccacgagct | acccggagga | gcgggaggcg | ccaagctcta | gatctagaaa | gaggtaaggg | 1500 |
| tttaagggat | ggttggttgg | tggggtatta | atgtttaatt | acctggagca | cctgcctgaa | 1560 |
| atcacttttt | ttcaggttgg | aagcttatgg | aagatgccaa | aaacattaag | aagggcccag | 1620 |
| cgccattcta | cccactcgag | gacgggaccg | ccggcgagca | gctgcacaaa | gccatgaagc | 1680 |
| gctacgccct | ggtgcccggc | accatcgcct | ttaccgacgc | acatatcgag | gtggacatta | 1740 |
| cctacgccga | gtacttcgag | atgagcgttc | ggctggcaga | agctatgaag | cgctatgggc | 1800 |
| tgaatacaaa | ccatcggatc | gtggtgtgca | gcgagaatag | cttgcagttc | ttcatgcccg | 1860 |
| tgttgggtgc | cctgttcatc | ggtgtggctg | tggccccagc | taacgacatc | tacaacgagc | 1920 |
| gcgagctgct | gaacagcatg | ggcatcagcc | agcccaccgt | cgtattcgtg | agcaagaaag | 1980 |
| ggctgcaaaa | gatcctcaac | gtgcaaaaga | agctaccgat | catacaaaag | atcatcatca | 2040 |
| tggatagcaa | gaccgactac | cagggcttcc | aaagcatgta | caccttcgtg | acttccatt | 2100 |
| tgccacccgg | cttcaacgag | tacgacttcg | tgcccgagag | cttcgaccgg | gacaaaacca | 2160 |
| tcgccctgat | catgaacagt | agtggcagta | ccggattgcc | caagggcgta | gccctaccgc | 2220 |

```
accgcaccgc ttgtgtccga ttcagtcatg cccgcgaccc catcttcggc aaccagatca    2280
tccccgacac cgctatcctc agcgtggtgc catttcacca cggcttcggc atgttcacca    2340
cgctgggcta cttgatctgc ggctttcggg tcgtgctcat gtaccgcttc gaggaggagc    2400
tattcttgcg cagcttgcaa gactataaga ttcaatctgc cctgctggtg cccacactat    2460
ttagcttctt cgctaagagc actctcatcg acaagtacga cctaagcaac ttgcacgaga    2520
tcgccagcgg cggggcgccg ctcagcaagg aggtaggtga ggccgtggcc aaacgcttcc    2580
acctaccagg catccgccag ggctacggcc tgacagaaac aaccagcgcc attctgatca    2640
cccccgaagg ggacgacaag cctggcgcag taggcaaggt ggtgcccttc ttcgaggcta    2700
aggtggtgga cttggacacc ggtaagacac tgggtgtgaa ccagcgcggc gagctgtgcg    2760
tccgtggccc catgatcatg agcggctacg ttaacaaccc cgaggctaca aacgctctca    2820
tcgacaagga cggctggctg cacagcggcg acatcgccta ctgggacgag gacgagcact    2880
tcttcatcgt ggaccggctg aagagcctga tcaaatacaa gggctaccag gtagccccag    2940
ccgaactgga gagcatcctg ctgcaacacc ccaacatctt cgacgccggg gtcgccggcc    3000
tgcccgacga cgatgccggc gagctgcccg ccgcagtcgt cgtgctggaa cacggtaaaa    3060
ccatgaccga aaggagatc gtggactatg tggccagcca ggttacaacc gccaagaagc    3120
tgcgcggtgg tgttgtgttc gtggacgagg tgcctaaagg actgaccggc aagttggacg    3180
cccgcaagat ccgcgagatt ctcattaagg ccaagaaggg cggcaagatc gccgtgtaat    3240
tcgaaacgtc acgtccatct tgagcatctg acttctggct aaataaaaga tctttatttt    3300
cattagatct gtgtgttggt tttttgtgtg cgtcgagatc cacggccgca ggaacccct a    3360 gtgatggagt tggccactcc ctctctgcgc gctcgctcgc tcactgaggc cgggcgacca    3420
aaggtcgccc gacgcccggg ctttgcccgg gcggcctcag tgagcgagcg agcgcgcagc    3480
tgcctgcagg ggcgcctgat gcggtatttt ctccttacgc atctgtgcgg tatttcacac    3540
cgcatacgtc aaagcaacca tagtacgcgc cctgtagcgg cgcattaagc gcggcgggtg    3600
tggtggttac gcgcagcgtg accgctacac ttgccagcgc cctagcgccc gctccctttcg    3660 ctttcttccc ttcctttctc gccacgttcg ccggctttcc ccgtcaagct ctaaatcggg    3720
ggctcccttt agggttccga tttagtgctt tacggcacct cgaccccaaa aaacttgatt    3780
tgggtgatgg ttcacgtagt gggccatcgc cctgatagac ggttttttcgc cctttgacgt    3840 tggagtccac gttctttaat agtggactct tgttccaaac tggaacaaca ctcaaccct a    3900 tctcgggcta ttcttttgat ttataaggga ttttgccgat ttcggcctat tggttaaaaa    3960
atgagctgat ttaacaaaaa tttaacgcga attttaacaa aatattaacg tttacaattt    4020
tatggtgcac tctcagtaca atctgctctg atgccgcata gttaagccag ccccgacacc    4080
cgccaacacc cgctgacgcg ccctgacggg cttgtctgct cccggcatcc gcttacagac    4140
aagctgtgac cgtctccggg agctgcatgt gtcagaggtt ttcaccgtca tcaccgaaac    4200
gcgcgagacg aaagggcctc gtgatacgcc tatttttata ggttaatgtc atgataataa    4260
tggtttctta gacgtcaggt ggcacttttc ggggaaatgt gcgcggaacc cctatttgtt    4320
tatttttcta aatacattca aatatgtatc cgctcatgag acaataaccc tgataaatgc    4380
ttcaataata ttgaaaaagg aagagtatga gtattcaaca tttccgtgtc gcccttattc    4440 cctttttgc ggcatttgc cttcctgttt ttgctcaccc agaaacgctg gtgaaagtaa    4500
aagatgctga agatcagttg ggtgcacgag tgggttacat cgaactggat ctcaacagcg    4560
gtaagatcct tgagagtttt cgccccgaag aacgttttcc aatgatgagc acttttaaag    4620
```

```
ttctgctatg tggcgcggta ttatcccgta ttgacgccgg gcaagagcaa ctcggtcgcc    4680
gcatacacta ttctcagaat gacttggttg agtactcacc agtcacagaa aagcatctta    4740
cggatggcat gacagtaaga gaattatgca gtgctgccat aaccatgagt gataacactg    4800
cggccaactt acttctgaca acgatcggag gaccgaagga gctaaccgct tttttgcaca    4860
acatggggga tcatgtaact cgccttgatc gttgggaacc ggagctgaat gaagccatac    4920
caaacgacga gcgtgacacc acgatgcctg tagcaatggc aacaacgttg cgcaaactat    4980
taactggcga actacttact ctagcttccc ggcaacaatt aatagactgg atggaggcgg    5040
ataaagttgc aggaccactt ctgcgctcgg cccttccggc tggctggttt attgctgata    5100
aatctggagc cggtgagcgt gggtctcgcg gtatcattgc agcactgggg ccagatggta    5160
agccctcccg tatcgtagtt atctacacga cggggagtca ggcaactatg gatgaacgaa    5220
atagacagat cgctgagata ggtgcctcac tgattaagca ttggtaactg tcagaccaag    5280
tttactcata tatactttag attgatttaa aacttcattt ttaatttaaa aggatctagg    5340
tgaagatcct ttttgataat ctcatgacca aaatccctta acgtgagttt tcgttccact    5400
gagcgtcaga ccccgtagaa aagatcaaag gatcttcttg agatcctttt tttctgcgcg    5460
taatctgctg cttgcaaaca aaaaaaccac cgctaccagc ggtggtttgt ttgccggatc    5520
aagagctacc aactcttttt ccgaaggtaa ctggcttcag cagagcgcag ataccaaata    5580
ctgtccttct agtgtagccg tagttaggcc accacttcaa gaactctgta gcaccgccta    5640
catacctcgc tctgctaatc ctgttaccag tggctgctgc cagtggcgat aagtcgtgtc    5700
ttaccgggtt ggactcaaga cgatagttac cggataaggc gcagcggtcg ggctgaacgg    5760
ggggttcgtg cacacagccc agcttggagc gaacgaccta caccgaactg agatacctac    5820
agcgtgagct atgagaaagc gccacgcttc ccgaagggag aaaggcggac aggtatccgg    5880
taagcggcag ggtcggaaca ggagagcgca cgagggagct tccaggggga aacgcctggt    5940
atctttatag tcctgtcggg tttcgccacc tctgacttga gcgtcgattt ttgtgatgct    6000
cgtcaggggg gcggagccta tggaaaaacg ccagcaacgc ggccttttta cggttcctgg    6060
ccttttgctg ccttttgct c                                              6081
```

<210> SEQ ID NO 38
<211> LENGTH: 6013
<212> TYPE: DNA
<213> ORGANISM: Artificial Sequence
<220> FEATURE:
<223> OTHER INFORMATION: AAV-CRE02-CSK-SH5-SPc5-12-MVM-Luc-pA

<400> SEQUENCE: 38

```
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggccgaca ggtgcggttc ccggagcgca ggcgcacaca tgcacccacc    180
ggcgaacgcg gtgaccctcg ccccacccca tcccctccgg cgggcaactg ggtcgggtca    240
ggaggggcaa acccgctagg gagacactcc atatacggcc cggcccgcgt tacctgggac    300
cgggccaacc cgctccttct ttggtcaacg caggggaccc gggcggggc ccaggccgcg    360 aaccggccga gggaggggc tctagtgccc aacacccaaa tatggctcga agggcagc     420 gacattcctg cggggtggcg cggagggaat gcccgcgggc tatataaaac ctgagcagag    480
ggacaagcgg ccaccgcagc ggacagcgcc aagtgaagcc tcgcttcccc tccgcggcga    540
```

```
ccagggcccg agccgagagt agcagttgta gctacccgcc caggtagggg cgcgccacgc    600
gtcagtttac tcaccaggga ttcagaggca gcactgctga accctgagcc cttggcacat    660
caggttggct gtcagaagtc ggcctttgta catacacagt tcccttgtga ggcccagctg    720
cgtgtcctag gagcggggcc tctctccaca gcagagctca gcctctcaag tgtatggaca    780
gcacgggtgc ctgatgggtg gatttagcca tgagttgaag gtggcttggg gagaatgaga    840
gttctagaga tagggagaag gggttgccaa taggagagtg gaattcctga gcacctcgtc    900
acaggcagcc gacagaacat gagccgcagg gcccaggcta tttatacctc gcctgtcact    960
atcagggtcc ccacagctcc ccccacctcc agccacacac agcaggtcct tttgctcttt   1020
ctggtcccct ctctactcct cccctccct acctaaggta cccaacgcgt tacgtggcca    1080
ccgccttcgg caccatcctc acgacaccca aatatggcga cgggtgagga atggtgggga   1140
gttatttta gagcggtgag gaaggtgggc aggcagcagg tgttggcgct ctaaaaataa    1200
ctcccgggag ttattttag agcggaggaa tggtggacac ccaaatatgg cgacggttcc    1260
tcacccgtcg ccatatttgg gtgtccgcc tcggccgggg ccgcattcct gggggccggg    1320
cggtgctccc gcccgcctcg ataaaaggct ccggggccgg cggcggccca cgagctaccc    1380
ggaggagcgg gaggcgccaa gctctagatc tagaaagagg taagggttta agggatggtt    1440
ggttggtggg gtattaatgt ttaattacct ggagcacctg cctgaaatca ctttttttca    1500
ggttggaagc ttatgaaga tgccaaaaac attaagaagg gccagcgcc attctaccca     1560
ctcgaggacg ggaccgccgg cgagcagctg cacaaagcca tgaagcgcta cgccctggtg   1620
cccggcacca tcgcctttac cgacgcacat atcgaggtgg acattaccta cgccgagtac   1680
ttcgagatga gcgttcggct ggcagaagct atgaagcgct atgggctgaa tacaaaccat   1740
cggatcgtgt tgtgcagcga gaatagcttg cagttcttca tgcccgtgtt gggtgccctg   1800
ttcatcggtg tggctgtggc cccagctaac gacatctaca acgagcgcga gctgctgaac   1860
agcatgggca tcagccagcc caccgtcgta ttcgtgagca gaaagggct gcaaaagatc    1920
ctcaacgtgc aaaagaagct accgatcata caaaagatca tcatcatgga tagcaagacc   1980
gactaccagg gcttccaaag catgtacacc ttcgtgactt cccatttgcc acccggcttc   2040
aacgagtacg acttcgtgcc cgagagcttc gaccgggaca aaaccatcgc cctgatcatg   2100
aacagtagtg gcagtaccgg attgcccaag ggcgtagccc taccgcaccg caccgcttgt   2160
gtccgattca gtcatgcccg cgaccccatc ttcggcaacc agatcatccc cgacaccgct   2220
atcctcagcg tggtgccatt tcaccacggc ttcggcatgt tcaccacgct gggctacttg   2280
atctgcggct ttcgggtcgt gctcatgtac cgcttcgagg aggagctatt cttgcgcagc   2340
ttgcaagact ataagattca atctgccctg ctggtgccca cactatttag cttcttcgct   2400
aagagcactc tcatcgacaa gtacgaccta agcaacttgc acgagatcgc cagcggcggg   2460
gcgccgctca gcaaggaggt aggtgaggcc gtggccaaac gcttccacct accaggcatc   2520
cgccagggct acggcctgac agaaacaacc agcgccattc tgatcacccc cgaagggga    2580
gacaagcctg gcgcagtagg caaggtggtg cccttcttcg aggctaaggt ggtggacttg   2640
gacaccggta agacactggg tgtgaaccag gcgggcgagc tgtgcgtccg tggccccatg   2700
atcatgagcg gctacgttaa caacccgag gctacaaacg ctctcatcga caaggacggc    2760
tggctgcaca gcggcgacat cgcctactgg gacgaggacg agcacttctt catcgtggac   2820
cggctgaaga gcctgatcaa atacaagggc taccaggtag ccccagccga actggagagc   2880
atcctgctgc aacaccccaa catcttcgac gccggggtcg ccggcctgcc cgacgacgat   2940
```

```
gccggcgagc tgcccgccgc agtcgtcgtg ctggaacacg gtaaaaccat gaccgagaag    3000
gagatcgtgg actatgtggc cagccaggtt acaaccgcca agaagctgcg cggtggtgtt    3060
gtgttcgtgg acgaggtgcc taaaggactg accggcaagt tggacgcccg caagatccgc    3120
gagattctca ttaaggccaa gaagggcggc aagatcgccg tgtaattcga aacgtcaagt    3180
ccatcttgag catctgactt ctggctaaat aaaagatctt tattttcatt agatctgtgt    3240
gttggttttt tgtgtgcgtc gagatccacg gccgcaggaa cccctagtga tggagttggc    3300
cactccctct ctgcgcgctc gctcgctcac tgaggccggg cgaccaaagg tcgcccgacg    3360
cccgggcttt gcccgggcgg cctcagtgag cgagcgagcg cgcagctgcc tgcaggggcg    3420
cctgatgcgg tattttctcc ttacgcatct gtgcggtatt tcacaccgca tacgtcaaag    3480
caaccatagt acgcgccctg tagcggcgca ttaagcgcgg cgggtgtggt ggttacgcgc    3540
agcgtgaccg ctacacttgc cagcgcccta gcgcccgctc ctttcgcttt cttcccttcc    3600
tttctcgcca cgttcgccgg ctttccccgt caagctctaa atcgggggct ccctttaggg    3660
ttccgattta gtgctttacg gcacctcgac cccaaaaaac ttgatttggg tgatggttca    3720
cgtagtgggc catcgccctg atagacggtt tttcgccctt tgacgttgga gtccacgttc    3780
tttaatagtg gactcttgtt ccaaactgga acaacactca accctatctc gggctattct    3840
tttgatttat aagggatttt gccgatttcg gcctattggt taaaaaatga gctgatttaa    3900
caaaaattta acgcgaattt taacaaaata ttaacgttta caattttatg gtgcactctc    3960
agtacaatct gctctgatgc cgcatagtta agccagcccc gacacccgcc aacacccgct    4020
gacgcgccct gacgggcttg tctgctcccg gcatccgctt acagacaagc tgtgaccgtc    4080
tccgggagct gcatgtgtca gaggttttca ccgtcatcac cgaaacgcgc gagacgaaag    4140
ggcctcgtga tacgcctatt tttataggtt aatgtcatga taataatggt ttcttagacg    4200
tcaggtggca cttttcgggg aaatgtgcgc ggaaccccta tttgtttatt tttctaaata    4260
cattcaaata tgtatccgct catgagacaa taaccctgat aaatgcttca ataatattga    4320
aaaaggaaga gtatgagtat tcaacatttc cgtgtcgccc ttattccctt ttttgcggca    4380
ttttgccttc ctgtttttgc tcacccagaa acgctggtga agtaaaagat gctgaagat    4440 cagttgggtg cacgagtggg ttacatcgaa ctggatctca acagcggtaa gatccttgag    4500
agttttcgcc ccgaagaacg ttttccaatg atgagcactt taaagttct gctatgtggc    4560 gcggtattat cccgtattga cgccgggcaa gagcaactcg gtcgccgcat acactattct    4620
cagaatgact tggttgagta ctcaccagtc acagaaaagc atcttacgga tggcatgaca    4680
gtaagagaat tatgcagtgc tgccataacc atgagtgata acactgcggc caacttactt    4740
ctgacaacga tcgaggaccg aaggagcta accgcttttt tgcacaacat ggggatcat    4800 gtaactcgcc ttgatcgttg ggaaccggag ctgaatgaag ccataccaaa cgacgagcgt    4860
gacaccacga tgcctgtagc aatggcaaca acgttgcgca aactattaac tggcgaacta    4920
cttactctag cttcccggca acaattaata gactggatgg aggcggataa agttgcagga    4980
ccacttctgc gctcggccct tccggctggc tggtttattg ctgataaatc tggagccggt    5040
gagcgtgggt ctcgcggtat cattgcagca ctggggccag atggtaagcc ctcccgtatc    5100
gtagttatct acacgacggg gagtcaggca actatggatg aacgaaatag acagatcgct    5160
gagataggtg cctcactgat taagcattgg taactgtcag accaagttta ctcatatata    5220
ctttagattg atttaaaact tcattttaa tttaaaagga tctaggtgaa gatcctttt    5280
```

```
gataatctca tgaccaaaat cccttaacgt gagttttcgt tccactgagc gtcagacccc    5340
gtagaaaaga tcaaaggatc ttcttgagat ccttttttc tgcgcgtaat ctgctgcttg    5400
caaacaaaaa aaccaccgct accagcggtg gtttgtttgc cggatcaaga gctaccaact    5460
cttttttccga aggtaactgg cttcagcaga gcgcagatac caaatactgt ccttctagtg    5520
tagccgtagt taggccacca cttcaagaac tctgtagcac cgcctacata cctcgctctg    5580
ctaatcctgt taccagtggc tgctgccagt ggcgataagt cgtgtcttac cgggttggac    5640
tcaagacgat agttaccgga taaggcgcag cggtcgggct gaacggggggg ttcgtgcaca    5700
cagcccagct tggagcgaac gacctacacc gaactgagat acctacagcg tgagctatga    5760
gaaagcgcca cgcttcccga agggagaaag gcggacaggt atccggtaag cggcagggtc    5820
ggaacaggag agcgcacgag ggagcttcca gggggaaacg cctggtatct ttatagtcct    5880
gtcgggtttc gccacctctg acttgagcgt cgatttttgt gatgctcgtc aggggggcgg    5940
agcctatgga aaaacgccag caacgcggcc ttttttacggt tcctggcctt tgctggcct    6000
tttgctcaca tgt                                                       6013
```

<210> SEQ ID NO 39
<211> LENGTH: 6502
<212> TYPE: DNA
<213> ORGANISM: Artificial Sequence
<220> FEATURE:
<223> OTHER INFORMATION: AAV-CRE06-CRE04-CSK-SH5-SPc5-12-MVM-Luc-pA

<400> SEQUENCE: 39

```
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggccgggc caggggacgg tggcttctac gtgcttggga cgttcccagc     180
caccgtccca tgttcccggc gggggggccag ctgtccccac cgccagccca actcagcact     240
tggtcagggt atcagcttgg tgggggggcg tgagcccagc cctggggcg gctcagccca     300
tacaaggcca tggggctggg cgcaaagcat gcctgggttc agggtgggta tggtgcggga    360
gcagggaggt gagaggctca gctgccctcc agaactcctc cctggggaca ccccctccca    420
gccaatagca cagcctaggt cccctatat aaggccacgg ctgctggccc ttcctttggg    480
tcagtgtcac ctccaggata cagacagccc cccttcagcc cagcccagcc aggtacggcg    540
cgccgtcgac ggatcccctt ttagagaatc cacacctgtc ccagttgctg ggttccacta    600
ccaaagtga attgcaacta ttttaggagc acttaagcac atccgaaaaa tgagtgattc    660
tgttctggcc cacaccacat cactgatgta cccccttaaa gcatgtccct gagttcatca    720
cagaagactg ctcctcctgt gccctccaca aggttagaac tgtccttgtc ttagggaaaa    780
aggagagaga gagagagaga gagagagaga gagagagaga gagagagaga gagggacagg    840
caccaactgg gtaacctctg ctgacccca ctctacttta ccataagtag ctccaaatcc    900
ttctagaaaa tctgaaaggc atagcccccat atatcagtga tataaataga acctgcagca    960
ggctctggta aatgatgact acaaggtgga ctgggaggca gcccggcctt ggcaggcatc   1020
atcctctaaa tataaagatg agtttgttca gcctttgcag aaggaggatc cgtcgacggc   1080
gcgccacgcg tcagtttact caccagggat tcagaggcag cactgctgaa ccctgagccc   1140
ttggcacatc aggttggctg tcagaagtcg gcctttgtac atacacagtt cccttgtgag   1200
gcccagctgc gtgtcctagg agcggggcct ctctccacag cagagctcag cctctcaagt   1260
gtatggacag cacgggtgcc tgatgggtgg atttagccat gagttgaagg tggcttgggg   1320
```

```
agaatgagag ttctagagat agggagaagg ggttgccaat aggagagtgg aattcctgag    1380
cacctcgtca caggcagccg acagaacatg agccgcaggg cccaggctat ttatacctcg    1440
cctgtcacta tcagggtccc cacagctccc cccacctcca gccacacaca gcaggtcctt    1500
ttgctctttc tggtcccttc tctactcctc cccctcccta cctaaggtac caacgcgtt     1560 acgtggccac cgccttcggc accatcctca cgacacccaa atatggcgac gggtgaggaa    1620
tggtggggag ttattttag agcggtgagg aaggtgggca ggcagcaggt gttggcgctc     1680
taaaaataac tcccgggagt tattttaga gcggaggaat ggtggacacc caaatatggc     1740
gacggttcct cacccgtcgc catatttggg tgtccgccct cggccggggc cgcattcctg    1800
ggggccgggc ggtgctcccg cccgcctcga taaaaggctc cggggccggc ggcggcccac    1860
gagctacccg gaggagcggg aggcgccaag ctctagatct agaaagaggt aagggtttaa    1920
gggatggttg gttggtgggg tattaatgtt taattacctg gagcacctgc ctgaaatcac    1980
tttttttcag gttggaagct tatggaagat gccaaaaaca ttaagaaggg cccagcgcca    2040
ttctacccac tcgaggacgg gaccgccggc gagcagctgc acaaagccat gaagcgctac    2100
gccctggtgc ccggcaccat cgcctttacc gacgcacata tcgaggtgga cattacctac    2160
gccgagtact tcgagatgag cgttcggctg gcagaagcta tgaagcgcta tgggctgaat    2220
acaaaccatc ggatcgtggt gtgcagcgag aatagcttgc agttcttcat gcccgtgttg    2280
ggtgccctgt tcatcggtgt ggctgtggcc ccagctaacg acatctacaa cgagcgcgag    2340
ctgctgaaca gcatgggcat cagccagccc accgtcgtat tcgtgagcaa gaaagggctg    2400
caaaagatcc tcaacgtgca aaagaagcta ccgatcatac aaaagatcat catcatggat    2460
agcaagaccg actaccaggg cttccaaagc atgtacacct tcgtgacttc ccatttgcca    2520
cccggcttca acgagtacga cttcgtgccc gagagcttcg accgggacaa aaccatcgcc    2580
ctgatcatga acagtagtgg cagtaccgga ttgcccaagg gcgtagccct accgcaccgc    2640
accgcttgtg tccgattcag tcatgcccgc gaccccatct tcggcaacca gatcatcccc    2700
gacaccgcta tcctcagcgt ggtgccattt caccacggct tcggcatgtt caccacgctg    2760
ggctacttga tctgcggctt tcgggtcgtg ctcatgtacc gcttcgagga ggagctattc    2820
ttgcgcagct tgcaagacta taagattcaa tctgccctgc tggtgcccac actatttagc    2880
ttcttcgcta agagcactct catcgacaag tacgacctaa gcaacttgca cgagatcgcc    2940
agcggcgggg cgccgctcag caaggaggta ggtgaggccg tggccaaacg cttccaccta    3000
ccaggcatcc gccagggcta cggcctgaca gaaacaacca gcgccattct gatcacccc     3060 gaaggggacg acaagcctgg cgcagtaggc aaggtggtgc ccttcttcga ggctaaggtg    3120
gtggacttgg acaccggtaa gacactgggt gtgaaccagc gcggcgagct gtgcgtccgt    3180
ggccccatga tcatgagcgg ctacgttaac aaccccgagg ctacaaacgc tctcatcgac    3240
aaggacggct ggctgcacag cggcgacatc gcctactggg acgaggacga gcacttcttc    3300
atcgtggacc ggctgaagag cctgatcaaa tacaagggct accaggtagc cccagccgaa    3360
ctggagagca tcctgctgca acaccccaac atcttcgacg ccggggtcgc cggcctgccc    3420
gacgacgatg ccggcgagct gccgccgca gtcgtcgtgc tggaacacgg taaaaccatg     3480
accgagaagg agatcgtgga ctatgtggcc agccaggtta caaccgccaa gaagctgcgc    3540
ggtggtgttg tgttcgtgga cgaggtgcct aaaggactga ccggcaagtt ggacgcccgc    3600
aagatccgcg agattctcat taaggccaag aagggcggca agatcgccgt gtaattcgaa    3660
```

```
acgtctagtc catcttgagc atctgacttc tggctaaata aaagatctttt attttcatta    3720
gatctgtgtg ttggtttttt gtgtgcgtcg agatccacgg ccgcaggaac ccctagtgat    3780
ggagttggcc actccctctc tgcgcgctcg ctcgctcact gaggccgggc gaccaaaggt    3840
cgcccgacgc ccgggctttg cccggcggc ctcagtgagc gagcgagcgc gcagctgcct     3900
gcaggggcgc ctgatgcggt attttctcct tacgcatctg tgcggtattt cacaccgcat    3960
acgtcaaagc aaccatagta cgcgcccgtg agcggcgcat taagcgcggc gggtgtggtg    4020
gttacgcgca gcgtgaccgc tacacttgcc agcgccctag cgcccgctcc tttcgctttc    4080
ttcccttcct ttctcgccac gttcgccggc tttccccgtc aagctctaaa tcggggctc     4140
cctttagggt tccgatttag tgctttacgg cacctcgacc ccaaaaaact tgatttgggt    4200
gatggttcac gtagtgggcc atcgccctga tagacggttt ttcgcccttt gacgttggag    4260
tccacgttct ttaatagtgg actcttgttc caaactggaa caacactcaa ccctatctcg    4320
ggctattctt ttgatttata agggattttg ccgatttcgg cctattggtt aaaaaatgag    4380
ctgatttaac aaaaatttaa cgcgaatttt aacaaaatat taacgtttac aattttatgg    4440
tgcactctca gtacaatctg ctctgatgcc gcatagttaa gccagccccg acacccgcca    4500
acacccgctg acgcgccctg acgggcttgt ctgctcccgg catccgctta cagacaagct    4560
gtgaccgtct ccgggagctg catgtgtcag aggttttcac cgtcatcacc gaaacgcgcg    4620
agacgaaagg gcctcgtgat acgcctattt ttataggtta atgtcatgat aataatggtt    4680
tcttagacgt caggtggcac ttttcgggga atgtgcgcg gaacccctat ttgtttattt     4740
ttctaaatac attcaaatat gtatccgctc atgagacaat aaccctgata aatgcttcaa    4800
taatattgaa aaaggaagag tatgagtatt caacatttcc gtgtcgccct tattcccttt    4860
tttgcggcat tttgccttcc tgttttgct cacccagaaa cgctggtgaa agtaaaagat     4920
gctgaagatc agttgggtgc acgagtgggt tacatcgaac tggatctcaa cagcggtaag    4980
atccttgaga gttttcgccc cgaagaacgt tttccaatga tgagcacttt taaagttctg    5040
ctatgtggcg cggtattatc ccgtattgac gccgggcaag agcaactcgg tcgccgcata    5100
cactattctc agaatgactt ggttgagtac tcaccagtca cagaaaagca tcttacggat    5160
ggcatgacag taagagaatt atgcagtgct gccataacca tgagtgataa cactgcggcc    5220
aacttacttc tgacaacgat cggaggaccg aaggagctaa ccgcttttt gcacaacatg     5280
ggggatcatg taactcgcct tgatcgttgg gaaccggagc tgaatgaagc cataccaaac    5340
gacgagcgtg acaccacgat gcctgtagca atggcaacaa cgttgcgcaa actattaact    5400
ggcgaactac ttactctagc ttcccggcaa caattaatag actggatgga ggcggataaa    5460
gttgcaggac cacttctgcg ctcggccctt ccggctggct ggtttattgc tgataaatct    5520
ggagccggtg agcgtgggtc tcgcggtatc attgcagcac tggggccaga tggtaagccc    5580
tcccgtatcg tagttatcta cacgacgggg agtcaggcaa ctatggatga acgaaataga    5640
cagatcgctg agataggtgc ctcactgatt aagcattggt aactgtcaga ccaagtttac    5700
tcatatatac tttagattga tttaaaactt cattttaat ttaaaaggat ctaggtgaag     5760
atcctttttg ataatctcat gaccaaaatc ccttaacgtg agttttcgtt ccactgagcg    5820
tcagaccccg tagaaaagat caaaggatct tcttgagatc ctttttttct gcgcgtaatc    5880
tgctgcttgc aaacaaaaaa accaccgcta ccagcggtgg tttgtttgcc ggatcaagag    5940
ctaccaactc tttttccgaa ggtaactggc ttcagcagag cgcagatacc aaatactgtc    6000
cttctagtgt agccgtagtt aggccaccac ttcaagaact ctgtagcacc gcctacatac    6060
```

```
ctcgctctgc taatcctgtt accagtggct gctgccagtg gcgataagtc gtgtcttacc    6120 ggggttggact caagacgata gttaccggat aaggcgcagc ggtcgggctg aacggggggt    6180
tcgtgcacac agcccagctt ggagcgaacg acctacaccg aactgagata cctacagcgt    6240
gagctatgag aaagcgccac gcttcccgaa gggagaaagg cggacaggta tccggtaagc    6300
ggcagggtcg aacaggaga gcgcacgagg gagcttccag ggggaaacgc ctggtatctt    6360
tatagtcctg tcgggtttcg ccacctctga cttgagcgtc gatttttgtg atgctcgtca    6420
ggggggcgga gcctatggaa aaacgccagc aacgcggcct ttttacggtt cctggccttt    6480
tgctggcctt ttgctcacat gt                                             6502

<210> SEQ ID NO 40
<211> LENGTH: 6513
<212> TYPE: DNA
<213> ORGANISM: Artificial Sequence
<220> FEATURE:
<223> OTHER INFORMATION: AAV-CRE04-CRE06-CSK-SH5-SPc5-12-MVM-Luc-pA

<400> SEQUENCE: 40
acatgtcctg caggcagctg cgcgctcgct cgctcactga ggccgcccgg gcaaagcccg      60
ggcgtcgggc gacctttggt cgcccggcct cagtgagcga gcgagcgcgc agagagggag     120
tggccaactc catcactagg ggttcctgcg gcccctttta gagaatccac acctgtccca     180
gttgctgggt tccactacca aaagtgaatt gcaactattt taggagcact taagcacatc     240
cgaaaaatga gtgattctgt tctggcccac accacatcac tgatgtaccc ccttaaagca     300
tgtccctgag ttcatcacag aagactgctc ctcctgtgcc ctccacaagg ttagaactgt     360
ccttgtctta gggaaaaagg agagagagag agagagagag agagagagag agagagagag     420
agagagagag ggacaggcac caactgggta acctctgctg accccactc tactttacca     480 taagtagctc caaatccttc tagaaaatct gaaaggcata gccccatata tcagtgatat     540
aaatagaacc tgcagcaggc tctggtaaat gatgactaca aggtggactg ggaggcagcc     600
cggccttggc aggcatcatc ctctaaatat aaagatgagt ttgttcagcc tttgcagaag     660
gaggcgcgcc gtcgacggat ccgggccagg ggacggtggc ttctacgtgc ttgggacgtt     720
cccagccacc gtcccatgtt cccggcgggg ggccagctgt ccccaccgcc agcccaactc     780
agcacttggt cagggtatca gcttggtggg ggggcgtgag cccagcccct ggggcggctc     840
agcccataca aggccatggg gctgggcgca aagcatgcct gggttcaggg tgggtatggt     900
gcgggagcag ggaggtgaga ggctcagctg ccctccagaa ctcctccctg ggacaaccc     960 ctcccagcca atagcacagc ctaggtcccc ctatataagg ccacggctgc tggcccttcc    1020
tttgggtcag tgtcacctcc aggatacaga cagccccct tcagcccagc ccagccaggt    1080
acggatccgt cgacggcgcg ccacgcgtca gtttactcac cagggattca gaggcagcac    1140
tgctgaaccc tgagccctgg gcacatcagg ttggctgtca gaagtcggcc tttgtacata    1200
cacagttccc ttgtgaggcc cagctgcgtg tcctaggagc ggggcctctc tccacagcag    1260
agctcagcct ctcaagtgta tggacagcac gggtgcctga tggtggatt tagccatgag    1320 ttgaaggtgg cttggggaga atgagagttc tagatagg gagaagggt tgccaatagg    1380 agagtggaat tcctgagcac ctcgtcacag gcagccgaca gaacatgagc cgcagggccc    1440
aggctattta tacctcgcct gtcactatca gggtccccac agctcccccc acctccagcc    1500
acacacagca ggtccttttg ctctttctgg tcccttctct actcctcccc ctccctacct    1560
```

-continued

| | | | | |
|---|---|---|---|---|
| aaggtaccca | acgcgttacg | tggccaccgc | cttcggcacc | atcctcacga cacccaaata | 1620 |
| tggcgacggg | tgaggaatgg | tggggagtta | ttttagagc | ggtgaggaag gtgggcaggc | 1680 |
| agcaggtgtt | ggcgctctaa | aaataactcc | cgggagttat | ttttagagcg gaggaatggt | 1740 |
| ggacacccaa | atatggcgac | ggttcctcac | ccgtcgccat | atttgggtgt ccgccctcgg | 1800 |
| ccggggccgc | attcctgggg | gccggcggt | gctcccgccc | gcctcgataa aaggctccgg | 1860 |
| ggccggcggc | ggcccacgag | ctacccggag | gagcgggagg | cgccaagctc tagatctaga | 1920 |
| aagaggtaag | ggtttaaggg | atggttggtt | ggtggggtat | taatgtttaa ttacctggag | 1980 |
| cacctgcctg | aaatcacttt | ttttcaggtt | ggaagcttat | ggaagatgcc aaaaacatta | 2040 |
| agaagggccc | agcgccattc | tacccactcg | aggacgggac | cgccggcgag cagctgcaca | 2100 |
| aagccatgaa | gcgctacgcc | ctggtgcccg | gcaccatcgc | ctttaccgac gcacatatcg | 2160 |
| aggtggacat | tacctacgcc | gagtacttcg | agatgagcgt | tcggctggca gaagctatga | 2220 |
| agcgctatgg | gctgaataca | aaccatcgga | tcgtggtgtg | cagcgagaat agcttgcagt | 2280 |
| tcttcatgcc | cgtgttgggt | gccctgttca | tcggtgtggc | tgtggcccca gctaacgaca | 2340 |
| tctacaacga | gcgcgagctg | ctgaacagca | tgggcatcag | ccagcccacc gtcgtattcg | 2400 |
| tgagcaagaa | agggctgcaa | aagatcctca | acgtgcaaaa | gaagctaccg atcatacaaa | 2460 |
| agatcatcat | catggatagc | aagaccgact | accagggctt | ccaaagcatg tacaccttcg | 2520 |
| tgacttccca | tttgccaccc | ggcttcaacg | agtacgactt | cgtgcccgag agcttcgacc | 2580 |
| gggacaaaac | catcgccctg | atcatgaaca | gtagtggcag | taccggattg cccaagggcg | 2640 |
| tagccctacc | gcaccgcacc | gcttgtgtcc | gattcagtca | tgcccgcgac ccatcttcg | 2700 |
| gcaaccagat | catccccgac | accgctatcc | tcagcgtggt | gccatttcac cacggcttcg | 2760 |
| gcatgttcac | cacgctgggc | tacttgatct | gcggctttcg | ggtcgtgctc atgtaccgct | 2820 |
| tcgaggagga | gctattcttg | cgcagcttgc | aagactataa | gattcaatct gccctgctgg | 2880 |
| tgcccacact | atttagcttc | ttcgctaaga | gcactctcat | cgacaagtac gacctaagca | 2940 |
| acttgcacga | gatcgccagc | ggcggggcgc | cgctcagcaa | ggaggtaggt gaggccgtgg | 3000 |
| ccaaacgctt | ccacctacca | ggcatccgcc | agggctacgg | cctgacagaa caaccagcg | 3060 |
| ccattctgat | cacccccgaa | ggggacgaca | agcctggcgc | agtaggcaag gtggtgccct | 3120 |
| tcttcgaggc | taaggtggtg | gacttggaca | ccggtaagac | actgggtgtg aaccagcgcg | 3180 |
| gcgagctgtg | cgtccgtggc | cccatgatca | tgagcggcta | cgttaacaac cccgaggcta | 3240 |
| caaacgctct | catcgacaag | gacggctggc | tgcacagcgg | cgacatcgcc tactgggacg | 3300 |
| aggacgagca | cttcttcatc | gtggaccggc | tgaagagcct | gatcaaatac aagggctacc | 3360 |
| aggtagcccc | agccgaactg | gagagcatcc | tgctgcaaca | ccccaacatc ttcgacgccg | 3420 |
| gggtcgccgg | cctgcccgac | gacgatgccg | gcgagctgcc | cgccgcagtc gtcgtgctgg | 3480 |
| aacacggtaa | aaccatgacc | gagaaggaga | tcgtggacta | tgtggccagc caggttacaa | 3540 |
| ccgccaagaa | gctgcgcggt | ggtgttgtgt | tcgtggacga | ggtgcctaaa ggactgaccg | 3600 |
| gcaagttgga | cgcccgcaag | atccgcgaga | ttctcattaa | ggccaagaag ggcggcaaga | 3660 |
| tcgccgtgta | attcgaaacg | tcacgtccat | cttgagcatc | tgacttctgg ctaaataaaa | 3720 |
| gatctttatt | ttcattagat | ctgtgtgttg | gttttttgtg | tgcgtcgaga tccacggccg | 3780 |
| caggaacccc | tagtgatgga | gttggccact | ccctctctgc | gcgctcgctc gctcactgag | 3840 |
| gccgggcgac | caaaggtcgc | ccgacgcccg | ggctttgccc | gggcggcctc agtgagcgag | 3900 |
| cgagcgcgca | gctgcctgca | ggggcgcctg | atgcggtatt | ttctccttac gcatctgtgc | 3960 |

-continued

```
ggtatttcac accgcatacg tcaaagcaac catagtacgc gccctgtagc ggcgcattaa    4020
gcgcggcggg tgtggtggtt acgcgcagcg tgaccgctac acttgccagc gccctagcgc    4080
ccgctccttt cgctttcttc ccttcctttc tcgccacgtt cgccggcttt ccccgtcaag    4140
ctctaaatcg ggggctccct ttagggttcc gatttagtgc tttacggcac ctcgacccca    4200
aaaaacttga tttgggtgat ggttcacgta gtgggccatc gccctgatag acggttttc    4260 gcccttgac gttggagtcc acgttcttta atagtggact cttgttccaa actgaacaa     4320 cactcaaccc tatctcgggc tattcttttg atttataagg gattttgccg atttcggcct   4380
attggttaaa aaatgagctg atttaacaaa aatttaacgc gaattttaac aaaatattaa   4440
cgtttacaat tttatggtgc actctcagta caatctgctc tgatgccgca tagttaagcc   4500
agccccgaca cccgccaaca cccgctgacg cgccctgacg ggcttgtctg ctcccggcat   4560
ccgcttacag acaagctgtg accgtctccg ggagctgcat gtgtcagagg ttttcaccgt   4620
catcaccgaa acgcgcgaga cgaaagggcc tcgtgatacg cctatttta taggttaatg    4680 tcatgataat aatggtttct tagacgtcag gtggcacttt tcggggaaat gtgcgcggaa   4740
cccctatttg tttatttttc taaatacatt caaatatgta tccgctcatg agacaataac   4800
cctgataaat gcttcaataa tattgaaaaa ggaagagtat gagtattcaa catttccgtg   4860
tcgcccttat tcccttttt gcggcatttt gccttcctgt ttttgctcac ccagaaacgc    4920
tggtgaaagt aaaagatgct gaagatcagt tgggtgcacg agtgggttac atcgaactgg   4980
atctcaacag cggtaagatc cttgagagtt tcgccccga agaacgtttt ccaatgatga    5040
gcacttttaa agttctgcta tgtggcgcgg tattatcccg tattgacgcc gggcaagagc   5100
aactcggtcg ccgcatacac tattctcaga atgacttggt tgagtactca ccagtcacag   5160
aaaagcatct tacggatggc atgacagtaa gagaattatg cagtgctgcc ataaccatga   5220
gtgataacac tgcggccaac ttacttctga acaacgatcgg aggaccgaag gagctaaccg   5280
cttttttgca acatggggg gatcatgtaa ctcgccttga tcgttgggaa ccggagctga   5340
atgaagccat accaaacgac gagcgtgaca ccacgatgcc tgtagcaatg gcaacaacgt   5400
tgcgcaaact attaactggc gaactactta ctctagcttc ccggcaacaa ttaatagact   5460
ggatggaggc ggataaagtt gcaggaccac ttctgcgctc ggcccttccg gctggctggt   5520
ttattgctga taaatctgga gccggtgagc gtgggtctcg cggtatcatt gcagcactgg   5580
ggccagatgg taagccctcc cgtatcgtag ttatctacac gacggggagt caggcaacta   5640
tggatgaacg aaatagacag atcgctgaga taggtgcctc actgattaag cattggtaac   5700
tgtcagacca agtttactca tatatacttt agattgattt aaaacttcat ttttaattta   5760
aaaggatcta ggtgaagatc cttttgata atctcatgac caaaatccct taacgtgagt   5820
tttcgttcca ctgagcgtca ccccgtag aaaagatcaa aggatcttct tgagatcctt    5880 ttttctgcg cgtaatctgc tgcttgcaaa caaaaaaacc accgctacca gcggtggttt    5940
gtttgccgga tcaagagcta ccaactcttt ttccgaaggt aactggcttc agcagagcgc   6000
agataccaaa tactgtcctt ctagtgtagc cgtagttagg ccaccacttc aagaactctg    6060
tagcaccgcc tacatacctc gctctgctaa tcctgttacc agtggctgct gccagtggcg    6120
ataagtcgtg tcttaccggg ttggactcaa gacgatagtt accggataag gcgcagcgt    6180 cgggctgaac ggggggttcg tgcacacagc ccagcttgga gcgaacgacc tacaccgaac   6240
tgagatacct acagcgtgag ctatgagaaa gcgccacgct tcccgaaggg agaaaggcgg    6300
```

```
acaggtatcc ggtaagcggc agggtcggaa caggagagcg cacgagggag cttccagggg    6360
gaaacgcctg gtatctttat agtcctgtcg ggtttcgcca cctctgactt gagcgtcgat    6420 tttttgtgatg ctcgtcaggg gggcggagcc tatggaaaaa cgccagcaac gcggccttttt   6480 tacggttcct ggccttttgc tggccttttg ctc                                 6513

<210> SEQ ID NO 41
<211> LENGTH: 6445
<212> TYPE: DNA
<213> ORGANISM: Artificial Sequence
<220> FEATURE:
<223> OTHER INFORMATION: AAV-CRE02-CRE06-CSK-SH5-SPc5-12-MVM-Luc-pA

<400> SEQUENCE: 41
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact    120
aggggttcct gcggccgaca ggtgcggttc ccggagcgca ggcgcacaca tgcacccacc    180
ggcgaacgcg gtgaccctcg ccccacccca tcccctccgg cgggcaactg ggtcgggtca    240
ggaggggcaa acccgctagg gagacactcc atatacggcc cggcccgcgt tacctgggac    300
cgggccaacc cgctccttct ttggtcaacg caggggaccc gggcggggc ccaggccgcg     360 aaccggccga gggaggggc tctagtgccc aacacccaaa tatggctcga aagggcagc      420 gacattcctg cggggtggcg cggagggaat gcccgcgggc tatataaaac ctgagcagag    480
ggacaagcgg ccaccgcagc ggacagcgcc aagtgaagcc tcgcttcccc tccgcggcga    540
ccagggcccg agccgagagt agcagttgta gctacccgcc caggtagggg cgcgccgtcg    600
acggatccgg gccaggggac ggtggcttct acgtgcttgg gacgttccca gccaccgtcc    660
catgttcccg gcggggggcc agctgtcccc accgccagcc caactcagca cttggtcagg    720
gtatcagctt ggtgggggg cgtgagccca gccctgggg cggctcagcc catacaaggc     780 catgggctg gcgcaaagc atgcctgggt tcagggtggg tatggtgcgg gagcaggag       840 gtgagaggct cagctgccct ccagaactcc tccctgggga caacccctcc cagccaatag   900
cacagcctag gtcccctat ataaggccac ggctgctggc ccttcctttg ggtcagtgtc     960
acctccagga tacagacagc ccccttcag cccagcccag ccaggtacgg atccgtcgac    1020
ggcgcgccac gcgtcagttt actcaccagg gattcagagg cagcactgct gaaccctgag   1080
cccttggcac atcaggttgg ctgtcagaag tcggcctttg tacatacaca gttcccttgt   1140
gaggcccagc tgcgtgtcct aggagcgggg cctctctcca cagcagagct cagcctctca   1200
agtgtatgga cagcacgggt gcctgatggg tggatttagc catgagttga aggtggcttg   1260
gggagaatga gagttctaga gatagggaga aggggttgcc aataggagag tggaattcct   1320
gagcacctcg tcacaggcag ccgacagaac atgagccgca gggcccaggc tatttatacc   1380
tcgcctgtca ctatcagggt ccccacagct cccccacct ccagccacac acagcaggtc    1440
cttttgctct ttctggtccc ttctctactc ctcccccctcc ctacctaagg tacccaacgc  1500
gttacgtggc caccgccttc ggcaccatcc tcacgacacc caaatatggc gacgggtgag   1560
gaatggtggg gagttattt tagagcgtg aggaaggtgg gcaggcagca ggtgttggcg     1620
ctctaaaaat aactcccggg agttattttt agagcggagg aatggtggac acccaaatat   1680
ggcgacggtt cctcacccgt cgccatattt gggtgtccgc cctcggccgg ggccgcattc   1740
ctgggggccg ggcggtgctc ccgcccgcct cgataaaagg ctccggggcc ggcggcggcc   1800
cacgagctac ccggaggagc gggaggcgcc aagctctaga tctagaaaga ggtaagggtt   1860
```

```
taagggatgg ttggttggtg gggtattaat gtttaattac ctggagcacc tgcctgaaat    1920 cactttttt caggttggaa gcttatggaa gatgccaaaa acattaagaa gggcccagcg     1980
ccattctacc cactcgagga cgggaccgcc ggcgagcagc tgcacaaagc catgaagcgc    2040
tacgccctgg tgcccggcac catcgccttt accgacgcac atatcgaggt ggacattacc    2100
tacgccgagt acttcgagat gagcgttcgg ctggcagaag ctatgaagcg ctatgggctg    2160
aatacaaacc atcggatcgt ggtgtgcagc gagaatagct tgcagttctt catgcccgtg    2220
ttgggtgccc tgttcatcgg tgtggctgtg gccccagcta acgacatcta caacgagcgc    2280
gagctgctga acagcatggg catcagccag cccaccgtcg tattcgtgag caagaaaggg    2340
ctgcaaaaga tcctcaacgt gcaaaagaag ctaccgatca tacaaaagat catcatcatg    2400
gatagcaaga ccgactacca gggcttccaa agcatgtaca ccttcgtgac ttcccatttg    2460
ccacccggct tcaacgagta cgacttcgtg cccgagagct tcgaccggga caaaaccatc    2520
gccctgatca tgaacagtag tggcagtacc ggattgccca agggcgtagc cctaccgcac    2580
cgcaccgctt gtgtccgatt cagtcatgcc cgcgacccca tcttcggcaa ccagatcatc    2640
cccgacaccg ctatcctcag cgtggtgcca tttcaccacg gcttcggcat gttcaccacg    2700
ctgggctact tgatctgcgg cttccgggtc gtgctcatgt accgcttcga ggaggagcta    2760
ttcttgcgca gcttgcaaga ctataagatt caatctgccc tgctggtgcc cacactattt    2820
agcttcttcg ctaagagcac tctcatcgac aagtacgacc taagcaactt gcacgagatc    2880
gccagcggcg gggcgccgct cagcaaggag gtaggtgagg ccgtggccaa acgcttccac    2940
ctaccaggca tccgccaggg ctacggcctg acagaaacaa ccagcgccat tctgatcacc    3000
cccgaagggg acgacaagcc tggcgcagta ggcaaggtgg tgcccttctt cgaggctaag    3060
gtggtggact tggacaccgg taagacactg ggtgtgaacc agcgcggcga gctgtgcgtc    3120
cgtggcccca tgatcatgag cggctacgtt aacaacccg aggctacaaa cgctctcatc    3180
gacaaggacg gctggctgca cagcggcgac atcgcctact gggacgagga cgagcacttc    3240
ttcatcgtgg accggctgaa gagcctgatc aaatacaagg gctaccaggt agccccagcc    3300
gaactggaga gcatcctgct gcaacacccc aacatcttcg acgccgggt cgccggcctg    3360 cccgacgacg atgccggcga gctgcccgcc gcagtcgtcg tgctggaaca cggtaaaacc    3420
atgaccgaga aggagatcgt ggactatgtg gccagccagg ttacaaccgc caagaagctg    3480
cgcggtggtg ttgtgttcgt ggacgaggtg cctaaaggac tgaccggcaa gttggacgcc    3540
cgcaagatcc gcgagattct cattaaggcc aagaagggcg gcaagatcgc cgtgtaattc    3600
gaaacgtcaa gtccatcttg agcatctgac ttctggctaa ataaaagatc tttattttca    3660
ttagatctgt gtgttggttt tttgtgtgcg tcgagatcca cggccgcagg aacccctagt    3720
gatggagttg gccactccct ctctgcgcgc tcgctcgctc actgaggccg ggcgaccaaa    3780
ggtcgcccga cgcccgggct ttgcccggc ggcctcagtg agcgagcgag cgcgcagctg    3840
cctgcagggg cgcctgatgc ggtattttct ccttacgcat ctgtgcggta tttcacaccg    3900
catacgtcaa agcaaccata gtacgcgccc tgtagcggcg cattaagcgc ggcgggtgtg    3960
gtggttacgc gcagcgtgac cgctacactt gccagcgccc tagcgcccgc tcctttcgct    4020
ttcttccctt cctttctcgc cacgttcgcc ggctttcccc gtcaagctct aaatcggggg    4080 ctcccttag ggttccgatt tagtgcttta cggcacctcg accccaaaaa acttgatttg    4140
ggtgatggtt cacgtagtgg gccatcgccc tgatagacgg ttttcgccc tttgacgttg    4200
```

```
gagtccacgt tctttaatag tggactcttg ttccaaactg gaacaacact caaccctatc    4260
tcgggctatt cttttgattt ataagggatt ttgccgattt cggcctattg gttaaaaaat    4320
gagctgattt aacaaaaatt taacgcgaat tttaacaaaa tattaacgtt tacaatttta    4380
tggtgcactc tcagtacaat ctgctctgat gccgcatagt taagccagcc ccgacacccg    4440
ccaacacccg ctgacgcgcc ctgacgggct tgtctgctcc cggcatccgc ttacagacaa    4500
gctgtgaccg tctccgggag ctgcatgtgt cagaggtttt caccgtcatc accgaaacgc    4560
gcgagacgaa agggcctcgt gatacgccta ttttatagg ttaatgtcat gataataatg    4620
gtttcttaga cgtcaggtgg cacttttcgg ggaaatgtgc gcggaaccc tatttgttta    4680 ttttctaaa tacattcaaa tatgtatccg ctcatgagac aataaccctg ataaatgctt    4740
caataatatt gaaaaggaa gagtatgagt attcaacatt tccgtgtcgc ccttattccc    4800
ttttttgcgg cattttgcct tcctgttttt gctcacccag aaacgctggt gaaagtaaaa    4860
gatgctgaag atcagttggg tgcacgagtg ggttacatcg aactggatct caacagcggt    4920
aagatccttg agagttttcg ccccgaagaa cgttttccaa tgatgagcac ttttaaagtt    4980
ctgctatgtg gcgcggtatt atcccgtatt gacgccgggc aagagcaact cggtcgccgc    5040
atacactatt ctcagaatga cttggttgag tactcaccag tcacagaaaa gcatcttacg    5100
gatggcatga cagtaagaga attatgcagt gctgccataa ccatgagtga taacactgcg    5160
gccaacttac ttctgacaac gatcggagga ccgaaggagc taaccgcttt tttgcacaac    5220 atggggatc atgtaactcg ccttgatcgt tgggaaccgg agctgaatga agccatacca    5280
aacgacgagc gtgacaccac gatgcctgta gcaatggcaa caacgttgcg caaactatta    5340
actggcgaac tacttactct agcttcccgg caacaattaa tagactggat ggaggcggat    5400
aaagttgcag gaccacttct gcgctcggcc cttccggctg gctggtttat tgctgataaa    5460
tctggagccg gtgagcgtgg gtctcgcggt atcattgcag cactggggcc agatggtaag    5520
ccctcccgta tcgtagttat ctacacgacg gggagtcagg caactatgga tgaacgaaat    5580
agacagatcg ctgagatagg tgcctcactg attaagcatt ggtaactgtc agaccaagtt    5640
tactcatata ctttagat tgatttaaaa cttcattttt aatttaaaag gatctaggtg    5700
aagatccttt ttgataatct catgaccaaa atcccttaac gtgagttttc gttccactga    5760
gcgtcagacc ccgtagaaaa gatcaaagga tcttcttgag atcctttttt tctgcgcgta    5820
atctgctgct tgcaaacaaa aaaaccaccg ctaccagcgg tggtttgttt gccggatcaa    5880
gagctaccaa ctctttttcc gaaggtaact ggcttcagca gagcgcagat accaaatact    5940
gtccttctag tgtagccgta gttaggccac cacttcaaga actctgtagc accgcctaca    6000
tacctcgctc tgctaatcct gttaccagtg gctgctgcca gtggcgataa gtcgtgtctt    6060
accgggttgg actcaagacg atagttaccg gataaggcgc agcggtcggg ctgaacgggg    6120
ggttcgtgca cacagcccag cttggagcga acgacctaca ccgaactgag atacctacag    6180
cgtgagctat gagaaagcgc cacgcttccc gaagggagaa aggcggacag gtatccggta    6240
agcggcaggg tcggaacagg agagcgcacg agggagcttc caggggggaaa cgcctggtat    6300 ctttatagtc ctgtcgggtt tcgccacctc tgacttgagc gtcgattttt gtgatgctcg    6360
tcaggggggc ggagcctatg gaaaaacgcc agcaacgcgg cctttttacg gttcctggcc    6420
ttttgctggc cttttgctca catgt                                          6445

<210> SEQ ID NO 42
<211> LENGTH: 6554
```

<212> TYPE: DNA
<213> ORGANISM: Artificial Sequence
<220> FEATURE:
<223> OTHER INFORMATION: AAV-CRE02-CRE04-CSK-SH5-SPc5-12-MVM-Luc-pA

<400> SEQUENCE: 42

```
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggccgaca ggtgcggttc ccggagcgca ggcgcacaca tgcacccacc     180
ggcgaacgcg gtgaccctcg ccccacccca tccctccgg cgggcaactg ggtcgggtca      240
ggaggggcaa acccgctagg gagacactcc atatacggcc cggcccgcgt tacctgggac     300
cgggccaacc cgctccttct ttggtcaacg caggggaccc gggcggggc ccaggccgcg      360
aaccggccga gggaggggc tctagtgccc aacacccaaa tatggctcga aagggcagc      420
gacattcctg cggggtggcg cggagggaat gcccgcgggc tatataaaac ctgagcagag     480
ggacaagcgg ccaccgcagc ggacagcgcc aagtgaagcc tcgcttcccc tccgcggcga     540
ccagggcccg agccgagagt agcagttgta gctacccgcc caggtagggg cgcgccgtcg     600
acggatcccc ttttagagaa tccacacctg tcccagttgc tggttccac taccaaaagt      660
gaattgcaac tattttagga gcacttaagc acatccgaaa aatgagtgat tctgttctgg     720
cccacaccac atcactgatg taccccctta agcatgtcc ctgagttcat cacagaagac      780
tgctcctcct gtgccctcca caaggttaga actgtccttg tcttagggaa aaaggagaga     840
gagagagaga gagagagaga gagagagaga gagagagaga gagagggaca ggcaccaact     900
gggtaacctc tgctgacccc cactctactt taccataagt agctccaaat ccttctagaa     960
aatctgaaag gcatagcccc atatatcagt gatataaata gaacctgcag caggctctgg    1020
taaatgatga ctacaaggtg gactgggagg cagcccggcc ttggcaggca tcatcctcta    1080
aatataaaga tgagtttgtt cagcctttgc agaaggagga tccgtcgacg gcgcgccacg    1140
cgtcagttta ctcaccaggg attcagaggc agcactgctg aaccctgagc ccttggcaca    1200
tcaggttggc tgtcagaagt cggcctttgt acatacacag ttcccttgtg aggcccagct    1260
gcgtgtccta ggagcggggc ctctctccac agcagagctc agcctctcaa gtgtatggac    1320
agcacgggtg cctgatgggt ggatttagcc atgagttgaa ggtggcttgg ggagaatgag    1380
agttctagag ataggagaa ggggttgcca ataggagagt ggaattcctg agcacctcgt     1440
cacaggcagc cgacagaaca tgagccgcag ggcccaggct atttatacct cgcctgtcac    1500
tatcagggtc cccacagctc cccccacctc cagccacaca cagcaggtcc ttttgctctt    1560
tctggtccct tctctactcc tcccctccc tacctaaggt acccaacgcg ttacgtggcc      1620
accgccttcg gcaccatcct cacgacaccc aaatatggcg acgggtgagg aatggtgggg    1680
agttattttt agagcggtga ggaaggtggg caggcagcag gtgttggcgc tctaaaaata    1740
actcccggga gttattttta gagcggagga atggtgaca cccaaatatg cgacgttc       1800
ctcacccgtc gccatatttg ggtgtccgcc ctcggccggg gccgcattcc tgggggccgg    1860
gcggtgctcc cgcccgcctc gataaaaggc tccggggccg gcggcggccc acgagctacc    1920
cggaggagcg ggaggcgcca agctctagat ctagaaagag gtaagggttt aagggatggt    1980
tggttggtgg ggtattaatg tttaattacc tggagcacct gcctgaaatc actttttttc    2040
aggttggaag cttatggaag atgccaaaaa cattaagaag gcccagcgc cattctaccc      2100
actcgaggac gggaccgccg gcgagcagct gcacaaagcc atgaagcgct acgccctggt    2160
```

```
gcccggcacc atcgccttta ccgacgcaca tatcgaggtg gacattacct acgccgagta    2220
cttcgagatg agcgttcggc tggcagaagc tatgaagcgc tatgggctga atacaaacca    2280
tcggatcgtg gtgtgcagcg agaatagctt gcagttcttc atgcccgtgt tgggtgccct    2340
gttcatcggt gtggctgtgg ccccagctaa cgacatctac aacgagcgcg agctgctgaa    2400
cagcatgggc atcagccagc ccaccgtcgt attcgtgagc aagaaagggc tgcaaaagat    2460
cctcaacgtg caaagaaagc taccgatcat acaaaagatc atcatcatgg atagcaagac    2520
cgactaccag ggcttccaaa gcatgtacac cttcgtgact cccatttgc cacccggctt    2580 caacgagtac gacttcgtgc ccgagagctt cgaccgggac aaaaccatcg ccctgatcat    2640
gaacagtagt ggcagtaccg gattgcccaa gggcgtagcc ctaccgcacc gcaccgcttg    2700
tgtccgattc agtcatgccc gcgacccat cttcggcaac cagatcatcc ccgacaccgc    2760
tatcctcagc gtggtgccat tcaccacgg cttcggcatg ttcaccacgc tgggctactt    2820
gatctgcggc tttcgggtcg tgctcatgta ccgcttcgag gaggagctat tcttgcgcag    2880
cttgcaagac tataagattc aatctgccct gctggtgccc acactattta gcttcttcgc    2940
taagagcact ctcatcgaca agtacgacct aagcaacttg cacgagatcg ccagcggcgg    3000
ggcgccgctc agcaaggagg taggtgaggc cgtggccaaa cgcttccacc taccaggcat    3060
ccgccagggc tacggcctga cagaaacaac cagcgccatt ctgatcaccc ccgaagggga    3120
cgacaagcct ggcgcagtag caaggtggt gcccttcttc gaggctaagg tggtggactt    3180
ggacaccggt aagacactgg gtgtgaacca gcgcggcgag ctgtgcgtcc gtggccccat    3240
gatcatgagc ggctacgtta caaccccga ggctacaaac gctctcatcg acaaggacgg    3300
ctggctgcac agcggcgaca tcgcctactg ggacgaggac gagcacttct tcatcgtgga    3360
ccggctgaag agcctgatca aatacaaggg ctaccaggta gccccagccg aactggagag    3420
catcctgctg caacacccca acatcttcga cgccggggtc gccggcctgc ccgacgacga    3480
tgccggcgag ctgcccgccg cagtcgtcgt gctggaacac ggtaaaacca tgaccgagaa    3540
ggagatcgtg gactatgtgg ccagccaggt tacaaccgcc aagaagctgc gcggtggtgt    3600
tgtgttcgtg gacgaggtgc ctaaaggact gaccggcaag ttggacgccc gcaagatccg    3660
cgagattctc attaaggcca agaagggcgg caagatcgcc gtgtaattcg aaacgtcaag    3720
tccatcttga gcatctgact tctggctaaa taaaagatct ttattttcat tagatctgtg    3780
tgttggtttt ttgtgtgcgt cgagatccac ggccgcagga acccctagtg atggagttgg    3840
ccactccctc tctgcgcgct cgctcgctca ctgaggccgg gcgaccaaag gtcgcccgac    3900
gcccgggctt tgcccgggcg gcctcagtga gcgagcgagc gcgcagctgc ctgcaggggc    3960
gcctgatgcg gtattttctc cttacgcatc tgtgcggtat ttcacaccgc atacgtcaaa    4020
gcaaccatag tacgcgccct gtagcggcgc attaagcgcg gcgggtgtgg tggttacgcg    4080
cagcgtgacc gctacacttg ccagcgccct agcgcccgct cctttcgctt tcttcccttc    4140
ctttctcgcc acgttcgccg gctttccccg tcaagctcta aatcggggc tccctttagg    4200 gttccgattt agtgctttac ggcacctcga ccccaaaaaa cttgatttgg gtgatggttc    4260
acgtagtggg ccatcgccct gatagacggt ttttcgccct tgacgttgg agtccacgtt    4320 ctttaatagt ggactcttgt tccaaactgg aacaacactc aaccctatct cgggctattc    4380
ttttgattta agggattt tgccgatttc ggcctattgg ttaaaaaatg agctgattta    4440
acaaaaattt aacgcgaatt ttaacaaat attaacgttt acaattttat ggtgcactct    4500
cagtacaatc tgctctgatg ccgcatagtt aagccagccc cgacacccgc caacacccgc    4560
```

```
tgacgcgccc tgacgggctt gtctgctccc ggcatccgct tacagacaag ctgtgaccgt    4620
ctccgggagc tgcatgtgtc agaggttttc accgtcatca ccgaaacgcg cgagacgaaa    4680
gggcctcgtg atacgcctat ttttataggt taatgtcatg ataataatgg tttcttagac    4740
gtcaggtggc acttttcggg gaaatgtgcg cggaacccct atttgtttat ttttctaaat    4800
acattcaaat atgtatccgc tcatgagaca ataaccctga taaatgcttc aataatattg    4860
aaaaaggaag agtatgagta ttcaacattt ccgtgtcgcc cttattccct ttttttgcggc    4920 attttgcctt cctgtttttg ctcacccaga aacgctggtg aaagtaaaag atgctgaaga    4980
tcagttgggt gcacgagtgg gttacatcga actggatctc aacagcggta agatccttga    5040
gagttttcgc cccgaagaac gttttccaat gatgagcact tttaaagttc tgctatgtgg    5100
cgcggtatta tcccgtattg acgccgggca agagcaactc ggtcgccgca tacactattc    5160
tcagaatgac ttggttgagt actcaccagt cacagaaaag catcttacgg atggcatgac    5220
agtaagagaa ttatgcagtg ctgccataac catgagtgat aacactgcgg ccaacttact    5280
tctgacaacg atcggaggac cgaaggagct aaccgctttt ttgcacaaca tgggggatca    5340
tgtaactcgc cttgatcgtt gggaaccgga gctgaatgaa gccataccaa acgacgagcg    5400
tgacaccacg atgcctgtag caatggcaac aacgttgcgc aaactattaa ctggcgaact    5460
acttactcta gcttcccggc aacaattaat agactggatg gaggcggata aagttgcagg    5520
accacttctg cgctcggccc ttccggctgg ctggtttatt gctgataaat ctggagccgg    5580
tgagcgtggg tctcgcggta tcattgcagc actggggcca gatggtaagc cctcccgtat    5640
cgtagttatc tacacgacgg ggagtcaggc aactatggat gaacgaaata gacagatcgc    5700
tgagataggt gcctcactga ttaagcattg gtaactgtca gaccaagttt actcatatat    5760
actttagatt gatttaaaac ttcatttta atttaaaagg atctaggtga agatcctttt    5820
tgataatctc atgaccaaaa tcccttaacg tgagttttcg ttccactgag cgtcagaccc    5880
cgtagaaaag atcaaaggat cttcttgaga tccttttttt ctgcgcgtaa tctgctgctt    5940
gcaaacaaaa aaaccaccgc taccagcggt ggtttgtttg ccggatcaag agctaccaac    6000 tcttttccg aaggtaactg gcttcagcag agcgcagata ccaaatactg tccttctagt    6060
gtagccgtag ttaggccacc acttcaagaa ctctgtagca ccgcctacat acctcgctct    6120
gctaatcctg ttaccagtgg ctgctgccag tggcgataag tcgtgtctta ccgggttgga    6180
ctcaagacga tagttaccgg ataaggcgca gcggtcgggc tgaacggggg gttcgtgcac    6240
acagcccagc ttgagcgaa cgacctacac cgaactgaga tacctacagc gtgagctatg    6300
agaaagcgcc acgcttcccg aagggagaaa ggcggacagg tatccggtaa gcggcagggt    6360
cggaacagga gagcgcacga gggagcttcc agggggaaac gcctggtatc tttatagtcc    6420
tgtcgggttt cgccacctct gacttgagcg tcatttttg tgatgctcgt caggggggcg    6480
gagcctatgg aaaaacgcca gcaacgcggc ctttttacgg ttcctggcct tttgctggcc    6540
ttttgctcac atgt                                                     6554
```

<210> SEQ ID NO 43
<211> LENGTH: 6986
<212> TYPE: DNA
<213> ORGANISM: Artificial Sequence
<220> FEATURE:
<223> OTHER INFORMATION: AAV-CRE02-CRE04-CRE06-CSK-SH5-SPc5-12-MVM-Luc-pA

<400> SEQUENCE: 43

```
cctgcaggca gctgcgcgct cgctcgctca ctgaggccgc ccgggcgtcg ggcgacctt     60 ggtcgcccgg cctcagtgag cgagcgagcg cgcagagagg gagtggccaa ctccatcact   120
aggggttcct gcggccgaca ggtgcggttc ccggagcgca ggcgcacaca tgcacccacc   180
ggcgaacgcg gtgaccctcg ccccaccccc tcccctccgg cgggcaactg gtcgggtca   240 ggagggcaa acccgctagg gagacactcc atatacggcc cggcccgcgt tacctgggac    300
cgggccaacc cgctccttct ttggtcaacg caggggaccc gggcggggc ccaggccgcg    360 aaccggccga gggagggggc tctagtgccc aacacccaaa tatggctcga aagggcagc    420 gacattcctg cggggtggcg cggagggaat ccccgcgggc tatataaaac ctgagcagag   480
ggacaagcgg ccaccgcagc ggacagcgcc aagtgaagcc tcgcttcccc tccgcggcga   540
ccagggcccg agccgagagt agcagttgta gctacccgcc caggtagggg cgcgcccgta   600
cggtcgacgg atccccttt agagaatcca cacctgtccc agttgctggg ttccactacc   660
aaaagtgaat tgcaactatt ttaggagcac ttaagcacat ccgaaaaatg agtgattctg   720
ttctggccca caccacatca ctgatgtacc cccttaaagc atgtccctga gttcatcaca   780
gaagactgct cctcctgtgc cctccacaag gttagaactg tccttgtctt agggaaaaag   840
gagagagaga gagagagaga gagagagaga gagagagaga gagagagaga gggacaggca   900
ccaactgggt aacctctgct gaccccact ctactttacc ataagtagct ccaaatcctt    960
ctagaaaatc tgaaaggcat agccccatat atcagtgata taaatagaac ctgcagcagg  1020
ctctggtaaa tgatgactac aaggtggact gggaggcagc ccggccttgg caggcatcat  1080
cctctaaata taaagatgag tttgttcagc cttttgcagaa ggaggcgcgc cgtcgacgga  1140
tccgggccag gggacggtgg cttctacgtg cttgggacgt tcccagccac cgtcccatgt   1200
tcccggcggg gggccagctg tccccaccgc cagcccaact cagcacttgg tcagggtatc   1260
agcttggtgg gggggcgtga gcccagcccc tggggcggct cagcccatac aaggccatgg   1320
ggctgggcgc aaagcatgcc tgggttcagg gtgggtatgg tgcgggagca gggaggtgag   1380
aggctcagct gccctccaga actcctccct ggggacaacc cctcccagcc aatagcacag   1440
cctaggtccc cctatataag gccacggctg ctggcccttc ctttgggtca gtgtcacctc   1500
caggatacag acagcccccc ttcagcccag cccagccagg tacggatccg tcgaccgtac   1560
gggcgcgcca cgcgtcagtt tactcaccag ggattcagag gcagcactgc tgaaccctga   1620
gcccttggca catcaggttg gctgtcagaa gtcggccttt gtacatacac agttcccttg   1680
tgaggcccag ctgcgtgtcc taggagcggg gcctctctcc acagcagagc tcagcctctc   1740
aagtgtatgg acagcacggg tgcctgatgg gtggatttag ccatgagttg aaggtggctt   1800
ggggagaatg agagttctag agataggag aaggggttgc caataggaga gtggaattcc    1860
tgagcacctc gtcacaggca gccgacagaa catgagccgc agggcccagg ctatttatac   1920
ctcgcctgtc actatcaggg tccccacagc tccccccacc tccagccaca cacagcaggt   1980
ccttttgctc tttctggtcc cttctctact cctccccctc cctacctaag gtacccaacg   2040
cgttacgtgg ccaccgcctt cggcaccatc ctcacgacac ccaaatatgg cgacgggtga   2100
ggaatggtgg ggagttattt ttagagcggt gaggaaggtg ggcaggcagc aggtgttggc   2160
gctctaaaaa taactcccgg gagttatttt tagagcggag gaatggtgga cacccaaata   2220
tggcgacggt tcctcacccg tcgccatatt tgggtgtccg ccctcggccg gggccgcatt   2280 cctggggcc gggcggtgct cccgcccgcc tcgataaaag gctccggggc cggcggcggc    2340
```

```
ccacgagcta cccggaggag cgggaggcgc caagctctag atctagaaag aggtaagggt      2400
ttaagggatg gttggttggt ggggtattaa tgtttaatta cctggagcac ctgcctgaaa      2460
tcactttttt tcaggttgga agcttatgga agatgccaaa aacattaaga agggcccagc      2520
gccattctac ccactcgagg acgggaccgc cggcgagcag ctgcacaaag ccatgaagcg      2580
ctacgccctg gtgcccggca ccatcgcctt taccgacgca catatcgagg tggacattac      2640
ctacgccgag tacttcgaga tgagcgttcg gctggcagaa gctatgaagc gctatgggct      2700
gaatacaaac catcggatcg tggtgtgcag cgagaatagc ttgcagttct tcatgcccgt      2760
gttgggtgcc ctgttcatcg gtgtggctgt ggcccagct aacgacatct acaacgagcg      2820
cgagctgctg aacagcatgg gcatcagcca gcccaccgtc gtattcgtga gcaagaaagg      2880
gctgcaaaag atcctcaacg tgcaaaagaa gctaccgatc atacaaaaga tcatcatcat      2940
ggatagcaag accgactacc agggcttcca aagcatgtac accttcgtga cttcccattt      3000
gccacccggc ttcaacgagt acgacttcgt gcccgagagc ttcgaccggg acaaaaccat      3060
cgccctgatc atgaacagta gtggcagtac cggattgccc aagggcgtag ccctaccgca      3120
ccgcaccgct tgtgtccgat tcagtcatgc ccgcgacccc atcttcggca accagatcat      3180
ccccgacacc gctatcctca gcgtggtgcc atttcaccac ggcttcggca tgttcaccac      3240
gctgggctac ttgatctgcg gctttcgggt cgtgctcatg taccgcttcg aggaggagct      3300
attcttgcgc agcttgcaag actataagat tcaatctgcc ctgctggtgc ccacactatt      3360
tagcttcttc gctaagagca ctctcatcga caagtacgac ctaagcaact gcacgagat      3420 cgccagcggc ggggcgccgc tcagcaagga ggtaggtgag gccgtggcca aacgcttcca      3480
cctaccaggc atccgccagg gctacggcct gacagaaaca accagcgcca ttctgatcac      3540
ccccgaaggg gacgacaagc ctggcgcagt aggcaaggtg gtgcccttct tcgaggctaa      3600
ggtggtggac ttggacaccg gtaagacact gggtgtgaac cagcgcggcg agctgtgcgt      3660 ccgtggccc atgatcatga gcggctacgt taacaacccc gaggctacaa acgctctcat      3720
cgacaaggac ggctggctgc acagcggcga catcgcctac tgggacgagg acgagcactt      3780
cttcatcgtg gaccggctga agagcctgat caaatacaag ggctaccagg tagccccagc      3840
cgaactggag agcatcctgc tgcaacaccc caacatcttc gacgccgggg tcgccggcct      3900
gcccgacgac gatgccggcg agctgcccgc cgcagtcgtc gtgctggaac acggtaaaac      3960
catgaccgag aaggagatcg tggactatgt ggccagccag gttacaaccg ccaagaagct      4020
gcgcggtggt gttgtgttcg tggacgaggt gcctaaagga ctgaccggca agttggacgc      4080
ccgcaagatc cgcgagattc tcattaaggc caagaagggc ggcaagatcg ccgtgtaatt      4140
cgaaacgtca agtccatctt gagcatctga cttctggcta aataaaagat ctttatttc      4200 attagatctg tgtgttggtt ttttgtgtgc gtcgagatcc acggccgcag gaacccctag      4260
tgatggagtt ggccactccc tctctgcgcg ctcgctcgct cactgaggcc gggcgaccaa      4320
aggtcgcccg acgcccgggc tttgcccggg cggcctcagt gagcgagcga gcgcgcagct      4380
gcctgcaggg gcgcctgatg cggtattttt ccttacgca tctgtgcggt atttcacacc      4440
gcatacgtca aagcaaccat agtacgcgcc ctgtagcggc gcattaagcg cggcgggtgt      4500
ggtggttacg cgcagcgtga ccgctacact tgccagcgcc ctagcgcccg ctcctttcgc      4560
tttcttccct ccttttctcg ccacgttcgc cggctttccc cgtcaagctc taaatcgggg      4620
gctcccttta gggttccgat ttagtgcttt acggcacctc gaccccaaaa aacttgattt      4680
gggtgatggt tcacgtagtg ggccatcgcc ctgatagacg ttttttcgcc ctttgacgtt      4740
```

```
ggagtccacg ttctttaata gtggactctt gttccaaact ggaacaacac tcaaccctat    4800
ctcgggctat tcttttgatt tataagggat tttgccgatt tcggcctatt ggttaaaaaa    4860
tgagctgatt taacaaaaat ttaacgcgaa ttttaacaaa atattaacgt ttacaatttt    4920
atggtgcact ctcagtacaa tctgctctga tgccgcatag ttaagccagc ccgacaccc     4980 gccaacaccc gctgacgcgc cctgacgggc ttgtctgctc ccggcatccg cttacagaca    5040
agctgtgacc gtctccggga gctgcatgtg tcagaggttt tcaccgtcat caccgaaacg    5100
cgcgagacga aagggcctcg tgatacgcct atttttatag gttaatgtca tgataataat    5160
ggtttcttag acgtcaggtg gcacttttcg gggaaatgtg cgcggaaccc ctatttgttt    5220
attttcctaa atacattcaa atatgtatcc gctcatgaga caataaccct gataaatgct    5280
tcaataatat tgaaaaagga agagtatgag tattcaacat ttccgtgtcg cccttattcc    5340
cttttttgcg gcattttgcc ttcctgtttt tgctcaccca gaaacgctgg tgaaagtaaa    5400
agatgctgaa gatcagttgg gtgcacgagt gggttacatc gaactggatc tcaacagcgg    5460
taagatcctt gagagttttc gccccgaaga acgttttcca atgatgagca cttttaaagt    5520
tctgctatgt ggcgcggtat tatcccgtat tgacgccggg caagagcaac tcggtcgccg    5580
catacactat tctcagaatg acttggttga gtactcacca gtcacagaaa agcatcttac    5640
ggatggcatg acagtaagag aattatgcag tgctgccata accatgagtg ataacactgc    5700
ggccaactta cttctgacaa cgatcggagg accgaaggag ctaaccgctt ttttgcacaa    5760
catgggggat catgtaactc gccttgatcg ttgggaaccg gagctgaatg aagccatacc    5820
aaacgacgag cgtgacacca cgatgcctgt agcaatggca acaacgttgc gcaaactatt    5880
aactggcgaa ctacttactc tagcttcccg gcaacaatta atagactgga tggaggcgga    5940
taaagttgca ggaccacttc tgcgctcggc ccttccggct ggctggttta ttgctgataa    6000
atctggagcc ggtgagcgtg ggtctcgcgg tatcattgca gcactggggc cagatggtaa    6060
gccctcccgt atcgtagtta tctacacgac ggggagtcag gcaactatgg atgaacgaaa    6120
tagacagatc gctgagatag gtgcctcact gattaagcat tggtaactgt cagaccaagt    6180
ttactcatat atactttaga ttgatttaaa acttcatttt taatttaaaa ggatctaggt    6240
gaagatcctt tttgataatc tcatgaccaa aatcccttaa cgtgagtttt cgttccactg    6300
agcgtcagac cccgtagaaa agatcaaagg atcttcttga tccttttttt tctgcgcgt    6360 aatctgctgc ttgcaaacaa aaaaaccacc gctaccagcg gtggtttgtt tgccggatca    6420
agagctacca actctttttc cgaaggtaac tggcttcagc agagcgcaga taccaaatac    6480
tgtccttcta gtgtagccgt agttaggcca ccacttcaag aactctgtag caccgcctac    6540
atacctcgct ctgctaatcc tgttaccagt ggctgctgcc agtggcgata agtcgtgtct    6600
taccgggttg gactcaagac gatagttacc ggataaggcg cagcggtcgg gctgaacggg    6660
gggttcgtgc acacagccca gcttggagcg aacgacctac accgaactga gatacctaca    6720
gcgtgagcta tgagaaagcg ccacgcttcc cgaagggaga aaggcggaca ggtatccggt    6780
aagcggcagg gtcggaacag gagagcgcac gagggagctt ccaggggga acgcctggta    6840 tctttatagt cctgtcgggt ttcgccacct ctgacttgag cgtcgatttt tgtgatgctc    6900
gtcagggggg cggagcctat ggaaaaacgc cagcaacgcg gcctttttac ggttcctggc    6960
cttttgctgg ccttttgctc acatgt                                         6986
```

<210> SEQ ID NO 44

<211> LENGTH: 4428
<212> TYPE: DNA
<213> ORGANISM: Artificial Sequence
<220> FEATURE:
<223> OTHER INFORMATION: AAV- SPc5-12-MVM-hB-SG-pA

<400> SEQUENCE: 44

| | | | | | |
|---|---|---|---|---|---|
| acatgtcctg | caggcagctg | cgcgctcgct | cgctcactga | ggccgcccgg gcaaagcccg | 60 |
| ggcgtcgggc | gacctttggt | cgcccggcct | cagtgagcga | gcgagcgcgc agagagggag | 120 |
| tggccaactc | catcactagg | ggttcctgcg | gccggcgcgc | cacgcgtggt acccaacgcg | 180 |
| ttacgtggcc | accgccttcg | gcaccatcct | cacgacaccc | aaatatggcg acgggtgagg | 240 |
| aatggtgggg | agttattttt | agagcggtga | ggaaggtggg | caggcagcag gtgttggcgc | 300 |
| tctaaaaata | actcccggga | gttatttttta | gagcggagga | atggtggaca cccaaatatg | 360 |
| gcgacggttc | ctcacccgtc | gccatatttg | ggtgtccgcc | ctcggccggg gccgcattcc | 420 |
| tgggggccgg | gcggtgctcc | cgcccgcctc | gataaaaggc | tccggggccg gcggcggccc | 480 |
| acgagctacc | cggaggagcg | ggaggcgcca | agctctagat | ctagaaagag gtaagggttt | 540 |
| aagggatggt | tggttggtgg | ggtattaatg | tttaattacc | tggagcacct gcctgaaatc | 600 |
| acttttttttc | aggttggaag | cttgccacca | tggcggcagc | ggcggcggcg gctgcagaac | 660 |
| agcaaagttc | caatggtcct | gtaaagaagt | ccatgcgtga | aaggctgtt gagagaagga | 720 |
| gtgtcaataa | agagcacaac | agtaacttta | agctggata | cattccgatt gatgaagatc | 780 |
| gtctccacaa | aacagggttg | agaggaagaa | agggcaattt | agccatctgt gtgattatcc | 840 |
| tcttgtttat | cctggctgtc | atcaatttaa | taataacact | tgttatttgg gccgtgattc | 900 |
| gcattggacc | aaatggctgt | gatagtatgg | agtttcatga | agtggcctg cttcgattta | 960 |
| agcaagtatc | tgcatgggga | gtgatccacc | ctctttataa | aagcacagta ggaggaaggc | 1020 |
| gaaatgaaaa | tttggtcatc | actggcaaca | accagccttat | tgttttttcag caagggacaa | 1080 |
| caaagctcag | tgtagaaaac | aacaaaaactt | ctattacaag | tgacatcggc atgcagtttt | 1140 |
| ttgacccgag | gactcaaaat | atcttattca | gcacagacta | tgaaactcat gagtttcatt | 1200 |
| tgccaagtgg | agtgaaaagt | ttgaatgttc | aaaaggcatc | tactgaaagg attaccagca | 1260 |
| atgctaccag | tgatttaaat | ataaaagttg | atgggcgtgc | tattgtgcgt ggaaatgaag | 1320 |
| gtgtattcat | tatgggcaaa | accattgaat | tcacatggg | tggtaatatg gagttaaagg | 1380 |
| cggaaaacag | tatcatccta | aatggatctg | tgatggtcag | caccacccgc ctacccagtt | 1440 |
| cctccagtgg | agaccagttg | ggtagtggtg | actgggtacg | ctacaagctc tgcatgtgtg | 1500 |
| ctgatgggac | gctcttcaag | gtgcaagtaa | ccagccagaa | catgggctgc caaatctcag | 1560 |
| acaacccctg | tggaaacact | cattaattcg | aaacgttgtg | tccatcttga gcatctgact | 1620 |
| tctggctaaa | taaagatct | ttattttcat | tagatctgtg | tgttggtttt ttgtgtgcgt | 1680 |
| cgagatccac | ggccgcagga | accctagtg | atggagttgg | ccactccctc tctgcgcgct | 1740 |
| cgctcgctca | ctgaggccgg | gcgaccaaag | gtcgcccgac | gcccgggctt tgcccgggcg | 1800 |
| gcctcagtga | gcgagcgagc | gcgcagctgc | ctgcaggggc | gcctgatgcg gtattttctc | 1860 |
| cttacgcatc | tgtgcggtat | ttcacaccgc | atacgtcaaa | gcaaccatag tacgcgcccc | 1920 |
| gtagcggcgc | attaagcgcg | gcgggtgtgg | tggttacgcg | cagcgtgacc gctacacttg | 1980 |
| ccagcgccct | agcgcccgct | cctttcgctt | tcttcccttc | ctttctcgcc acgttcgccg | 2040 |
| gctttccccg | tcaagctcta | aatcgggggc | tccctttagg | gttccgattt agtgctttac | 2100 |
| ggcacctcga | ccccaaaaaa | cttgatttgg | gtgatggttc | acgtagtggg ccatcgccct | 2160 |

```
gatagacggt ttttcgccct ttgacgttgg agtccacgtt ctttaatagt ggactcttgt    2220
tccaaactgg aacaacactc aaccctatct cgggctattc ttttgattta aagggattt    2280 tgccgatttc ggcctattgg ttaaaaaatg agctgattta acaaaaattt aacgcgaatt    2340
ttaacaaaat attaacgttt acaattttat ggtgcactct cagtacaatc tgctctgatg    2400
ccgcatagtt aagccagccc cgacacccgc caacacccgc tgacgcgccc tgacgggctt    2460
gtctgctccc ggcatccgct tacagacaag ctgtgaccgt ctccgggagc tgcatgtgtc    2520
agaggttttc accgtcatca ccgaaacgcg cgagacgaaa gggcctcgtg atacgcctat    2580
ttttataggt taatgtcatg ataataatgg tttcttagac gtcaggtggc acttttcggg    2640
gaaatgtgcg cggaacccct atttgtttat ttttctaaat acattcaaat atgtatccgc    2700
tcatgagaca taaccctga taaatgcttc aataatattg aaaaaggaag agtatgagta    2760
ttcaacattt ccgtgtcgcc cttattccct tttttgcggc attttgcctt cctgtttttg    2820
ctcacccaga aacgctggtg aaagtaaaag atgctgaaga tcagttgggt gcacgagtgg    2880
gttacatcga actggatctc aacagcggta agatccttga gttttcgc cccgaagaac    2940 gttttccaat gatgagcact tttaaagttc tgctatgtgg cgcggtatta tcccgtattg    3000
acgccgggca agagcaactc ggtcgccgca tacactattc tcagaatgac ttggttgagt    3060
actcaccagt cacagaaaag catcttacgg atggcatgac agtaagagaa ttatgcagtg    3120
ctgccataac catgagtgat aacactgcgg ccaacttact tctgacaacg atcggaggac    3180
cgaaggagct aaccgctttt ttgcacaaca tgggggatca tgtaactcgc cttgatcgtt    3240
gggaaccgga gctgaatgaa gccataccaa acgacgagcg tgacaccacg atgcctgtag    3300
caatggcaac aacgttgcgc aaactattaa ctggcgaact acttactcta gcttcccggc    3360
aacaattaat agactggatg gaggcggata agttgcagg accacttctg cgctcggccc    3420
ttccggctgg ctggtttatt gctgataaat ctggagccgg tgagcgtggg tctcgcggta    3480
tcattgcagc actggggcca gatggtaagc cctcccgtat cgtagttatc tacacgacgg    3540
ggagtcaggc aactatggat gaacgaaata gacagatcgc tgagataggt gcctcactga    3600
ttaagcattg gtaactgtca gaccaagttt actcatatat actttagatt gatttaaaac    3660
ttcattttta atttaaaagg atctaggtga agatcctttt tgataatctc atgaccaaaa    3720
tcccttaacg tgagttttcg ttccactgag cgtcagaccc cgtagaaaag atcaaaggat    3780
cttcttgaga tccttttttt ctgcgcgtaa tctgctgctt gcaaacaaaa aaaccaccgc    3840
taccagcggt ggtttgtttg ccggatcaag agctaccaac tcttttttcg aaggtaactg    3900
gcttcagcag agcgcagata ccaaatactg tccttctagt gtagccgtag ttaggccacc    3960
acttcaagaa ctctgtagca ccgcctacat acctcgctct gctaatcctg ttaccagtgg    4020
ctgctgccag tggcgataag tcgtgtctta ccgggttgga ctcaagacga tagttaccgg    4080
ataaggcgca gcggtcgggc tgaacggggg gttcgtgcac acagcccagc ttggagcgaa    4140
cgacctacac cgaactgaga tacctacagc gtgagctatg agaaagcgcc acgcttcccg    4200
aagggagaaa ggcggacagg tatccggtaa gcggcagggt cggaacagga gagcgcacga    4260
gggagcttcc agggggaaac gcctggtatc tttatagtcc tgtcgggttt cgccacctct    4320
gacttgagcg tcgatttttg tgatgctcgt cagggggggcg gagcctatgg aaaaacgcca    4380
gcaacgcggc cttttacgg ttcctggcct tttgctggcc ttttgctc                  4428

<210> SEQ ID NO 45
```

<211> LENGTH: 4428
<212> TYPE: DNA
<213> ORGANISM: Artificial Sequence
<220> FEATURE:
<223> OTHER INFORMATION: AAV- SPc5-12-MVM-hB-SGco-pA

<400> SEQUENCE: 45

| | | | | | |
|---|---|---|---|---|---|
| acatgtcctg | caggcagctg | cgcgctcgct | cgctcactga | ggccgcccgg gcaaagcccg | 60 |
| ggcgtcgggc | gacctttggt | cgcccggcct | cagtgagcga | gcgagcgcgc agagagggag | 120 |
| tggccaactc | catcactagg | ggttcctgcg | gccggcgcgc | cacgcgtggt acccaacgcg | 180 |
| ttacgtggcc | accgccttcg | gcaccatcct | cacgacaccc | aaatatggcg acgggtgagg | 240 |
| aatggtgggg | agttattttt | agagcggtga | ggaaggtggg | caggcagcag gtgttggcgc | 300 |
| tctaaaaata | actcccggga | gttattttta | gagcggagga | atggtggaca cccaaatatg | 360 |
| gcgacggttc | ctcacccgtc | gccatatttg | ggtgtccgcc | ctcggccggg gccgcattcc | 420 |
| tgggggccgg | gcggtgctcc | cgcccgcctc | gataaaaggc | tccggggccg gcggcggccc | 480 |
| acgagctacc | cggaggagcg | ggaggcgcca | agctctagat | ctagaaagag gtaagggttt | 540 |
| aagggatggt | tggttggtgg | ggtattaatg | tttaattacc | tggagcacct gcctgaaatc | 600 |
| acttttttc | aggttggaag | cttgccacca | tggctgctgc | cgctgctgct gcagctgaac | 660 |
| agcaatctag | caacggcccc | gtgaagaaat | ccatgcgcga | aaggccgtc gagcggagat | 720 |
| ctgtgaacaa | agagcacaac | agcaacttca | aggccggcta | catccccatc gacgaggaca | 780 |
| gactgcacaa | gacaggcctg | agaggcagaa | agggcaatct | ggccatctgc gtgatcatcc | 840 |
| tgctgttcat | cctggccgtg | atcaacctga | tcatcaccct | ggtcatctgg gccgtgatta | 900 |
| gaatcggccc | caacggctgc | gacagcatgg | aatttcacga | gagcggcctg ctgcggttca | 960 |
| aacaggtgtc | cgatatgggc | gtgatccatc | cactgtacaa | gagcaccgtt ggcggcagaa | 1020 |
| gaaacgagaa | tctggtcatc | accggcaaca | accagcctat | cgtgtttcag cagggcacca | 1080 |
| ccaagctgag | cgtggaaaac | aacaagacca | gcatcaccag | cgacatcggc atgcagttct | 1140 |
| tcgaccccag | aacacagaac | atcctgttca | gcaccgacta | cgagacacac gagttccatc | 1200 |
| tgcctagcgg | cgtgaagtcc | ctgaatgtgc | agaaggccag | caccgagaga atcaccagca | 1260 |
| atgccacctc | cgacctgaac | atcaaagtgg | acggcagagc | catcgtgcgg ggaaatgagg | 1320 |
| gcgtgttcat | catgggcaag | accatcgagt | tccacatggg | cggcaacatg gaactgaagg | 1380 |
| ccgagaacag | catcatcctg | aacggcagcg | tgatggtgtc | caccacaaga ctgccaagca | 1440 |
| gcagctctgg | cgatcagctt | ggatctggcg | actgggtccg | atacaagctg tgtatgtgtg | 1500 |
| ccgacggcac | cctgttcaag | gtgcaagtga | caagccagaa | catgggctgc cagatcagcg | 1560 |
| acaacccttg | cggcaatacc | cactgattcg | aaacgttgtg | tccatcttga gcatctgact | 1620 |
| tctggctaaa | taaagatct | ttattttcat | tagatctgtg | tgttggtttt ttgtgtgcgt | 1680 |
| cgagatccac | ggccgcagga | accctagtg | atggagttgg | ccactccctc tctgcgcgct | 1740 |
| cgctcgctca | ctgaggccgg | gcgaccaaag | gtcgcccgac | gcccgggctt tgcccgggcg | 1800 |
| gcctcagtga | gcgagcgagc | gcgcagctgc | ctgcaggggc | gcctgatgcg gtattttctc | 1860 |
| cttacgcatc | tgtgcggtat | ttcacaccgc | atacgtcaaa | gcaaccatag tacgcgcccc | 1920 |
| gtagcggcgc | attaagcgcg | gcgggtgtgg | tggttacgcg | cagcgtgacc gctacacttg | 1980 |
| ccagcgccct | agcgcccgct | cctttcgctt | tcttcccttc | ctttctcgcc acgttcgccg | 2040 |
| gctttccccg | tcaagctcta | aatcgggggc | tccctttagg | gttccgattt agtgctttac | 2100 |
| ggcacctcga | ccccaaaaaa | cttgatttgg | gtgatggttc | acgtagtggg ccatcgccct | 2160 |

```
gatagacggt ttttcgccct tgacgttgg agtccacgtt ctttaatagt ggactcttgt    2220
tccaaactgg aacaacactc aaccctatct cgggctattc ttttgattta aagggattt    2280 tgccgatttc ggcctattgg ttaaaaaatg agctgattta acaaaaattt aacgcgaatt    2340
ttaacaaaat attaacgttt acaattttat ggtgcactct cagtacaatc tgctctgatg    2400
ccgcatagtt aagccagccc cgacacccgc caacacccgc tgacgcgccc tgacgggctt    2460
gtctgctccc ggcatccgct tacagacaag ctgtgaccgt ctccgggagc tgcatgtgtc    2520
agaggttttc accgtcatca ccgaaacgcg cgagacgaaa gggcctcgtg atacgcctat    2580
ttttataggt taatgtcatg ataataatgg tttcttagac gtcaggtggc acttttcggg    2640
gaaatgtgcg cggaacccct atttgtttat ttttctaaat acattcaaat atgtatccgc    2700
tcatgagaca taaccctga taaatgcttc aataatattg aaaaggaag agtatgagta     2760 ttcaacattt ccgtgtcgcc cttattccct ttttgcggc attttgcctt cctgtttttg    2820
ctcacccaga aacgctggtg aaagtaaaag atgctgaaga tcagttgggt gcacgagtgg    2880
gttacatcga actggatctc aacagcggta agatccttga gttttcgc cccgaagaac     2940 gttttccaat gatgagcact tttaaagttc tgctatgtgg cgcggtatta tcccgtattg    3000
acgccgggca agagcaactc ggtcgccgca tacactattc tcagaatgac ttggttgagt    3060
actcaccagt cacagaaaag catcttacgg atggcatgac agtaagagaa ttatgcagtg    3120
ctgccataac catgagtgat aacactgcgg ccaacttact tctgacaacg atcggaggac    3180
cgaaggagct aaccgctttt ttgcacaaca tgggggatca tgtaactcgc cttgatcgtt    3240
gggaaccgga gctgaatgaa gccataccaa acgacgagcg tgacaccacg atgcctgtag    3300
caatggcaac aacgttgcgc aaactattaa ctggcgaact acttactcta gcttcccggc    3360
aacaattaat agactggatg gaggcggata agttgcagg accacttctg cgctcggccc     3420
ttccggctgg ctggtttatt gctgataaat ctggagccgg tgagcgtggg tctcgcggta    3480
tcattgcagc actggggcca gatggtaagc cctcccgtat cgtagttatc tacacgacgg    3540
ggagtcaggc aactatggat gaacgaaata gacagatcgc tgagataggt gcctcactga    3600
ttaagcattg gtaactgtca gaccaagttt actcatatat actttagatt gatttaaaac    3660
ttcattttta atttaaaagg atctaggtga agatcctttt tgataatctc atgaccaaaa    3720
tcccttaacg tgagttttcg ttccactgag cgtcagaccc cgtagaaaag atcaaaggat    3780
cttcttgaga tccttttttt ctgcgcgtaa tctgctgctt gcaaacaaaa aaaccaccgc    3840
taccagcggt ggtttgtttg ccggatcaag agctaccaac tcttttttcg aaggtaactg    3900
gcttcagcag agcgcagata ccaaatactg tccttctagt gtagccgtag ttaggccacc    3960
acttcaagaa ctctgtagca ccgcctacat acctcgctct gctaatcctg ttaccagtgg    4020
ctgctgccag tggcgataag tcgtgtctta ccgggttgga ctcaagacga tagttaccgg    4080
ataaggcgca gcggtcgggc tgaacggggg gttcgtgcac acagcccagc ttggagcgaa    4140
cgacctacac cgaactgaga tacctacagc gtgagctatg agaaagcgcc acgcttcccg    4200
aagggagaaa ggcggacagg tatccggtaa gcggcagggt cggaacagga gagcgcacga    4260
gggagcttcc agggggaaac gcctggtatc tttatagtcc tgtcgggttt cgccacctct    4320
gacttgagcg tcgatttttg tgatgctcgt caggggggcg gagcctatgg aaaaacgcca    4380
gcaacgcggc ctttttacgg ttcctggcct tttgctggcc ttttgctc                4428
```

<210> SEQ ID NO 46

<211> LENGTH: 5118
<212> TYPE: DNA
<213> ORGANISM: Artificial Sequence
<220> FEATURE:
<223> OTHER INFORMATION: AAV-SPc5-12-MVM-Luc-pA

<400> SEQUENCE: 46

| | | | | | |
|---|---|---|---|---|---|
| acatgtcctg | caggcagctg | cgcgctcgct | cgctcactga | ggccgcccgg gcaaagcccg | 60 |
| ggcgtcgggc | gacctttggt | cgcccggcct | cagtgagcga | gcgagcgcgc agagagggag | 120 |
| tggccaactc | catcactagg | ggttcctgcg | gccggcgcgc | cacgcgtggt acccaacgcg | 180 |
| ttacgtggcc | accgccttcg | gcaccatcct | cacgacaccc | aaatatggcg acgggtgagg | 240 |
| aatggtgggg | agttattttt | agagcggtga | ggaaggtggg | caggcagcag gtgttggcgc | 300 |
| tctaaaaata | actcccggga | gttatttta | gagcggagga | atggtggaca cccaaatatg | 360 |
| gcgacggttc | ctcacccgtc | gccatatttg | ggtgtccgcc | ctcggccggg gccgcattcc | 420 |
| tgggggccgg | gcggtgctcc | cgcccgcctc | gataaaaggc | tccggggccg gcggcggccc | 480 |
| acgagctacc | cggaggagcg | ggaggcgcca | agctctagat | ctagaaagag gtaagggttt | 540 |
| aagggatggt | tggttggtgg | ggtattaatg | tttaattacc | tggagcacct gcctgaaatc | 600 |
| acttttttc | aggttggaag | cttatggaag | atgccaaaaa | cattaagaag ggcccagcgc | 660 |
| cattctaccc | actcgaagac | gggaccgccg | gcgagcagct | gcacaaagcc atgaagcgct | 720 |
| acgccctggt | gccggcacc | atcgccttta | ccgacgcaca | tatcgaggtg acattacct | 780 |
| acgccgagta | cttcgagatg | agcgttcggc | tggcagaagc | tatgaagcgc tatgggctga | 840 |
| atacaaacca | tcgatcgtg | gtgtgcagcg | agaatagctt | gcagttcttc atgcccgtgt | 900 |
| tgggtgccct | gttcatcggt | gtggctgtgg | ccccagctaa | cgacatctac aacgagcgcg | 960 |
| agctgctgaa | cagcatgggc | atcagccagc | ccaccgtcgt | attcgtgagc aagaaagggc | 1020 |
| tgcaaaagat | cctcaacgtg | caaagaagc | taccgatcat | acaaaagatc atcatcatgg | 1080 |
| atagcaagac | cgactaccag | ggcttccaaa | gcatgtacac | cttcgtgact tcccatttgc | 1140 |
| cacccggctt | caacgagtac | gacttcgtgc | ccgagagctt | cgaccgggac aaaaccatcg | 1200 |
| ccctgatcat | gaacagtagt | ggcagtaccg | gattgcccaa | gggcgtagcc ctaccgcacc | 1260 |
| gcaccgcttg | tgtccgattc | agtcatgccc | gcgacccat | cttcggcaac cagatcatcc | 1320 |
| ccgacaccgc | tatcctcagc | gtggtgccat | tcaccacgg | cttcggcatg ttcaccacgc | 1380 |
| tgggctactt | gatctgcggc | tttcgggtcg | tgctcatgta | ccgcttcgag gaggagctat | 1440 |
| tcttgcgcag | cttgcaagac | tataagattc | aatctgccct | gctggtgccc acactattta | 1500 |
| gcttcttcgc | taagagcact | ctcatcgaca | agtacgacct | aagcaacttg cacgagatcg | 1560 |
| ccagcggcgg | ggcgccgctc | agcaaggagg | taggtgaggc | cgtggccaaa cgcttccacc | 1620 |
| taccaggcat | ccgccagggc | tacggcctga | cagaaacaac | cagcgccatt ctgatcaccc | 1680 |
| ccgaagggga | cgacaagcct | ggcgcagtag | gcaaggtggt | gcccttcttc gaggctaagg | 1740 |
| tggtggactt | ggacaccggt | aagacactgg | gtgtgaacca | gcgcggcgag ctgtgcgtcc | 1800 |
| gtggccccat | gatcatgagc | ggctacgtta | caaccccga | ggctacaaac gctctcatcg | 1860 |
| acaaggacgg | ctggctgcac | agcggcgaca | tcgcctactg | gacgaggac gagcacttct | 1920 |
| tcatcgtgga | ccggctgaag | agcctgatca | aatacaaggg | ctaccaggta gccccagccg | 1980 |
| aactggagag | catcctgctg | caacacccca | acatcttcga | cgccgggtc gccggcctgc | 2040 |
| ccgacgacga | tgccggcgag | ctgcccgccg | cagtcgtcgt | gctggaacac ggtaaaacca | 2100 |
| tgaccgagaa | ggagatcgtg | gactatgtgg | ccagccaggt | tacaaccgcc aagaagctgc | 2160 |

```
gcggtggtgt tgtgttcgtg gacgaggtgc ctaaaggact gaccggcaag ttggacgccc    2220
gcaagatccg cgagattctc attaaggcca agaagggcgg caagatcgcc gtgtaattcg    2280
aaacgttgtg tccatcttga gcatctgact tctggctaaa taaaagatct ttattttcat    2340
tagatctgtg tgttggtttt ttgtgtgcgt cgagatccac ggccgcagga accctagtg     2400 atggagttgg ccactccctc tctgcgcgct cgctcgctca ctgaggccgg cgaccaaag     2460 gtcgcccgac gcccgggctt tgcccggcg gcctcagtga gcgagcgagc gcgcagctgc    2520
ctgcaggggc gcctgatgcg gtattttctc cttacgcatc tgtgcggtat ttcacaccgc    2580
atacgtcaaa gcaaccatag tacgcgccct gtagcggcgc attaagcgcg cgggtgtgg     2640 tggttacgcg cagcgtgacc gctacacttg ccagcgccct agcgcccgct cctttcgctt    2700
tcttcccttc ctttctcgcc acgttcgccg gctttccccg tcaagctcta atcgggggc     2760 tcccttaagg gttccgattt agtgctttac ggcacctcga ccccaaaaaa cttgatttgg    2820
gtgatggttc acgtagtggg ccatcgccct gatagacggt ttttcgccct tgacgttgg     2880 agtccacgtt ctttaatagt ggactcttgt tccaaactgg aacaacactc aaccctatct    2940
cgggctattc ttttgattta agggattt tgccgatttc ggcctattgg ttaaaaaatg      3000
agctgattta acaaaaattt aacgcgaatt ttaacaaaat attaacgttt acaatttat     3060 ggtgcactct cagtacaatc tgctctgatg ccgcatagtt aagccagccc cgacacccgc    3120
caacacccgc tgacgcgccc tgacgggctt gtctgctccc ggcatccgct tacagacaag    3180
ctgtgaccgt ctccgggagc tgcatgtgtc agaggttttc accgtcatca ccgaaacgcg    3240
cgagacgaaa gggcctcgtg atacgcctat ttttataggt taatgtcatg ataataatgg    3300
tttcttagac gtcaggtggc acttttcggg gaaatgtgcg cggaacccct atttgtttat    3360
ttttctaaat acattcaaat atgtatccgc tcatgagaca ataaccctga taaatgcttc    3420
aataatattg aaaaaggaag agtatgagta ttcaacattt ccgtgtcgcc cttattccct    3480 ttttttgcggc attttgcctt cctgtttttg ctcacccaga aacgctggtg aaagtaaaag    3540
atgctgaaga tcagttgggt gcacgagtgg gttacatcga actggatctc aacagcggta    3600
agatccttga gagttttcgc cccgaagaac gttttccaat gatgagcact tttaaagttc    3660
tgctatgtgg cgcggtatta tcccgtattg acgccgggca agagcaactc ggtcgccgca    3720
tacactattc tcagaatgac ttggttgagt actcaccagt cacagaaaag catcttacgg    3780
atggcatgac agtaagagaa ttatgcagtg ctgccataac catgagtgat aacactgcgg    3840
ccaacttact tctgacaacg atcggaggac cgaaggagct aaccgctttt ttgcacaaca    3900
tgggggatca tgtaactcgc cttgatcgtt gggaaccgga gctgaatgaa gccataccaa    3960
acgacgagcg tgacaccacg atgcctgtag caatggcaac aacgttgcgc aaactattaa    4020
ctggcgaact acttactcta gcttcccggc aacaattaat agactggatg gaggcggata    4080
aagttgcagg accacttctg cgctcggccc ttccggctgg ctggtttatt gctgataaat    4140
ctggagccgg tgagcgtggg tctcgcggta tcattgcagc actggggcca gatggtaagc    4200
cctcccgtat cgtagttatc tacacgacgg ggagtcaggc aactatggat gaacgaaata    4260
gacagatcgc tgagataggt gcctcactga ttaagcattg gtaactgtca gaccaagttt    4320
actcatatat actttagatt gatttaaaac ttcatttta atttaaaagg atctaggtga    4380
agatcctttt tgataatctc atgaccaaaa tcccttaacg tgagttttcg ttccactgag    4440
cgtcagaccc cgtagaaaag atcaaaggat cttcttgaga tcctttttt ctgcgcgtaa    4500
```

-continued

```
tctgctgctt gcaaacaaaa aaaccaccgc taccagcggt ggtttgtttg ccggatcaag    4560
agctaccaac tcttttttccg aaggtaactg gcttcagcag agcgcagata ccaaatactg    4620
tccttctagt gtagccgtag ttaggccacc acttcaagaa ctctgtagca ccgcctacat    4680
acctcgctct gctaatcctg ttaccagtgg ctgctgccag tggcgataag tcgtgtctta    4740
ccgggttgga ctcaagacga tagttaccgg ataaggcgca gcggtcgggc tgaacggggg    4800
gttcgtgcac acagcccagc ttggagcgaa cgacctacac cgaactgaga tacctacagc    4860
gtgagctatg agaaagcgcc acgcttcccg aagggagaaa ggcggacagg tatccggtaa    4920
gcggcagggt cggaacagga gagcgcacga ggggagcttcc aggggggaaac gcctggtatc    4980 tttatagtcc tgtcgggttt cgccacctct gacttgagcg tcgatttttg tgatgctcgt    5040
caggggggcg gagcctatgg aaaaacgcca gcaacgcggc cttttttacgg ttcctggcct    5100 tttgctggcc ttttgctc                                                  5118
```

<210> SEQ ID NO 47
<211> LENGTH: 5572
<212> TYPE: DNA
<213> ORGANISM: Artificial Sequence
<220> FEATURE:
<223> OTHER INFORMATION: AAV- CSK-SH5-SPc5-12-MVM-Luc-pA

<400> SEQUENCE: 47

```
acatgtcctg caggcagctg cgcgctcgct cgctcactga ggccgcccgg gcaaagcccg      60
ggcgtcgggc gacctttggt cgcccggcct cagtgagcga gcgagcgcgc agagagggag     120
tggccaactc catcactagg ggttcctgcg gccggcgcgc cacgcgtcag tttactcacc     180
agggattcag aggcagcact gctgaaccct gagcccttgg cacatcaggt tggctgtcag     240
aagtcggcct ttgtacatac acagttccct tgtgaggccc agctgcgtgt cctaggagcg     300
gggcctctct ccacagcaga gctcagcctc tcaagtgtat ggacagcacg ggtgcctgat     360
gggtggattt agccatgagt tgaaggtggc ttggggagaa tgagagttct agagataggg     420
agaaggggtt gccaatagga gagtggaatt cctgagcacc tcgtcacagg cagccgacag     480
aacatgagcc gcagggccca ggctatttat acctcgcctg tcactatcag ggtccccaca     540
gctcccccca cctccagcca cacacagcag gtccttttgc tctttctggt cccttctcta     600
ctcctccccc tccctaccta aggtacccaa cgcgttacgt ggccaccgcc ttcggcacca     660
tcctcacgac acccaaatat ggcgacgggt gaggaatggt ggggagttat ttttagagcg     720
gtgaggaagg tggcaggca gcaggtgttg gcgctctaaa aataactccc gggagttatt     780
tttagagcgg aggaatggtg gacacccaaa tatggcgacg gttcctcacc cgtcgccata     840
tttgggtgtc cgccctcggc cggggccgca ttcctggggg ccgggcggtg ctcccgcccg     900
cctcgataaa aggctccggg gccggcggcg gcccacgagc tacccggagg agcgggaggc     960
gccaagctct agatctagaa agaggtaagg gtttaaggga tggttggttg gtggggtatt    1020
aatgtttaat tacctggagc acctgcctga aatcactttt tttcaggttg gaagcttatg    1080
gaagatgcca aaaacattaa gaagggccca gcgccattct acccactcga ggacgggacc    1140 gccgcgagc agctgcacaa agccatgaag cgctacgccc tggtgccgg caccatcgcc    1200 tttaccgacg cacatatcga ggtggacatt acctacgccg agtacttcga gatgagcgtt    1260
cggctggcag aagctatgaa gcgctatggg ctgaatacaa accatcggat cgtggtgtgc    1320
agcgagaata gcttgcagtt cttcatgccc gtgttgggtg ccctgttcat cggtgtggct    1380 gtggcccag ctaacgacat ctacaacgag cgcgagctgc tgaacagcat gggcatcagc    1440
```

```
cagcccaccg tcgtattcgt gagcaagaaa gggctgcaaa agatcctcaa cgtgcaaaag   1500
aagctaccga tcatacaaaa gatcatcatc atggatagca agaccgacta ccagggcttc   1560
caaagcatgt acaccttcgt gacttcccat ttgccacccg gcttcaacga gtacgacttc   1620
gtgcccgaga gcttcgaccg ggacaaaacc atcgccctga tcatgaacag tagtggcagt   1680
accggattgc caagggcgt agccctaccg caccgcaccg cttgtgtccg attcagtcat   1740
gcccgcgacc ccatcttcgg caaccagatc atccccgaca ccgctatcct cagcgtggtg   1800
ccatttcacc acggcttcgg catgttcacc acgctgggct acttgatctg cggctttcgg   1860
gtcgtgctca tgtaccgctt cgaggaggag ctattcttgc gcagcttgca agactataag   1920
attcaatctg ccctgctggt gcccacacta tttagcttct tcgctaagag cactctcatc   1980
gacaagtacg acctaagcaa cttgcacgag atcgccagcg gcgggggcgcc gctcagcaag   2040 gaggtaggtg aggccgtggc caaacgcttc cacctaccag gcatccgcca gggctacggc   2100
ctgacagaaa caaccagcgc cattctgatc accccgaag gggacgacaa gcctggcgca   2160
gtaggcaagg tggtgcccct tcttcgaggct aaggtggtgg acttggacac cggtaagaca   2220
ctgggtgtga accagcgcgg cgagctgtgc gtccgtggcc ccatgatcat gagcggctac   2280
gttaacaacc ccgaggctac aaacgctctc atcgacaagg acggctggct gcacagcggc   2340
gacatcgcct actgggacga ggacgagcac ttcttcatcg tggaccggct gaagagcctg   2400
atcaaataca agggctacca ggtagcccca gccgaactgg agagcatcct gctgcaacac   2460
cccaacatct tcgacgccgg ggtcgccggc ctgcccgacg acgatgccgg cgagctgccc   2520
gccgcagtcg tcgtgctgga acacggtaaa accatgaccg agaaggagat cgtggactat   2580
gtggccagcc aggttacaac cgccaagaag ctgcgcggtg gtgttgtgtt cgtggacgag   2640
gtgcctaaag gactgaccgg caagttggac gcccgcaaga tccgcgagat tctcattaag   2700
gccaagaagg gcggcaagat cgccgtgtaa ttcgaaacgt tcggtccatc ttgagcatct   2760
gacttctggc taaataaaag atctttattt tcattagatc tgtgtgttgg ttttttgtgt   2820
gcgtcgagat ccacggccgc aggaaccccct agtgatggag ttggccactc cctctctgcg   2880
cgctcgctcg ctcactgagg ccgggcgacc aaaggtcgcc cgacgcccgg gctttgcccg   2940
ggcggcctca gtgagcgagc gagcgcgcag ctgcctgcag gggcgcctga tgcggtattt   3000
tctccttacg catctgtgcg gtatttcaca ccgcatacgt caaagcaacc atagtacgcg   3060
ccctgtagcg gcgcattaag cgcggcgggt gtggtggtta cgcgcagcgt gaccgctaca   3120
cttgccagcg ccctagcgcc cgctcctttc gctttcttcc cttcctttct cgccacgttc   3180
gccggctttc cccgtcaagc tctaaatcgg gggctccctt tagggttccg atttagtgct   3240
ttacggcacc tcgaccccaa aaaacttgat ttgggtgatg gttcacgtag tgggccatcg   3300
ccctgataga cggttttcg ccctttgacg ttggagtcca cgttctttaa tagtggactc   3360
ttgttccaaa ctggaacaac actcaaccct atctcgggct attcttttga tttataaggg   3420
attttgccga tttcggccta ttggttaaaa aatgagctga tttaacaaaa atttaacgcg   3480
aattttaaca aaatattaac gtttacaatt ttatggtgca ctctcagtac aatctgctct   3540
gatgccgcat agttaagcca gccccgacac ccgccaacac ccgctgacgc gccctgacgg   3600
gcttgtctgc tcccggcatc cgcttacaga caagctgtga ccgtctccgg gagctgcatg   3660
tgtcagaggt tttcaccgtc atcaccgaaa cgcgcgagac gaaagggcct cgtgatacgc   3720
ctatttttat aggttaatgt catgataata atggtttctt agacgtcagg tggcactttt   3780
```

-continued

```
cggggaaatg tgcgcggaac ccctatttgt ttatttttct aaatacattc aaatatgtat    3840
ccgctcatga gacaataacc ctgataaatg cttcaataat attgaaaaag gaagagtatg    3900
agtattcaac atttccgtgt cgcccttatt ccctttttg cggcattttg ccttcctgtt    3960
tttgctcacc cagaaacgct ggtgaaagta aaagatgctg aagatcagtt gggtgcacga    4020
gtgggttaca tcgaactgga tctcaacagc ggtaagatcc ttgagagttt tcgccccgaa    4080
gaacgttttc caatgatgag cacttttaaa gttctgctat gtggcgcggt attatcccgt    4140
attgacgccg ggcaagagca actcggtcgc cgcatacact attctcagaa tgacttggtt    4200
gagtactcac cagtcacaga aaagcatctt acggatggca tgacagtaag agaattatgc    4260
agtgctgcca taaccatgag tgataacact gcggccaact tacttctgac aacgatcgga    4320
ggaccgaagg agctaaccgc ttttttgcac aacatggggg atcatgtaac tcgccttgat    4380
cgttgggaac cggagctgaa tgaagccata ccaaacgacg agcgtgacac cacgatgcct    4440
gtagcaatgg caacaacgtt gcgcaaacta ttaactggcg aactacttac tctagcttcc    4500
cggcaacaat taatagactg gatggaggcg gataaagttg caggaccact tctgcgctcg    4560
gcccttccgg ctggctggtt tattgctgat aaatctggag ccggtgagcg tgggtctcgc    4620
ggtatcattg cagcactggg gccagatggt aagccctccc gtatcgtagt tatctacacg    4680
acggggagtc aggcaactat ggatgaacga aatagacaga tcgctgagat aggtgcctca    4740
ctgattaagc attggtaact gtcagaccaa gtttactcat atatacttta gattgattta    4800
aaacttcatt tttaatttaa aaggatctag gtgaagatcc tttttgataa tctcatgacc    4860
aaaatccctt aacgtgagtt ttcgttccac tgagcgtcag accccgtaga aaagatcaaa    4920
ggatcttctt gagatccttt ttttctgcgc gtaatctgct gcttgcaaac aaaaaaacca    4980
ccgctaccag cggtggtttg tttgccggat caagagctac caactctttt tccgaaggta    5040
actggcttca gcagagcgca gataccaaat actgtccttc tagtgtagcc gtagttaggc    5100
caccacttca agaactctgt agcaccgcct acatacctcg ctctgctaat cctgttacca    5160
gtggctgctg ccagtggcga taagtcgtgt cttaccgggt tggactcaag acgatagtta    5220
ccggataagg cgcagcggtc gggctgaacg gggggttcgt gcacacagcc cagcttggag    5280
cgaacgacct acaccgaact gagatacta cagcgtgagc tatgagaaag cgccacgctt    5340
cccgaaggga aaaggcgga caggtatccg gtaagcggca gggtcggaac aggagagcgc    5400
acgagggagc ttccaggggg aaacgcctgg tatctttata gtcctgtcgg gtttcgccac    5460
ctctgacttg agcgtcgatt tttgtgatgc tcgtcagggg gcggagcct atggaaaaac    5520
gccagcaacg cggccttttt acggttcctg gccttttgct ggccttttgc tc            5572
```

<210> SEQ ID NO 48
<211> LENGTH: 20
<212> TYPE: DNA
<213> ORGANISM: Artificial Sequence
<220> FEATURE:
<223> OTHER INFORMATION: Luc Forward primer for titration

<400> SEQUENCE: 48
cccaccgtcg tattcgtgag                                                20

<210> SEQ ID NO 49
<211> LENGTH: 21
<212> TYPE: DNA
<213> ORGANISM: Artificial Sequence
<220> FEATURE:
<223> OTHER INFORMATION: Luc Reverse primer for titration

<400> SEQUENCE: 49
tcagggcgat ggttttgtcc c         21

<210> SEQ ID NO 50
<211> LENGTH: 19
<212> TYPE: DNA
<213> ORGANISM: Artificial Sequence
<220> FEATURE:
<223> OTHER INFORMATION: beta-sarcoglycan Forward primer for titration

<400> SEQUENCE: 50
agggatggtt ggttggtgg         19

<210> SEQ ID NO 51
<211> LENGTH: 19
<212> TYPE: DNA
<213> ORGANISM: Artificial Sequence
<220> FEATURE:
<223> OTHER INFORMATION: beta-sarcoglycan Reverse primer for titration

<400> SEQUENCE: 51
ggcaggtgct ccaggtaat         19

<210> SEQ ID NO 52
<211> LENGTH: 20
<212> TYPE: DNA
<213> ORGANISM: Artificial Sequence
<220> FEATURE:
<223> OTHER INFORMATION: beta-sarcoglycan Forward primer for RT-PCR

<400> SEQUENCE: 52
catcacaagt gacatcggca         20

<210> SEQ ID NO 53
<211> LENGTH: 19
<212> TYPE: DNA
<213> ORGANISM: Artificial Sequence
<220> FEATURE:
<223> OTHER INFORMATION: beta-sarcoglycan Reverse primer for RT-PCR

<400> SEQUENCE: 53
tggcagccca tgttctggc         19

<210> SEQ ID NO 54
<211> LENGTH: 20
<212> TYPE: DNA
<213> ORGANISM: Artificial Sequence
<220> FEATURE:
<223> OTHER INFORMATION: GAPDH Forward primer for RT-PCR

<400> SEQUENCE: 54
tgtgtccgtc gtggatctga         20

<210> SEQ ID NO 55
<211> LENGTH: 22
<212> TYPE: DNA
<213> ORGANISM: Artificial Sequence
<220> FEATURE:
<223> OTHER INFORMATION: GAPDH Reverse primer for RT-PCR

<400> SEQUENCE: 55
gcctgcttca ccaccttctt ga         22

<210> SEQ ID NO 56

```
<211> LENGTH: 798
<212> TYPE: DNA
<213> ORGANISM: Artificial Sequence
<220> FEATURE:
<223> OTHER INFORMATION: MHCK7 promoter

<400> SEQUENCE: 56
tagttcatag cccatatatg gagttccgct agaagctgca tgtctaagct agacccttca      60
gattaaaaat aactgaggta agggcctggg taggggaggt ggtgtgagac gctcctgtct     120
ctcctctatc tgcccatcgg ccctttgggg aggaggaatg tgcccaagga ctaaaaaaag    180
gccatggagc cagaggggcg agggcaacag acctttcatg gcaaaccctt ggggccctgc   240
tgtctagcat gccccactac gggtctaggc tgcccatgta aggaggcaag gcctggggac     300
acccgagatg cctggttata attaacccag acatgtggct gccccccccc ccccaacacc     360
tgctgcctct aaaaataacc ctgtccctgg tggatccccct gcatgcgaag atcttcgaac    420
aaggctgtgg gggactgagg gcaggctgta acaggcttgg gggccagggc ttatacgtgc   480
ctgggactcc caaagtatta ctgttccatg ttccggcga agggccagct gtccccgcc      540 agctagactc agcacttagt ttaggaacca gtgagcaagt cagcccttgg ggcagcccat    600
acaaggccat ggggctgggc aagctgcacg cctgggtccg gggtgggcac ggtgcccggg   660
caacgagctg aaagctcatc tgctctcagg ggcccctccc tggggacagc ccctcctggc    720
tagtcacacc ctgtaggctc ctctatataa cccaggggca caggggctgc cctcattcta   780
ccaccacctc cacagcac                                                   798

<210> SEQ ID NO 57
<211> LENGTH: 1426
<212> TYPE: DNA
<213> ORGANISM: Artificial Sequence
<220> FEATURE:
<223> OTHER INFORMATION: desmin promoter

<400> SEQUENCE: 57
acacacctac tagtaacccc tccagctggt gatggcaggt ctagggtagg accagtgact      60
ggctcctaat cgagcactct attttcaggg tttgcattcc aaaagggtca ggtccaagag    120
ggacctggag tgccaagtgg aggtgtagag gcacggccag tacccatgga gaatggtgga    180
tgtccttagg ggttagcaag tgccgtgtgc taaggagggg gctttggagg ttgggcaggc    240
cctctgtggg gctccatttt tgtggggggtg ggggctggag cattataggg ggtgggaagt    300
gattggggct gtcaccctag ccttccttat ctgacgccca cccatgcctc tcaggtacc    360 ccctgccccc cacagctcct ctcctgtgcc ttgtttccca gccatgcgtt ctcctctata    420
aatacccgct ctggtatttg ggttggcag ctgttgctgc cagggagatg gttgggttga    480
catgcggctc ctgacaaaac acaaacccct ggtgtgtgtg ggcgtgggtg gtgtgagtag    540
ggggatgaat cagggagggg gcgggggacc caggggcag gagccacaca agtctgtgc     600 ggggggtggga gcgcacatag caattggaaa ctgaaagctt atcagaccct ttctggaaat    660
cagcccactg tttataaact tgaggcccca ccctcgacag taccggggag gaagagggcc    720
tgcactagtc cagagggaaa ctgaggctca gggctagctc gcccatagac atacatggca    780
ggcaggcttt ggccaggatc cctccgcctg ccaggcgtct cctgccctc ccttcctgcc     840 tagagacccc caccctcaag cctggctggt ctttgcctga gacccaaacc tcttcgactt    900
caagagaata tttaggaaca aggtggttta gggccttttcc tggaacagg ccttgacccct    960 ttaagaaatg acccaaagtc tctccttgac caaaaagggg accctcaaac taagggaag   1020
```

| | |
|---|---|
| cctctcttct gctgtctccc ctgaccccac tcccccccac cccaggacga ggagataacc | 1080 |
| agggctgaaa gaggcccgcc tgggggctgc agacatgctt gctgcctgcc ctggcgaagg | 1140 |
| attggcaggc ttgcccgtca caggaccccc gctggctgac tcaggggcgc aggcctcttg | 1200 |
| cgggggagct ggcctccccg cccccacggc cacgggccgc cctttcctgg caggacagcg | 1260 |
| ggatcttgca gctgtcaggg gaggggaggc ggggctgat gtcaggaggg atacaaatag | 1320 |
| tgccgacggc tgggggccct gtctcccctc gccgcatcca ctctccggcc ggccgcctgc | 1380 |
| ccgccgcctc ctccgtgcgc ccgccagcct cgcccgcgcc gtcacc | 1426 |

<210> SEQ ID NO 58
<211> LENGTH: 2859
<212> TYPE: DNA
<213> ORGANISM: Homo sapiens

<400> SEQUENCE: 58

| | |
|---|---|
| atgggagtga ggcacccgcc ctgctcccac cggctcctgg ccgtctgcgc cctcgtgtcc | 60 |
| ttggcaaccg ctgcactcct ggggcacatc ctactccatg atttcctgct ggttccccga | 120 |
| gagctgagtg gctcctcccc agtcctggag gagactcacc cagctcacca gcagggagcc | 180 |
| agcagaccag ggccccggga tgcccaggca caccccggcc gtcccagagc agtgcccaca | 240 |
| cagtgcgacg tccccccaa cagccgcttc gattgcgccc ctgacaaggc catcacccag | 300 |
| gaacagtgcg aggcccgcgg ctgttgctac atccctgcaa gcagggggct gcagggagcc | 360 |
| cagatggggc agccctggtg cttcttccca cccagctacc ccagctacaa gctggagaac | 420 |
| ctgagctcct ctgaaatggg ctacacggcc accctgaccc gtaccacccc caccttcttc | 480 |
| cccaaggaca tcctgaccct gcggctggac gtgatgatgg agactgagaa ccgcctccac | 540 |
| ttcacgatca aagatccagc taacaggcgc tacgaggtgc ccttggagac cccgcatgtc | 600 |
| cacagccggg caccgtcccc actctacagc gtggagttct ccgaggagcc cttcggggtg | 660 |
| atcgtgcgcc ggcagctgga cggccgcgtg ctgctgaaca cgacggtggc gccctgttc | 720 |
| tttgcggacc agttccttca gctgtccacc tcgctgccct cgcagtatat cacaggcctc | 780 |
| gccgagcacc tcagtcccct gatgctcagc accagctgga ccaggatcac cctgtggaac | 840 |
| cgggaccttg cgcccacgcc cggtgcgaac ctctacgggt ctcacccttt ctacctggcg | 900 |
| ctggaggacg gcgggtcggc acacggggtg ttcctgctaa acagcaatgc catggatgtg | 960 |
| gtcctgcagc cgagccctgc ccttagctgg aggtcgacag gtgggatcct ggatgtctac | 1020 |
| atcttcctgg gccagagcc caagagcgtg gtgcagcagt acctggacgt tgtgggatac | 1080 |
| ccgttcatgc cgccatactg gggcctgggc ttccacctgt gccgctgggg ctactcctcc | 1140 |
| accgctatca cccgccaggt ggtggagaac atgaccaggg cccacttccc cctggacgtc | 1200 |
| cagtggaacg acctggacta catggactcc cggagggact tcacgttcaa caaggatggc | 1260 |
| ttccgggact ccaggccat ggtgcaggag ctgcaccagg gcggccggcg ctacatgatg | 1320 |
| atcgtggatc ctgccatcag cagctcgggc cctgccggga gctacaggcc ctacgacgag | 1380 |
| ggtctgcgga gggggtttt catcaccaac gagaccggcc agccgctgat tgggaaggta | 1440 |
| tggcccgggt ccactgcctt ccccgacttc accaacccca cagccctggc ctggtgggag | 1500 |
| gacatggtgg ctgagttcca tgaccaggtg cccttcgacg gcatgtggat tgacatgaac | 1560 |
| gagccttcca acttcatcag gggctctgag gacggctgcc ccaacaatga gctgagaac | 1620 |
| ccaccctacg tgcctggggt ggttgggggg accctccagg cggccaccat ctgtgcctcc | 1680 |

| | |
|---|---|
| agccaccagt ttctctccac acactacaac ctgcacaacc tctacggcct gaccgaagcc | 1740 |
| atcgcctccc acagggcgct ggtgaaggct cggggggacac gcccatttgt gatctcccgc | 1800 |
| tcgacctttg ctggccacgg ccgatacgcc ggccactgga cggggacgt gtggagctcc | 1860 |
| tgggagcagc tcgcctcctc cgtgccagaa atcctgcagt ttaacctgct gggggtgcct | 1920 |
| ctggtcgggg ccgacgtctg cggcttcctg ggcaacacct cagaggagct gtgtgtgcgc | 1980 |
| tggacccagc tgggggcctt ctaccccttc atgcggaacc acaacagcct gctcagtctg | 2040 |
| ccccaggagc cgtacagctt cagcgagccg gcccagcagg ccatgaggaa ggccctcacc | 2100 |
| ctgcgctacg cactcctccc ccacctctac acactgttcc accaggccca cgtcgcgggg | 2160 |
| gagaccgtgg cccggcccct cttcctggag ttccccaagg actctagcac ctggactgtg | 2220 |
| gaccaccagc tcctgtgggg ggaggccctg ctcatcaccc cagtgctcca ggccgggaag | 2280 |
| gccgaagtga ctggctactt ccccttgggc acatggtacg acctgcagac ggtgccagta | 2340 |
| gaggcccttg gcagcctccc accccaccct gcagctcccc gtgagccagc catccacagc | 2400 |
| gaggggcagt gggtgacgct gccggccccc ctggacacca tcaacgtcca cctccgggct | 2460 |
| gggtacatca tccccctgca gggccctggc ctcacaacca cagagtcccg ccagcagccc | 2520 |
| atggccctgc tgtggcccct gaccaagggt ggggaggccc gaggggagct gttctgggac | 2580 |
| gatggagaga gcctggaagt gctggagcga ggggcctaca cacaggtcat cttcctggcc | 2640 |
| aggaataaca cgatcgtgaa tgagctggta cgtgtgacca gtgagggagc tggcctgcag | 2700 |
| ctgcagaagg tgactgtcct gggcgtggcc acggcgcccc agcaggtcct ctccaacggt | 2760 |
| gtccctgtct ccaacttcac ctacagcccc gacaccaagg tcctggacat ctgtgtctcg | 2820 |
| ctgttgatgg gagagcagtt tctcgtcagc tggtgttag | 2859 |

<210> SEQ ID NO 59
<211> LENGTH: 2859
<212> TYPE: DNA
<213> ORGANISM: Artificial Sequence
<220> FEATURE:
<223> OTHER INFORMATION: codon-optimized human acid alpha-glucosidase gene (hGAAco)

<400> SEQUENCE: 59

| | |
|---|---|
| atgggcgtca gacatcctcc atgttctcac agactgctgg ccgtgtgtgc tctggtgtct | 60 |
| cttgctacag ctgccctgct gggacatatc ctgctgcacg attttctgct ggtgcccaga | 120 |
| gagctgtctg gcagctctcc tgtgctggaa gaaacacacc ctgcacatca gcagggcgcc | 180 |
| tctagacctg gacctagaga tgctcaagcc catcctggca gacctagagc cgtgcctaca | 240 |
| cagtgtgacg tgccacctaa cagcagattc gactgcgccc tgacaaggc catcacacaa | 300 |
| gagcagtgtg aagccagagg ctgctgctac attcctgcca acaaggact gcagggcgct | 360 |
| cagatgggac agccttggtg cttcttccca ccatcttacc ccagctacaa gctggaaaac | 420 |
| ctgagcagca cgagatggg ctacaccgcc acactgacca gaaccacacc tacattcttc | 480 |
| ccaaaggaca tcctgacact gcggctggac gtgatgatgg aaaccgagaa ccggctgcac | 540 |
| ttcaccatca aggaccccgc caatagaaga tacgaggtgc ccctggaaac ccctcacgtg | 600 |
| cactctagag ccccatctcc actgtacagc gtggaattca gcgaggaacc ctttggcgtg | 660 |
| atcgtgcgga gacagctgga tgcagagtg ctgctgaata ccacagtggc ccctctgttc | 720 |
| ttcgccgacc agtttctgca gctgagcaca agcctgccta gccagtatat cacaggcctg | 780 |
| gccgaacacc tgtctccact gatgctgagc accagctgga ccagaatcac cctgtggaac | 840 |

```
agagatctgg cccctacacc tggcgccaat ctgtacggct ctcacccttt ttatctggcc    900
ctggaagatg gcggaagcgc ccacggtgtc tttctgctga acagcaacgc catggacgtg    960
gtgctgcaac catctcctgc tctgtcttgg agaagcaccg gcggcatcct ggacgtgtac   1020
atctttctgg gacccgagcc taagagcgtg gtgcagcagt atctggatgt cgtgggctac   1080
cccttcatgc ctccttattg gggcctgggc ttccacctgt gtagatgggg atacagctcc   1140
accgccatca ccagacaggt ggtggaaaac atgacccggg ctcacttccc actggatgtg   1200
cagtggaacg acctggacta catggactcc agacgggact tcacctttaa caaggacggc   1260
ttcagagact cccccgccat ggtgcaagaa ctgcatcaag gcggcagacg gtacatgatg   1320
atcgtggatc ctgccatctc ttctagcggc cctgccggaa gctacagacc ttatgatgag   1380
ggcctgagaa gaggcgtgtt catcaccaat gagacaggcc agcctctgat cggcaaagtg   1440
tggcctggaa gcaccgcctt tccagacttc accaatccaa ccgctctggc ttggtgggaa   1500
gatatggtgg ccgagttcca cgatcaggtg cccttcgatg gcatgtggat cgacatgaac   1560
gagcccagca acttcatcag gggcagcgag gatggctgcc caacaacga actggaaaat   1620
cctccttacg tgccaggcgt tgtcggagga acactgcagg ccgccacaat ttgtgccagc   1680
agccatcagt ttctgagcac ccactacaac ctgcacaacc tgtacggcct gaccgaggcc   1740
attgcctctc atagagccct ggttaaggcc agaggcaccc ggccttttgt gatcagcaga   1800
agcacatttg ccggccacgg cagatatgcc ggacattgga caggggacgt ttggtctagt   1860
tgggagcagc tggcctctag cgtgcccgag atcctgcagt ttaatctgct gggagtgccc   1920
ctcgtgggag ccgatgtttg tggatttctg ggcaacacct ccgaggaact gtgcgtcaga   1980
tggacacagc tgggcgcctt ctatcccttc atgagaaacc acaacagcct gctgagcctg   2040
cctcaagagc cttacagctt tagcgaaccc gcacagcagg ccatgagaaa ggccctgact   2100
ctgagatacg ctctgctgcc ccacctgtac accctgtttc atcaagctca tgtggccggc   2160
gagacagtgg ccagaccact gtttctggaa ttccccaagg acagcagcac ctggacagtg   2220
gatcatcagc tgctctgggg agaagccctg ctcattacac ctgtgctgca ggctggcaag   2280
gccgaagtga caggatactt tcccctcggc acttggtacg acctgcagac agttcctgtg   2340
gaagctctgg gatctctgcc tccacctcct gctgctccta gagagcctgc cattcactct   2400
gaaggccagt gggttacact gcccgctcca ctggacacca tcaatgtgca cctgagagcc   2460
ggctacatca tccctctgca aggccctgga ctgaccacaa ccgaaagcag acagcagcca   2520
atggctctgg ccgtggctct gacaaaaggc ggagaagcta gaggcgaact gttctgggat   2580
gacggcgaga gcctggaagt gctggaacgg ggagcctaca cacaagtgat ctttctcgcc   2640
cggaacaaca ccatcgtgaa cgaactcgtc agagtgacca gtgaaggtgc cggactgcag   2700
ctccagaaag tgacagtgct tggagtggcc acagcacccc agcaggtttt gtctaatggc   2760
gtgcccgtgt ccaacttcac atacagcccct gacaccaagg tgctggacat ctgtgtgtct   2820
ctgctgatgg gcgagcagtt cctggtgtcc tggtgttga                          2859
```